US 8,486,422 B2

(12) United States Patent
Verhagen et al.

(10) Patent No.: US 8,486,422 B2
(45) Date of Patent: Jul. 16, 2013

(54) METHODS OF ACTIVATING CLOSTRIDIAL TOXINS

(75) Inventors: Marc F. Verhagen, Irvine, CA (US);
Dean G. Stathakis, Irvine, CA (US);
Lance E. Steward, Irvine, CA (US)

(73) Assignees: Allergan, Inc.; Irvine, Inc.

( * ) Notice: Subject to any disclaimer, the term of this patent is extended or adjusted under 35 U.S.C. 154(b) by 345 days.

(21) Appl. No.: 12/669,447

(22) PCT Filed: Jun. 27, 2008

(86) PCT No.: PCT/US2008/068504
§ 371 (c)(1),
(2), (4) Date: Jan. 15, 2010

(87) PCT Pub. No.: WO2009/014854
PCT Pub. Date: Jan. 29, 2009

(65) Prior Publication Data
US 2010/0286371 A1  Nov. 11, 2010

Related U.S. Application Data

(60) Provisional application No. 60/952,112, filed on Jul. 26, 2007.

(51) Int. Cl.
*A61K 39/08* (2006.01)
(52) U.S. Cl.
USPC ................................. 424/239.1; 424/247.1
(58) Field of Classification Search
None
See application file for complete search history.

(56) References Cited

U.S. PATENT DOCUMENTS

2002/0137886 A1 * 9/2002 Lin et al. ................... 530/350
2008/0241881 A1 * 10/2008 Steward et al. ............ 435/69.1

FOREIGN PATENT DOCUMENTS

WO  WO 2006/076902  *  7/2006

OTHER PUBLICATIONS

Barrett et al, "Evolutionary Lines of Cysteine Peptidases", Biol. Chem., vol. 362, pp. 727-733, 2001.
Dargatz et al, "The heterodimeric protease clostripain from *Clostridium histolyticum* is encodd by a single gene", MolGen Genet, 240, pp. 140-145, 1993.
Dekleva et al, "Nicking of Single Chain *Clostridium Botulinum* Type A Neurotoxin by an Endogenous Protease", Biochemical and Biophysical Research Communications, vol. 162, No. 2, pp. 767-772, 1989.
Dekleva et al, "Purification and Characterization of a Protease from *Clostridium botulinum* Type A That Nicks Single-Chain Type A Botulinum Neurotoxin into the Di-Chain Form", Journal of Bacteriology, vol. 172, No. 5, pp. 2498-2503, 1990.
Gilles et al, "Primary structure of α-clostripain light chain", Eur. J. Biochem., 145, pp. 469-476, 1984.
Kembhavi et al, "Clostripain: characterization of the active site", FEBS, vol. 283, No. 3, pp. 277-280, 1991.
Mitchell et al, "Purification and Properties of Clostridiopeptidase B (Clostripain)", The Journal of Biological Chemistry, vol. 243, No. 18, pp. 4683-4692, 1968.
Mitchell et al, "Clostripain", 635, 1970.
Sebaihia et al, "Genome sequence of a Proteolytic (Group I) *Clostridium botulinum* strain Hall A and comparative analysis of the clostridial genomes", Genome Res, pp. 1082, 2007.
Seddon et al, "Proteolytic activity of *Clostridium difficile*", J. Med. Microbiol., vol. 36, pp. 307-311, 1992.
Ullmann et al, "The specificity of clostripain from *Clostridium histolyticum* Mapping the S' subsites via acyl transfer to amino acid and peptides", Eur. J. Biochem, 223, pp. 865-872, 1994.
Witte et al, "Heterologous expression of the clostripain gene from *Clostridium histolyticum* in *Escherichia coli* and *Bacillus subtilis*: maturation of the clostripain precursor is coupled with self-activation", Microbiology, 140, pp. 1175-1182, 1994.

* cited by examiner

*Primary Examiner* — Mark Navarro
*Assistant Examiner* — Khatol Shahnan-Shah
(74) *Attorney, Agent, or Firm* — Kenton Abel; Debra Condino

(57) ABSTRACT

The specification discloses modified Clostridial toxins comprising an exogenous Clostridial toxin di-chain loop protease cleavage site located within the di-chain loop region; polynucleotide molecules encoding such modified Clostridial toxins; method of producing such modified Clostridial toxins, method of activating such modified Clostridial toxins and methods of activating recombinantly-expressed Clostridial toxins.

2 Claims, 3 Drawing Sheets

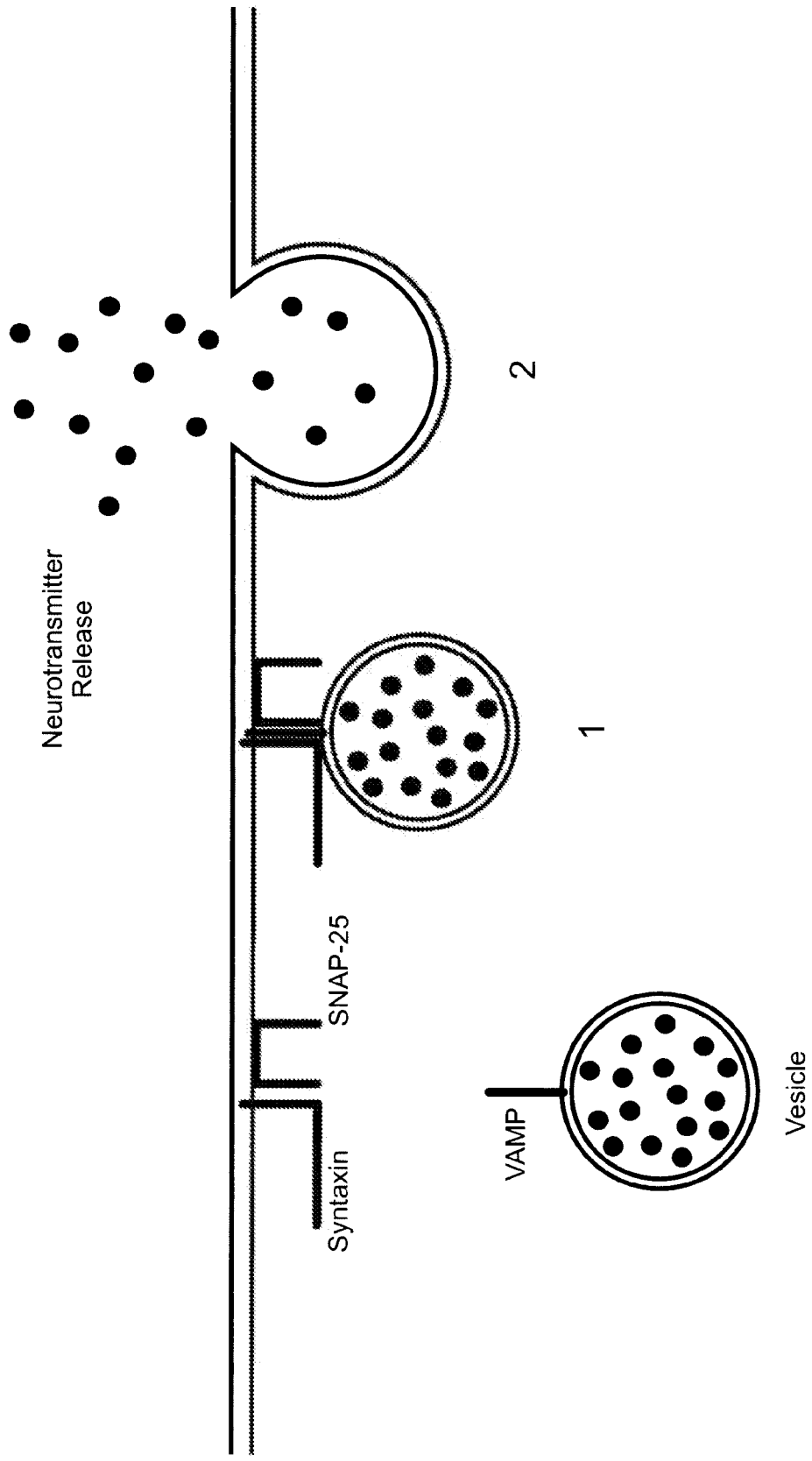

FIG. 2b.

Toxin
Heavy Chain Binding Domain
Receptor System
Heavy Chain Translocation Domain
Light Chain

METHODS OF ACTIVATING CLOSTRIDIAL TOXINS

This Non-Provisional Patent Application claims priority pursuant to 35 U.S.C. §119(e) to U.S. Provisional Patent Application Ser. No. 60/952,112 filed Jul. 26, 2007, which is hereby incorporated by reference in its entirety.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, Tetanus neurotoxin (TeNT), Baratium neurotoxin (BaNT) and Butyricum neurotoxin (BuNT) to inhibit neuronal transmission are being exploited in a wide variety of therapeutic and cosmetic applications, see e.g., William J. Lipham, COSMETIC AND CLINICAL APPLICATIONS OF BOTULINUM TOXIN (Slack, Inc., 2004). Clostridial toxins commercially available as pharmaceutical compositions include, BoNT/A preparations, such as, e.g., BOTOX® (Allergan, Inc., Irvine, Calif.), Dysport®/Reloxin®, (Beaufour Ipsen, Porton Down, England), Linurase® (Prollenium, Inc., Ontario, Canada), Neuronox® (Medy-Tox, Inc., Ochang-myeon, South Korea) BTX-A (Lanzhou Institute Biological Products, China) and Xeomin® (Merz Pharmaceuticals, GmbH., Frankfurt, Germany); and BoNT/B preparations, such as, e.g., MyoBloc™/NeuroBloc™ (Elan Pharmaceuticals, San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

The increasing use of Clostridial toxin therapies in treating a wider range of human afflictions necessitates increasing the efficiency with which these toxins are produced. However, meeting the needs for the ever increasing demand for such toxin treatments may become difficult. One outstanding problem is that all Clostridial toxins need to be converted into the di-chain form of the molecule in order to achieve optimal activity. Historically, this conversion has been done in one of two ways. The first method simply purifies a Clostridial toxin di-chain from the bacterial strain itself, thereby relying on the naturally-occurring endogenous protease used to convert the single-chain form of the toxin into the di-chain form. The second method utilizes an exogenous protease that converts the single-chain form into the di-chain by either taking advantage of a fortuitous cleavage site found in the appropriate location or by genetically engineering a protease cleavage site of commonly used, commercially available exogenous proteases. However, there are several drawbacks to both of these methods. For example, methods employing an endogenous protease produce low toxin yields because native Clostridial strains usually produce little toxin. In addition these strains are poorly suited for research, thus hindering the efforts to genetic manipulation Clostridial toxins to improve their therapeutic and cosmetic attributes. Lastly, several Clostridial strains do not produce the endogenous protease necessary to convert the single-chain form of the toxin to the di-chain form. A drawback to the use of exogenous proteases is a lack of protease specificity that results in inactive toxin because of proteolytic cleavage in inappropriate locations. In addition, many of the currently available proteases are from animal sources that lack Good Manufacture Standard (GMS) approval, requiring additional purification steps during the manufacturing process. Thus, methods currently used to convert the single-chain form of the toxin into the di-chain form are inefficient, cumbersome and/or lead to higher overall production costs. These drawbacks represent a significant obstacle to the overall commercial production of Clostridial toxins and are thus a major problem since di-chain forms of these toxins are needed for scientific, therapeutic and cosmetic applications. In addition, both the amount of Clostridial toxins anticipated for future therapies and the demand for toxins with enhanced therapeutic properties are increasing. Therefore, there is a need to develop better methods for producing Clostridial toxin di-chain molecules in order to meet this need.

The present invention provides modified Clostridial toxins that rely on a novel method of converting the single-chain form of the toxin into the di-chain form and novel methods of convering single-chain Clostridial toxins. These and related advantages are useful for various clinical, therapeutic and cosmetic applications, such as, e.g., the treatment of neuromuscular disorders, neuropathic disorders, eye disorders, pain, muscle injuries, headache, cardiovascular diseases, neuropsychiatric disorders, endocrine disorders, cancers, otic disorders and hyperkinetic facial lines, as well as, other disorders where a Clostridial toxin administration to a mammal can produce a beneficial effect.

BRIEF DESCRIPTION OF THE DRAWINGS

FIG. 2 shows a schematic of the current paradigm of neurotransmitter release and Clostridial toxin intoxication in a central and peripheral neuron. FIG. 2a shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed. FIG. 2b shows a schematic of the intoxication mechanism for tetanus and botulinum toxin activity in a central and peripheral neuron. This intoxication process can be described as comprising four steps: 1) receptor binding, where a Clostridial toxin binds to a Clostridial receptor system and initiates the intoxication process; 2) complex internalization, where after toxin binding, a vesicle containing the toxin/receptor system complex is endocytosed into the cell; 3) light chain translocation, where multiple events result in the release of the active light chain into the cytoplasm; and 4) enzymatic target modification, where the active light chain of Clostridial toxin proteolytically cleaves its target SNARE substrate, such as, e.g., SNAP-25, VAMP or Syntaxin, thereby preventing vesicle docking and neurotransmitter release.

DETAILED DESCRIPTION

Figure 1:
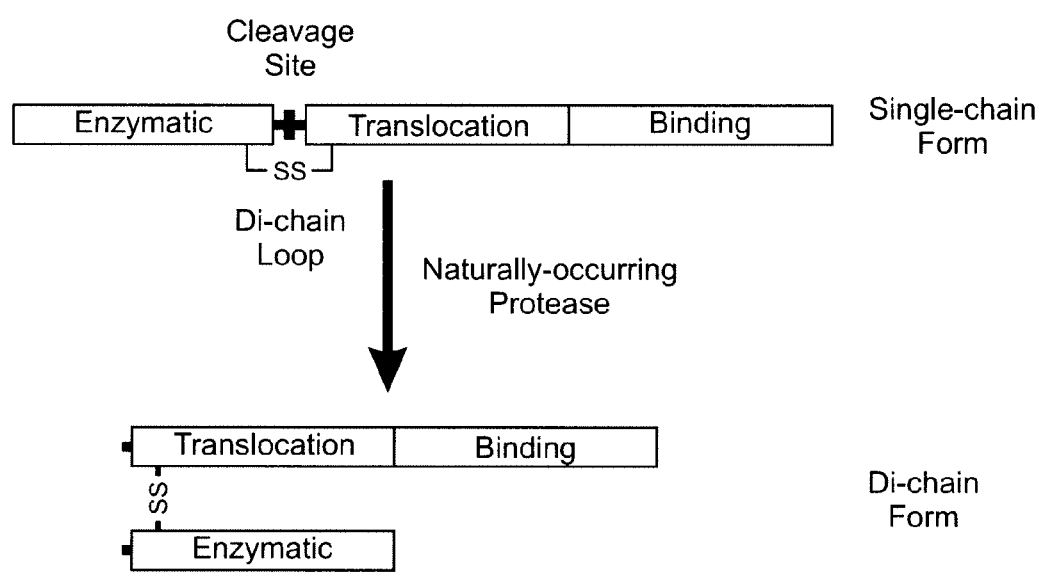
FIG. 1 shows a schematic of the current paradigm of Clostridial toxin posttranslational processing. Clostridial toxins are translated as a single-chain polypeptide of approximately 150 kDa comprising an enzymatic domain, a translocation domain and a binding domain. A disulfide bridge formed from a cysteine residue in the enzymatic domain and a cysteine residue from the translocation domain form a di-chain loop. Within this di-chain loop is a protease cleavage site for a naturally-occurring protease that can be produced endogenously from the Clostridial strain synthesizing the toxin, or exogenously from a source found in the environment. Cleavage of the protease cleavage site by the naturally-occurring protease converts the single-chain form of the toxin into the di-chain form. The di-chain form of the toxin is held together by the disulfide bond and non-covalent interactions between the two chains.

Clostridia toxins produced by *Clostridium botulinum*, *Clostridium tetani*, *Clostridium baratii* and *Clostridium butyricum* are the most widely used in therapeutic and cosmetic treatments of humans and other mammals. Strains of *C. botulinum* produce seven antigenically-distinct types of Botulinum toxins (BoNTs), which have been identified by investigating botulism outbreaks in man (BoNT/A, /B, /E and /F), animals (BoNT/C1 and /D), or isolated from soil (BoNT/G). BoNTs possess approximately 35% amino acid identity with each other and share the same functional domain organization and overall structural architecture. It is recognized by those of skill in the art that within each type of Clostridial toxin there can be subtypes that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific subtypes showing approximately 89% amino acid identity when compared to another BoNT/A subtype. While all seven BoNT serotypes have similar structure and pharmacological properties, each also displays heterogeneous bacteriological characteristics. In contrast, tetanus toxin (TeNT) is produced by a uniform group of *C. tetani*. Two other species of *Clostridia*, *C. baratii* and *C. butyricum*, also produce toxins, BaNT and BuNT respectively, which are similar to BoNT/F and BoNT/E, respectively.

Clostridial toxins are each translated as a single chain polypeptide of approximately 150 kDa that is subsequently cleaved by proteolytic scission within a disulfide loop by a naturally-occurring protease (FIG. 1). This cleavage occurs within the discrete di-chain loop region created between two cysteine residues that form a disulfide bridge. This posttranslational processing yields a di-chain molecule comprising an approximately 50 kDa light chain (LC) and an approximately 100 kDa heavy chain (HC) held together by the single disulfide bond and non-covalent interactions between the two chains. The naturally-occurring protease used to convert the single chain molecule into the di-chain is currently not known. In some bacterial serotypes, such as, e.g., a BoNT/A, a BoNT/B proteolytic, a BoNT/F proteolytic, a BaNT proteolytic strain, or a TeNT, the naturally-occurring protease is produced endogenously by the bacteria serotype and cleavage occurs within the cell before the toxin is release into the environment. However, in other bacterial serotypes, such as, e.g., a BoNT/B nonproteolytic, a BoNT/C1, a BoNT/D, a BoNT/E, a BoNT/F nonproteolytic, a BoNT/G, a BaNT nonproteolytic, or a BuNT, the bacterial strain appears not to produce appreciable amounts of an endogenous protease capable of converting the single chain form of the toxin into the di-chain form. In these situations, the toxin is released from the cell as a single-chain toxin which is subsequently converted into the di-chain form by a naturally-occurring protease found in the environment.

The present invention discloses novel methods that can convert the single-chain polypeptide form of a recombinantly-expressed Clostridial toxin or a modified Clostridial toxins into the di-chain form using the enzymatic activity of a di-chain loop protease isolated from a Clostridial bacteria strain. The present specification discloses several proteases having proteolytic activity for the cleavage site within the di-chain loop region. Thus discovery has lead to the development of methods of activating recombinantly-expressed Clostridial toxins, irrespective of whether these recombinantly-expressed Clostridial toxins are 1) Clostridial toxins capable of cleavage by a di-chain protease expressed within the Clostridial bacterial strain expressing that toxin, such as, e.g., a BoNT/A, a BoNT/B proteolytic, a BoNT/F proteolytic, a BaNT proteolytic, or a TeNT baterical strain; or 2) modified Clostridial toxins comprising a cleavage site within the di-chain loop region that can be cleaved the di-chain proteases disclosed, such as, e.g., a Clostridial toxin from a BoNT/B nonproteolytic, a BoNT/C1, a BoNT/D, a BoNT/E, a BoNT/F nonproteolytic, a BoNT/G, a BaNT nonproteolytic, or BuNT, bacterial strain modified to include the di-chain loop region from a Clostridial toxin produced by a BoNT/A, a BoNT/B proteolytic or a BoNT/F proteolytic bacterial strain.

As a non-limiting example, BoNT/A expressed naturally from *Clostridia botulinum* serotype A strain is produced in its di-chain polypeptide form. This is because the single-chain polypeptide is converted into its di-chain form by a di-chain loop protease produced by the bacterium. However, when a BoNT/A is recombinantly expresses, such as, e.g., in an *E. coli* bacterial strain, this conversion does not occur since *E. coli* strains do not express the di-chain loop protease. As a result, recombinantly expresses BoNT/A is primarily isolated in its single-chain polypeptide form, a form that is approximately 100 times less active than the di-chain form. Thus, the presently disclosed methods of activating recombinantly-expressed Clostridial toxins include methods that convert a recombinantly expressed single-chain BoNT/A into its di-chain form using a BoNT/A di-chain protease disclosed in the present specification.

As another non-limiting example, BoNT/E expressed naturally from *Clostridia botulinum* serotype E strain is produced in its single-chain polypeptide form. This is because the *C. botulinum* serotype E bacterium does not express a di-chain loop protease cabaple of cleaving the toxin within the di-chain loop region. Similarly, when a BoNT/E is recombinantly expresses, such as, e.g., in an *E. coli* bacterial strain, this conversion does not occur since *E. coli* strains also do not express the di-chain loop protease. Thus, the present specification discloses modified Clostridial toxins comprising a di-chain loop protease cleavage site from a Clostridial toxin expressed in a *Clostridia botulinum* strain expressing an endogenous di-chain loop protease, such as, e.g., a modified BoNT/E comprising a BoNT/A di-chain loop region including a BoNT/A di-chain loop protease cleavage site. This can be accomplished, for instance, by replacing the naturally-occurring di-chain loop region from BoNT/E with a di-chain loop region including the di-chain loop protease cleavage site from BoNT/A. Using such a modified BoNT/E, the presently disclosed methods of activating recombinantly-expressed Clostridial toxins include methods that convert a recombinantly expressed single-chain modified BoNT/E into its di-chain form using a BoNT/A di-chain protease disclosed in the present specification.

Aspects of the present invention provide modified Clostridial toxins comprising an exogenous Clostridial toxin di-chain loop including a Clostridial toxin di-chain loop protease cleavage site from a different Clostridial toxin. It is envisioned that the exogenous di-chain loop region can replace the endogenous di-chain loop region or be in addition to the endogenous di-chain loop region. It is also envisioned that any Clostridial toxin di-chain loop region including a di-chain loop protease cleavage site can be used. including, without limitation, a BoNT/A di-chain loop region including a di-chain loop protease cleavage site, a BoNT/B di-chain loop region including a di-chain loop protease cleavage site, a BoNT/C1 di-chain loop region including a di-chain loop protease cleavage site, a BoNT/D di-chain loop region including a di-chain loop protease cleavage site, a BoNT/E di-chain loop region including a di-chain loop protease cleavage site, a BoNT/F di-chain loop region including a di-chain loop protease cleavage site, a BoNT/G di-chain loop region including a di-chain loop protease cleavage site, a TeNT di-chain loop region including a di-chain loop protease cleavage site, a BaNT di-chain loop region including a di-chain loop protease cleavage site and a BuNT di-chain loop region including a di-chain loop protease cleavage site.

Other aspects of the present invention provide polynucleotide molecules encoding modified Clostridial toxins comprising an exogenous Clostridial toxin di-chain loop including a Clostridial toxin di-chain loop protease cleavage site from a different Clostridial toxin.

Other aspects of the present invention provide methods of producing a modified Clostridial toxin comprising an exogenous Clostridial toxin di-chain loop including a Clostridial toxin di-chain loop protease cleavage site from a different Clostridial toxin. Other aspects of the present invention provide methods of producing in a cell a modified Clostridial toxin comprising an exogenous Clostridial toxin di-chain loop including a Clostridial toxin di-chain loop protease cleavage site from a different Clostridial toxin.

Other aspects of the present invention provide methods of activating a modified Clostridial toxin comprising an exogenous Clostridial toxin di-chain loop including a Clostridial toxin di-chain loop protease cleavage site from a different Clostridial toxin.

Yet other aspects of the present invention provide methods of activating a modified Clostridial toxin comprising an exogenous Clostridial toxin di-chain loop including a Clostridial toxin di-chain loop protease cleavage site from a different Clostridial toxin.

Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC ($H_N$) that facilitates release of the LC from intracellular vesicles into the cytoplasm of the target cell; and 3) a binding domain found within the carboxyl-terminal half of the HC ($H_C$) that determines the binding activity and binding specificity of the toxin to the receptor complex located at the surface of the target cell. The $H_C$ domain comprises two distinct structural features of roughly equal size that indicate function and are designated the $H_{CN}$ and $H_{CC}$ subdomains. Table 1 gives approximate boundary regions for each domain found in exemplary Clostridial toxins.

The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of type. Although the applicants have no wish to be limited by the following description, the intoxication mechanism can be described as comprising at least four steps: 1) receptor binding, 2) complex internalization, 3) light chain translocation, and 4) enzymatic target modification (see FIG. 2). The process is initiated when the $H_C$ domain of a Clostridial toxin binds to a toxin-specific receptor complex located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote formation di-chain form of the toxin. Once activated, light chain endopeptidase of the toxin is released from the intracellular vesicle into the cytosol where it specifically targets one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release*, 82(5) Biochimie. 427-446 (2000); Kathryn Turton et al., *Botulinum and Tetanus Neurotoxins: Structure,*

TABLE 1

Clostridial Toxin Reference Sequences and Regions

| Toxin | SEQ ID NO: | LC | $H_N$ | $H_{CN}$ | $H_{CC}$ |
|---|---|---|---|---|---|
| BoNT/A | 1 | M1-K448 | A449-I873 | I874-P1110 | Y1111-L1296 |
| BoNT/B | 2 | M1-K441 | A442-I860 | L861-E1097 | Y1098-E1291 |
| BoNT/C1 | 3 | M1-K449 | T450-I868 | N869-E1111 | Y1112-E1291 |
| BoNT/D | 4 | M1-R445 | D446-I864 | N865-E1098 | Y1099-E1276 |
| BoNT/E | 5 | M1-R422 | K423-I847 | K848-E1085 | Y1086-K1252 |
| BoNT/F | 6 | M1-K439 | A440-I866 | K867-K1105 | Y1106-E1274 |
| BoNT/G | 7 | M1-K446 | S447-I865 | S866-Q1105 | Y1106-E1297 |
| TeNT | 8 | M1-A457 | S458-L881 | K882-E1127 | Y1128-D1315 |
| BaNT | 9 | M1-K431 | N432-I857 | I858-K1094 | Y1095-E1268 |
| BuNT | 10 | M1-R422 | K423-I847 | K848-E1085 | Y1086-K1251 |

*Function and Therapeutic Utility,* 27(11) Trends Biochem. Sci. 552-558. (2002); Giovanna Lalli et al., *The Journey of Tetanus and Botulinum Neurotoxins in Neurons,* 11(9) Trends Microbiol. 431-437, (2003).

Aspects of the present invention provide, in part, a Clostridial toxin. As used herein, the term "Clostridial toxin" means any polypeptide that can execute the overall cellular mechanism whereby a Clostridial toxin enters a neuron and inhibits neurotransmitter release and encompasses the binding of a Clostridial toxin to a low or high affinity receptor complex, the internalization of the toxin/receptor complex, the translocation of the Clostridial toxin light chain into the cytoplasm and the enzymatic modification of a Clostridial toxin substrate.

A Clostridial toxin includes, without limitation, naturally occurring Clostridial toxin variants, such as, e.g., Clostridial toxin isoforms and Clostridial toxin subtypes; non-naturally occurring Clostridial toxin variants, such as, e.g., conservative Clostridial toxin variants, non-conservative Clostridial toxin variants, Clostridial toxin chimeric variants and active Clostridial toxin fragments thereof, or any combination thereof. As used herein, the term "Clostridial toxin variant," whether naturally-occurring or non-naturally-occurring, means a Clostridial toxin that has at least one amino acid change from the corresponding region of the disclosed reference sequences (see Table 1) and can be described in percent identity to the corresponding region of that reference sequence. As non-limiting examples, a BoNT/A variant comprising amino acids 1-1296 of SEQ ID NO: 1 will have at least one amino acid difference, such as, e.g., an amino acid substitution, deletion or addition, as compared to the amino acid region 1-1296 of SEQ ID NO: 1; a BoNT/B variant comprising amino acids 1-1291 of SEQ ID NO: 2 will have at least one amino acid difference, such as, e.g., an amino acid substitution, deletion or addition, as compared to the amino acid region 1-1291 of SEQ ID NO: 2; a BoNT/C1 variant comprising amino acids 1-1291 of SEQ ID NO: 3 will have at least one amino acid difference, such as, e.g., an amino acid substitution, deletion or addition, as compared to the amino acid region 1-1291 of SEQ ID NO: 3; a BoNT/D variant comprising amino acids 1-1276 of SEQ ID NO: 4 will have at least one amino acid difference, such as, e.g., an amino acid substitution, deletion or addition, as compared to the amino acid region 1-1276 of SEQ ID NO: 4; a BoNT/E variant comprising amino acids 1-1252 of SEQ ID NO: 5 will have at least one amino acid difference, such as, e.g., an amino acid substitution, deletion or addition, as compared to the amino acid region 1-1252 of SEQ ID NO: 5; a BoNT/F variant comprising amino acids 1-1274 of SEQ ID NO: 6 will have at least one amino acid difference, such as, e.g., an amino acid substitution, deletion or addition, as compared to the amino acid region 1-1274 of SEQ ID NO: 6; a BoNT/G variant comprising amino acids 1-1297 of SEQ ID NO: 7 will have at least one amino acid difference, such as, e.g., an amino acid substitution, deletion or addition, as compared to the amino acid region 1-1297 of SEQ ID NO: 7; a TeNT variant comprising amino acids 1-1315 of SEQ ID NO: 8 will have at least one amino acid difference, such as, e.g., an amino acid substitution, deletion or addition, as compared to the amino acid region 1-1315 of SEQ ID NO: 8; a BaNT variant comprising amino acids 1-1268 of SEQ ID NO: 9 will have at least one amino acid difference, such as, e.g., an amino acid substitution, deletion or addition, as compared to the amino acid region 1-1268 of SEQ ID NO: 9; and a BuNT variant comprising amino acids 1-1251 of SEQ ID NO: 10 will have at least one amino acid difference, such as, e.g., an amino acid substitution, deletion or addition, as compared to the amino acid region 1-1251 of SEQ ID NO: 10.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice,* 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments,* 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, Match-Box: *A Fundamentally New Algorithm for the Simultaneous Alignment of Several Protein Sequences,* 8(5) CABIOS 501-509 (1992); Gibbs sampling, see, e.g., C. E. Lawrence et al., *Detecting Subtle Sequence Signals: A Gibbs Sampling Strategy for Multiple Alignment,* 262(5131) Science 208-214 (1993); Align-M, see, e.g., Ivo Van Walle et al., *Align-M—A New Algorithm for Multiple Alignment of Highly Divergent Sequences,* 20(9) Bioinformatics: 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison,* 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment,* 302(1) J. Mol. Biol. 205-217 (2000); MUSCLE, see, e.g., Robert C. Edgar, *MUSCLE: Multiple Sequence Alignment With High Score Accuracy and High Throughput,* 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment,* 6(1) BMC Bioinformatics 66 (2005).

As used herein, the term "naturally occurring Clostridial toxin variant" means any Clostridial toxin produced without the aid of any human manipulation, including, without limitation, Clostridial toxin isoforms produced from alternatively-spliced transcripts, Clostridial toxin isoforms produced by spontaneous mutation and Clostridial toxin subtypes. Non-limiting examples of a Clostridial toxin isoform include, e.g., BoNT/A isoforms, BoNT/B isoforms, BoNT/C1 isoforms, BoNT/D isoforms, BoNT/E isoforms, BoNT/F isoforms, BoNT/G isoforms, TeNT isoforms, BaNT isoforms, and BuNT isoforms. Non-limiting examples of a Clostridial toxin subtype include, e.g., BoNT/A subtypes BoNT/A1, BoNT/A2, BoNT/A3 and BoNT/A4; BoNT/B subtypes BoNT/B1, BoNT/B2, BoNT/B bivalent and BoNT/B nonproteolytic; BoNT/C1 subtypes BoNT/C1-1 and BoNT/C1-2; BoNT/E subtypes BoNT/E1, BoNT/E2 and BoNT/E3; and BoNT/F subtypes BoNT/F1, BoNT/F2, BoNT/F3 and BoNT/F4.

As used herein, the term "non-naturally occurring Clostridial toxin variant" means any Clostridial toxin produced with the aid of human manipulation, including, without limitation, Clostridial toxins produced by genetic engineering using random mutagenesis or rational design and Clostridial toxins produced by chemical synthesis. Non-limiting examples of non-naturally occurring Clostridial toxin variants include, e.g., conservative Clostridial toxin variants, non-conservative Clostridial toxin variants, Clostridial toxin chimeric variants and active Clostridial toxin fragments.

As used herein, the term "conservative Clostridial toxin variant" means a Clostridial toxin that has at least one amino acid substituted by another amino acid or an amino acid analog that has at least one property similar to that of the original amino acid from the reference Clostridial toxin sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin variant can function in substantially the same manner as the reference Clostridial toxin on which the conservative Clostridial toxin variant is based, and can be substituted for the reference Clostridial toxin in any aspect of the present invention. A conservative Clostridial toxin variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin on which the conservative Clostridial toxin variant is based. A conservative Clostridial toxin variant can also substitute at least 10 contiguous amino acids, at least 15 contiguous amino acids, at least 20 contiguous amino acids, or at least 25 contiguous amino acids from the reference Clostridial toxin on which the conservative Clostridial toxin variant is based, that possess at least 50% amino acid identity, 65% amino acid identity, 75% amino acid identity, 85% amino acid identity or 95% amino acid identity to the reference Clostridial toxin on which the conservative Clostridial toxin variant is based. Non-limiting examples of a conservative Clostridial toxin variant include, e.g., conservative BoNT/A variants, conservative BoNT/B variants, conservative BoNT/C1 variants, conservative BoNT/D variants, conservative BoNT/E variants, conservative BoNT/F variants, conservative BoNT/G variants, conservative TeNT variants, conservative BaNT variants and conservative BuNT variants.

As used herein, the term "non-conservative Clostridial toxin variant" means a Clostridial toxin in which 1) at least one amino acid is deleted from the reference Clostridial toxin on which the non-conservative Clostridial toxin variant is based; 2) at least one amino acid added to the reference Clostridial toxin on which the non-conservative Clostridial toxin is based; or 3) at least one amino acid is substituted by another amino acid or an amino acid analog that does not share any property similar to that of the original amino acid from the reference Clostridial toxin sequence (Table 1). A non-conservative Clostridial toxin variant can function in substantially the same manner as the reference Clostridial toxin on which the non-conservative Clostridial toxin variant is based, and can be substituted for the reference Clostridial toxin in any aspect of the present invention. A non-conservative Clostridial toxin variant can delete one or more amino acids, two or more amino acids, three or more amino acids, four or more amino acids, five or more amino acids, and ten or more amino acids from the reference Clostridial toxin on which the non-conservative Clostridial toxin variant is based. A non-conservative Clostridial toxin variant can add one or more amino acids, two or more amino acids, three or more amino acids, four or more amino acids, five or more amino acids, and ten or more amino acids to the reference Clostridial toxin on which the non-conservative Clostridial toxin variant is based. A non-conservative Clostridial toxin variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin on which the non-conservative Clostridial toxin variant is based. A non-conservative Clostridial toxin variant can also substitute at least 10 contiguous amino acids, at least 15 contiguous amino acids, at least 20 contiguous amino acids, or at least 25 contiguous amino acids from the reference Clostridial toxin on which the non-conservative Clostridial toxin variant is based, that possess at least 50% amino acid identity, 65% amino acid identity, 75% amino acid identity, 85% amino acid identity or 95% amino acid identity to the reference Clostridial toxin on which the non-conservative Clostridial toxin variant is based. Non-limiting examples of a non-conservative Clostridial toxin variant include, e.g., non-conservative BoNT/A variants, non-conservative BoNT/B variants, non-conservative BoNT/C1 variants, non-conservative BoNT/D variants, non-conservative BoNT/E variants, non-conservative BoNT/F variants, non-conservative BoNT/G variants, non-conservative TeNT variants, non-conservative BaNT variants and non-conservative BuNT variants.

As used herein, the term "Clostridial toxin chimeric variant" means a molecule comprising at least a portion of a Clostridial toxin and at least a portion of at least one other protein to form a toxin with at least one property different from the reference Clostridial toxins of Table 1. One class of Clostridial toxin chimeric variant comprises a modified Clostridial toxin were the endogenous cell binding domain of a naturally-occurring Clostridial toxin is either modified or replaced with a cell binding domain of another molecule. Such modified Clostridial toxin possesses an altered cell binding activity because the modified toxin can, e.g., use the same receptor present on the surface of a naturally occurring Clostridial toxin target cell, referred to as an enhanced cell binding activity for a naturally-occurring Clostridial toxin target cell; use a different receptor present on the surface of a naturally occurring Clostridial toxin target cell, referred to as an altered cell binding activity for a naturally-occurring Clostridial toxin target cell, or use a different receptor present on the surface of the non-Clostridial toxin target cell, referred to as an altered cell binding activity for a non-naturally-occurring Clostridial toxin target cell.

A Clostridial toxin chimeric variant can be a modified Clostridial toxin with an enhanced cell binding activity capable of intoxicating a naturally occurring Clostridial toxin target cell, e.g., a motor neuron. One way this enhanced binding activity is achieved by modifying the endogenous targeting domain of a naturally-occurring Clostridial toxin in order to enhance a cell binding activity of the toxin for its naturally-occurring receptor. Such modifications to a targeting domain result in, e.g., a enhanced cell binding activity that increases binding affinity for an endogenous Clostridial toxin receptor present on a naturally-occurring Clostridial toxin target cell; an enhanced cell binding activity that increases binding specificity for a subgroup of endogenous Clostridial toxin receptors present on a naturally-occurring Clostridial toxin target cell; or an enhanced cell binding activity that increases both binding affinity and binding specificity. Non-limiting examples of modified Clostridial toxins an enhanced cell binding activity for a naturally-occurring Clostridial toxin receptor are described in, e.g., Lance E. Steward, et al., Modified Clostridial Toxins with Enhanced Targeting Capabilities For Endogenous Clostridial Toxin Receptors, International Patent Publication No. 2006/008956 (Mar. 14, 2006), Lance E. Steward, Modified Clostridial Toxins with Enhanced Translocation Capability and Enhanced Targeting Activity, U.S. patent application Ser. No. 11/776,043 (Jul. 11, 2007), each of which is hereby incorporated by reference in its entirety.

A Clostridial toxin chimeric variant can be a modified Clostridial toxin with an altered cell binding activity capable of intoxicating a naturally occurring Clostridial toxin target cell, e.g., a motor neuron. One way this altered capability is achieved by replacing the endogenous targeting domain of a naturally-occurring Clostridial toxin with a targeting domain of another molecule that selectively binds to a different receptor present on the surface of a naturally occurring Clostridial toxin target cell. Such a modification to a targeting domain results in a modified toxin that is able to selectively bind to a non-Clostridial toxin receptor (target receptor) present on a Clostridial toxin target cell. This enhanced binding activity for a naturally occurring Clostridial toxin target cell allows for lower effective doses of a modified Clostridial toxin to be administered to an individual because more toxin will be delivered to the target cell. Thus, modified Clostridial toxins with an enhanced binding activity will reduce the undesirable dispersal of the toxin to areas not targeted for treatment, thereby reducing or preventing the undesirable side-effects associated with diffusion of a Clostridial toxin to an unwanted location. Non-limiting examples of modified Clostridial toxins with an altered cell binding capability for a Clostridial toxin target cell are described in, e.g., Lance E. Steward et al., Modified Clostridial Toxins with Altered Targeting Capabilities For Clostridial Toxin Target Cells, International Patent Publication No. 2006/009831 (Mar. 14, 2005); Lance E. Steward et al., Multivalent Clostridial Toxin Derivatives and Methods of Their Use, U.S. Patent Publication No. 2006/0211619 (Sep. 21, 2006); and Lance E. Steward, Modified Clostridial Toxins with Enhanced Translocation Capabilities and Altered Targeting Activity for Clostridial Toxin Target Cells, U.S. patent application Ser. No. 11/776,052, (Jul. 11, 2007), each of which is hereby incorporated by reference in its entirety.

A Clostridial toxin chimeric variant can be a modified Clostridial toxin with an altered cell binding activity capable of intoxicating a cell other than a naturally occurring Clostridial toxin target cell, e.g., a cell other than a motor neuron. These modified toxins achieve this intoxication by using a target receptor present on non-Clostridial toxin target cell. This re-targeted capability is achieved by replacing a naturally-occurring targeting domain of a Clostridial toxin with a targeting domain showing a selective binding activity for a non-Clostridial toxin receptor present in a non-Clostridial toxin target cell. Such modifications to a targeting domain result in a modified toxin that is able to selectively bind to a non-Clostridial toxin receptor (target receptor) present on a non-Clostridial toxin target cell (re-targeted). A modified Clostridial toxin with an altered targeting activity for a non-Clostridial toxin target cell can bind to a target receptor, translocate into the cytoplasm, and exert its proteolytic effect on the SNARE complex of the non-Clostridial toxin target cell. Non-limiting examples of modified Clostridial toxins with an altered targeting activity for a non-Clostridial toxin target cell are described in, e.g., Keith A. Foster et al., Clostridial Toxin Derivatives Able To Modify Peripheral Sensory Afferent Functions, U.S. Pat. No. 5,989,545 (Nov. 23, 1999); Clifford C. Shone et al., Recombinant Toxin Fragments, U.S. Pat. No. 6,461,617 (Oct. 8, 2002); Conrad P. Quinn et al., Methods and Compounds for the Treatment of Mucus Hypersecretion, U.S. Pat. No. 6,632,440 (Oct. 14, 2003); Lance E. Steward et al., Methods And Compositions For The Treatment Of Pancreatitis, U.S. Pat. No. 6,843,998 (Jan. 18, 2005); Stephan Donovan, Clostridial Toxin Derivatives and Methods For Treating Pain, U.S. Pat. No. 7,138,127 (Nov. 21, 2006); Keith A. Foster et al., Inhibition of Secretion from Non-Neural Cells, U.S. Patent Publication 2003/0180289 (Sep. 25, 2003); J. Oliver Dolly et al., Activatable Recombinant Neurotoxins, U.S. Pat. No. 7,132,259 (Nov. 7, 2006); Keith A. Foster et al., Re-targeted Toxin Conjugates, International Patent Publication WO 2005/023309 (Mar. 17, 2005); Lance E. Steward et al., Multivalent Clostridial Toxin Derivatives and Methods of Their Use, U.S. patent application Ser. No. 11/376,696 (Mar. 15, 2006); Keith A. Foster, Fusion Proteins, International Patent Publication WO 2006/059093 (Jun. 8, 2005); Keith A. Foster, Non-Cytotoxic Protein Conjugates, International Patent Publication WO 2006/059105 (Jun. 8, 2005); and Lance E. Steward, Modified Clostridial Toxins with Enhanced Translocation Capabilities and Altered Targeting Capabilities for Non-Clostridial Toxin Target Cells, U.S. patent application Ser. No. 11/776,075 (Jul. 11, 2007), each of which is hereby incorporated by reference in its entirety. The ability to re-target the therapeutic effects associated with Clostridial toxins has greatly extended the number of medicinal applications able to use a Clostridial toxin therapy. As a non-limiting example, modified Clostridial toxins retargeted to sensory neurons are useful in treating various kinds of chronic pain, such as, e.g., hyperalgesia and allodynia, neuropathic pain and inflammatory pain, see, e.g., Foster, supra, (1999); and Donovan, supra, (2006); and Stephan Donovan, Method For Treating Neurogenic Inflammation Pain with Botulinum Toxin and Substance P Components, U.S. Pat. No. 7,022,329 (Apr. 4, 2006). As another non-limiting example, modified Clostridial toxins retargeted to pancreatic cells are useful in treating pancreatitis, see, e.g., Steward, supra, (2005).

Thus, in an embodiment, a Clostridial toxin chimeric variant can comprise a modified Clostridial toxin disclosed in the present specification where the binding domain comprises an enhanced cell binding activity capable of intoxicating a naturally occurring Clostridial toxin target cell. In another embodiment, a Clostridial toxin chimeric variant can comprise a modified Clostridial toxin disclosed in the present specification where the binding domain comprises an altered cell binding activity capable of intoxicating a naturally occurring Clostridial toxin target cell. In still another embodiment, a Clostridial toxin chimeric variant can comprise a modified Clostridial toxin disclosed in the present specification where the binding domain comprises an altered cell binding activity capable of intoxicating a non-naturally occurring Clostridial toxin target cell.

It is also envisioned that any of a variety of Clostridial toxin fragments can be useful in aspects of the present invention with the proviso that these active fragments can execute the overall cellular mechanism whereby a Clostridial toxin proteolytically cleaves a substrate. Thus, aspects of this embodiment can include Clostridial toxin fragments having a length of, e.g., at least 300 amino acids, at least 400 amino acids, at least 500 amino acids, at least 600 amino acids, at least 700 amino acids, at least 800 amino acids, at least 900 amino acids, at least 1000 amino acids, at least 1100 amino acids and at least 1200 amino acids. Other aspects of this embodiment, can include Clostridial toxin fragments having a length of, e.g., at most 300 amino acids, at most 400 amino acids, at most 500 amino acids, at most 600 amino acids, at most 700 amino acids, at most 800 amino acids, at most 900 amino acids, at most 1000 amino acids, at most 1100 amino acids and at most 1200 amino acids.

It is also envisioned that any of a variety of Clostridial toxin fragments comprising the light chain can be useful in aspects of the present invention with the proviso that these light chain fragments can specifically target the core components of the neurotransmitter release apparatus and thus participate in executing the overall cellular mechanism whereby a Clostridial toxin proteolytically cleaves a substrate. The light chains of Clostridial toxins are approximately 420-460 amino acids in length and comprise an enzymatic domain (Table 1). Research has shown that the entire length of a Clostridial toxin light chain is not necessary for the enzymatic activity of the enzymatic domain. As a non-limiting example, the first eight amino acids of the BoNT/A light chain (residues 1-8 of SEQ ID NO: 1) are not required for enzymatic activity. As another non-limiting example, the first eight amino acids of the TeNT light chain (residues 1-8 of SEQ ID NO: 8) are not required for enzymatic activity. Likewise, the carboxyl-terminus of the light chain is not necessary for activity. As a non-limiting example, the last 32 amino acids of the BoNT/A light chain (residues 417-448 of SEQ ID NO: 1) are not required for enzymatic activity. As another non-limiting example, the last 31 amino acids of the TeNT light chain (residues 427-457 of SEQ ID NO: 8) are not required for enzymatic activity. Thus, aspects of this embodiment can include Clostridial toxin light chains comprising an enzymatic domain having a length of, e.g., at least 350 amino acids, at least 375 amino acids, at least 400 amino acids, at least 425 amino acids and at least 450 amino acids. Other aspects of this embodiment can include Clostridial toxin light chains comprising an enzymatic domain having a length of, e.g., at most 350 amino acids, at most 375 amino acids, at most 400 amino acids, at most 425 amino acids and at most 450 amino acids.

It is also envisioned that any of a variety of Clostridial toxin $H_N$ regions comprising a translocation domain can be useful in aspects of the present invention with the proviso that these active fragments can facilitate the release of the LC from intracellular vesicles into the cytoplasm of the target cell and thus participate in executing the overall cellular mechanism whereby a Clostridial toxin proteolytically cleaves a substrate. The $H_N$ regions from the heavy chains of Clostridial toxins are approximately 410-430 amino acids in length and comprise a translocation domain (Table 1). Research has shown that the entire length of a $H_N$ region from a Clostridial toxin heavy chain is not necessary for the translocating activity of the translocation domain. Thus, aspects of this embodiment can include Clostridial toxin $H_N$ regions comprising a translocation domain having a length of, e.g., at least 350 amino acids, at least 375 amino acids, at least 400 amino acids and at least 425 amino acids. Other aspects of this embodiment can include Clostridial toxin $H_N$ regions comprising translocation domain having a length of, e.g., at most 350 amino acids, at most 375 amino acids, at most 400 amino acids and at most 425 amino acids.

It is also envisioned that any of a variety of Clostridial toxin $H_C$ regions comprising a binding domain can be useful in aspects of the present invention with the proviso that these active fragments can determine the binding activity and binding specificity of the toxin to the receptor complex located at the surface of the target cell execute the overall cellular mechanism whereby a Clostridial toxin proteolytically cleaves a substrate. The $H_C$ regions from the heavy chains of Clostridial toxins are approximately 400-440 amino acids in length and comprise a binding domain (Table 1). Research has shown that the entire length of a $H_C$ region from a Clostridial toxin heavy chain is not necessary for the binding activity of the binding domain. Thus, aspects of this embodiment can include Clostridial toxin $H_C$ regions comprising a binding domain having a length of, e.g., at least 350 amino acids, at least 375 amino acids, at least 400 amino acids and at least 425 amino acids. Other aspects of this embodiment can include Clostridial toxin $H_C$ regions comprising a binding domain having a length of, e.g., at most 350 amino acids, at most 375 amino acids, at most 400 amino acids and at most 425 amino acids.

Thus, in an embodiment, a Clostridial toxin comprises a Clostridial toxin enzymatic domain, a Clostridial toxin translocation domain and a Clostridial toxin binding domain. In an aspect of this embodiment, a Clostridial toxin comprises a naturally occurring Clostridial toxin variant, such as, e.g., a Clostridial toxin isoform or a Clostridial toxin subtype. In another aspect of this embodiment, a Clostridial toxin comprises a non-naturally occurring Clostridial toxin variant, such as, e.g., a conservative Clostridial toxin variant, a non-conservative Clostridial toxin variant or an active Clostridial toxin fragment, or any combination thereof. In another aspect of this embodiment, a Clostridial toxin comprises a Clostridial toxin enzymatic domain or an active fragment thereof, a Clostridial toxin translocation domain or an active fragment thereof, a Clostridial toxin binding domain or an active fragment thereof, or any combination thereof. In other aspects of this embodiment, a Clostridial toxin can comprise a BoNT/A, a BoNT/B, a BoNT/C1, a BoNT/D, a BoNT/E, a BoNT/F, a BoNT/G, a TeNT, a BaNT or a BuNT.

In another embodiment, a Clostridial toxin comprises a BoNT/A. In an aspect of this embodiment, a BoNT/A comprises a BoNT/A enzymatic domain, a BoNT/A translocation domain and a BoNT/A binding domain. In another aspect of this embodiment, a BoNT/A comprises SEQ ID NO: 1. In another aspect of this embodiment, a BoNT/A comprises a naturally occurring BoNT/A variant, such as, e.g., a BoNT/A isoform or a BoNT/A subtype. In another aspect of this embodiment, a BoNT/A comprises a naturally occurring BoNT/A variant of SEQ ID NO: 1, such as, e.g., a BoNT/A isoform of SEQ ID NO: 1 or a BoNT/A subtype of SEQ ID NO: 1. In still another aspect of this embodiment, a BoNT/A comprises a non-naturally occurring BoNT/A variant, such as, e.g., a conservative BoNT/A variant, a non-conservative BoNT/A variant or an active BoNT/A fragment, or any combination thereof. In still another aspect of this embodiment, a BoNT/A comprises a non-naturally occurring BoNT/A variant of SEQ ID NO: 1, such as, e.g., a conservative BoNT/A variant of SEQ ID NO: 1, a non-conservative BoNT/A variant of SEQ ID NO: 1 or an active BoNT/A fragment of SEQ ID NO: 1, or any combination thereof. In yet another aspect of this embodiment, a BoNT/A comprises a BoNT/A enzymatic domain or an active fragment thereof, a BoNT/A translocation domain or an active fragment thereof, a BoNT/A binding domain or an active fragment thereof, or any combination thereof. In yet another aspect of this embodiment, a BoNT/A comprising a BoNT/A enzymatic domain of amino acids 1-448 from SEQ ID NO: 1 or an active fragment thereof, a BoNT/A translocation domain of amino acids 449-871 from SEQ ID NO: 1 or an active fragment thereof, a BoNT/A binding domain of amino acids 872-1296 from SEQ ID NO: 1 or an active fragment thereof, and any combination thereof.

In other aspects of this embodiment, a BoNT/A comprises a polypeptide having, e.g., at least 70% amino acid identity with SEQ ID NO: 1, at least 75% amino acid identity with the SEQ ID NO: 1, at least 80% amino acid identity with SEQ ID NO: 1, at least 85% amino acid identity with SEQ ID NO: 1, at least 90% amino acid identity with SEQ ID NO: 1 or at least 95% amino acid identity with SEQ ID NO: 1. In yet other aspects of this embodiment, a BoNT/A comprises a polypeptide having, e.g., at most 70% amino acid identity with SEQ ID NO: 1, at most 75% amino acid identity with the SEQ ID NO: 1, at most 80% amino acid identity with SEQ ID NO: 1, at most 85% amino acid identity with SEQ ID NO: 1, at most 90% amino acid identity with SEQ ID NO: 1 or at most 95% amino acid identity with SEQ ID NO: 1.

In other aspects of this embodiment, a BoNT/A comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 1. In yet other aspects of this embodiment, a BoNT/A comprises a polypeptide having, e.g., at most one, two, three, four, five, six, seven, eight, nine, 10, 20, 30, 40, 50, 100, 200 or 500 non-contiguous amino acid deletions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 non-contiguous amino acid deletions relative to SEQ ID NO: 1. In still other aspects of this embodiment, a BoNT/A comprises a polypeptide having, e.g., at most one, two, three, four, five, six, seven, eight, nine, 10, 20, 30, 40, 50, 100, 200 or 500 non-contiguous amino acid additions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 non-contiguous amino acid additions relative to SEQ ID NO: 1.

In other aspects of this embodiment, a BoNT/A comprises a polypeptide having, e.g., at most one, two, three, four, five, six, seven, eight, nine, 10, 20, 30, 40, 50, 100, 200 or 500 contiguous amino acid substitutions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 contiguous amino acid substitutions relative to SEQ ID NO: 1. In yet other aspects of this embodiment, a BoNT/A comprises a polypeptide having, e.g., at most one, two, three, four, five, six, seven, eight, nine, 10, 20, 30, 40, 50, 100, 200 or 500 contiguous amino acid deletions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 contiguous amino acid deletions relative to SEQ ID NO: 1. In still other aspects of this embodiment, a BoNT/A comprises a polypeptide having, e.g., at most one, two, three, four, five, six, seven, eight, nine, 10, 20, 30, 40, 50, 100, 200 or 500 contiguous amino acid additions relative to SEQ ID NO: 1. In other aspects of this embodiment, a BoNT/A comprises a polypeptide having, e.g., at least one, two, three, four, five, six, seven, eight, nine, 10, 20, 30, 40, 50, 100, 200 or 500 contiguous amino acid additions relative to SEQ ID NO: 1.

In another embodiment, a Clostridial toxin comprises a BoNT/B. In an aspect of this embodiment, a BoNT/B comprises a BoNT/B enzymatic domain, a BoNT/B translocation domain and a BoNT/B binding domain. In another aspect of this embodiment, a BoNT/B comprises SEQ ID NO: 2. In another aspect of this embodiment, a BoNT/B comprises a naturally occurring BoNT/B variant, such as, e.g., a BoNT/B isoform or a BoNT/B subtype. In another aspect of this embodiment, a BoNT/B comprises a naturally occurring BoNT/B variant of SEQ ID NO: 2, such as, e.g., a BoNT/B isoform of SEQ ID NO: 2 or a BoNT/B subtype of SEQ ID NO: 2. In still another aspect of this embodiment, a BoNT/B comprises a non-naturally occurring BoNT/B variant, such as, e.g., a conservative BoNT/B variant, a non-conservative BoNT/B variant or an active BoNT/B fragment, or any combination thereof. In still another aspect of this embodiment, a BoNT/B comprises a non-naturally occurring BoNT/B variant of SEQ ID NO: 2, such as, e.g., a conservative BoNT/B variant of SEQ ID NO: 2, a non-conservative BoNT/B variant of SEQ ID NO: 2 or an active BoNT/B fragment of SEQ ID NO: 2, or any combination thereof. In yet another aspect of this embodiment, a BoNT/B comprising a BoNT/B enzymatic domain or an active fragment thereof, a BoNT/B translocation domain or active fragment thereof, a BoNT/B binding domain or active fragment thereof, and any combination thereof. In yet another aspect of this embodiment, a BoNT/B comprising a BoNT/B enzymatic domain of amino acids 1-441 from SEQ ID NO: 2 or active fragment thereof, a BoNT/B translocation domain of amino acids 442-858 from SEQ ID NO: 2 or active fragment thereof, a BoNT/B binding domain of amino acids 859-1291 from SEQ ID NO: 2 or active fragment thereof, and any combination thereof.

In other aspects of this embodiment, a BoNT/B comprises a polypeptide having, e.g., at least 70% amino acid identity with SEQ ID NO: 2, at least 75% amino acid identity with the SEQ ID NO: 2, at least 80% amino acid identity with SEQ ID NO: 2, at least 85% amino acid identity with SEQ ID NO: 2, at least 90% amino acid identity with SEQ ID NO: 2 or at least 95% amino acid identity with SEQ ID NO: 2. In yet other aspects of this embodiment, a BoNT/B comprises a polypeptide having, e.g., at most 70% amino acid identity with SEQ ID NO: 2, at most 75% amino acid identity with the SEQ ID NO: 2, at most 80% amino acid identity with SEQ ID NO: 2, at most 85% amino acid identity with SEQ ID NO: 2, at most 90% amino acid identity with SEQ ID NO: 2 or at most 95% amino acid identity with SEQ ID NO: 2.

In other aspects of this embodiment, a BoNT/B comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 2. In yet other aspects of this embodiment, a BoNT/B comprises a polypeptide having, e.g., at most one, two, three, four, five, six, seven, eight, nine, 10, 20, 30, 40, 50, 100, 200 or 500 non-contiguous amino acid deletions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 non-contiguous amino acid deletions relative to SEQ ID NO: 2. In still other aspects of this embodiment, a BoNT/B comprises a polypeptide having, e.g., at most one, two, three, four, five, six, seven, eight, nine, 10, 20, 30, 40, 50, 100, 200 or 500 non-contiguous amino acid additions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 non-contiguous amino acid additions relative to SEQ ID NO: 2.

In other aspects of this embodiment, a BoNT/B comprises a polypeptide having, e.g., at most one, two, three, four, five, six, seven, eight, nine, 10, 20, 30, 40, 50, 100, 200 or 500 contiguous amino acid substitutions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 contiguous amino acid substitutions relative to SEQ ID NO: 2. In yet other aspects of this embodiment, a BoNT/B comprises a polypeptide having, e.g., at most one, two, three, four, five, six, seven, eight, nine, 10, 20, 30, 40, 50, 100, 200 or 500 contiguous amino acid deletions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 contiguous amino acid deletions relative to SEQ ID NO: 2. In still other aspects of this embodiment, a BoNT/B comprises a polypeptide having, e.g., at most one, two, three, four, five, six, seven, eight, nine, 10, 20, 30, 40, 50, 100, 200 or 500 contiguous amino acid additions relative to SEQ ID NO: 2. In other aspects of this embodiment, a BoNT/B comprises a polypeptide having, e.g., at least one, two, three, four, five, six, seven, eight, nine, 10, 20, 30, 40, 50, 100, 200 or 500 contiguous amino acid additions relative to SEQ ID NO: 2.

In another embodiment, a Clostridial toxin comprises a BoNT/C1. In an aspect of this embodiment, a BoNT/C1 comprises a BoNT/C1 enzymatic domain, a BoNT/C1 translocation domain and a BoNT/C1 binding domain. In another aspect of this embodiment, a BoNT/C1 comprises SEQ ID NO: 3. In another aspect of this embodiment, a BoNT/C1 comprises a naturally occurring BoNT/C1 variant, such as, e.g., a BoNT/C1 isoform or a BoNT/C1 subtype. In another aspect of this embodiment, a BoNT/C1 comprises a naturally occurring BoNT/C1 variant of SEQ ID NO: 3, such as, e.g., a BoNT/C1 isoform of SEQ ID NO: 3 or a BoNT/C1 subtype of SEQ ID NO: 3. In still another aspect of this embodiment, a BoNT/C1 comprises a non-naturally occurring BoNT/C1 variant, such as, e.g., a conservative BoNT/C1 variant, a non-conservative BoNT/C1 variant or an active BoNT/C1 fragment, or any combination thereof. In still another aspect of this embodiment, a BoNT/C1 comprises a non-naturally occurring BoNT/C1 variant of SEQ ID NO: 3, such as, e.g., a conservative BoNT/C1 variant of SEQ ID NO: 3, a non-conservative BoNT/C1 variant of SEQ ID NO: 3 or an active BoNT/C1 fragment of SEQ ID NO: 3, or any combination thereof. In yet another aspect of this embodiment, a BoNT/C1 comprises a BoNT/C1 enzymatic domain or active fragment thereof, a BoNT/C1 translocation domain or active fragment thereof, a BoNT/C1 binding domain or active fragment thereof, and any combination thereof. In yet another aspect of this embodiment, a BoNT/C1 comprises a BoNT/C1 enzymatic domain of amino acid 1-449 from SEQ ID NO: 3 or active fragment thereof, a BoNT/C1 translocation domain of amino acids 450-866 from SEQ ID NO: 3 or active fragment thereof, a BoNT/C1 binding domain of amino acids 867-1291 from SEQ ID NO: 3 or active fragment thereof, and any combination thereof.

In other aspects of this embodiment, a BoNT/C1 comprises a polypeptide having, e.g., at least 70% amino acid identity with SEQ ID NO: 3, at least 75% amino acid identity with the SEQ ID NO: 3, at least 80% amino acid identity with SEQ ID NO: 3, at least 85% amino acid identity with SEQ ID NO: 3, at least 90% amino acid identity with SEQ ID NO: 3 or at least 95% amino acid identity with SEQ ID NO: 3. In yet other aspects of this embodiment, a BoNT/C1 comprises a polypeptide having, e.g., at most 70% amino acid identity with SEQ ID NO: 3, at most 75% amino acid identity with the SEQ ID NO: 3, at most 80% amino acid identity with SEQ ID NO: 3, at most 85% amino acid identity with SEQ ID NO: 3, at most 90% amino acid identity with SEQ ID NO: 3 or at most 95% amino acid identity with SEQ ID NO: 3.

In other aspects of this embodiment, a BoNT/C1 comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 3. In yet other aspects of this embodiment, a BoNT/C1 comprises a polypeptide having, e.g., at most one, two, three, four, five, six, seven, eight, nine, 10, 20, 30, 40, 50, 100, 200 or 500 non-contiguous amino acid deletions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 non-contiguous amino acid deletions relative to SEQ ID NO: 3. In still other aspects of this embodiment, a BoNT/C1 comprises a polypeptide having, e.g., at most one, two, three, four, five, six, seven, eight, nine, 10, 20, 30, 40, 50, 100, 200 or 500 non-contiguous amino acid additions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 non-contiguous amino acid additions relative to SEQ ID NO: 3.

In other aspects of this embodiment, a BoNT/C1 comprises a polypeptide having, e.g., at most one, two, three, four, five, six, seven, eight, nine, 10, 20, 30, 40, 50, 100, 200 or 500 contiguous amino acid substitutions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 contiguous amino acid substitutions relative to SEQ ID NO: 3. In yet other aspects of this embodiment, a BoNT/C1 comprises a polypeptide having, e.g., at most one, two, three, four, five, six, seven, eight, nine, 10, 20, 30, 40, 50, 100, 200 or 500 contiguous amino acid deletions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 contiguous amino acid deletions relative to SEQ ID NO: 3. In still other aspects of this embodiment, a BoNT/C1 comprises a polypeptide having, e.g., at most one, two, three, four, five, six, seven, eight, nine, 10, 20, 30, 40, 50, 100, 200 or 500 contiguous amino acid additions relative to SEQ ID NO: 3. In other aspects of this embodiment, a BoNT/C1 comprises a polypeptide having, e.g., at least one, two, three, four, five, six, seven, eight, nine, 10, 20, 30, 40, 50, 100, 200 or 500 contiguous amino acid additions relative to SEQ ID NO: 3.

In another embodiment, a Clostridial toxin comprises a BoNT/D. In an aspect of this embodiment, a BoNT/D comprises a BoNT/D enzymatic domain, a BoNT/D translocation domain and a BoNT/D binding domain. In another aspect of this embodiment, a BoNT/D comprises SEQ ID NO: 4. In another aspect of this embodiment, a BoNT/D comprises a naturally occurring BoNT/D variant, such as, e.g., a BoNT/D isoform or a BoNT/D subtype. In another aspect of this embodiment, a BoNT/D comprises a naturally occurring BoNT/D variant of SEQ ID NO: 4, such as, e.g., a BoNT/D isoform of SEQ ID NO: 4 or a BoNT/D subtype of SEQ ID NO: 4. In still another aspect of this embodiment, a BoNT/D comprises a non-naturally occurring BoNT/D variant, such as, e.g., a conservative BoNT/D variant, a non-conservative BoNT/D variant or an active BoNT/D fragment, or any combination thereof. In still another aspect of this embodiment, a BoNT/D comprises a non-naturally occurring BoNT/D variant of SEQ ID NO: 4, such as, e.g., a conservative BoNT/D variant of SEQ ID NO: 4, a non-conservative BoNT/D variant of SEQ ID NO: 4 or an active BoNT/D fragment of SEQ ID NO: 4, or any combination thereof. In yet another aspect of this embodiment, a BoNT/D comprises a BoNT/D enzymatic domain or an active fragment thereof, a BoNT/D translocation domain or an active fragment thereof, a BoNT/D binding domain or an active fragment thereof, or any combination thereof. In yet another aspect of this embodiment, a BoNT/D comprising a BoNT/D enzymatic domain of amino acids 1-445 from SEQ ID NO: 4 or an active fragment thereof, a BoNT/D translocation domain of amino acids 446-862 from SEQ ID NO: 4 or an active fragment thereof, a BoNT/D binding domain of amino acids 863-1276 from SEQ ID NO: 4 or an active fragment thereof, and any combination thereof.

In other aspects of this embodiment, a BoNT/D comprises a polypeptide having, e.g., at least 70% amino acid identity with SEQ ID NO: 4, at least 75% amino acid identity with the SEQ ID NO: 4, at least 80% amino acid identity with SEQ ID NO: 4, at least 85% amino acid identity with SEQ ID NO: 4, at least 90% amino acid identity with SEQ ID NO: 4 or at least 95% amino acid identity with SEQ ID NO: 4. In yet other aspects of this embodiment, a BoNT/D comprises a polypeptide having, e.g., at most 70% amino acid identity with SEQ ID NO: 4, at most 75% amino acid identity with the SEQ ID NO: 4, at most 80% amino acid identity with SEQ ID NO: 4, at most 85% amino acid identity with SEQ ID NO: 4, at most 90% amino acid identity with SEQ ID NO: 4 or at most 95% amino acid identity with SEQ ID NO: 4.

In other aspects of this embodiment, a BoNT/D comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 4. In yet other aspects of this embodiment, a BoNT/D comprises a polypeptide having, e.g., at most one, two, three, four, five, six, seven, eight, nine, 10, 20, 30, 40, 50, 100, 200 or 500 non-contiguous amino acid deletions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 non-contiguous amino acid deletions relative to SEQ ID NO: 4. In still other aspects of this embodiment, a BoNT/D comprises a polypeptide having, e.g., at most one, two, three, four, five, six, seven, eight, nine, 10, 20, 30, 40, 50, 100, 200 or 500 non-contiguous amino acid additions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 non-contiguous amino acid additions relative to SEQ ID NO: 4.

In other aspects of this embodiment, a BoNT/D comprises a polypeptide having, e.g., at most one, two, three, four, five, six, seven, eight, nine, 10, 20, 30, 40, 50, 100, 200 or 500 contiguous amino acid substitutions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 contiguous amino acid substitutions relative to SEQ ID NO: 4. In yet other aspects of this embodiment, a BoNT/D comprises a polypeptide having, e.g., at most one, two, three, four, five, six, seven, eight, nine, 10, 20, 30, 40, 50, 100, 200 or 500 contiguous amino acid deletions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 contiguous amino acid deletions relative to SEQ ID NO: 4. In still other aspects of this embodiment, a BoNT/D comprises a polypeptide having, e.g., at most one, two, three, four, five, six, seven, eight, nine, 10, 20, 30, 40, 50, 100, 200 or 500 contiguous amino acid additions relative to SEQ ID NO: 4. In other aspects of this embodiment, a BoNT/D comprises a polypeptide having, e.g., at least one, two, three, four, five, six, seven, eight, nine, 10, 20, 30, 40, 50, 100, 200 or 500 contiguous amino acid additions relative to SEQ ID NO: 4.

In another embodiment, a Clostridial toxin comprises a BoNT/E. In an aspect of this embodiment, a BoNT/E comprises a BoNT/E enzymatic domain, a BoNT/E translocation domain and a BoNT/E binding domain. In another aspect of this embodiment, a BoNT/E comprises SEQ ID NO: 5. In another aspect of this embodiment, a BoNT/E comprises a naturally occurring BoNT/E variant, such as, e.g., a BoNT/E isoform or a BoNT/E subtype. In another aspect of this embodiment, a BoNT/E comprises a naturally occurring BoNT/E variant of SEQ ID NO: 5, such as, e.g., a BoNT/E isoform of SEQ ID NO: 5 or a BoNT/E subtype of SEQ ID NO: 5. In still another aspect of this embodiment, a BoNT/E comprises a non-naturally occurring BoNT/E variant, such as, e.g., a conservative BoNT/E variant, a non-conservative BoNT/E variant or an active BoNT/E fragment, or any combination thereof. In still another aspect of this embodiment, a BoNT/E comprises a non-naturally occurring BoNT/E variant of SEQ ID NO: 5, such as, e.g., a conservative BoNT/E variant of SEQ ID NO: 5, a non-conservative BoNT/E variant of SEQ ID NO: 5 or an active BoNT/E fragment of SEQ ID NO: 5, or any combination thereof. In yet another aspect of this embodiment, a BoNT/E comprising a BoNT/E enzymatic domain or an active fragment thereof, a BoNT/E translocation domain or active fragment thereof, a BoNT/E binding domain or active fragment thereof, and any combination thereof. In yet another aspect of this embodiment, a BoNT/E comprising a BoNT/E enzymatic domain of amino acids 1-422 from SEQ ID NO: 5 or active fragment thereof, a BoNT/E translocation domain of amino acids 423-845 from SEQ ID NO: 5 or active fragment thereof, a BoNT/E binding domain of amino acids 846-1252 from SEQ ID NO: 5 or active fragment thereof, and any combination thereof.

In other aspects of this embodiment, a BoNT/E comprises a polypeptide having, e.g., at least 70% amino acid identity with SEQ ID NO: 5, at least 75% amino acid identity with the SEQ ID NO: 5, at least 80% amino acid identity with SEQ ID NO: 5, at least 85% amino acid identity with SEQ ID NO: 5, at least 90% amino acid identity with SEQ ID NO: 5 or at least 95% amino acid identity with SEQ ID NO: 5. In yet other aspects of this embodiment, a BoNT/E comprises a polypeptide having, e.g., at most 70% amino acid identity with SEQ ID NO: 5, at most 75% amino acid identity with the SEQ ID NO: 5, at most 80% amino acid identity with SEQ ID NO: 5, at most 85% amino acid identity with SEQ ID NO: 5, at most 90% amino acid identity with SEQ ID NO: 5 or at most 95% amino acid identity with SEQ ID NO: 5.

In other aspects of this embodiment, a BoNT/E comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 5. In yet other aspects of this embodiment, a BoNT/E comprises a polypeptide having, e.g., at most one, two, three, four, five, six, seven, eight, nine, 10, 20, 30, 40, 50, 100, 200 or 500 non-contiguous amino acid deletions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 non-contiguous amino acid deletions relative to SEQ ID NO: 5. In still other aspects of this embodiment, a BoNT/E comprises a polypeptide having, e.g., at most one, two, three, four, five, six, seven, eight, nine, 10, 20, 30, 40, 50, 100, 200 or 500 non-contiguous amino acid additions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 non-contiguous amino acid additions relative to SEQ ID NO: 5.

In other aspects of this embodiment, a BoNT/E comprises a polypeptide having, e.g., at most one, two, three, four, five, six, seven, eight, nine, 10, 20, 30, 40, 50, 100, 200 or 500 contiguous amino acid substitutions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 contiguous amino acid substitutions relative to SEQ ID NO: 5. In yet other aspects of this embodiment, a BoNT/E comprises a polypeptide having, e.g., at most one, two, three, four, five, six, seven, eight, nine, 10, 20, 30, 40, 50, 100, 200 or 500 contiguous amino acid deletions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 contiguous amino acid deletions relative to SEQ ID NO: 5. In still other aspects of this embodiment, a BoNT/E comprises a polypeptide having, e.g., at most one, two, three, four, five, six, seven, eight, nine, 10, 20, 30, 40, 50, 100, 200 or 500 contiguous amino acid additions relative to SEQ ID NO: 5. In other aspects of this embodiment, a BoNT/E comprises a polypeptide having, e.g., at least one, two, three, four, five, six, seven, eight, nine, 10, 20, 30, 40, 50, 100, 200 or 500 contiguous amino acid additions relative to SEQ ID NO: 5.

In another embodiment, a Clostridial toxin comprises a BoNT/F. In an aspect of this embodiment, a BoNT/F comprises a BoNT/F enzymatic domain, a BoNT/F translocation domain and a BoNT/F binding domain. In another aspect of this embodiment, a BoNT/F comprises SEQ ID NO: 6. In another aspect of this embodiment, a BoNT/F comprises a naturally occurring BoNT/F variant, such as, e.g., a BoNT/F isoform or a BoNT/F subtype. In another aspect of this embodiment, a BoNT/F comprises a naturally occurring BoNT/F variant of SEQ ID NO: 6, such as, e.g., a BoNT/F isoform of SEQ ID NO: 6 or a BoNT/F subtype of SEQ ID NO: 6. In still another aspect of this embodiment, a BoNT/F comprises a non-naturally occurring BoNT/F variant, such as, e.g., a conservative BoNT/F variant, a non-conservative BoNT/F variant or an active BoNT/F fragment, or any combination thereof. In still another aspect of this embodiment, a BoNT/F comprises a non-naturally occurring BoNT/F variant of SEQ ID NO: 6, such as, e.g., a conservative BoNT/F variant of SEQ ID NO: 6, a non-conservative BoNT/F variant of SEQ ID NO: 6 or an active BoNT/F fragment of SEQ ID NO: 6, or any combination thereof. In yet another aspect of this embodiment, a BoNT/F comprises a BoNT/F enzymatic domain or active fragment thereof, a BoNT/F translocation domain or active fragment thereof, a BoNT/F binding domain or active fragment thereof, and any combination thereof. In yet another aspect of this embodiment, a BoNT/F comprises a BoNT/F enzymatic domain of amino acid 1-439 from SEQ ID NO: 6 or active fragment thereof, a BoNT/F translocation domain of amino acids 440-864 from SEQ ID NO: 6 or active fragment thereof, a BoNT/F binding domain of amino acids 865-1274 from SEQ ID NO: 6 or active fragment thereof, and any combination thereof.

In other aspects of this embodiment, a BoNT/F comprises a polypeptide having, e.g., at least 70% amino acid identity with SEQ ID NO: 6, at least 75% amino acid identity with the SEQ ID NO: 6, at least 80% amino acid identity with SEQ ID NO: 6, at least 85% amino acid identity with SEQ ID NO: 6, at least 90% amino acid identity with SEQ ID NO: 6 or at least 95% amino acid identity with SEQ ID NO: 6. In yet other aspects of this embodiment, a BoNT/F comprises a polypeptide having, e.g., at most 70% amino acid identity with SEQ ID NO: 6, at most 75% amino acid identity with the SEQ ID NO: 6, at most 80% amino acid identity with SEQ ID NO: 6, at most 85% amino acid identity with SEQ ID NO: 6, at most 90% amino acid identity with SEQ ID NO: 6 or at most 95% amino acid identity with SEQ ID NO: 6.

In other aspects of this embodiment, a BoNT/F comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 6. In yet other aspects of this embodiment, a BoNT/F comprises a polypeptide having, e.g., at most one, two, three, four, five, six, seven, eight, nine, 10, 20, 30, 40, 50, 100, 200 or 500 non-contiguous amino acid deletions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 non-contiguous amino acid deletions relative to SEQ ID NO: 6. In still other aspects of this embodiment, a BoNT/F comprises a polypeptide having, e.g., at most one, two, three, four, five, six, seven, eight, nine, 10, 20, 30, 40, 50, 100, 200 or 500 non-contiguous amino acid additions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 non-contiguous amino acid additions relative to SEQ ID NO: 6.

In other aspects of this embodiment, a BoNT/F comprises a polypeptide having, e.g., at most one, two, three, four, five, six, seven, eight, nine, 10, 20, 30, 40, 50, 100, 200 or 500 contiguous amino acid substitutions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 contiguous amino acid substitutions relative to SEQ ID NO: 6. In yet other aspects of this embodiment, a BoNT/F comprises a polypeptide having, e.g., at most one, two, three, four, five, six, seven, eight, nine, 10, 20, 30, 40, 50, 100, 200 or 500 contiguous amino acid deletions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 contiguous amino acid deletions relative to SEQ ID NO: 6. In still other aspects of this embodiment, a BoNT/F comprises a polypeptide having, e.g., at most one, two, three, four, five, six, seven, eight, nine, 10, 20, 30, 40, 50, 100, 200 or 500 contiguous amino acid additions relative to SEQ ID NO: 6. In other aspects of this embodiment, a BoNT/F comprises a polypeptide having, e.g., at least one, two, three, four, five, six, seven, eight, nine, 10, 20, 30, 40, 50, 100, 200 or 500 contiguous amino acid additions relative to SEQ ID NO: 6.

In another embodiment, a Clostridial toxin comprises a BoNT/G. In an aspect of this embodiment, a BoNT/G comprises a BoNT/G enzymatic domain, a BoNT/G translocation domain and a BoNT/G binding domain. In another aspect of this embodiment, a BoNT/G comprises SEQ ID NO: 7. In another aspect of this embodiment, a BoNT/G comprises a naturally occurring BoNT/G variant, such as, e.g., a BoNT/G isoform or a BoNT/G subtype. In another aspect of this embodiment, a BoNT/G comprises a naturally occurring BoNT/G variant of SEQ ID NO: 7, such as, e.g., a BoNT/G isoform of SEQ ID NO: 7 or a BoNT/G subtype of SEQ ID NO: 7. In still another aspect of this embodiment, a BoNT/G comprises a non-naturally occurring BoNT/G variant, such as, e.g., a conservative BoNT/G variant, a non-conservative BoNT/G variant or an active BoNT/G fragment, or any combination thereof. In still another aspect of this embodiment, a BoNT/D comprises a non-naturally occurring BoNT/G variant of SEQ ID NO: 7, such as, e.g., a conservative BoNT/G variant of SEQ ID NO: 7, a non-conservative BoNT/G variant of SEQ ID NO: 7 or an active BoNT/G fragment of SEQ ID NO: 7, or any combination thereof. In yet another aspect of this embodiment, a BoNT/G comprises a BoNT/G enzymatic domain or an active fragment thereof, a BoNT/G translocation domain or an active fragment thereof, a BoNT/G binding domain or an active fragment thereof, or any combination thereof. In yet another aspect of this embodiment, a BoNT/G comprising a BoNT/G enzymatic domain of amino acids 1-446 from SEQ ID NO: 7 or an active fragment thereof, a BoNT/G translocation domain of amino acids 447-863 from SEQ ID NO: 7 or an active fragment thereof, a BoNT/G binding domain of amino acids 864-1297 from SEQ ID NO: 7 or an active fragment thereof, and any combination thereof.

In other aspects of this embodiment, a BoNT/G comprises a polypeptide having, e.g., at least 70% amino acid identity with SEQ ID NO: 7, at least 75% amino acid identity with the SEQ ID NO: 7, at least 80% amino acid identity with SEQ ID NO: 7, at least 85% amino acid identity with SEQ ID NO: 7, at least 90% amino acid identity with SEQ ID NO: 7 or at least 95% amino acid identity with SEQ ID NO: 7. In yet other aspects of this embodiment, a BoNT/G comprises a polypeptide having, e.g., at most 70% amino acid identity with SEQ ID NO: 7, at most 75% amino acid identity with the SEQ ID NO: 7, at most 80% amino acid identity with SEQ ID NO: 7, at most 85% amino acid identity with SEQ ID NO: 7, at most 90% amino acid identity with SEQ ID NO: 7 or at most 95% amino acid identity with SEQ ID NO: 7.

In other aspects of this embodiment, a BoNT/G comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 7. In yet other aspects of this embodiment, a BoNT/G comprises a polypeptide having, e.g., at most one, two, three, four, five, six, seven, eight, nine, 10, 20, 30, 40, 50, 100, 200 or 500 non-contiguous amino acid deletions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 non-contiguous amino acid deletions relative to SEQ ID NO: 7. In still other aspects of this embodiment, a BoNT/G comprises a polypeptide having, e.g., at most one, two, three, four, five, six, seven, eight, nine, 10, 20, 30, 40, 50, 100, 200 or 500 non-contiguous amino acid additions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 non-contiguous amino acid additions relative to SEQ ID NO: 7.

In other aspects of this embodiment, a BoNT/G comprises a polypeptide having, e.g., at most one, two, three, four, five, six, seven, eight, nine, 10, 20, 30, 40, 50, 100, 200 or 500 contiguous amino acid substitutions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 contiguous amino acid substitutions relative to SEQ ID NO: 7. In yet other aspects of this embodiment, a BoNT/G comprises a polypeptide having, e.g., at most one, two, three, four, five, six, seven, eight, nine, 10, 20, 30, 40, 50, 100, 200 or 500 contiguous amino acid deletions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 contiguous amino acid deletions relative to SEQ ID NO: 7. In still other aspects of this embodiment, a BoNT/G comprises a polypeptide having, e.g., at most one, two, three, four, five, six, seven, eight, nine, 10, 20, 30, 40, 50, 100, 200 or 500 contiguous amino acid additions relative to SEQ ID NO: 7. In other aspects of this embodiment, a BoNT/G comprises a polypeptide having, e.g., at least one, two, three, four, five, six, seven, eight, nine, 10, 20, 30, 40, 50, 100, 200 or 500 contiguous amino acid additions relative to SEQ ID NO: 7.

In another embodiment, a Clostridial toxin comprises a TeNT. In an aspect of this embodiment, a TeNT comprises a TeNT enzymatic domain, a TeNT translocation domain and a TeNT binding domain. In an aspect of this embodiment, a TeNT comprises SEQ ID NO: 8. In another aspect of this embodiment, a TeNT comprises a naturally occurring TeNT variant, such as, e.g., a TeNT isoform or a TeNT subtype. In another aspect of this embodiment, a TeNT comprises a naturally occurring TeNT variant of SEQ ID NO: 8, such as, e.g., a TeNT isoform of SEQ ID NO: 8 or a TeNT subtype of SEQ ID NO: 8. In still another aspect of this embodiment, a TeNT comprises a non-naturally occurring TeNT variant, such as, e.g., a conservative TeNT variant, a non-conservative TeNT variant or an active TeNT fragment, or any combination thereof. In still another aspect of this embodiment, a TeNT comprises a non-naturally occurring TeNT variant of SEQ ID NO: 8, such as, e.g., a conservative TeNT variant of SEQ ID NO: 8, a non-conservative TeNT variant of SEQ ID NO: 8 or an active TeNT fragment of SEQ ID NO: 8, or any combination thereof. In yet another aspect of this embodiment, a TeNT comprising a TeNT enzymatic domain or an active fragment thereof, a TeNT translocation domain or active fragment thereof, a TeNT binding domain or active fragment thereof, and any combination thereof. In yet another aspect of this embodiment, a TeNT comprising a TeNT enzymatic domain of amino acids 1-457 from SEQ ID NO: 8 or active fragment thereof, a TeNT translocation domain of amino acids 458-879 from SEQ ID NO: 8 or active fragment thereof, a TeNT binding domain of amino acids 880-1315 from SEQ ID NO: 8 or active fragment thereof, and any combination thereof.

In other aspects of this embodiment, a TeNT comprises a polypeptide having, e.g., at least 70% amino acid identity with SEQ ID NO: 8, at least 75% amino acid identity with the SEQ ID NO: 8, at least 80% amino acid identity with SEQ ID NO: 8, at least 85% amino acid identity with SEQ ID NO: 8, at least 90% amino acid identity with SEQ ID NO: 8 or at least 95% amino acid identity with SEQ ID NO: 8. In yet other aspects of this embodiment, a TeNT comprises a polypeptide having, e.g., at most 70% amino acid identity with SEQ ID NO: 8, at most 75% amino acid identity with the SEQ ID NO: 8, at most 80% amino acid identity with SEQ ID NO: 8, at most 85% amino acid identity with SEQ ID NO: 8, at most 90% amino acid identity with SEQ ID NO: 8 or at most 95% amino acid identity with SEQ ID NO: 8.

In other aspects of this embodiment, a TeNT comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 8. In yet other aspects of this embodiment, a TeNT comprises a polypeptide having, e.g., at most one, two, three, four, five, six, seven, eight, nine, 10, 20, 30, 40, 50, 100, 200 or 500 non-contiguous amino acid deletions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 non-contiguous amino acid deletions relative to SEQ ID NO: 8. In still other aspects of this embodiment, a TeNT comprises a polypeptide having, e.g., at most one, two, three, four, five, six, seven, eight, nine, 10, 20, 30, 40, 50, 100, 200 or 500 non-contiguous amino acid additions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 non-contiguous amino acid additions relative to SEQ ID NO: 8.

In other aspects of this embodiment, a TeNT comprises a polypeptide having, e.g., at most one, two, three, four, five, six, seven, eight, nine, 10, 20, 30, 40, 50, 100, 200 or 500 contiguous amino acid substitutions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 contiguous amino acid substitutions relative to SEQ ID NO: 8. In yet other aspects of this embodiment, a TeNT comprises a polypeptide having, e.g., at most one, two, three, four, five, six, seven, eight, nine, 10, 20, 30, 40, 50, 100, 200 or 500 contiguous amino acid deletions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 contiguous amino acid deletions relative to SEQ ID NO: 8. In still other aspects of this embodiment, a TeNT comprises a polypeptide having, e.g., at most one, two, three, four, five, six, seven, eight, nine, 10, 20, 30, 40, 50, 100, 200 or 500 contiguous amino acid additions relative to SEQ ID NO: 8. In other aspects of this embodiment, a TeNT comprises a polypeptide having, e.g., at least one, two, three, four, five, six, seven, eight, nine, 10, 20, 30, 40, 50, 100, 200 or 500 contiguous amino acid additions relative to SEQ ID NO: 8.

In another embodiment, a Clostridial toxin comprises a BaNT. In an aspect of this embodiment, a BaNT comprises a BaNT enzymatic domain, a BaNT translocation domain and a BaNT binding domain. In another aspect of this embodiment, a BaNT comprises SEQ ID NO: 9. In another aspect of this embodiment, a BaNT comprises a naturally occurring BaNT variant, such as, e.g., a BaNT isoform or a BaNT subtype. In another aspect of this embodiment, a BaNT comprises a naturally occurring BaNT variant of SEQ ID NO: 9, such as, e.g., a BaNT isoform of SEQ ID NO: 9 or a BaNT subtype of SEQ ID NO: 9. In still another aspect of this embodiment, a BaNT comprises a non-naturally occurring BaNT variant, such as, e.g., a conservative BaNT variant, a non-conservative BaNT variant or an active BaNT fragment, or any combination thereof. In still another aspect of this embodiment, a BaNT comprises a non-naturally occurring BaNT variant of SEQ ID NO: 9, such as, e.g., a conservative BaNT variant of SEQ ID NO: 9, a non-conservative BaNT variant of SEQ ID NO: 9 or an active BaNT fragment of SEQ ID NO: 9, or any combination thereof. In yet another aspect of this embodiment, a BaNT comprises a BaNT enzymatic domain or an active fragment thereof, a BaNT translocation domain or an active fragment thereof, a BaNT binding domain or an active fragment thereof, or any combination thereof. In yet another aspect of this embodiment, a BaNT comprising a BaNT enzymatic domain of amino acids 1-448 from SEQ ID NO: 9 or an active fragment thereof, a BaNT translocation domain of amino acids 449-871 from SEQ ID NO: 9 or an active fragment thereof, a BaNT binding domain of amino acids 872-1296 from SEQ ID NO: 9 or an active fragment thereof, and any combination thereof.

In other aspects of this embodiment, a BaNT comprises a polypeptide having, e.g., at least 70% amino acid identity with SEQ ID NO: 9, at least 75% amino acid identity with the SEQ ID NO: 9, at least 80% amino acid identity with SEQ ID NO: 9, at least 85% amino acid identity with SEQ ID NO: 9, at least 90% amino acid identity with SEQ ID NO: 9 or at least 95% amino acid identity with SEQ ID NO: 9. In yet other aspects of this embodiment, a BaNT comprises a polypeptide having, e.g., at most 70% amino acid identity with SEQ ID NO: 9, at most 75% amino acid identity with the SEQ ID NO: 9, at most 80% amino acid identity with SEQ ID NO: 9, at most 85% amino acid identity with SEQ ID NO: 9, at most 90% amino acid identity with SEQ ID NO: 9 or at most 95% amino acid identity with SEQ ID NO: 9.

In other aspects of this embodiment, a BaNT comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 9. In other aspects of this embodiment, a BaNT comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 9. In yet other aspects of this embodiment, a BaNT comprises a polypeptide having, e.g., at most one, two, three, four, five, six, seven, eight, nine, 10, 20, 30, 40, 50, 100, 200 or 500 non-contiguous amino acid deletions relative to SEQ ID NO: 9. In other aspects of this embodiment, a BaNT comprises a polypeptide having, e.g., at least one, two, three, four, five, six, seven, eight, nine, 10, 20, 30, 40, 50, 100, 200 or 500 non-contiguous amino acid deletions relative to SEQ ID NO: 9. In still other aspects of this embodiment, a BaNT comprises a polypeptide having, e.g., at most one, two, three, four, five, six, seven, eight, nine, 10, 20, 30, 40, 50, 100, 200 or 500 non-contiguous amino acid additions relative to SEQ ID NO: 9. In other aspects of this embodiment, a BaNT comprises a polypeptide having, e.g., at least one, two, three, four, five, six, seven, eight, nine, 10, 20, 30, 40, 50, 100, 200 or 500 non-contiguous amino acid additions relative to SEQ ID NO: 9.

In other aspects of this embodiment, a BaNT comprises a polypeptide having, e.g., at most one, two, three, four, five, six, seven, eight, nine, 10, 20, 30, 40, 50, 100, 200 or 500 contiguous amino acid substitutions relative to SEQ ID NO:

9. In other aspects of this embodiment, a BaNT comprises a polypeptide having, e.g., at least one, two, three, four, five, six, seven, eight, nine, 10, 20, 30, 40, 50, 100, 200 or 500 contiguous amino acid substitutions relative to SEQ ID NO: 9. In yet other aspects of this embodiment, a BaNT comprises a polypeptide having, e.g., at most one, two, three, four, five, six, seven, eight, nine, 10, 20, 30, 40, 50, 100, 200 or 500 contiguous amino acid deletions relative to SEQ ID NO: 9. In other aspects of this embodiment, a BaNT comprises a polypeptide having, e.g., at least one, two, three, four, five, six, seven, eight, nine, 10, 20, 30, 40, 50, 100, 200 or 500 contiguous amino acid deletions relative to SEQ ID NO: 9. In still other aspects of this embodiment, a BaNT comprises a polypeptide having, e.g., at most one, two, three, four, five, six, seven, eight, nine, 10, 20, 30, 40, 50, 100, 200 or 500 contiguous amino acid additions relative to SEQ ID NO: 9. In other aspects of this embodiment, a BaNT comprises a polypeptide having, e.g., at least one, two, three, four, five, six, seven, eight, nine, 10, 20, 30, 40, 50, 100, 200 or 500 contiguous amino acid additions relative to SEQ ID NO: 9.

In another embodiment, a Clostridial toxin comprises a BuNT. In an aspect of this embodiment, a BuNT comprises a BuNT enzymatic domain, a BuNT translocation domain and a BuNT binding domain. In another aspect of this embodiment, a BuNT comprises SEQ ID NO: 10. In another aspect of this embodiment, a BuNT comprises a naturally occurring BuNT variant, such as, e.g., a BuNT isoform or a BuNT subtype. In another aspect of this embodiment, a BuNT comprises a naturally occurring BuNT variant of SEQ ID NO: 10, such as, e.g., a BuNT isoform of SEQ ID NO: 10 or a BuNT subtype of SEQ ID NO: 10. In still another aspect of this embodiment, a BuNT comprises a non-naturally occurring BuNT variant, such as, e.g., a conservative BuNT variant, a non-conservative BuNT variant or an active BuNT fragment, or any combination thereof. In still another aspect of this embodiment, a BuNT comprises a non-naturally occurring BuNT variant of SEQ ID NO: 10, such as, e.g., a conservative BuNT variant of SEQ ID NO: 10, a non-conservative BuNT variant of SEQ ID NO: 10 or an active BuNT fragment of SEQ ID NO: 10, or any combination thereof. In yet another aspect of this embodiment, a BuNT comprises a BuNT enzymatic domain or an active fragment thereof, a BuNT translocation domain or an active fragment thereof, a BuNT binding domain or an active fragment thereof, or any combination thereof. In yet another aspect of this embodiment, a BuNT comprising a BuNT enzymatic domain of amino acids 1-448 from SEQ ID NO: 10 or an active fragment thereof, a BuNT translocation domain of amino acids 449-871 from SEQ ID NO: 10 or an active fragment thereof, a BuNT binding domain of amino acids 872-1296 from SEQ ID NO: 10 or an active fragment thereof, and any combination thereof.

In other aspects of this embodiment, a BuNT comprises a polypeptide having, e.g., at least 70% amino acid identity with SEQ ID NO: 10, at least 75% amino acid identity with the SEQ ID NO: 10, at least 80% amino acid identity with SEQ ID NO: 10, at least 85% amino acid identity with SEQ ID NO: 10, at least 90% amino acid identity with SEQ ID NO: 10 or at least 95% amino acid identity with SEQ ID NO: 10. In yet other aspects of this embodiment, a BuNT comprises a polypeptide having, e.g., at most 70% amino acid identity with SEQ ID NO: 10, at most 75% amino acid identity with the SEQ ID NO: 10, at most 80% amino acid identity with SEQ ID NO: 10, at most 85% amino acid identity with SEQ ID NO: 10, at most 90% amino acid identity with SEQ ID NO: 10 or at most 95% amino acid identity with SEQ ID NO: 10.

In other aspects of this embodiment, a BuNT comprises a polypeptide having, e.g., at most one, two, three, four, five, six, seven, eight, nine, 10, 20, 30, 40, 50, 100, 200 or 500 non-contiguous amino acid substitutions relative to SEQ ID NO: 10. In other aspects of this embodiment, a BuNT comprises a polypeptide having, e.g., at least one, two, three, four, five, six, seven, eight, nine, 10, 20, 30, 40, 50, 100, 200 or 500 non-contiguous amino acid substitutions relative to SEQ ID NO: 10. In yet other aspects of this embodiment, a BuNT comprises a polypeptide having, e.g., at most one, two, three, four, five, six, seven, eight, nine, 10, 20, 30, 40, 50, 100, 200 or 500 non-contiguous amino acid deletions relative to SEQ ID NO: 10. In other aspects of this embodiment, a BuNT comprises a polypeptide having, e.g., at least one, two, three, four, five, six, seven, eight, nine, 10, 20, 30, 40, 50, 100, 200 or 500 non-contiguous amino acid deletions relative to SEQ ID NO: 10. In still other aspects of this embodiment, a BuNT comprises a polypeptide having, e.g., at most one, two, three, four, five, six, seven, eight, nine, 10, 20, 30, 40, 50, 100, 200 or 500 non-contiguous amino acid additions relative to SEQ ID NO: 10. In other aspects of this embodiment, a BuNT comprises a polypeptide having, e.g., at least one, two, three, four, five, six, seven, eight, nine, 10, 20, 30, 40, 50, 100, 200 or 500 non-contiguous amino acid additions relative to SEQ ID NO: 10.

In other aspects of this embodiment, a BuNT comprises a polypeptide having, e.g., at most one, two, three, four, five, six, seven, eight, nine, 10, 20, 30, 40, 50, 100, 200 or 500 contiguous amino acid substitutions relative to SEQ ID NO: 10. In other aspects of this embodiment, a BuNT comprises a polypeptide having, e.g., at least one, two, three, four, five, six, seven, eight, nine, 10, 20, 30, 40, 50, 100, 200 or 500 contiguous amino acid substitutions relative to SEQ ID NO: 10. In yet other aspects of this embodiment, a BuNT comprises a polypeptide having, e.g., at most one, two, three, four, five, six, seven, eight, nine, 10, 20, 30, 40, 50, 100, 200 or 500 contiguous amino acid deletions relative to SEQ ID NO: 10. In other aspects of this embodiment, a BuNT comprises a polypeptide having, e.g., at least one, two, three, four, five, six, seven, eight, nine, 10, 20, 30, 40, 50, 100, 200 or 500 contiguous amino acid deletions relative to SEQ ID NO: 10. In still other aspects of this embodiment, a BuNT comprises a polypeptide having, e.g., at most one, two, three, four, five, six, seven, eight, nine, 10, 20, 30, 40, 50, 100, 200 or 500 contiguous amino acid additions relative to SEQ ID NO: 10. In other aspects of this embodiment, a BuNT comprises a polypeptide having, e.g., at least one, two, three, four, five, six, seven, eight, nine, 10, 20, 30, 40, 50, 100, 200 or 500 contiguous amino acid additions relative to SEQ ID NO: 10.

As mentioned above, a Clostridial toxin is converted from a single polypeptide form into a di-chain molecule by proteolytic cleavage. The location of the di-chain loop protease cleavage site for Clostridial toxins is shown (Table 2). Cleavage within the di-chain loop does not appear to be confined to a single peptide bond. Thus, cleavage of a Clostridial toxin with a naturally-occurring di-chain loop protease results in the lost of several residues centered around the original cleavage site. This loss is limited to a few amino acids located between the two cysteine residues that form the disulfide bridge. As a non-limiting example, BoNT/A single-chain polypeptide cleavage ultimately results in the loss of a ten amino acids within the di-chain loop. For BoNTs, cleavage at K448-A449 converts the single-chain form of BoNT/A into the di-chain form; cleavage at K441-A442 converts the single-chain form of BoNT/B into the di-chain form; cleavage at K449-T450 converts the single-chain form of BoNT/C1 into the di-chain form; cleavage at R445-D446 converts the single-chain form of BoNT/D into the di-chain form; cleavage at R422-K423 converts the single-chain form of BoNT/E into the di-chain form; cleavage at K439-A440 converts the single-chain form of BoNT/F into the di-chain form; and cleavage at K446-5447 converts the single-chain form of BoNT/G into the di-chain form. Proteolytic cleavage of the single-chain form of TeNT at of A457-5458 results in the di-chain form. Proteolytic cleavage of the single-chain form of BaNT at of K431-N432 results in the di-chain form. Proteolytic cleavage of the single-chain form of BuNT at of R422-K423 results in the di-chain form.

TABLE 2

Di-chain Loop Region of Clostridial Toxins

| Toxin | SEQ ID NO: | Di-Chain Loop Region Including a Di-Chain Protease Cleavage Site |
|---|---|---|
| BoNT/A | 11 | CVRGIITSKTKSLDKGYNK*----ALNDLC |
| BoNT/B | 12 | CKSVK*------------------APGIC |
| BoNT/C1 | 13 | CHKAIDGRSLYNK*-----------TLDC |
| BoNT/D | 14 | CLRLTKNSR*---------------DDSTC |
| BoNT/E | 15 | CKNIVSVKGIR*-------------KSIC |
| BoNT/F | 16 | CKSVIPRKGTK*-----------APPRLC |
| BoNT/G | 17 | CKPVMYKNTGK*--------------SEQC |
| TeNT | 18 | CKKIIPPTNIRENLYNRTA*SLTDLGGELC |
| BaNT | 19 | CKSIVSKKGTK*--------------NSLC |
| BuNT | 20 | CKNIVSVKGIR*--------------KSIC |

The amino acid sequence displayed are as follows:
BoNT/A, residues 430-454 of SEQ ID NO: 1;
BoNT/B, residues 437-446 of SEQ ID NO: 2;
BoNT/C1, residues 437-453 of SEQ ID NO: 3;
BoNT/D, residues 437-450 of SEQ ID NO: 4;
BoNT/E, residues 412-426 of SEQ ID NO: 5;
BoNT/F, residues 429-445 of SEQ ID NO: 6;
BoNT/G, residues 436-450 of SEQ ID NO: 7;
TeNT, residues 439-467 of SEQ ID NO: 8;
BaNT, residues 421-435 of SEQ ID NO: 9; and
BuNT, residues 412-426 of SEQ ID NO: 10.
An asterisks (*) indicates the peptide bond of the $P_1$-$P_{1'}$ cleavage site that is believed to be cleaved by a Clostridial toxin di-chain loop protease.

However, it should also be noted that additional cleavage sites within the di-chain loop also appear to be cleaved resulting in the generation of a small peptide fragment being lost. As a non-limiting example, BoNT/A single-chain polypeptide cleavage ultimately results in the loss of a ten amino acid fragment within the di-chain loop. Thus, cleavage at S441-L442 converts the single polypeptide form of BoNT/A into the di-chain form; cleavage at G444-I445 converts the single polypeptide form of BoNT/B into the di-chain form; cleavage at S445-L446 converts the single polypeptide form of BoNT/C1 into the di-chain form; cleavage at K442-N443 converts the single polypeptide form of BoNT/D into the di-chain form; cleavage at K419-G420 converts the single polypeptide form of BoNT/E into the di-chain form; cleavage at K423-S424 converts the single polypeptide form of BoNT/E into the di-chain form; cleavage at K436-G437 converts the single polypeptide form of BoNT/F into the di-chain form; cleavage at T444-G445 converts the single polypeptide form of BoNT/G into the di-chain form; and cleavage at E448-Q449 converts the single polypeptide form of BoNT/G into the di-chain form.

Aspects of the present invention provide, in part, a Clostridial toxin di-chain loop region. As used herein, the term "Clostridial toxin di-chain loop region" means the loop region of a Clostridial toxin formed by a disulfide bridge located between the LC domain and the HC domain of a naturally-occurring Clostridial toxin. A Clostridial toxin di-chain loop region includes, without limitation, a BoNT/A di-chain loop region, a BoNT/B di-chain loop region, a BoNT/C1 di-chain loop region, a BoNT/D di-chain loop region, a BoNT/E di-chain loop region, a BoNT/F di-chain loop region, a BoNT/G di-chain loop region, a TeNT di-chain loop region, a BaNT di-chain loop region, and a BuNT di-chain loop region. A non-limiting example of a BoNT/A di-chain loop region is amino acid sequence CVRGIITSK-TKSLDKGYNKALNDLC (SEQ ID NO: 11). A non-limiting example of a BoNT/B di-chain loop region is the amino acid sequence CKSVKAPGIC (SEQ ID NO: 12). A non-limiting example of a BoNT/C1 di-chain loop region is the amino acid sequence CHKAIDGRSLYNKTLDC (SEQ ID NO: 13). A non-limiting example of a BoNT/D di-chain loop region is the amino acid sequence CLRLTKNSRDDSTC (SEQ ID NO: 14). A non-limiting example of a BoNT/E di-chain loop region is the amino acid sequence CKNIVS-VKGIRKSIC (SEQ ID NO: 15). A non-limiting example of a BoNT/F di-chain loop region is the amino acid sequence CKSVIPRKGTKAPPRLC (SEQ ID NO: 16). A non-limiting example of a BoNT/G di-chain loop region is the amino acid sequence CKPVMYKNTGKSEQC (SEQ ID NO: 17). A non-limiting example of a TeNT di-chain loop region is the amino acid sequence CKKIIPPTNIRENLYNRTASLT-DLGGELC (SEQ ID NO: 18). A non-limiting example of a BaNT di-chain loop region is the amino acid sequence CKSIVSKKGTKNSLC (SEQ ID NO: 19). A non-limiting example of a BuNT di-chain loop region is the amino acid sequence CKNIVSVKGIRKSIC (SEQ ID NO: 20). As discussed below, SEQ ID NO: 11 through SEQ IN NO: 20 can serve as reference Clostridial toxin di-chain loop region sequences.

A Clostridial toxin di-chain loop region useful in aspects of the invention includes, without limitation, naturally occurring Clostridial toxin di-chain loop region; naturally occurring Clostridial toxin di-chain loop region variants; and non-naturally-occurring Clostridial toxin di-chain loop region variants, such as, e.g., conservative Clostridial toxin di-chain loop region variants, non-conservative Clostridial toxin di-chain loop region variants and Clostridial toxin di-chain loop region peptidomimetics. As used herein, the term "Clostridial toxin di-chain loop region variant," whether naturally-occurring or non-naturally-occurring, means a Clostridial toxin di-chain loop region that has at least one amino acid change from the corresponding region of the disclosed reference sequences and can be described in percent identity to the corresponding region of that reference sequence. Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

As used herein, the term "naturally occurring Clostridial toxin di-chain loop region variant" means any Clostridial toxin di-chain loop region produced without the aid of any human manipulation, including, without limitation, Clostridial toxin di-chain loop region isoforms produced from alternatively-spliced transcripts, Clostridial toxin di-chain loop region isoforms produced by spontaneous mutation and Clostridial toxin di-chain loop region subtypes. Non-limiting examples of a Clostridial toxin di-chain loop region isoform include, e.g., BoNT/A di-chain loop region isoforms, BoNT/B di-chain loop region isoforms, BoNT/C1 di-chain loop region isoforms, BoNT/D di-chain loop region isoforms, BoNT/E di-chain loop region isoforms, BoNT/F di-chain loop region isoforms, BoNT/G di-chain loop region isoforms, TeNT di-chain loop region isoforms, BaNT di-chain loop region isoforms, and BuNT di-chain loop region isoforms. Non-limiting examples of a Clostridial toxin subtype include, e.g., BoNT/A di-chain loop region subtypes such as, e.g., a BoNT/A1 di-chain loop region, a BoNT/A2 di-chain loop region, a BoNT/A3 di-chain loop region and a BoNT/A4 di-chain loop region; BoNT/B di-chain loop region subtypes, such as, e.g., a BoNT/B1 di-chain loop region, a BoNT/B2 di-chain loop region, a BoNT/B bivalent di-chain loop region and a BoNT/B nonproteolytic di-chain loop region; BoNT/C1 di-chain loop region subtypes, such as, e.g., a BoNT/C1-1 di-chain loop region and a BoNT/C1-2 di-chain loop region; BoNT/E di-chain loop region subtypes, such as, e.g., a BoNT/E1 di-chain loop region, a BoNT/E2 di-chain loop region and a BoNT/E3 di-chain loop region; and BoNT/F di-chain loop region subtypes, such as, e.g., a BoNT/F1 di-chain loop region, a BoNT/F2 di-chain loop region, a BoNT/F3 di-chain loop region and a BoNT/F4 di-chain loop region.

As used herein, the term "non-naturally occurring Clostridial toxin di-chain loop region variant" means any Clostridial toxin di-chain loop region produced with the aid of human manipulation, including, without limitation, Clostridial toxin di-chain loop region variants produced by genetic engineering using random mutagenesis or rational design and Clostridial toxin di-chain loop region variants produced by chemical synthesis. Non-limiting examples of non-naturally occurring Clostridial toxin di-chain loop region variants include, e.g., conservative Clostridial toxin di-chain loop region variants, non-conservative Clostridial toxin di-chain loop region variants and Clostridial toxin di-chain loop region peptidomimetics.

As used herein, the term "conservative Clostridial toxin di-chain loop region variant" means a Clostridial toxin di-chain loop region that has at least one amino acid substituted by another amino acid or an amino acid analog that has at least one property similar to that of the original amino acid from the reference Clostridial toxin di-chain loop region sequence. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin di-chain loop region variant can function in substantially the same manner as the reference Clostridial toxin di-chain loop region on which the conservative Clostridial toxin di-chain loop region variant is based, and can be substituted for the reference Clostridial toxin di-chain loop region in any aspect of the present invention. A conservative Clostridial toxin di-chain loop region variant may substitute one or more amino acids, two or more amino acids, three or more amino acids, four or more amino acids or five or more amino acids from the reference Clostridial toxin di-chain loop region on which the conservative Clostridial toxin di-chain loop region variant is based. A conservative Clostridial toxin di-chain loop region variant can also possess at least 50% amino acid identity, 65% amino acid identity, 75% amino acid identity, 85% amino acid identity or 95% amino acid identity to the reference Clostridial toxin di-chain loop region on which the conservative Clostridial toxin di-chain loop region variant is based. Non-limiting examples of a conservative Clostridial toxin di-chain loop region variant include, e.g., conservative BoNT/A di-chain loop region variants, conservative BoNT/B di-chain loop region variants, conservative BoNT/C1 di-chain loop region variants, conservative BoNT/D di-chain loop region variants, conservative BoNT/E di-chain loop region variants, conservative BoNT/F di-chain loop region variants, conservative BoNT/G di-chain loop region variants, conservative TeNT di-chain loop region variants, conservative BaNT di-chain loop region variants and conservative BuNT di-chain loop region variants.

As used herein, the term "non-conservative Clostridial toxin di-chain loop region variant" means a Clostridial toxin di-chain loop region in which 1) at least one amino acid is deleted from the reference Clostridial toxin di-chain loop region on which the non-conservative Clostridial toxin di-chain loop region variant is based; 2) at least one amino acid added to the reference Clostridial toxin di-chain loop region on which the non-conservative Clostridial toxin di-chain loop region is based; or 3) at least one amino acid is substituted by another amino acid or an amino acid analog that does not share any property similar to that of the original amino acid from the reference Clostridial toxin di-chain loop region sequence. A non-conservative Clostridial toxin di-chain loop region variant can function in substantially the same manner as the reference Clostridial toxin di-chain loop region on which the non-conservative Clostridial toxin di-chain loop region is based, and can be substituted for the reference Clostridial toxin di-chain loop region in any aspect of the present invention. A non-conservative Clostridial toxin di-chain loop region variant can add one or more amino acids, two or more amino acids, three or more amino acids, four or more amino acids, five or more amino acids, and ten or more amino acids to the reference Clostridial toxin di-chain loop region on which the non-conservative Clostridial toxin di-chain loop region variant is based. A non-conservative Clostridial toxin di-chain loop region may substitute one or more amino acids, two or more amino acids, three or more amino acids, four or more amino acids or five or more amino acids from the reference Clostridial toxin di-chain loop region on which the non-conservative Clostridial toxin di-chain loop region variant is based. A non-conservative Clostridial toxin di-chain loop region variant can also possess at least 50% amino acid identity, 65% amino acid identity, 75% amino acid identity, 85% amino acid identity or 95% amino acid identity to the reference Clostridial toxin di-chain loop region on which the non-conservative Clostridial toxin di-chain loop region variant is based. Non-limiting examples of a non-conservative Clostridial toxin di-chain loop region variant include, e.g., non-conservative BoNT/A di-chain loop region variants, non-conservative BoNT/B di-chain loop region variants, non-conservative BoNT/C1 di-chain loop region variants, non-conservative BoNT/D di-chain loop region variants, non-conservative BoNT/E di-chain loop region variants, non-conservative BoNT/F di-chain loop region variants, non-conservative BoNT/G di-chain loop region variants, non-conservative TeNT di-chain loop region variants, non-conservative BaNT di-chain loop region variants and non-conservative BuNT di-chain loop region variants.

As used herein, the term "Clostridial toxin di-chain loop region peptidomimetic" means a Clostridial toxin di-chain loop region that has at least one amino acid substituted by a non-natural oligomer that has at least one property similar to that of the first amino acid. Examples of properties include, without limitation, topography of a peptide primary structural element, functionality of a peptide primary structural element, topology of a peptide secondary structural element, functionality of a peptide secondary structural element, of the like, or any combination thereof. A Clostridial toxin di-chain loop region peptidomimetic can function in substantially the same manner as the reference Clostridial toxin di-chain loop region on which the Clostridial toxin di-chain loop region peptidomimetic is based, and can be substituted for the reference Clostridial toxin di-chain loop region in any aspect of the present invention. A Clostridial toxin di-chain loop region peptidomimetic may substitute one or more amino acids, two or more amino acids, three or more amino acids, four or more amino acids or five or more amino acids from the reference Clostridial toxin di-chain loop region on which the Clostridial toxin di-chain loop region peptidomimetic is based. A Clostridial toxin di-chain loop region peptidomimetic can also possess at least 50% amino acid identity, at least 65% amino acid identity, at least 75% amino acid identity, at least 85% amino acid identity or at least 95% amino acid identity to the reference Clostridial toxin di-chain loop region on which the Clostridial toxin di-chain loop region peptidomimetic is based. For examples of peptidomimetic methods see, e.g., Amy S. Ripka & Daniel H. Rich, Peptidomimetic design, 2(4) CURR. OPIN. CHEM. BIOL. 441-452 (1998); and M. Angels Estiarte & Daniel H. Rich, *Peptidomimetics for Drug Design*, 803-861 (BURGER'S MEDICINAL CHEMISTRY AND DRUG DISCOVERY Vol. 1 PRINCIPLE AND PRACTICE, Donald J. Abraham ed., Wiley-Interscience, 6$^{th}$ ed 2003). Non-limiting examples of a Clostridial toxin di-chain loop region peptidomimetic include, e.g., BoNT/A di-chain loop region peptidomimetics, BoNT/B di-chain loop region peptidomimetics, BoNT/C1 di-chain loop region peptidomimetics, BoNT/D di-chain loop region peptidomimetics, BoNT/E di-chain loop region peptidomimetics, BoNT/F di-chain loop region peptidomimetics, BoNT/G di-chain loop region peptidomimetics, TeNT di-chain loop region peptidomimetics, BaNT di-chain loop region peptidomimetics and BuNT di-chain loop region peptidomimetics.

Aspects of the present invention provide, in part, a Clostridial toxin di-chain loop protease cleavage site. As used herein, the term "Clostridial toxin di-chain loop protease cleavage site" means means a $P_1$-$P_1$ scissile bond located within a Clostridial toxin di-chain loop region, together with adjacent or non-adjacent recognition elements, or both, sufficient for detectable proteolysis at the scissile bond by a Clostridial toxin di-chain loop protease under conditions suitable for Clostridial toxin di-chain loop protease activity. A Clostridial toxin di-chain loop region includes, without limitation, a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site, a TeNT di-chain loop protease cleavage site, a BaNT di-chain loop protease cleavage site, and a BuNT di-chain loop protease cleavage site. Non-limiting examples of a BoNT/A di-chain loop protease cleavage site include the S441-L442 scissile bond and the K448-A449 scissile bond. Non-limiting examples of a BoNT/B di-chain loop protease cleavage site include the K441-A442 scissile bond and the G444-I445 scissile bond. Non-limiting examples of a BoNT/C1 di-chain loop protease cleavage site include the S445-L446 scissile bond and the K449-T450 scissile bond. Non-limiting examples of a BoNT/D di-chain loop protease cleavage site include the K442-N443 scissile bond and the R445-D446 scissile bond. Non-limiting examples of a BoNT/E di-chain loop protease cleavage site include the K419-G420 scissile bond, the R422-K423 scissile bond, and the K423-S424 scissile bond. Non-limiting examples of a BoNT/F di-chain loop protease cleavage site include the K436-G437 scissile bond and the K439-A440 scissile bond. Non-limiting examples of a BoNT/G di-chain loop protease cleavage site include the T444-G445 scissile bond, the K446-S447 scissile bond, and the E448-Q449 scissile bond. A non-limiting example of a TeNT di-chain loop protease cleavage site is the A457-S458 scissile bond. A non-limiting example of a BaNT di-chain loop protease cleavage site is the K431-N432 scissile bond. A non-limiting example of a BuNT di-chain loop protease cleavage site is the R422-K423 scissile bond.

Thus, in an embodiment, a modified Clostridial toxin comprises a BoNT/A di-chain loop region. In an aspect of this embodiment, a modified Clostridial toxin comprises a BoNT/A di-chain loop region including a BoNT/A di-chain loop protease cleavage site. In another aspect of this embodiment, a modified Clostridial toxin comprises a BoNT/A di-chain loop region including a BoNT/A di-chain loop protease cleavage site comprising the S441-L442 scissile bond. In another aspect of this embodiment, a modified Clostridial toxin comprises a BoNT/A di-chain loop region including a BoNT/A di-chain loop protease cleavage site comprising the K448-A449 scissile bond. In yet another aspect of this embodiment, a modified Clostridial toxin comprises the BoNT/A di-chain loop region of SEQ ID NO: 11.

In another aspect of this embodiment, a modified Clostridial toxin comprises a naturally occurring BoNT/A di-chain loop region variant. In another aspect of this embodiment, a modified Clostridial toxin comprises a naturally occurring BoNT/A di-chain loop region variant, such as, e.g., a BoNT/A di-chain loop region isoform, or a BoNT/A di-chain loop region subtype. In another aspect of this embodiment, a modified Clostridial toxin comprises a naturally occurring BoNT/A di-chain loop region variant of SEQ ID NO: 11, such as, e.g., a BoNT/A di-chain loop region isoform of SEQ ID NO: 11; or a BoNT/A di-chain loop region subtype of SEQ ID NO: 11. In still another aspect of this embodiment, a modified Clostridial toxin comprises a non-naturally occurring BoNT/A di-chain loop region variant, such as, e.g., a conservative BoNT/A di-chain loop region variant, a non-conservative BoNT/A di-chain loop region variant or a BoNT/A di-chain loop region peptidomimetic, or any combination thereof. In still another aspect of this embodiment, a modified Clostridial toxin comprises a non-naturally occurring BoNT/A di-chain loop region variant of SEQ ID NO: 11, such as, e.g., a conservative BoNT/A di-chain loop region variant of SEQ ID NO: 11, a non-conservative BoNT/A di-chain loop region variant of SEQ ID NO: 11 or a BoNT/A di-chain loop region peptidomimetic of SEQ ID NO: 11, or any combination thereof.

In other aspects of this embodiment, a modified Clostridial toxin comprises a BoNT/A di-chain loop region having, e.g., at least 50% amino acid identity with SEQ ID NO: 11, at least 60% amino acid identity with the SEQ ID NO: 11, at least 70% amino acid identity with SEQ ID NO: 11, at least 80% amino acid identity with SEQ ID NO: 11, or at least 90% amino acid identity with SEQ ID NO: 11. In still other aspects of this embodiment, a modified Clostridial toxin comprises a BoNT/A di-chain loop region having, e.g., at most 50% amino acid identity with SEQ ID NO: 11, at most 60% amino acid identity with the SEQ ID NO: 11, at most 70% amino acid identity with SEQ ID NO: 11, at most 80% amino acid identity with SEQ ID NO: 11, or at most 90% amino acid identity with SEQ ID NO: 11.

In other aspects of this embodiment, a modified Clostridial toxin comprises a BoNT/A di-chain loop region having, e.g., at most one, two, three, four, five, six, seven, eight, nine or ten non-contiguous amino acid substitutions relative to SEQ ID NO: 11. In still other aspects of this embodiment, a modified Clostridial toxin comprises a BoNT/A di-chain loop region having, e.g., at least one, two, three, four, five, six, seven, eight, nine or ten non-contiguous amino acid substitutions relative to SEQ ID NO: 11. In yet other aspects of this embodiment, a modified Clostridial toxin comprises a BoNT/A di-chain loop region having, e.g., at most one, two, three, four, five, six, seven, eight, nine or ten non-contiguous amino acid additions relative to SEQ ID NO: 11. In yet other aspects of this embodiment, a modified Clostridial toxin comprises a BoNT/A di-chain loop region having, e.g., at least one, two, three, four, five, six, seven, eight, nine or ten non-contiguous amino acid additions relative to SEQ ID NO: 11. In still other aspects of this embodiment, a modified Clostridial toxin comprises a BoNT/A di-chain loop region having, e.g., at most one, two, three, four, five, six, seven, eight, nine or ten non-contiguous amino acid deletions relative to SEQ ID NO: 11. In still other aspects of this embodiment, a modified Clostridial toxin comprises a BoNT/A di-chain loop region having, e.g., at least one, two, three, four, five, six, seven, eight, nine or ten non-contiguous amino acid deletions relative to SEQ ID NO: 11.

In other aspects of this embodiment, a modified Clostridial toxin comprises a BoNT/A di-chain loop region having, e.g., at most one, two, three, four, five, six, seven, eight, nine or ten contiguous amino acid substitutions relative to SEQ ID NO: 11. In still other aspects of this embodiment, a modified Clostridial toxin comprises a BoNT/A di-chain loop region having, e.g., at least one, two, three, four, five, six, seven, eight, nine or ten contiguous amino acid substitutions relative to SEQ ID NO: 11. In yet other aspects of this embodiment, a modified Clostridial toxin comprises a BoNT/A di-chain loop region having, e.g., at most one, two, three, four, five, six, seven, eight, nine or ten contiguous amino acid additions relative to SEQ ID NO: 11. In yet other aspects of this embodiment, a modified Clostridial toxin comprises a BoNT/A di-chain loop region having, e.g., at least one, two, three, four, five, six, seven, eight, nine or ten contiguous amino acid additions relative to SEQ ID NO: 11. In still other aspects of this embodiment, a modified Clostridial toxin comprises a BoNT/A di-chain loop region having, e.g., at most one, two, three, four, five, six, seven, eight, nine or ten contiguous amino acid deletions relative to SEQ ID NO: 11. In still other aspects of this embodiment, a modified Clostridial toxin comprises a BoNT/A di-chain loop region having, e.g., at least one, two, three, four, five, six, seven, eight, nine or ten contiguous amino acid deletions relative to SEQ ID NO: 11.

In another embodiment, a modified Clostridial toxin comprises a BoNT/B di-chain loop region. In an aspect of this embodiment, a modified Clostridial toxin comprises a BoNT/B di-chain loop region including a BoNT/B di-chain loop protease cleavage site. In another aspect of this embodiment, a modified Clostridial toxin comprises a BoNT/B di-chain loop region including a BoNT/B di-chain loop protease cleavage site comprising the K441-A442 scissile bond. In another aspect of this embodiment, a modified Clostridial toxin comprises a BoNT/B di-chain loop region including a BoNT/B di-chain loop protease cleavage site comprising the G444-I445 scissile bond. In yet another aspect of this embodiment, a modified Clostridial toxin comprises the BoNT/B di-chain loop region of SEQ ID NO: 12.

In another aspect of this embodiment, a modified Clostridial toxin comprises a naturally occurring BoNT/B di-chain loop region variant. In another aspect of this embodiment, a modified Clostridial toxin comprises a naturally occurring BoNT/B di-chain loop region variant, such as, e.g., a BoNT/B di-chain loop region isoform, or a BoNT/B di-chain loop region subtype. In another aspect of this embodiment, a modified Clostridial toxin comprises a naturally occurring BoNT/B di-chain loop region variant of SEQ ID NO: 12, such as, e.g., a BoNT/B di-chain loop region isoform of SEQ ID NO: 12; or a BoNT/B di-chain loop region subtype of SEQ ID NO: 12. In still another aspect of this embodiment, a modified Clostridial toxin comprises a non-naturally occurring BoNT/B di-chain loop region variant, such as, e.g., a conservative BoNT/B di-chain loop region variant, a non-conservative BoNT/B di-chain loop region variant or a BoNT/B di-chain loop region peptidomimetic, or any combination thereof. In still another aspect of this embodiment, a modified Clostridial toxin comprises a non-naturally occurring BoNT/B di-chain loop region variant of SEQ ID NO: 12, such as, e.g., a conservative BoNT/B di-chain loop region variant of SEQ ID NO: 12, a non-conservative BoNT/B di-chain loop region variant of SEQ ID NO: 12 or a BoNT/B di-chain loop region peptidomimetic of SEQ ID NO: 12, or any combination thereof.

In other aspects of this embodiment, a modified Clostridial toxin comprises a BoNT/B di-chain loop region having, e.g., at least 50% amino acid identity with SEQ ID NO: 12, at least 60% amino acid identity with the SEQ ID NO: 12, at least 70% amino acid identity with SEQ ID NO: 12, at least 80% amino acid identity with SEQ ID NO: 12, or at least 90% amino acid identity with SEQ ID NO: 12. In still other aspects of this embodiment, a modified Clostridial toxin comprises a BoNT/B di-chain loop region having, e.g., at most 50% amino acid identity with SEQ ID NO: 12, at most 60% amino acid identity with the SEQ ID NO: 12, at most 70% amino acid identity with SEQ ID NO: 12, at most 80% amino acid identity with SEQ ID NO: 12, or at most 90% amino acid identity with SEQ ID NO: 12.

In other aspects of this embodiment, a modified Clostridial toxin comprises a BoNT/B di-chain loop region having, e.g., at most one, two, three, four, or five non-contiguous amino acid substitutions relative to SEQ ID NO: 12. In still other aspects of this embodiment, a modified Clostridial toxin comprises a BoNT/B di-chain loop region having, e.g., at least one, two, three, four, or five non-contiguous amino acid substitutions relative to SEQ ID NO: 12. In yet other aspects of this embodiment, a modified Clostridial toxin comprises a BoNT/B di-chain loop region having, e.g., at most one, two, three, four, or five non-contiguous amino acid additions relative to SEQ ID NO: 12. In yet other aspects of this embodiment, a modified Clostridial toxin comprises a BoNT/B di-chain loop region having, e.g., at least one, two, three, four, or five non-contiguous amino acid additions relative to SEQ ID NO: 12. In still other aspects of this embodiment, a modified Clostridial toxin comprises a BoNT/B di-chain loop region having, e.g., at most one, two, three, four, or five non-contiguous amino acid deletions relative to SEQ ID NO: 12. In still other aspects of this embodiment, a modified Clostridial toxin comprises a BoNT/B di-chain loop region having, e.g., at least one, two, three, four, or five non-contiguous amino acid deletions relative to SEQ ID NO: 12.

In other aspects of this embodiment, a modified Clostridial toxin comprises a BoNT/B di-chain loop region having, e.g., at most one, two, three, four, or five contiguous amino acid substitutions relative to SEQ ID NO: 12. In still other aspects of this embodiment, a modified Clostridial toxin comprises a BoNT/B di-chain loop region having, e.g., at least one, two, three, four, or five contiguous amino acid substitutions relative to SEQ ID NO: 12. In yet other aspects of this embodiment, a modified Clostridial toxin comprises a BoNT/B di-chain loop region having, e.g., at most one, two, three, four, or five contiguous amino acid additions relative to SEQ ID NO: 12. In yet other aspects of this embodiment, a modified Clostridial toxin comprises a BoNT/B di-chain loop region having, e.g., at least one, two, three, four, or five contiguous amino acid additions relative to SEQ ID NO: 12. In still other aspects of this embodiment, a modified Clostridial toxin comprises a BoNT/B di-chain loop region having, e.g., at most one, two, three, four, or five contiguous amino acid deletions relative to SEQ ID NO: 12. In still other aspects of this embodiment, a modified Clostridial toxin comprises a BoNT/B di-chain loop region having, e.g., at least one, two, three, four, or five contiguous amino acid deletions relative to SEQ ID NO: 12.

In another embodiment, a modified Clostridial toxin comprises a BoNT/C1 di-chain loop region. In an aspect of this embodiment, a modified Clostridial toxin comprises a BoNT/C1 di-chain loop region including a BoNT/C1 di-chain loop protease cleavage site. In another aspect of this embodiment, a modified Clostridial toxin comprises a BoNT/C1 di-chain loop region including a BoNT/C1 di-chain loop protease cleavage site comprising the S445-L446 scissile bond. In another aspect of this embodiment, a modified Clostridial toxin comprises a BoNT/C1 di-chain loop region including a BoNT/C1 di-chain loop protease cleavage site comprising the K449-T450 scissile bond. In yet another aspect of this embodiment, a modified Clostridial toxin comprises the BoNT/C1 di-chain loop region of SEQ ID NO: 13.

In another aspect of this embodiment, a modified Clostridial toxin comprises a naturally occurring BoNT/C1 di-chain loop region variant. In another aspect of this embodiment, a modified Clostridial toxin comprises a naturally occurring BoNT/C1 di-chain loop region variant, such as, e.g., a BoNT/C1 di-chain loop region isoform, or a BoNT/C1 di-chain loop region subtype. In another aspect of this embodiment, a modified Clostridial toxin comprises a naturally occurring BoNT/C1 di-chain loop region variant of SEQ ID NO: 13, such as, e.g., a BoNT/C1 di-chain loop region isoform of SEQ ID NO: 13; or a BoNT/C1 di-chain loop region subtype of SEQ ID NO: 13. In still another aspect of this embodiment, a modified Clostridial toxin comprises a non-naturally occurring BoNT/C1 di-chain loop region variant, such as, e.g., a conservative BoNT/C1 di-chain loop region variant, a non-conservative BoNT/C1 di-chain loop region variant or a BoNT/C1 di-chain loop region peptidomimetic, or any combination thereof. In still another aspect of this embodiment, a modified Clostridial toxin comprises a non-naturally occurring BoNT/C1 di-chain loop region variant of SEQ ID NO: 13, such as, e.g., a conservative BoNT/C1 di-chain loop region variant of SEQ ID NO: 13, a non-conservative BoNT/C1 di-chain loop region variant of SEQ ID NO: 13 or a BoNT/C1 di-chain loop region peptidomimetic of SEQ ID NO: 13, or any combination thereof.

In other aspects of this embodiment, a modified Clostridial toxin comprises a BoNT/C1 di-chain loop region having, e.g., at least 50% amino acid identity with SEQ ID NO: 13, at least 60% amino acid identity with the SEQ ID NO: 13, at least 70% amino acid identity with SEQ ID NO: 13, at least 80% amino acid identity with SEQ ID NO: 13, or at least 90% amino acid identity with SEQ ID NO: 13. In still other aspects of this embodiment, a modified Clostridial toxin comprises a BoNT/C1 di-chain loop region having, e.g., at most 50% amino acid identity with SEQ ID NO: 13, at most 60% amino acid identity with the SEQ ID NO: 13, at most 70% amino acid identity with SEQ ID NO: 13, at most 80% amino acid identity with SEQ ID NO: 13, or at most 90% amino acid identity with SEQ ID NO: 13.

In other aspects of this embodiment, a modified Clostridial toxin comprises a BoNT/C1 di-chain loop region having, e.g., at most one, two, three, four, five, six, seven, eight, nine or ten non-contiguous amino acid substitutions relative to SEQ ID NO: 13. In still other aspects of this embodiment, a modified Clostridial toxin comprises a BoNT/C1 di-chain loop region having, e.g., at least one, two, three, four, five, six, seven, eight, nine or ten non-contiguous amino acid substitutions relative to SEQ ID NO: 13. In yet other aspects of this embodiment, a modified Clostridial toxin comprises a BoNT/C1 di-chain loop region having, e.g., at most one, two, three, four, five, six, seven, eight, nine or ten non-contiguous amino acid additions relative to SEQ ID NO: 13. In yet other aspects of this embodiment, a modified Clostridial toxin comprises a BoNT/C1 di-chain loop region having, e.g., at least one, two, three, four, five, six, seven, eight, nine or ten non-contiguous amino acid additions relative to SEQ ID NO: 13. In still other aspects of this embodiment, a modified Clostridial toxin comprises a BoNT/C1 di-chain loop region having, e.g., at most one, two, three, four, five, six, seven, eight, nine or ten non-contiguous amino acid deletions relative to SEQ ID NO: 13. In still other aspects of this embodiment, a modified Clostridial toxin comprises a BoNT/C1 di-chain loop region having, e.g., at least one, two, three, four, five, six, seven, eight, nine or ten non-contiguous amino acid deletions relative to SEQ ID NO: 13.

In other aspects of this embodiment, a modified Clostridial toxin comprises a BoNT/C1 di-chain loop region having, e.g., at most one, two, three, four, five, six, seven, eight, nine or ten contiguous amino acid substitutions relative to SEQ ID NO: 13. In still other aspects of this embodiment, a modified Clostridial toxin comprises a BoNT/C1 di-chain loop region having, e.g., at least one, two, three, four, five, six, seven, eight, nine or ten contiguous amino acid substitutions relative to SEQ ID NO: 13. In yet other aspects of this embodiment, a modified Clostridial toxin comprises a BoNT/C1 di-chain loop region having, e.g., at most one, two, three, four, five, six, seven, eight, nine or ten contiguous amino acid additions relative to SEQ ID NO: 13. In yet other aspects of this embodiment, a modified Clostridial toxin comprises a BoNT/C1 di-chain loop region having, e.g., at least one, two, three, four, five, six, seven, eight, nine or ten contiguous amino acid additions relative to SEQ ID NO: 13. In still other aspects of this embodiment, a modified Clostridial toxin comprises a BoNT/C1 di-chain loop region having, e.g., at most one, two, three, four, five, six, seven, eight, nine or ten contiguous amino acid deletions relative to SEQ ID NO: 13. In still other aspects of this embodiment, a modified Clostridial toxin comprises a BoNT/C1 di-chain loop region having, e.g., at least one, two, three, four, five, six, seven, eight, nine or ten contiguous amino acid deletions relative to SEQ ID NO: 13.

In another embodiment, a modified Clostridial toxin comprises a BoNT/D di-chain loop region. In an aspect of this embodiment, a modified Clostridial toxin comprises a BoNT/D di-chain loop region including a BoNT/D di-chain loop protease cleavage site. In another aspect of this embodiment, a modified Clostridial toxin comprises a BoNT/D di-chain loop region including a BoNT/D di-chain loop protease cleavage site comprising the K442-N443 scissile bond. In another aspect of this embodiment, a modified Clostridial toxin comprises a BoNT/D di-chain loop region including a BoNT/D di-chain loop protease cleavage site comprising the R445-D446 scissile bond. In yet another aspect of this embodiment, a modified Clostridial toxin comprises the BoNT/D di-chain loop region of SEQ ID NO: 14.

In another aspect of this embodiment, a modified Clostridial toxin comprises a naturally occurring BoNT/D di-chain loop region variant. In another aspect of this embodiment, a modified Clostridial toxin comprises a naturally occurring BoNT/D di-chain loop region variant, such as, e.g., a BoNT/D di-chain loop region isoform, or a BoNT/D di-chain loop region subtype. In another aspect of this embodiment, a modified Clostridial toxin comprises a naturally occurring BoNT/D di-chain loop region variant of SEQ ID NO: 14, such as, e.g., a BoNT/D di-chain loop region isoform of SEQ ID NO: 14; or a BoNT/D di-chain loop region subtype of SEQ ID NO: 14. In still another aspect of this embodiment, a modified Clostridial toxin comprises a non-naturally occurring BoNT/D di-chain loop region variant, such as, e.g., a conservative BoNT/D di-chain loop region variant, a non-conservative BoNT/D di-chain loop region variant or a BoNT/D di-chain loop region peptidomimetic, or any combination thereof. In still another aspect of this embodiment, a modified Clostridial toxin comprises a non-naturally occurring BoNT/D di-chain loop region variant of SEQ ID NO: 14, such as, e.g., a conservative BoNT/D di-chain loop region variant of SEQ ID NO: 14, a non-conservative BoNT/D di-chain loop region variant of SEQ ID NO: 14 or a BoNT/D di-chain loop region peptidomimetic of SEQ ID NO: 14, or any combination thereof.

In other aspects of this embodiment, a modified Clostridial toxin comprises a BoNT/D di-chain loop region having, e.g., at least 50% amino acid identity with SEQ ID NO: 14, at least 60% amino acid identity with the SEQ ID NO: 14, at least 70% amino acid identity with SEQ ID NO: 14, at least 80% amino acid identity with SEQ ID NO: 14, or at least 90% amino acid identity with SEQ ID NO: 14. In still other aspects of this embodiment, a modified Clostridial toxin comprises a BoNT/D di-chain loop region having, e.g., at most 50% amino acid identity with SEQ ID NO: 14, at most 60% amino acid identity with the SEQ ID NO: 14, at most 70% amino acid identity with SEQ ID NO: 14, at most 80% amino acid identity with SEQ ID NO: 14, or at most 90% amino acid identity with SEQ ID NO: 14.

In other aspects of this embodiment, a modified Clostridial toxin comprises a BoNT/D di-chain loop region having, e.g., at most one, two, three, four, five, six, or seven non-contiguous amino acid substitutions relative to SEQ ID NO: 14. In still other aspects of this embodiment, a modified Clostridial toxin comprises a BoNT/D di-chain loop region having, e.g., at least one, two, three, four, five, six, or seven non-contiguous amino acid substitutions relative to SEQ ID NO: 14. In yet other aspects of this embodiment, a modified Clostridial toxin comprises a BoNT/D di-chain loop region having, e.g., at most one, two, three, four, five, six, or seven non-contiguous amino acid additions relative to SEQ ID NO: 14. In yet other aspects of this embodiment, a modified Clostridial toxin comprises a BoNT/D di-chain loop region having, e.g., at least one, two, three, four, five, six, or seven non-contiguous amino acid additions relative to SEQ ID NO: 14. In still other aspects of this embodiment, a modified Clostridial toxin comprises a BoNT/D di-chain loop region having, e.g., at most one, two, three, four, five, six, or seven non-contiguous amino acid deletions relative to SEQ ID NO: 14. In still other aspects of this embodiment, a modified Clostridial toxin comprises a BoNT/D di-chain loop region having, e.g., at least one, two, three, four, five, six, or seven non-contiguous amino acid deletions relative to SEQ ID NO: 14.

In other aspects of this embodiment, a modified Clostridial toxin comprises a BoNT/D di-chain loop region having, e.g., at most one, two, three, four, five, six, or seven contiguous amino acid substitutions relative to SEQ ID NO: 14. In still other aspects of this embodiment, a modified Clostridial toxin comprises a BoNT/D di-chain loop region having, e.g., at least one, two, three, four, five, six, or seven contiguous amino acid substitutions relative to SEQ ID NO: 14. In yet other aspects of this embodiment, a modified Clostridial toxin comprises a BoNT/D di-chain loop region having, e.g., at most one, two, three, four, five, six, or seven contiguous amino acid additions relative to SEQ ID NO: 14. In yet other aspects of this embodiment, a modified Clostridial toxin comprises a BoNT/D di-chain loop region having, e.g., at least one, two, three, four, five, six, or seven contiguous amino acid additions relative to SEQ ID NO: 14. In still other aspects of this embodiment, a modified Clostridial toxin comprises a BoNT/D di-chain loop region having, e.g., at most one, two, three, four, five, six, or seven contiguous amino acid deletions relative to SEQ ID NO: 14. In still other aspects of this embodiment, a modified Clostridial toxin comprises a BoNT/D di-chain loop region having, e.g., at least one, two, three, four, five, six, or seven contiguous amino acid deletions relative to SEQ ID NO: 14.

In another embodiment, a modified Clostridial toxin comprises a BoNT/E di-chain loop region. In an aspect of this embodiment, a modified Clostridial toxin comprises a BoNT/E di-chain loop region including a BoNT/E di-chain loop protease cleavage site. In another aspect of this embodiment, a modified Clostridial toxin comprises a BoNT/E di-chain loop region including a BoNT/E di-chain loop protease cleavage site comprising the K419-G420 scissile bond. In another aspect of this embodiment, a modified Clostridial toxin comprises a BoNT/E di-chain loop region including a BoNT/E di-chain loop protease cleavage site comprising the R422-K423 scissile bond. In another aspect of this embodiment, a modified Clostridial toxin comprises a BoNT/E di-chain loop region including a BoNT/E di-chain loop protease cleavage site comprising the K423-5424 scissile bond. In yet another aspect of this embodiment, a modified Clostridial toxin comprises the BoNT/E di-chain loop region of SEQ ID NO: 15.

In another aspect of this embodiment, a modified Clostridial toxin comprises a naturally occurring BoNT/E di-chain loop region variant. In another aspect of this embodiment, a modified Clostridial toxin comprises a naturally occurring BoNT/E di-chain loop region variant, such as, e.g., a BoNT/E di-chain loop region isoform, or a BoNT/E di-chain loop region subtype. In another aspect of this embodiment, a modified Clostridial toxin comprises a naturally occurring BoNT/E di-chain loop region variant of SEQ ID NO: 15, such as, e.g., a BoNT/E di-chain loop region isoform of SEQ ID NO: 15; or a BoNT/E di-chain loop region subtype of SEQ ID NO: 15. In still another aspect of this embodiment, a modified Clostridial toxin comprises a non-naturally occurring BoNT/E di-chain loop region variant, such as, e.g., a conservative BoNT/E di-chain loop region variant, a non-conservative BoNT/E di-chain loop region variant or a BoNT/E di-chain loop region peptidomimetic, or any combination thereof. In still another aspect of this embodiment, a modified Clostridial toxin comprises a non-naturally occurring BoNT/E di-chain loop region variant of SEQ ID NO: 15, such as, e.g., a conservative BoNT/E di-chain loop region variant of SEQ ID NO: 15, a non-conservative BoNT/E di-chain loop region variant of SEQ ID NO: 15 or a BoNT/E di-chain loop region peptidomimetic of SEQ ID NO: 15, or any combination thereof.

In other aspects of this embodiment, a modified Clostridial toxin comprises a BoNT/E di-chain loop region having, e.g., at least 50% amino acid identity with SEQ ID NO: 15, at least 60% amino acid identity with the SEQ ID NO: 15, at least 70% amino acid identity with SEQ ID NO: 15, at least 80% amino acid identity with SEQ ID NO: 15, or at least 90% amino acid identity with SEQ ID NO: 15. In still other aspects of this embodiment, a modified Clostridial toxin comprises a BoNT/E di-chain loop region having, e.g., at most 50% amino acid identity with SEQ ID NO: 15, at most 60% amino acid identity with the SEQ ID NO: 15, at most 70% amino acid identity with SEQ ID NO: 15, at most 80% amino acid identity with SEQ ID NO: 15, or at most 90% amino acid identity with SEQ ID NO: 15.

In other aspects of this embodiment, a modified Clostridial toxin comprises a BoNT/E di-chain loop region having, e.g., at most one, two, three, four, five, six, or seven non-contiguous amino acid substitutions relative to SEQ ID NO: 15. In still other aspects of this embodiment, a modified Clostridial toxin comprises a BoNT/E di-chain loop region having, e.g., at least one, two, three, four, five, six, or seven non-contiguous amino acid substitutions relative to SEQ ID NO: 15. In yet other aspects of this embodiment, a modified Clostridial toxin comprises a BoNT/E di-chain loop region having, e.g., at most one, two, three, four, five, six, or seven non-contiguous amino acid additions relative to SEQ ID NO: 15. In yet other aspects of this embodiment, a modified Clostridial toxin comprises a BoNT/E di-chain loop region having, e.g., at least one, two, three, four, five, six, or seven non-contiguous amino acid additions relative to SEQ ID NO: 15. In still other aspects of this embodiment, a modified Clostridial toxin comprises a BoNT/E di-chain loop region having, e.g., at most one, two, three, four, five, six, or seven non-contiguous amino acid deletions relative to SEQ ID NO: 15. In still other aspects of this embodiment, a modified Clostridial toxin comprises a BoNT/E di-chain loop region having, e.g., at least one, two, three, four, five, six, or seven non-contiguous amino acid deletions relative to SEQ ID NO: 15.

In other aspects of this embodiment, a modified Clostridial toxin comprises a BoNT/E di-chain loop region having, e.g., at most one, two, three, four, five, six, or seven contiguous amino acid substitutions relative to SEQ ID NO: 15. In still other aspects of this embodiment, a modified Clostridial toxin comprises a BoNT/E di-chain loop region having, e.g., at least one, two, three, four, five, six, or seven contiguous amino acid substitutions relative to SEQ ID NO: 15. In yet other aspects of this embodiment, a modified Clostridial toxin comprises a BoNT/E di-chain loop region having, e.g., at most one, two, three, four, five, six, or seven contiguous amino acid additions relative to SEQ ID NO: 15. In yet other aspects of this embodiment, a modified Clostridial toxin comprises a BoNT/E di-chain loop region having, e.g., at least one, two, three, four, five, six, or seven contiguous amino acid additions relative to SEQ ID NO: 15. In still other aspects of this embodiment, a modified Clostridial toxin comprises a BoNT/E di-chain loop region having, e.g., at most one, two, three, four, five, six, or seven contiguous amino acid deletions relative to SEQ ID NO: 15. In still other aspects of this embodiment, a modified Clostridial toxin comprises a BoNT/E di-chain loop region having, e.g., at least one, two, three, four, five, six, or seven contiguous amino acid deletions relative to SEQ ID NO: 15.

In another embodiment, a modified Clostridial toxin comprises a BoNT/F di-chain loop region. In an aspect of this embodiment, a modified Clostridial toxin comprises a BoNT/F di-chain loop region including a BoNT/F di-chain loop protease cleavage site. In another aspect of this embodiment, a modified Clostridial toxin comprises a BoNT/F di-chain loop region including a BoNT/F di-chain loop protease cleavage site comprising the K436-G437 scissile bond. In another aspect of this embodiment, a modified Clostridial toxin comprises a BoNT/F di-chain loop region including a BoNT/F di-chain loop protease cleavage site comprising the K439-A440 scissile bond. In yet another aspect of this embodiment, a modified Clostridial toxin comprises the BoNT/F di-chain loop region of SEQ ID NO: 16.

In another aspect of this embodiment, a modified Clostridial toxin comprises a naturally occurring BoNT/F di-chain loop region variant. In another aspect of this embodiment, a modified Clostridial toxin comprises a naturally occurring BoNT/F di-chain loop region variant, such as, e.g., a BoNT/F di-chain loop region isoform, or a BoNT/F di-chain loop region subtype. In another aspect of this embodiment, a modified Clostridial toxin comprises a naturally occurring BoNT/F di-chain loop region variant of SEQ ID NO: 16, such as, e.g., a BoNT/F di-chain loop region isoform of SEQ ID NO: 16; or a BoNT/F di-chain loop region subtype of SEQ ID NO: 16. In still another aspect of this embodiment, a modified Clostridial toxin comprises a non-naturally occurring BoNT/F di-chain loop region variant, such as, e.g., a conservative BoNT/F di-chain loop region variant, a non-conservative BoNT/F di-chain loop region variant or a BoNT/F di-chain loop region peptidomimetic, or any combination thereof. In still another aspect of this embodiment, a modified Clostridial toxin comprises a non-naturally occurring BoNT/F di-chain loop region variant of SEQ ID NO: 16, such as, e.g., a conservative BoNT/F di-chain loop region variant of SEQ ID NO: 16, a non-conservative BoNT/F di-chain loop region variant of SEQ ID NO: 16 or a BoNT/F di-chain loop region peptidomimetic of SEQ ID NO: 16, or any combination thereof.

In other aspects of this embodiment, a modified Clostridial toxin comprises a BoNT/F di-chain loop region having, e.g., at least 50% amino acid identity with SEQ ID NO: 16, at least 60% amino acid identity with the SEQ ID NO: 16, at least 70% amino acid identity with SEQ ID NO: 16, at least 80% amino acid identity with SEQ ID NO: 16, or at least 90% amino acid identity with SEQ ID NO: 16. In still other aspects of this embodiment, a modified Clostridial toxin comprises a BoNT/F di-chain loop region having, e.g., at most 50% amino acid identity with SEQ ID NO: 16, at most 60% amino acid identity with the SEQ ID NO: 16, at most 70% amino acid identity with SEQ ID NO: 16, at most 80% amino acid identity with SEQ ID NO: 16, or at most 90% amino acid identity with SEQ ID NO: 16.

In other aspects of this embodiment, a modified Clostridial toxin comprises a BoNT/F di-chain loop region having, e.g., at most one, two, three, four, five, six, seven, eight, nine or ten non-contiguous amino acid substitutions relative to SEQ ID NO: 16. In still other aspects of this embodiment, a modified Clostridial toxin comprises a BoNT/F di-chain loop region having, e.g., at least one, two, three, four, five, six, seven, eight, nine or ten non-contiguous amino acid substitutions relative to SEQ ID NO: 16. In yet other aspects of this embodiment, a modified Clostridial toxin comprises a BoNT/F di-chain loop region having, e.g., at most one, two, three, four, five, six, seven, eight, nine or ten non-contiguous amino acid additions relative to SEQ ID NO: 16. In yet other aspects of this embodiment, a modified Clostridial toxin comprises a BoNT/F di-chain loop region having, e.g., at least one, two, three, four, five, six, seven, eight, nine or ten non-contiguous amino acid additions relative to SEQ ID NO: 16. In still other aspects of this embodiment, a modified Clostridial toxin comprises a BoNT/F di-chain loop region having, e.g., at most one, two, three, four, five, six, seven, eight, nine or ten non-contiguous amino acid deletions relative to SEQ ID NO: 16. In still other aspects of this embodiment, a modified Clostridial toxin comprises a BoNT/F di-chain loop region having, e.g., at least one, two, three, four, five, six, seven, eight, nine or ten non-contiguous amino acid deletions relative to SEQ ID NO: 16.

In other aspects of this embodiment, a modified Clostridial toxin comprises a BoNT/F di-chain loop region having, e.g., at most one, two, three, four, five, six, seven, eight, nine or ten contiguous amino acid substitutions relative to SEQ ID NO:

16. In still other aspects of this embodiment, a modified Clostridial toxin comprises a BoNT/F di-chain loop region having, e.g., at least one, two, three, four, five, six, seven, eight, nine or ten contiguous amino acid substitutions relative to SEQ ID NO: 16. In yet other aspects of this embodiment, a modified Clostridial toxin comprises a BoNT/F di-chain loop region having, e.g., at most one, two, three, four, five, six, seven, eight, nine or ten contiguous amino acid additions relative to SEQ ID NO: 16. In yet other aspects of this embodiment, a modified Clostridial toxin comprises a BoNT/F di-chain loop region having, e.g., at least one, two, three, four, five, six, seven, eight, nine or ten contiguous amino acid additions relative to SEQ ID NO: 16. In still other aspects of this embodiment, a modified Clostridial toxin comprises a BoNT/F di-chain loop region having, e.g., at most one, two, three, four, five, six, seven, eight, nine or ten contiguous amino acid deletions relative to SEQ ID NO: 16. In still other aspects of this embodiment, a modified Clostridial toxin comprises a BoNT/F di-chain loop region having, e.g., at least one, two, three, four, five, six, seven, eight, nine or ten contiguous amino acid deletions relative to SEQ ID NO: 16.

In another embodiment, a modified Clostridial toxin comprises a BoNT/G di-chain loop region. In an aspect of this embodiment, a modified Clostridial toxin comprises a BoNT/G di-chain loop region including a BoNT/G di-chain loop protease cleavage site. In another aspect of this embodiment, a modified Clostridial toxin comprises a BoNT/G di-chain loop region including a BoNT/G di-chain loop protease cleavage site comprising the T444-G445 scissile bond. In another aspect of this embodiment, a modified Clostridial toxin comprises a BoNT/G di-chain loop region including a BoNT/G di-chain loop protease cleavage site comprising the K446-5447 scissile bond. In another aspect of this embodiment, a modified Clostridial toxin comprises a BoNT/G di-chain loop region including a BoNT/G di-chain loop protease cleavage site comprising the E448-Q449 scissile bond. In yet another aspect of this embodiment, a modified Clostridial toxin comprises the BoNT/G di-chain loop region of SEQ ID NO: 17.

In another aspect of this embodiment, a modified Clostridial toxin comprises a naturally occurring BoNT/G di-chain loop region variant. In another aspect of this embodiment, a modified Clostridial toxin comprises a naturally occurring BoNT/G di-chain loop region variant, such as, e.g., a BoNT/G di-chain loop region isoform, or a BoNT/G di-chain loop region subtype. In another aspect of this embodiment, a modified Clostridial toxin comprises a naturally occurring BoNT/G di-chain loop region variant of SEQ ID NO: 17, such as, e.g., a BoNT/G di-chain loop region isoform of SEQ ID NO: 17; or a BoNT/G di-chain loop region subtype of SEQ ID NO: 17. In still another aspect of this embodiment, a modified Clostridial toxin comprises a non-naturally occurring BoNT/G di-chain loop region variant, such as, e.g., a conservative BoNT/G di-chain loop region variant, a non-conservative BoNT/G di-chain loop region variant or a BoNT/G di-chain loop region peptidomimetic, or any combination thereof. In still another aspect of this embodiment, a modified Clostridial toxin comprises a non-naturally occurring BoNT/G di-chain loop region variant of SEQ ID NO: 17, such as, e.g., a conservative BoNT/G di-chain loop region variant of SEQ ID NO: 17, a non-conservative BoNT/G di-chain loop region variant of SEQ ID NO: 17 or a BoNT/G di-chain loop region peptidomimetic of SEQ ID NO: 17, or any combination thereof.

In other aspects of this embodiment, a modified Clostridial toxin comprises a BoNT/G di-chain loop region having, e.g., at least 50% amino acid identity with SEQ ID NO: 17, at least 60% amino acid identity with the SEQ ID NO: 17, at least 70% amino acid identity with SEQ ID NO: 17, at least 80% amino acid identity with SEQ ID NO: 17, or at least 90% amino acid identity with SEQ ID NO: 17. In still other aspects of this embodiment, a modified Clostridial toxin comprises a BoNT/G di-chain loop region having, e.g., at most 50% amino acid identity with SEQ ID NO: 17, at most 60% amino acid identity with the SEQ ID NO: 17, at most 70% amino acid identity with SEQ ID NO: 17, at most 80% amino acid identity with SEQ ID NO: 17, or at most 90% amino acid identity with SEQ ID NO: 17.

In other aspects of this embodiment, a modified Clostridial toxin comprises a BoNT/G di-chain loop region having, e.g., at most one, two, three, four, five, six, or seven non-contiguous amino acid substitutions relative to SEQ ID NO: 17. In still other aspects of this embodiment, a modified Clostridial toxin comprises a BoNT/G di-chain loop region having, e.g., at least one, two, three, four, five, six, or seven non-contiguous amino acid substitutions relative to SEQ ID NO: 17. In yet other aspects of this embodiment, a modified Clostridial toxin comprises a BoNT/G di-chain loop region having, e.g., at most one, two, three, four, five, six, or seven non-contiguous amino acid additions relative to SEQ ID NO: 17. In yet other aspects of this embodiment, a modified Clostridial toxin comprises a BoNT/G di-chain loop region having, e.g., at least one, two, three, four, five, six, or seven non-contiguous amino acid additions relative to SEQ ID NO: 17. In still other aspects of this embodiment, a modified Clostridial toxin comprises a BoNT/G di-chain loop region having, e.g., at most one, two, three, four, five, six, or seven non-contiguous amino acid deletions relative to SEQ ID NO: 17. In still other aspects of this embodiment, a modified Clostridial toxin comprises a BoNT/G di-chain loop region having, e.g., at least one, two, three, four, five, six, or seven non-contiguous amino acid deletions relative to SEQ ID NO: 17.

In other aspects of this embodiment, a modified Clostridial toxin comprises a BoNT/G di-chain loop region having, e.g., at most one, two, three, four, five, six, or seven contiguous amino acid substitutions relative to SEQ ID NO: 17. In still other aspects of this embodiment, a modified Clostridial toxin comprises a BoNT/G di-chain loop region having, e.g., at least one, two, three, four, five, six, or seven contiguous amino acid substitutions relative to SEQ ID NO: 17. In yet other aspects of this embodiment, a modified Clostridial toxin comprises a BoNT/G di-chain loop region having, e.g., at most one, two, three, four, five, six, or seven contiguous amino acid additions relative to SEQ ID NO: 17. In yet other aspects of this embodiment, a modified Clostridial toxin comprises a BoNT/G di-chain loop region having, e.g., at least one, two, three, four, five, six, or seven contiguous amino acid additions relative to SEQ ID NO: 17. In still other aspects of this embodiment, a modified Clostridial toxin comprises a BoNT/G di-chain loop region having, e.g., at most one, two, three, four, five, six, or seven contiguous amino acid deletions relative to SEQ ID NO: 17. In still other aspects of this embodiment, a modified Clostridial toxin comprises a BoNT/G di-chain loop region having, e.g., at least one, two, three, four, five, six, or seven contiguous amino acid deletions relative to SEQ ID NO: 17.

In another embodiment, a modified Clostridial toxin comprises a TeNT di-chain loop region. In an aspect of this embodiment, a modified Clostridial toxin comprises a TeNT di-chain loop region including a TeNT di-chain loop protease cleavage site. In another aspect of this embodiment, a modified Clostridial toxin comprises a TeNT di-chain loop region including a TeNT di-chain loop protease cleavage site comprising the A457-5458 scissile bond. In yet another aspect of this embodiment, a modified Clostridial toxin comprises the TeNT di-chain loop region of SEQ ID NO: 18.

In another aspect of this embodiment, a modified Clostridial toxin comprises a naturally occurring TeNT di-chain loop region variant. In another aspect of this embodiment, a modified Clostridial toxin comprises a naturally occurring TeNT di-chain loop region variant, such as, e.g., a TeNT di-chain loop region isoform, or a TeNT di-chain loop region subtype. In another aspect of this embodiment, a modified Clostridial toxin comprises a naturally occurring TeNT di-chain loop region variant of SEQ ID NO: 18, such as, e.g., a TeNT di-chain loop region isoform of SEQ ID NO: 18; or a TeNT di-chain loop region subtype of SEQ ID NO: 18. In still another aspect of this embodiment, a modified Clostridial toxin comprises a non-naturally occurring TeNT di-chain loop region variant, such as, e.g., a conservative TeNT di-chain loop region variant, a non-conservative TeNT di-chain loop region variant or a TeNT di-chain loop region peptidomimetic, or any combination thereof. In still another aspect of this embodiment, a modified Clostridial toxin comprises a non-naturally occurring TeNT di-chain loop region variant of SEQ ID NO: 18, such as, e.g., a conservative TeNT di-chain loop region variant of SEQ ID NO: 18, a non-conservative TeNT di-chain loop region variant of SEQ ID NO: 18 or a TeNT di-chain loop region peptidomimetic of SEQ ID NO: 18, or any combination thereof.

In other aspects of this embodiment, a modified Clostridial toxin comprises a TeNT di-chain loop region having, e.g., at least 50% amino acid identity with SEQ ID NO: 18, at least 60% amino acid identity with the SEQ ID NO: 18, at least 70% amino acid identity with SEQ ID NO: 18, at least 80% amino acid identity with SEQ ID NO: 18, or at least 90% amino acid identity with SEQ ID NO: 18. In still other aspects of this embodiment, a modified Clostridial toxin comprises a TeNT di-chain loop region having, e.g., at most 50% amino acid identity with SEQ ID NO: 18, at most 60% amino acid identity with the SEQ ID NO: 18, at most 70% amino acid identity with SEQ ID NO: 18, at most 80% amino acid identity with SEQ ID NO: 18, or at most 90% amino acid identity with SEQ ID NO: 18.

In other aspects of this embodiment, a modified Clostridial toxin comprises a TeNT di-chain loop region having, e.g., at most one, two, three, four, five, six, seven, eight, nine or ten non-contiguous amino acid substitutions relative to SEQ ID NO: 18. In still other aspects of this embodiment, a modified Clostridial toxin comprises a TeNT di-chain loop region having, e.g., at least one, two, three, four, five, six, seven, eight, nine or ten non-contiguous amino acid substitutions relative to SEQ ID NO: 18. In yet other aspects of this embodiment, a modified Clostridial toxin comprises a TeNT di-chain loop region having, e.g., at most one, two, three, four, five, six, seven, eight, nine or ten non-contiguous amino acid additions relative to SEQ ID NO: 18. In yet other aspects of this embodiment, a modified Clostridial toxin comprises a TeNT di-chain loop region having, e.g., at least one, two, three, four, five, six, seven, eight, nine or ten non-contiguous amino acid additions relative to SEQ ID NO: 18. In still other aspects of this embodiment, a modified Clostridial toxin comprises a TeNT di-chain loop region having, e.g., at most one, two, three, four, five, six, seven, eight, nine or ten non-contiguous amino acid deletions relative to SEQ ID NO: 18. In still other aspects of this embodiment, a modified Clostridial toxin comprises a TeNT di-chain loop region having, e.g., at least one, two, three, four, five, six, seven, eight, nine or ten non-contiguous amino acid deletions relative to SEQ ID NO: 18.

In other aspects of this embodiment, a modified Clostridial toxin comprises a TeNT di-chain loop region having, e.g., at most one, two, three, four, five, six, seven, eight, nine or ten contiguous amino acid substitutions relative to SEQ ID NO: 18. In still other aspects of this embodiment, a modified Clostridial toxin comprises a TeNT di-chain loop region having, e.g., at least one, two, three, four, five, six, seven, eight, nine or ten contiguous amino acid substitutions relative to SEQ ID NO: 18. In yet other aspects of this embodiment, a modified Clostridial toxin comprises a TeNT di-chain loop region having, e.g., at most one, two, three, four, five, six, seven, eight, nine or ten contiguous amino acid additions relative to SEQ ID NO: 18. In yet other aspects of this embodiment, a modified Clostridial toxin comprises a TeNT di-chain loop region having, e.g., at least one, two, three, four, five, six, seven, eight, nine or ten contiguous amino acid additions relative to SEQ ID NO: 18. In still other aspects of this embodiment, a modified Clostridial toxin comprises a TeNT di-chain loop region having, e.g., at most one, two, three, four, five, six, seven, eight, nine or ten contiguous amino acid deletions relative to SEQ ID NO: 18. In still other aspects of this embodiment, a modified Clostridial toxin comprises a TeNT di-chain loop region having, e.g., at least one, two, three, four, five, six, seven, eight, nine or ten contiguous amino acid deletions relative to SEQ ID NO: 18.

In another embodiment, a modified Clostridial toxin comprises a BaNT di-chain loop region. In an aspect of this embodiment, a modified Clostridial toxin comprises a BaNT di-chain loop region including a BaNT di-chain loop protease cleavage site. In another aspect of this embodiment, a modified Clostridial toxin comprises a BaNT di-chain loop region including a BaNT di-chain loop protease cleavage site comprising the K431-N432 scissile bond. In yet another aspect of this embodiment, a modified Clostridial toxin comprises the BaNT di-chain loop region of SEQ ID NO: 19.

In another aspect of this embodiment, a modified Clostridial toxin comprises a naturally occurring BaNT di-chain loop region variant. In another aspect of this embodiment, a modified Clostridial toxin comprises a naturally occurring BaNT di-chain loop region variant, such as, e.g., a BaNT di-chain loop region isoform, or a BaNT di-chain loop region subtype. In another aspect of this embodiment, a modified Clostridial toxin comprises a naturally occurring BaNT di-chain loop region variant of SEQ ID NO: 19, such as, e.g., a BaNT di-chain loop region isoform of SEQ ID NO: 19; or a BaNT di-chain loop region subtype of SEQ ID NO: 19. In still another aspect of this embodiment, a modified Clostridial toxin comprises a non-naturally occurring BaNT di-chain loop region variant, such as, e.g., a conservative BaNT di-chain loop region variant, a non-conservative BaNT di-chain loop region variant or a BaNT di-chain loop region peptidomimetic, or any combination thereof. In still another aspect of this embodiment, a modified Clostridial toxin comprises a non-naturally occurring BaNT di-chain loop region variant of SEQ ID NO: 19, such as, e.g., a conservative BaNT di-chain loop region variant of SEQ ID NO: 19, a non-conservative BaNT di-chain loop region variant of SEQ ID NO: 19 or a BaNT di-chain loop region peptidomimetic of SEQ ID NO: 19, or any combination thereof.

In other aspects of this embodiment, a modified Clostridial toxin comprises a BaNT di-chain loop region having, e.g., at least 50% amino acid identity with SEQ ID NO: 19, at least 60% amino acid identity with the SEQ ID NO: 19, at least 70% amino acid identity with SEQ ID NO: 19, at least 80% amino acid identity with SEQ ID NO: 19, or at least 90% amino acid identity with SEQ ID NO: 19. In still other aspects of this embodiment, a modified Clostridial toxin comprises a BaNT di-chain loop region having, e.g., at most 50% amino acid identity with SEQ ID NO: 19, at most 60% amino acid identity with the SEQ ID NO: 19, at most 70% amino acid identity with SEQ ID NO: 19, at most 80% amino acid identity with SEQ ID NO: 19, or at most 90% amino acid identity with SEQ ID NO: 19.

In other aspects of this embodiment, a modified Clostridial toxin comprises a BaNT di-chain loop region having, e.g., at most one, two, three, four, five, six, or seven non-contiguous amino acid substitutions relative to SEQ ID NO: 19. In still other aspects of this embodiment, a modified Clostridial toxin comprises a BaNT di-chain loop region having, e.g., at least one, two, three, four, five, six, or seven non-contiguous amino acid substitutions relative to SEQ ID NO: 19. In yet other aspects of this embodiment, a modified Clostridial toxin comprises a BaNT di-chain loop region having, e.g., at most one, two, three, four, five, six, or seven non-contiguous amino acid additions relative to SEQ ID NO: 19. In yet other aspects of this embodiment, a modified Clostridial toxin comprises a BaNT di-chain loop region having, e.g., at least one, two, three, four, five, six, or seven non-contiguous amino acid additions relative to SEQ ID NO: 19. In still other aspects of this embodiment, a modified Clostridial toxin comprises a BaNT di-chain loop region having, e.g., at most one, two, three, four, five, six, or seven non-contiguous amino acid deletions relative to SEQ ID NO: 19. In still other aspects of this embodiment, a modified Clostridial toxin comprises a BaNT di-chain loop region having, e.g., at least one, two, three, four, five, six, or seven non-contiguous amino acid deletions relative to SEQ ID NO: 19.

In other aspects of this embodiment, a modified Clostridial toxin comprises a BaNT di-chain loop region having, e.g., at most one, two, three, four, five, six, or seven contiguous amino acid substitutions relative to SEQ ID NO: 19. In still other aspects of this embodiment, a modified Clostridial toxin comprises a BaNT di-chain loop region having, e.g., at least one, two, three, four, five, six, or seven contiguous amino acid substitutions relative to SEQ ID NO: 19. In yet other aspects of this embodiment, a modified Clostridial toxin comprises a BaNT di-chain loop region having, e.g., at most one, two, three, four, five, six, or seven contiguous amino acid additions relative to SEQ ID NO: 19. In yet other aspects of this embodiment, a modified Clostridial toxin comprises a BaNT di-chain loop region having, e.g., at least one, two, three, four, five, six, or seven contiguous amino acid additions relative to SEQ ID NO: 19. In still other aspects of this embodiment, a modified Clostridial toxin comprises a BaNT di-chain loop region having, e.g., at most one, two, three, four, five, six, or seven contiguous amino acid deletions relative to SEQ ID NO: 19. In still other aspects of this embodiment, a modified Clostridial toxin comprises a BaNT di-chain loop region having, e.g., at least one, two, three, four, five, six, or seven contiguous amino acid deletions relative to SEQ ID NO: 19.

In another embodiment, a modified Clostridial toxin comprises a BuNT di-chain loop region. In an aspect of this embodiment, a modified Clostridial toxin comprises a BuNT di-chain loop region including a BuNT di-chain loop protease cleavage site. In another aspect of this embodiment, a modified Clostridial toxin comprises a BuNT di-chain loop region including a BuNT di-chain loop protease cleavage site comprising the K431-N432 scissile bond. In yet another aspect of this embodiment, a modified Clostridial toxin comprises the BuNT di-chain loop region of SEQ ID NO: 20.

In another aspect of this embodiment, a modified Clostridial toxin comprises a naturally occurring BuNT di-chain loop region variant. In another aspect of this embodiment, a modified Clostridial toxin comprises a naturally occurring BuNT di-chain loop region variant, such as, e.g., a BuNT di-chain loop region isoform, or a BuNT di-chain loop region subtype. In another aspect of this embodiment, a modified Clostridial toxin comprises a naturally occurring BuNT di-chain loop region variant of SEQ ID NO: 20, such as, e.g., a BuNT di-chain loop region isoform of SEQ ID NO: 20; or a BuNT di-chain loop region subtype of SEQ ID NO: 20. In still another aspect of this embodiment, a modified Clostridial toxin comprises a non-naturally occurring BuNT di-chain loop region variant, such as, e.g., a conservative BuNT di-chain loop region variant, a non-conservative BuNT di-chain loop region variant or a BuNT di-chain loop region peptidomimetic, or any combination thereof. In still another aspect of this embodiment, a modified Clostridial toxin comprises a non-naturally occurring BuNT di-chain loop region variant of SEQ ID NO: 20, such as, e.g., a conservative BuNT di-chain loop region variant of SEQ ID NO: 20, a non-conservative BuNT di-chain loop region variant of SEQ ID NO: 20 or a BuNT di-chain loop region peptidomimetic of SEQ ID NO: 20, or any combination thereof.

In other aspects of this embodiment, a modified Clostridial toxin comprises a BuNT di-chain loop region having, e.g., at least 50% amino acid identity with SEQ ID NO: 20, at least 60% amino acid identity with the SEQ ID NO: 20, at least 70% amino acid identity with SEQ ID NO: 20, at least 80% amino acid identity with SEQ ID NO: 20, or at least 90% amino acid identity with SEQ ID NO: 20. In still other aspects of this embodiment, a modified Clostridial toxin comprises a BuNT di-chain loop region having, e.g., at most 50% amino acid identity with SEQ ID NO: 20, at most 60% amino acid identity with the SEQ ID NO: 20, at most 70% amino acid identity with SEQ ID NO: 20, at most 80% amino acid identity with SEQ ID NO: 20, or at most 90% amino acid identity with SEQ ID NO: 20.

In other aspects of this embodiment, a modified Clostridial toxin comprises a BuNT di-chain loop region having, e.g., at most one, two, three, four, five, six, or seven non-contiguous amino acid substitutions relative to SEQ ID NO: 20. In still other aspects of this embodiment, a modified Clostridial toxin comprises a BuNT di-chain loop region having, e.g., at least one, two, three, four, five, six, or seven non-contiguous amino acid substitutions relative to SEQ ID NO: 20. In yet other aspects of this embodiment, a modified Clostridial toxin comprises a BuNT di-chain loop region having, e.g., at most one, two, three, four, five, six, or seven non-contiguous amino acid additions relative to SEQ ID NO: 20. In yet other aspects of this embodiment, a modified Clostridial toxin comprises a BuNT di-chain loop region having, e.g., at least one, two, three, four, five, six, or seven non-contiguous amino acid additions relative to SEQ ID NO: 20. In still other aspects of this embodiment, a modified Clostridial toxin comprises a BuNT di-chain loop region having, e.g., at most one, two, three, four, five, six, or seven non-contiguous amino acid deletions relative to SEQ ID NO: 20. In still other aspects of this embodiment, a modified Clostridial toxin comprises a BuNT di-chain loop region having, e.g., at least one, two, three, four, five, six, or seven non-contiguous amino acid deletions relative to SEQ ID NO: 20.

In other aspects of this embodiment, a modified Clostridial toxin comprises a BuNT di-chain loop region having, e.g., at most one, two, three, four, five, six, or seven contiguous amino acid substitutions relative to SEQ ID NO: 20. In still other aspects of this embodiment, a modified Clostridial toxin comprises a BuNT di-chain loop region having, e.g., at least one, two, three, four, five, six, or seven contiguous amino acid substitutions relative to SEQ ID NO: 20. In yet other aspects of this embodiment, a modified Clostridial toxin comprises a BuNT di-chain loop region having, e.g., at most one, two, three, four, five, six, or seven contiguous amino acid additions relative to SEQ ID NO: 20. In yet other aspects of this embodiment, a modified Clostridial toxin comprises a BuNT di-chain loop region having, e.g., at least one, two, three, four, five, six, or seven contiguous amino acid additions relative to SEQ ID NO: 20. In still other aspects of this embodiment, a modified Clostridial toxin comprises a BuNT di-chain loop region having, e.g., at most one, two, three, four, five, six, or seven contiguous amino acid deletions relative to SEQ ID NO: 20. In still other aspects of this embodiment, a modified Clostridial toxin comprises a BuNT di-chain loop region having, e.g., at least one, two, three, four, five, six, or seven contiguous amino acid deletions relative to SEQ ID NO: 20.

The di-chain loop region of the Clostridial toxin to be modified can be modified to include an exogenous Clostridial toxin di-chain loop region in addition to the naturally-occurring di-chain loop region (Table 3). In this type of modification, both di-chain loop regions are operably-linked in-frame to the modified Clostridial toxin as a fusion protein and both sites can be cleaved by their respective proteases. In such a modification, the cysteine residues from the exogenous di-chain loop region should not be included because the additional cysteine residues could interfere with the proper formation of the disulfide bridge necessary to for the loop structure. As a non-limiting example, a modified BoNT/E can comprise a di-chain loop containing both the naturally-occurring di-chain loop region and a BoNT/A di-chain loop region (e.g., SEQ ID NO: 11 minus the cysteine residues at position 1 and position 25) that can be cleaved by a BoNT/A di-chain loop protease found in *C. botulinum* serotype A.

TABLE 3

Examples of Modified Clostridial Toxins

| Enzymatic Domain | Di-Chain Loop Region[1] | Translocation Domain | Binding Domain |
|---|---|---|---|
| BoNT/B, BoNT/C1, BoNT/D, BoNT/E, BoNT/F, BoNT/G, TeNT, BaNT, or BuNT | BoNT/A | BoNT/B, BoNT/C1, BoNT/D, BoNT/E, BoNT/F, BoNT/G, TeNT, BaNT, or BuNT | BoNT/B, BoNT/C1, BoNT/D, BoNT/E, BoNT/F, BoNT/G, TeNT, BaNT, BuNT, or targeting moiety[2] |
| BoNT/A, BoNT/C1, BoNT/D, BoNT/E, BoNT/F, BoNT/G, TeNT, BaNT, or BuNT | BoNT/B | BoNT/A, BoNT/C1, BoNT/D, BoNT/E, BoNT/F, BoNT/G, TeNT, BaNT, or BuNT | BoNT/A, BoNT/C1, BoNT/D, BoNT/E, BoNT/F, BoNT/G, TeNT, BaNT, BuNT, or re-targeting moeity |
| BoNT/A, BoNT/B, BoNT/D, BoNT/E, BoNT/F, BoNT/G, TeNT, BaNT, or BuNT | BoNT/C1 | BoNT/A, BoNT/B, BoNT/D, BoNT/E, BoNT/F, BoNT/G, TeNT, BaNT, or BuNT | BoNT/A, BoNT/B, BoNT/D, BoNT/E, BoNT/F, BoNT/G, TeNT, BaNT, BuNT, or re-targeting moeity |
| BoNT/A, BoNT/B, BoNT/C1, BoNT/E, BoNT/F, BoNT/G, TeNT, BaNT, or BuNT | BoNT/D | BoNT/A, BoNT/B, BoNT/C1, BoNT/E, BoNT/F, BoNT/G, TeNT, BaNT, or BuNT | BoNT/A, BoNT/B, BoNT/C1, BoNT/E, BoNT/F, BoNT/G, TeNT, BaNT, BuNT, or re-targeting moeity |
| BoNT/A, BoNT/B, BoNT/C1, BoNT/D, BoNT/F, BoNT/G, TeNT, BaNT, or BuNT | BoNT/E | BoNT/A, BoNT/B, BoNT/C1, BoNT/D, BoNT/F, BoNT/G, TeNT, BaNT, or BuNT | BoNT/A, BoNT/B, BoNT/C1, BoNT/D, BoNT/F, BoNT/G, TeNT, BaNT, BuNT, or re-targeting moeity |
| BoNT/A, BoNT/B, BoNT/C1, BoNT/D, BoNT/E, BoNT/G, TeNT, BaNT, or BuNT | BoNT/F | BoNT/A, BoNT/B, BoNT/C1, BoNT/D, BoNT/E, BoNT/G, TeNT, BaNT, or BuNT | BoNT/A, BoNT/B, BoNT/C1, BoNT/D, BoNT/E, BoNT/G, TeNT, BaNT, BuNT, or re-targeting moeity |
| BoNT/A, BoNT/B, BoNT/C1, BoNT/D, BoNT/E, BoNT/F, TeNT, BaNT, or BuNT | BoNT/G | BoNT/A, BoNT/B, BoNT/C1, BoNT/D, BoNT/E, BoNT/F, TeNT, BaNT, or BuNT | BoNT/A, BoNT/B, BoNT/C1, BoNT/D, BoNT/E, BoNT/F, TeNT, BaNT, BuNT, or re-targeting moeity |
| BoNT/A, BoNT/B, BoNT/C1, BoNT/D, BoNT/E, BoNT/F, BoNT/G, BaNT, or BuNT | TeNT | BoNT/A, BoNT/B, BoNT/C1, BoNT/D, BoNT/E, BoNT/F, BoNT/G, BaNT, or BuNT | BoNT/A, BoNT/B, BoNT/C1, BoNT/D, BoNT/E, BoNT/F, BoNT/G, BaNT, BuNT, or re-targeting moeity |
| BoNT/A, BoNT/B, BoNT/C1, BoNT/D, BoNT/E, BoNT/F, BoNT/G, TeNT, or BuNT | BaNT | BoNT/A, BoNT/B, BoNT/C1, BoNT/D, BoNT/E, BoNT/F, BoNT/G, TeNT, or BuNT | BoNT/A, BoNT/B, BoNT/C1, BoNT/D, BoNT/E, BoNT/F, BoNT/G, TeNT, BuNT, or re-targeting moeity |

TABLE 3-continued

Examples of Modified Clostridial Toxins

| Enzymatic Domain | Di-Chain Loop Region[1] | Translocation Domain | Binding Domain |
|---|---|---|---|
| BoNT/A, BoNT/B, BoNT/C1, BoNT/D, BoNT/E, BoNT/F, BoNT/G, TeNT, or BaNT | BuNT | BoNT/A, BoNT/B, BoNT/C1, BoNT/D, BoNT/E, BoNT/F, BoNT/G, TeNT, or BaNT | BoNT/A, BoNT/B, BoNT/C1, BoNT/D, BoNT/E, BoNT/F, BoNT/G, TeNT, BaNT, or re-targeting moeity |

[1]Included in this category is the replacement of the endogenous Clostridial toxin di-chain loop with the indicated exogenous Clostridial toxin di-chain loop; replacement of the endogenous Clostridial toxin di-chain loop protease cleavage site with the indicated exogenous Clostridial toxin di-chain loop protease cleavage site; the addition of an exogenous Clostridial toxin di-chain loop from the indicated Clostridial toxin within the endogenous Clostridial toxin di-chain loop; and the addition of an exogenous Clostridial toxin di-chain loop protease cleavage site from the indicated Clostridial toxin within the endogenous Clostridial toxin di-chain loop.
[2]Targeting moeities suitable as binding domains disclosed in the present specification are described in Steward, supra, International Patent Publication No. 2006/008956; Steward, supra, U.S. patent application No. 11/776,043; Steward, supra, International Patent Publication No. 2006/009831; Steward, supra, U.S. Patent Publication No. 2006/0211619; Steward, supra, U.S. patent application No. 11/776,052; Foster, supra, U.S. Pat. No. 5,989,545; Shone, supra, U.S. Pat. No. 6,461,617; Quinn, supra, U.S. Pat. No. 6,632,440; Steward, supra, U.S. Pat. No. 6,843,998; Donovan, supra, U.S. Pat. No. 7,138,127; Foster, supra, U.S. Patent Publication 2003/0180289; Dolly, supra, U.S. Pat. No. 7,132,259; Foster, supra, International Patent Publication WO 2005/023309; Steward, supra, U.S. patent application No. 11/376,696; Foster, supra, International Patent Publication WO 2006/059093; Foster, supra, International Patent Publication WO 2006/059105; and Steward, supra, U.S. patent application No. 11/776,075.

The di-chain loop region of the Clostridial toxin to be modified can be modified to include an exogenous Clostridial toxin di-chain loop protease cleavage site in addition to the naturally-occurring di-chain loop protease cleavage site (Table 3). In this type of modification, both cleavage sites are operably-linked in-frame to a modified Clostridial toxin as a fusion protein and both sites can be cleaved by their respective proteases. As a non-limiting example, a modified BoNT/E can comprise a di-chain loop containing both the naturally-occurring di-chain loop protease cleavage site and a BoNT/A di-chain loop protease cleavage site that can be cleaved by a BoNT/A di-chain loop protease found in C. botulinum serotype A.

The di-chain loop region can also be modified to replace the naturally-occurring di-chain loop region with an exogenous Clostridial toxin di-chain loop region (Table 3). Such a Clostridial toxin di-chain loop region is operably-linked in-frame to a modified Clostridial toxin as a fusion protein. As a non-limiting example, a BoNT/E di-chain loop region (e.g., SEQ ID NO: 15) can be replaced by a BoNT/A di-chain loop region (e.g., SEQ ID NO: 11) that can be cleaved by a BoNT/A di-chain loop protease found in C. botulinum serotype A.

The di-chain loop region can also be modified to replace a naturally-occurring di-chain loop protease cleavage site with an exogenous Clostridial toxin di-chain loop protease cleavage site (Table 3). Such a Clostridial toxin di-chain loop protease cleavage site is operably-linked in-frame to a modified Clostridial toxin as a fusion protein. As a non-limiting example, the R422-K423 scissile bond of a BoNT/E di-chain loop region can be replaced by a K448-A449 scissile bond from a BoNT/A di-chain loop region that can be cleaved by a BoNT/A di-chain loop protease found in C. botulinum serotype A.

The naturally-occurring di-chain loop protease cleavage site can be made inoperable by altering at least the one of the amino acids flanking the peptide bond cleaved by the naturally-occurring protease, i.e., either $P_1$, $P_{1'}$, or both $P_1$ and $P_{1'}$. More extensive alterations can be made, with the proviso that the two cysteine residues of the di-chain loop region remain intact and formation of the disulfide bridge can still be acheived. Non-limiting examples of an amino acid alteration include deletion of an amino acid or replacement of the original amino acid with a different amino acid. These alterations can be made using standard mutagenesis procedures known to a person skilled in the art. In addition, non-limiting examples of mutagensis procedures, as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures within the scope of one skilled in the art and from the teaching herein.

Thus, in one embodiment, a naturally-occurring di-chain loop protease cleavage site is made inoperable by altering at least one of the amino acids flanking the peptide bond cleaved by a naturally-occurring protease. In aspects of this embodiment, the $P_1$ amino acid of the di-chain loop protease cleavage site is altered or the $P_{1'}$ amino acid of the di-chain loop protease cleavage site is altered. In other aspects of this embodiment, either K448 or A449 of BoNT/A is altered; either S441 or L442 of BoNT/A is altered; either K441 or A442 of BoNT/B is altered; either G444 or I445 of BoNT/B is altered; either K449 or T450 of BoNT/C1 is altered; either S445 or L446 of BoNT/C1 is altered; either R445 or D446 of BoNT/D is altered; either K442 or N443 of BoNT/D is altered; either R422 or K423 of BoNT/E is altered; either K419 or G420 of BoNT/E is altered; either K423 or S424 of BoNT/E is altered; either K439 or A440 of BoNT/F is altered; either K436 or G437 of BoNT/F is altered; either K446 or S447 of BoNT/G is altered; either T444 or G445 of BoNT/G is altered; either E448 or Q449 of BoNT/G is altered; or either A457 or S458 of TeNT is altered.

In another embodiment, a naturally-occurring di-chain loop protease cleavage site is made inoperable by altering the two amino acids flanking the peptide bond cleaved by a naturally-occurring protease, i.e., $P_1$ and $P_{1'}$. In other aspects of this embodiment, both K448 and A449 of BoNT/A are altered; both S441 and L442 of BoNT/A are altered; both K441 and A442 of BoNT/B are altered; both G444 and I445 of BoNT/B are altered; both K449 and T450 of BoNT/C1 are altered; both S445 and L446 of BoNT/C1 are altered; both R445 and D446 of BoNT/D are altered; both K442 and N443 of BoNT/D are altered; both R422 and K423 of BoNT/E are altered; both K419 and G420 of BoNT/E are altered; both K423 and S424 of BoNT/E are altered; both K439 and A440 of BoNT/F are altered; both K436 and G437 of BoNT/F are altered; both K446 and S447 of BoNT/G are altered; both T444 and G445 of BoNT/G are altered; both E448 and Q449 of BoNT/G are altered; or both A457 and S458 of TeNT are altered.

In other aspects of this embodiment, a naturally-occurring di-chain loop protease cleavage site is made inoperable by altering, e.g., at least two amino acids within the di-chain loop region; at least three amino acids within the di-chain loop region; at least four amino acids within the di-chain loop region; at least five amino acids within the di-chain loop region; at least six amino acids within the di-chain loop region; at least seven amino acids within the di-chain loop region; at least eight amino acids within the di-chain loop region; at least nine amino acids within the di-chain loop region; at least ten amino acids within the di-chain loop region; or at least 15 amino acids within the di-chain loop region. In still other aspects of this embodiment, a naturally-occurring di-chain loop protease cleavage site is made inoperable by altering one of the amino acids flanking the peptide bond cleaved by a naturally-occurring protease and, e.g., at least one more amino acid within the di-chain loop region; at least two more amino acids within the di-chain loop region; at least three more amino acids within the di-chain loop region; at least four more amino acids within the di-chain loop region; at least five more amino acids within the di-chain loop region; at least six more amino acids within the di-chain loop region; at least seven more amino acids within the di-chain loop region; at least eight more amino acids within the di-chain loop region; at least nine more amino acids within the di-chain loop region; at least ten more amino acids within the di-chain loop region; at least 15 more amino acids within the di-chain loop region. In yet other aspects of this embodiment, a naturally-occurring di-chain loop protease cleavage site is made inoperable by altering the two amino acids flanking the peptide bond cleaved by a naturally-occurring protease and, e.g., at least one more amino acid within the di-chain loop region; at least two more amino acids within the di-chain loop region; at least three more amino acids within the di-chain loop region; at least four more amino acids within the di-chain loop region; at least five more amino acids within the di-chain loop region; at least six more amino acids within the di-chain loop region; at least seven more amino acids within the di-chain loop region; at least eight more amino acids within the di-chain loop region; at least nine more amino acids within the di-chain loop region; at least ten more amino acids within the di-chain loop region; at least 15 more amino acids within the di-chain loop region.

In other aspects of this embodiment, a naturally-occurring di-chain loop protease cleavage site is made inoperable by altering, e.g., at most two amino acids within the di-chain loop region; at most three amino acids within the di-chain loop region; at most four amino acids within the di-chain loop region; at most five amino acids within the di-chain loop region; at most six amino acids within the di-chain loop region; at most seven amino acids within the di-chain loop region; at most eight amino acids within the di-chain loop region; at most nine amino acids within the di-chain loop region; at most ten amino acids within the di-chain loop region; or at most 15 amino acids within the di-chain loop region. In still other aspects of this embodiment, a naturally-occurring di-chain loop protease cleavage site is made inoperable by altering one of the amino acids flanking the peptide bond cleaved by a naturally-occurring protease and, e.g., at most one more amino acid within the di-chain loop region; at most two more amino acids within the di-chain loop region; at most three more amino acids within the di-chain loop region; at most four more amino acids within the di-chain loop region; at most five more amino acids within the di-chain loop region; at most six more amino acids within the di-chain loop region; at most seven more amino acids within the di-chain loop region; at most eight more amino acids within the di-chain loop region; at most nine more amino acids within the di-chain loop region; at most ten more amino acids within the di-chain loop region; at most 15 more amino acids within the di-chain loop region. In yet other aspects of this embodiment, a naturally-occurring di-chain loop protease cleavage site is made inoperable by altering the two amino acids flanking the peptide bond cleaved by a naturally-occurring protease and, e.g., at most one more amino acid within the di-chain loop region; at most two more amino acids within the di-chain loop region; at most three more amino acids within the di-chain loop region; at most four more amino acids within the di-chain loop region; at most five more amino acids within the di-chain loop region; at most six more amino acids within the di-chain loop region; at most seven more amino acids within the di-chain loop region; at most eight more amino acids within the di-chain loop region; at most nine more amino acids within the di-chain loop region; at most ten more amino acids within the di-chain loop region; at most 15 more amino acids within the di-chain loop region.

It is envisioned that the di-chain loop region of a Clostridial toxin can be modified to include any of the other Clostridial toxin di-chain loop regions. In aspects of this embodiment, a Clostridial toxin di-chain loop region can be modified to comprise, e.g., a BoNT/A di-chain loop region, a BoNT/B di-chain loop region, a BoNT/C1 di-chain loop region, a BoNT/D di-chain loop region, a BoNT/E di-chain loop region, a BoNT/F di-chain loop region, a BoNT/G di-chain loop region, a TeNT di-chain loop region, a BaNT di-chain loop region or a BuNT di-chain loop region. In other aspects of this embodiment, an exogenous Clostridial toxin di-chain loop region, in addition to the naturally-occurring protease cleavage site, can be modified to comprise, e.g., a BoNT/A di-chain loop region, a BoNT/B di-chain loop region, a BoNT/C1 di-chain loop region, a BoNT/D di-chain loop region, a BoNT/E di-chain loop region, a BoNT/F di-chain loop region, a BoNT/G di-chain loop region, a TeNT di-chain loop region, a BaNT di-chain loop region or a BuNT di-chain loop region.

In still other aspects of this embodiment, a di-chain loop of a Clostridial toxin can be modified to replace a naturally-occurring protease cleavage site with, e.g., a BoNT/A substrate cleavage site, a BoNT/B substrate cleavage site, a BoNT/C1 substrate cleavage site, a BoNT/D substrate cleavage site, a BoNT/E substrate cleavage site, a BoNT/F substrate cleavage site, a BoNT/G substrate cleavage site, a TeNT substrate cleavage site, a BaNT substrate cleavage site or a BuNT substrate cleavage site.

The location of the Clostridial toxin substrate cleavage site can be anywhere in the Clostridial toxin, with the proviso that cleavage of the site must occur between the two cysteine residues that form the single disulfide bridge of toxin. Thus, in aspects of this embodiment, location of a Clostridial toxin substrate cleavage site can be, e.g., anywhere in the BoNT/A of SEQ ID NO: 1, with the proviso that cleavage occurs between cysteine 430 and cysteine 454; anywhere in the BoNT/B of SEQ ID NO: 2, with the proviso that cleavage occurs between cysteine 437 and cysteine 446; anywhere in the BoNT/C1 of SEQ ID NO: 2, with the proviso that cleavage occurs between cysteine 437 and cysteine 453; anywhere in the BoNT/D of SEQ ID NO: 4, with the proviso that cleavage occurs between cysteine 437 and cysteine 450; anywhere in the BoNT/E of SEQ ID NO: 5, with the proviso that cleavage occurs between cysteine 412 and cysteine 426; anywhere in the BoNT/F of SEQ ID NO: 6, with the proviso that cleavage occurs between cysteine 429 and cysteine 445; anywhere in the BoNT/G of SEQ ID NO: 7, with the proviso that cleavage occurs between cysteine 436 and cysteine 450; or anywhere in the TeNT of SEQ ID NO: 8, with the proviso that cleavage occurs between cysteine 439 and cysteine 467.

It is understood that a modified Clostridial toxin disclosed in the present specification can optionally include one or more additional components. As a non-limiting example of an optional component, a modified Clostridial toxin can further comprise a flexible region comprising a flexible spacer. Non-limiting examples of a flexible spacer include, e.g., a G-spacer GGGGS (SEQ ID NO: 21) or an A-spacer EAAAK (SEQ ID NO: 22). A flexible region comprising flexible spacers can be used to adjust the length of a polypeptide region in order to optimize a characteristic, attribute or property of a polypeptide. Such a flexible region is operably-linked in-frame to the modified Clostridial toxin as a fusion protein. As a non-limiting example, a polypeptide region comprising one or more flexible spacers in tandem can be use to better expose a protease cleavage site thereby facilitating cleavage of that site by a protease. As another non-limiting example, a polypeptide region comprising one or more flexible spacers in tandem can be use to better present a ligand domain, thereby facilitating the binding of that ligand domain to its binding domain on a receptor.

Thus, in an embodiment, a modified Clostridial toxin disclosed in the present specification can further comprise a flexible region comprising a flexible spacer. In another embodiment, a modified Clostridial toxin disclosed in the present specification can further comprise flexible region comprising a plurality of flexible spacers in tandem. In aspects of this embodiment, a flexible region can comprise in tandem, e.g., at least 1 G-spacer, at least 2 G-spacers, at least 3 G-spacers, at least 4 G-spacers or at least 5 G-spacers. In other aspects of this embodiment, a flexible region can comprise in tandem, e.g., at most 1 G-spacer, at most 2 G-spacers, at most 3 G-spacers, at most 4 G-spacers or at most 5 G-spacers. In still other aspects of this embodiment, a flexible region can comprise in tandem, e.g., at least 1 A-spacer, at least 2 A-spacers, at least 3 A-spacers, at least 4 A-spacers or at least 5 A-spacers. In still other aspects of this embodiment, a flexible region can comprise in tandem, e.g., at most 1 A-spacer, at most 2 A-spacers, at most 3 A-spacers, at most 4 A-spacers or at most 5 A-spacers. In another aspect of this embodiment, a modified Clostridial toxin can comprise a flexible region comprising one or more copies of the same flexible spacers, one or more copies of different flexible-spacer regions, or any combination thereof.

As another non-limiting example of an optional component, a modified Clostridial toxin can further comprise an epitope-binding region. An epitope-binding region can be used in a wide variety of procedures involving, e.g., protein purification and protein visualization. Such an epitope-binding region is operably-linked in-frame to a modified Clostridial toxin as a fusion protein. Non-limiting examples of an epitope-binding region include, e.g., FLAG, Express™ (SEQ ID NO: 23), human Influenza virus hemagluttinin (HA) (SEQ ID NO: 24), human p62$^{c\text{-}Myc}$ protein (c-MYC) (SEQ ID NO: 25), Vesicular Stomatitis Virus Glycoprotein (VSV-G) (SEQ ID NO: 26), Substance P (SEQ ID NO: 27), glycoprotein-D precursor of Herpes simplex virus (HSV) (SEQ ID NO: 28), V5 (SEQ ID NO: 29), AU1 (SEQ ID NO: 30) and AU5 (SEQ ID NO: 31); affinity-binding, such as. e.g., polyhistidine (HIS) (SEQ ID NO: 32), streptavidin binding peptide (strep), and biotin or a biotinylation sequence; peptide-binding regions, such as. e.g., the glutathione binding domain of glutathione-S-transferase, the calmodulin binding domain of the calmodulin binding protein, and the maltose binding domain of the maltose binding protein. Non-limiting examples of specific protocols for selecting, making and using an appropriate binding peptide are described in, e.g., Epitope Tagging, pp. 17.90-17.93 (Sambrook and Russell, eds., MOLECULAR CLONING A LABORATORY MANUAL, Vol. 3, 3$^{rd}$ ed. 2001); ANTIBODIES: A LABORATORY MANUAL (Edward Harlow & David Lane, eds., Cold Spring Harbor Laboratory Press, 2$^{nd}$ ed. 1998); and USING ANTIBODIES: A LABORATORY MANUAL: PORTABLE PROTOCOL NO. I (Edward Harlow & David Lane, Cold Spring Harbor Laboratory Press, 1998). In addition, non-limiting examples of binding peptides as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures well within the scope of one skilled in the art and from the teaching herein.

Thus, in an embodiment, a modified Clostridial toxin disclosed in the present specification can further comprise an epitope-binding region. In another embodiment, a modified Clostridial toxin disclosed in the present specification can further comprises a plurality of epitope-binding regions. In aspects of this embodiment, a modified Clostridial toxin can comprise, e.g., at least 1 epitope-binding region, at least 2 epitope-binding regions, at least 3 epitope-binding regions, at least 4 epitope-binding regions or at least 5 epitope-binding regions. In other aspects of this embodiment, a modified Clostridial toxin can comprise, e.g., at most 1 epitope-binding region, at most 2 epitope-binding regions, at most 3 epitope-binding regions, at most 4 epitope-binding regions or at most 5 epitope-binding regions. In another aspect of this embodiment, a modified Clostridial toxin can comprise one or more copies of the same epitope-binding region, one or more copies of different epitope-binding regions, or any combination thereof.

The location of an epitope-binding region can be in various positions, including, without limitation, at the amino terminus of a modified Clostridial toxin, within a modified Clostridial toxin, or at the carboxyl terminus of a modified Clostridial toxin. Thus, in an embodiment, an epitope-binding region is located at the amino-terminus of a modified Clostridial toxin. In such a location, a start methionine should be placed in front of the epitope-binding region. In addition, it is known in the art that when adding a polypeptide that is operationally-linked to the amino terminus of another polypeptide comprising the start methionine that the original methionine residue can be deleted. This is due to the fact that the added polypeptide will contain a new start methionine and that the original start methionine may reduce optimal expression of the fusion protein. In aspects of this embodiment, an epitope-binding region located at the amino-terminus of a modified Clostridial toxin disclosed in the present specification can be, e.g., a FLAG, Express™ epitope-binding region, a human Influenza virus hemagluttinin (HA) epitope-binding region, a human p62$^{c\text{-}Myc}$ protein (c-MYC) epitope-binding region, a Vesicular Stomatitis Virus Glycoprotein (VSV-G) epitope-binding region, a Substance P epitope-binding region, a glycoprotein-D precursor of Herpes simplex virus (HSV) epitope-binding region, a V5 epitope-binding region, a AU1 epitope-binding region, a AU5 epitope-binding region, a polyhistidine epitope-binding region, a streptavidin binding peptide epitope-binding region, a biotin epitope-binding region, a biotinylation epitope-binding region, a glutathione binding domain of glutathione-S-transferase, a calmodulin binding domain of the calmodulin binding protein or a maltose binding domain of the maltose binding protein.

In another embodiment, an epitope-binding region is located at the carboxyl-terminus of a modified Clostridial toxin. In aspects of this embodiment, an epitope-binding region located at the carboxyl-terminus of a modified Clostridial toxin disclosed in the present specification can be, e.g., a FLAG, Express™ epitope-binding region, a human Influenza virus hemagluttinin (HA) epitope-binding region, a human p62$^{c-Myc}$ protein (c-MYC) epitope-binding region, a Vesicular Stomatitis Virus Glycoprotein (VSV-G) epitope-binding region, a Substance P epitope-binding region, a glycoprotein-D precursor of Herpes simplex virus (HSV) epitope-binding region, a V5 epitope-binding region, a AU1 epitope-binding region, a AU5 epitope-binding region, a polyhistidine epitope-binding region, a streptavidin binding peptide epitope-binding region, a biotin epitope-binding region, a biotinylation epitope-binding region, a glutathione binding domain of glutathione-S-transferase, a calmodulin binding domain of the calmodulin binding protein or a maltose binding domain of the maltose binding protein.

Aspects of the present invention provide, in part modified Clostridial toxins. As used herein, the term "modified Clostridial toxin" means any naturally-occurring Clostridial toxin or non-naturally occurring Clostridial toxin comprising at least 1) the replacement of a naturally-occurring di-chain loop protease cleavage site with a di-chain loop protease cleavage site from another Clostridial toxin, 2) the addition of a Clostridial toxin di-chain loop protease cleavage site as disclosed in the present specification into the di-chain loop region of a naturally-occurring Clostridial toxin, 3) the replacement of a naturally-occurring di-chain loop region with a di-chain loop region from another Clostridial toxin, or 4) the addition of a Clostridial toxin di-chain loop region as disclosed in the present specification into the di-chain loop region of a naturally-occurring Clostridial toxin.

It is understood that all such modifications do not substantially affect the ability of a Clostridial toxin to intoxicate a cell. As used herein, the term "do not substantially affect" means a Clostridial toxin can still execute the overall cellular mechanism whereby a Clostridial toxin enters a neuron and inhibits neurotransmitter release and encompasses the binding of a Clostridial toxin to a low or high affinity receptor complex, the internalization of the toxin/receptor complex, the translocation of the Clostridial toxin light chain into the cytoplasm and the enzymatic modification of a Clostridial toxin substrate. In aspects of this embodiment, the modified Clostridial toxin is, e.g., at least 10% as toxic as a naturally-occurring Clostridial toxin, at least 20% as toxic as a naturally-occurring Clostridial toxin, at least 30% as toxic as a naturally-occurring Clostridial toxin, at least 40% as toxic as a naturally-occurring Clostridial toxin, at least 50% as toxic as a naturally-occurring Clostridial toxin, at least 60% as toxic as a naturally-occurring Clostridial toxin, at least 70% as toxic as a naturally-occurring Clostridial toxin, at least 80% as toxic as a naturally-occurring Clostridial toxin, at least 90% as toxic as a naturally-occurring Clostridial toxin or at least 95% as toxic as a naturally-occurring Clostridial toxin. In aspects of this embodiment, the modified Clostridial toxin is, e.g., at most 10% as toxic as a naturally-occurring Clostridial toxin, at most 20% as toxic as a naturally-occurring Clostridial toxin, at most 30% as toxic as a naturally-occurring Clostridial toxin, at most 40% as toxic as a naturally-occurring Clostridial toxin, at most 50% as toxic as a naturally-occurring Clostridial toxin, at most 60% as toxic as a naturally-occurring Clostridial toxin, at most 70% as toxic as a naturally-occurring Clostridial toxin, at most 80% as toxic as a naturally-occurring Clostridial toxin, at most 90% as toxic as a naturally-occurring Clostridial toxin or at most 95% as toxic as a naturally-occurring Clostridial toxin.

Aspects of the present invention provide, in part, polynucleotide molecules. As used herein, the term "polynucleotide molecule" is synonymous with "nucleic acid molecule" and means a polymeric form of nucleotides, such as, e.g., ribonucleotides and deoxyribonucleotides, of any length. It is envisioned that any and all polynucleotide molecules that can encode a modified Clostridial toxin disclosed in the present specification can be useful, including, without limitation naturally-occurring and non-naturally-occurring DNA molecules and naturally-occurring and non-naturally-occurring RNA molecules. Non-limiting examples of naturally-occurring and non-naturally-occurring DNA molecules include single-stranded DNA molecules, double-stranded DNA molecules, genomic DNA molecules, cDNA molecules, vector constructs, such as, e.g., plasmid constructs, phagmid constructs, bacteriophage constructs, retroviral constructs and artificial chromosome constructs. Non-limiting examples of naturally-occurring and non-naturally-occurring RNA molecules include single-stranded RNA, double stranded RNA and mRNA.

Well-established molecular biology techniques that may be necessary to make a polynucleotide molecule encoding a modified Clostridial toxin disclosed in the present specification including, but not limited to, procedures involving polymerase chain reaction (PCR) amplification, restriction enzyme reactions, agarose gel electrophoresis, nucleic acid ligation, bacterial transformation, nucleic acid purification, nucleic acid sequencing and recombination-based techniques are routine procedures well within the scope of one skilled in the art and from the teaching herein. Non-limiting examples of specific protocols necessary to make a polynucleotide molecule encoding a modified Clostridial toxin are described in e.g., MOLECULAR CLONING A LABORATORY MANUAL, supra, (2001); and CURRENT PROTOCOLS IN MOLECULAR BIOLOGY (Frederick M. Ausubel et al., eds. John Wiley & Sons, 2004). Additionally, a variety of commercially available products useful for making a polynucleotide molecule encoding a modified Clostridial toxin are widely available. These protocols are routine procedures well within the scope of one skilled in the art and from the teaching herein.

Another aspect of the present invention provides a method of producing a modified Clostridial toxin comprising an exogenous Clostridial toxin di-chain loop region including a Clostridial toxin di-chain loop protease cleavage site from a different Clostridial toxin, such method comprising the step of expressing a polynucleotide molecule encoding a modified Clostridial toxin in a cell. Another aspect of the present invention provides a method of producing a modified Clostridial toxin comprising an exogenous Clostridial toxin di-chain loop region including a Clostridial toxin di-chain loop protease cleavage site from a different Clostridial toxin, such method comprising the steps of introducing an expression construct comprising a polynucleotide molecule encoding the modified Clostridial toxin into a cell and expressing the expression construct in the cell.

The methods disclosed in the present specification include, in part, a modified Clostridial toxin. It is envisioned that any and all modified Clostridial toxins disclosed in the present specification can be produced using the methods disclosed in the present specification. Thus, aspects of this embodiment include producing, without limitation, naturally occurring Clostridial toxins, naturally occurring Clostridial toxins variants, such as, e.g., Clostridial toxins isoforms and Clostridial toxins subtypes, non-naturally occurring Clostridial toxins variants, such as, e.g., conservative Clostridial toxins variants, non-conservative Clostridial toxins variants and Clostridial toxins fragments thereof, or any combination thereof.

The methods disclosed in the present specification include, in part, a polynucleotide molecule. It is envisioned that any and all polynucleotide molecules disclosed in the present specification can be used. Thus, aspects of this embodiment include, without limitation, naturally-occurring and non-naturally-occurring DNA molecules include single-stranded DNA molecules, double-stranded DNA molecules, genomic DNA molecules, cDNA molecules, vector constructs, such as, e.g., plasmid constructs, phagmid constructs, bacteriophage constructs, retroviral constructs and artificial chromosome constructs. Non-limiting examples of naturally-occurring and non-naturally-occurring RNA molecules include single-stranded RNA, double stranded RNA and mRNA.

The methods disclosed in the present specification include, in part, an expression construct. An expression construct comprises a polynucleotide molecule disclosed in the present specification operably-linked to an expression vector useful for expressing the polynucleotide molecule in a cell or cell-free extract. A wide variety of expression vectors can be employed for expressing a polynucleotide molecule encoding a modified Clostridial toxin, including, without limitation, a viral expression vector; a prokaryotic expression vector; eukaryotic expression vectors, such as, e.g., a yeast expression vector, an insect expression vector and a mammalian expression vector; and a cell-free extract expression vector. It is further understood that expression vectors useful to practice aspects of these methods may include those which express a modified Clostridial toxin under control of a constitutive, tissue-specific, cell-specific or inducible promoter element, enhancer element or both. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

Thus, aspects of this embodiment include, without limitation, a viral expression vector operably-linked to a polynucleotide molecule encoding a modified Clostridial toxin; a prokaryotic expression vector operably-linked to a polynucleotide molecule encoding a modified Clostridial toxin; a yeast expression vector operably-linked to a polynucleotide molecule encoding a modified Clostridial toxin; an insect expression vector operably-linked to a polynucleotide molecule encoding a modified Clostridial toxin; and a mammalian expression vector operably-linked to a polynucleotide molecule encoding a modified Clostridial toxin. Other aspects of this embodiment include, without limitation, expression constructs suitable for expressing a modified Clostridial toxin disclosed in the present specification using a cell-free extract comprising a cell-free extract expression vector operably linked to a polynucleotide molecule encoding a modified Clostridial toxin.

The methods disclosed in the present specification include, in part, a cell. It is envisioned that any and all cells can be used. Thus, aspects of this embodiment include, without limitation, prokaryotic cells including, without limitation, strains of aerobic, microaerophilic, capnophilic, facultative, anaerobic, gram-negative and gram-positive bacterial cells such as those derived from, e.g., *Escherichia coli, Bacillus subtilis, Bacillus licheniformis, Bacteroides fragilis, Clostridia perfringens, Clostridia difficile, Caulobacter crescentus, Lactococcus lactis, Methylobacterium extorquens, Neisseria meningirulls, Neisseria meningitidis, Pseudomonas fluorescens* and *Salmonella typhimurium*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; insect cells and cell lines derived from insects, such as, e.g., those derived from *Spodoptera frugiperda, Trichoplusia ni, Drosophila melanogaster* and *Manduca sexta*; and mammalian cells and cell lines derived from mammalian cells, such as, e.g., those derived from mouse, rat, hamster, porcine, bovine, equine, primate and human. Cell lines may be obtained from the American Type Culture Collection (2004); European Collection of Cell Cultures (2204); and the German Collection of Microorganisms and Cell Cultures (2004). Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae, GENERAL TECHNIQUES OF CELL CULTURE (Cambridge University Press, 1997); CELL AND TISSUE CULTURE: LABORATORY PROCEDURES (Alan Doyle et al eds., John Wiley and Sons, 1998); R. Ian Freshney, CULTURE OF ANIMAL CELLS: A MANUAL OF BASIC TECHNIQUE (Wiley-Liss, $4^{th}$ ed. 2000); ANIMAL CELL CULTURE: A PRACTICAL APPROACH (John R. W. Masters ed., Oxford University Press, $3^{rd}$ ed. 2000); MOLECULAR CLONING A LABORATORY MANUAL, supra, (2001); BASIC CELL CULTURE: A PRACTICAL APPROACH (John M. Davis, Oxford Press, $2^{nd}$ ed. 2002); and CURRENT PROTOCOLS IN MOLECULAR BIOLOGY, supra, (2004). These protocols are routine procedures within the scope of one skilled in the art and from the teaching herein.

The methods disclosed in the present specification include, in part, introducing into a cell a polynucleotide molecule. A polynucleotide molecule introduced into a cell can be transiently or stably maintained by that cell. Stably-maintained polynucleotide molecules may be extra-chromosomal and replicate autonomously, or they may be integrated into the chromosomal material of the cell and replicate non-autonomously. It is envisioned that any and all methods for introducing a polynucleotide molecule disclosed in the present specification into a cell can be used. Methods useful for introducing a nucleic acid molecule into a cell include, without limitation, chemical-mediated transfection such as, e.g., calcium phosphate-mediated, diethyl-aminoethyl (DEAE) dextran-mediated, lipid-mediated, polyethyleneimine (PEI)-mediated, polylysine-mediated and polybrene-mediated; physical-mediated tranfection, such as, e.g., biolistic particle delivery, microinjection, protoplast fusion and electroporation; and viral-mediated transfection, such as, e.g., retroviral-mediated transfection, see, e.g., Introducing Cloned Genes into Cultured Mammalian Cells, pp. 16.1-16.62 (Sambrook & Russell, eds., Molecular Cloning A Laboratory Manual, Vol. 3, $3^{rd}$ ed. 2001). One skilled in the art understands that selection of a specific method to introduce an expression construct into a cell will depend, in part, on whether the cell will transiently contain an expression construct or whether the cell will stably contain an expression construct. These protocols are routine procedures within the scope of one skilled in the art and from the teaching herein.

In an aspect of this embodiment, a chemical-mediated method, termed transfection, is used to introduce a polynucleotide molecule encoding a modified Clostridial toxin into a cell. In chemical-mediated methods of transfection the chemical reagent forms a complex with the nucleic acid that facilitates its uptake into the cells. Such chemical reagents include, without limitation, calcium phosphate-mediated, see, e.g., Martin Jordan & Florian Worm, *Transfection of Adherent and Suspended Cells by Calcium Phosphate,* 33(2) Methods 136-143 (2004); diethyl-aminoethyl (DEAE) dextran-mediated, lipid-mediated, cationic polymer-mediated like polyethyleneimine (PEI)-mediated and polylysine-mediated and polybrene-mediated, see, e.g., Chun Zhang et al., *Polyethylenimine Strategies for Plasmid Delivery to Brain-Derived Cells,* 33(2) Methods 144-150 (2004). Such chemical-mediated delivery systems can be prepared by standard methods and are commercially available, see, e.g., CellPhect Transfection Kit (Amersham Biosciences, Piscataway, N.J.); Mammalian Transfection Kit, Calcium phosphate and DEAE Dextran, (Stratagene, Inc., La Jolla, Calif.); Lipofectamine™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

In another aspect of this embodiment, a physical-mediated method is used to introduce a polynucleotide molecule encoding a modified Clostridial toxin into a cell. Physical techniques include, without limitation, electroporation, biolistic and microinjection. Biolistics and microinjection techniques perforate the cell wall in order to introduce the nucleic acid molecule into the cell, see, e.g., Jeike E. Biewenga et al., *Plasmid-Mediated Gene Transfer in Neurons Using the Biolistics Technique,* 71(1) J. Neurosci. Methods. 67-75 (1997); and John O'Brien & Sarah C. R. Lummis, *Biolistic and Diolistic Transfection: Using the Gene Gun to Deliver DNA and Lipophilic Dyes into Mammalian Cells,* 33(2) Methods 121-125 (2004). Electroporation, also termed electropermeabilization, uses brief, high-voltage, electrical pulses to create transient pores in the membrane through which the nucleic acid molecules enter and can be used effectively for stable and transient transfections of all cell types, see, e.g., M. Golzio et al., *In vitro and in vivo Electric Field-Mediated Permeabilization, Gene Transfer, and Expression,* 33(2) Methods 126-135 (2004); and Oliver Gresch et al., *New Non-Viral Method for Gene Transfer into Primary Cells,* 33(2) Methods 151-163 (2004).

In another aspect of this embodiment, a viral-mediated method, termed transduction, is used to introduce a polynucleotide molecule encoding a modified Clostridial toxin into a cell. In viral-mediated methods of transient transduction, the process by which viral particles infect and replicate in a host cell has been manipulated in order to use this mechanism to introduce a nucleic acid molecule into the cell. Viral-mediated methods have been developed from a wide variety of viruses including, without limitation, retroviruses, adenoviruses, adeno-associated viruses, herpes simplex viruses, picornaviruses, alphaviruses and baculoviruses, see, e.g., Armin Blesch, *Lentiviral and MLV based Retroviral Vectors for ex vivo and in vivo Gene Transfer,* 33(2) Methods 164-172 (2004); and Maurizio Federico, *From Lentiviruses to Lentivirus Vectors,* 229 Methods Mol. Biol. 3-15 (2003); E. M. Poeschla, *Non-Primate Lentiviral Vectors,* 5(5) Curr. Opin. Mol. Ther. 529-540 (2003); Karim Benihoud et al, *Adenovirus Vectors for Gene Delivery,* 10(5) Curr. Opin. Biotechnol. 440-447 (1999); H. Bueler, *Adeno-Associated Viral Vectors for Gene Transfer and Gene Therapy,* 380(6) Biol. Chem. 613-622 (1999); Chooi M. Lai et al., *Adenovirus and Adeno-Associated Virus Vectors,* 21(12) DNA Cell Biol. 895-913 (2002); Edward A. Burton et al., *Gene Delivery Using Herpes Simplex Virus Vectors,* 21(12) DNA Cell Biol. 915-936 (2002); Paola Grandi et al., *Targeting HSV Amplicon Vectors,* 33(2) Methods 179-186 (2004); Ilya Frolov et al., *Alphavirus-Based Expression Vectors: Strategies and Applications,* 93(21) Proc. Natl. Acad. Sci. U.S.A. 11371-11377 (1996); Markus U. Ehrengruber, *Alphaviral Gene Transfer in Neurobiology,* 59(1) Brain Res. Bull. 13-22 (2002); Thomas A. Kost & J. Patrick Condreay, *Recombinant Baculoviruses as Mammalian Cell Gene-Delivery Vectors,* 20(4) Trends Biotechnol. 173-180 (2002); and A. Huser & C. Hofmann, *Baculovirus Vectors: Novel Mammalian Cell Gene-Delivery Vehicles and Their Applications,* 3(1) Am. J. Pharmacogenomics 53-63 (2003).

Adenoviruses, which are non-enveloped, double-stranded DNA viruses, are often selected for mammalian cell transduction because adenoviruses handle relatively large polynucleotide molecules of about 36 kb, are produced at high titer, and can efficiently infect a wide variety of both dividing and non-dividing cells, see, e.g., Wim T. J. M. C. Hermens et al., *Transient Gene Transfer to Neurons and Glia: Analysis of Adenoviral Vector Performance in the CNS and PNS,* 71(1) J. Neurosci. Methods 85-98 (1997); and Hiroyuki Mizuguchi et al., *Approaches for Generating Recombinant Adenovirus Vectors,* 52(3) Adv. Drug Deliv. Rev. 165-176 (2001). Transduction using adenoviral-based system do not support prolonged protein expression because the nucleic acid molecule is carried from an episome in the cell nucleus, rather than being integrated into the host cell chromosome. Adenoviral vector systems and specific protocols for how to use such vectors are disclosed in, e.g., ViraPower™ Adenoviral Expression System (Invitrogen, Inc., Carlsbad, Calif.) and ViraPower™ Adenoviral Expression System Instruction Manual 25-0543 version A, Invitrogen, Inc., (Jul. 15, 2002); and AdEasy™ Adenoviral Vector System (Stratagene, Inc., La Jolla, Calif.) and AdEasy™ Adenoviral Vector System Instruction Manual 064004f, Stratagene, Inc.

Polynucleotide molecule delivery can also use single-stranded RNA retroviruses, such as, e.g., oncoretroviruses and lentiviruses. Retroviral-mediated transduction often produce transduction efficiencies close to 100%, can easily control the proviral copy number by varying the multiplicity of infection (MOI), and can be used to either transiently or stably transduce cells, see, e.g., Tiziana Tonini et al., *Transient Production Of Retroviral- and Lentiviral-Based Vectors For the Transduction of Mammalian Cells,* 285 Methods Mol. Biol. 141-148 (2004); Armin Blesch, *Lentiviral and MLV Based Retroviral Vectors for ex vivo and in vivo Gene Transfer,* 33(2) Methods 164-172 (2004); Félix Recillas-Targa, *Gene Transfer and Expression in Mammalian Cell Lines and Transgenic Animals,* 267 Methods Mol. Biol. 417-433 (2004); and Roland Wolkowicz et al., *Lentiviral Vectors for the Delivery of DNA into Mammalian Cells,* 246 Methods Mol. Biol. 391-411 (2004). Retroviral particles consist of an RNA genome packaged in a protein capsid, surrounded by a lipid envelope. The retrovirus infects a host cell by injecting its RNA into the cytoplasm along with the reverse transcriptase enzyme. The RNA template is then reverse transcribed into a linear, double stranded cDNA that replicates itself by integrating into the host cell genome. Viral particles are spread both vertically (from parent cell to daughter cells via the provirus) as well as horizontally (from cell to cell via virions). This replication strategy enables long-term persistent expression since the nucleic acid molecules of interest are stably integrated into a chromosome of the host cell, thereby enabling long-term expression of the protein. For instance, animal studies have shown that lentiviral vectors injected into a variety of tissues produced sustained protein expression for more than 1 year, see, e.g., Luigi Naldini et al., *In vivo Gene Delivery and Stable Transduction of Non-Dividing Cells By a Lentiviral Vector,* 272(5259) Science 263-267 (1996). The Oncoretroviruses-derived vector systems, such as, e.g., Moloney murine leukemia virus (MoMLV), are widely used and infect many different non-dividing cells. Lentiviruses can also infect many different cell types, including dividing and non-dividing cells and possess complex envelope proteins, which allows for highly specific cellular targeting.

Retroviral vectors and specific protocols for how to use such vectors are disclosed in, e.g., U.S. Patent Nos. Manfred Gossen & Hermann Bujard, *Tight Control of Gene Expression in Eukaryotic Cells By Tetracycline-Responsive Promoters,* U.S. Pat. No. 5,464,758 (Nov. 7, 1995) and Hermann Bujard & Manfred Gossen, *Methods for Regulating Gene Expression,* U.S. Pat. No. 5,814,618 (Sep. 29, 1998) David S. Hogness, *Polynucleotides Encoding Insect Steroid Hormone Receptor Polypeptides and Cells Transformed With Same,* U.S. Pat. No. 5,514,578 (May 7, 1996) and David S. Hogness, *Polynucleotide Encoding Insect Ecdysone Receptor,* U.S. Pat. No. 6,245,531 (Jun. 12, 2001); Elisabetta Vegeto et al., *Progesterone Receptor Having C. Terminal Hormone Binding Domain Truncations,* U.S. Pat. No. 5,364,791 (Nov. 15, 1994), Elisabetta Vegeto et al., *Mutated Steroid Hormone Receptors, Methods For Their Use and Molecular Switch For Gene Therapy,* U.S. Pat. No. 5,874,534 (Feb. 23, 1999) and Elisabetta Vegeto et al., *Mutated Steroid Hormone Receptors, Methods For Their Use and Molecular Switch For Gene Therapy,* U.S. Pat. No. 5,935,934 (Aug. 10, 1999). Furthermore, such viral delivery systems can be prepared by standard methods and are commercially available, see, e.g., BD™ Tet-Off and Tet-On Gene Expression Systems (BD Biosciences-Clonetech, Palo Alto, Calif.) and BD™ Tet-Off and Tet-On Gene Expression Systems User Manual, PT3001-1, BD Biosciences Clonetech, (Mar. 14, 2003), GeneSwitch™ System (Invitrogen, Inc., Carlsbad, Calif.) and GeneSwitch™ System A Mifepristone-Regulated Expression System for Mammalian Cells version D, 25-0313, Invitrogen, Inc., (Nov. 4, 2002); ViraPower™ Lentiviral Expression System (Invitrogen, Inc., Carlsbad, Calif.) and ViraPower™ Lentiviral Expression System Instruction Manual 25-0501 version E, Invitrogen, Inc., (Dec. 8, 2003); and Complete Control® Retroviral Inducible Mammalian Expression System (Stratagene, La Jolla, Calif.) and Complete Control® Retroviral Inducible Mammalian Expression System Instruction Manual, 064005e.

The methods disclosed in the present specification include, in part, expressing a modified Clostridial toxin from a polynucleotide molecule. It is envisioned that any of a variety of expression systems may be useful for expressing a modified Clostridial toxin from a polynucleotide molecule disclosed in the present specification, including, without limitation, cell-based systems and cell-free expression systems. Cell-based systems include, without limitation, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and *E. coli* extracts and generally are equivalent to the method disclosed herein. Expression of a polynucleotide molecule using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin, Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heterologous Proteins,* 80(9) Curr. Sci. 1121-1128, (2001). These protocols are routine procedures well within the scope of one skilled in the art and from the teaching herein.

A variety of cell-based expression procedures are useful for expressing a modified Clostridial toxin encoded by polynucleotide molecule disclosed in the present specification. Examples included, without limitation, viral expression systems, prokaryotic expression systems, yeast expression systems, baculoviral expression systems, insect expression systems and mammalian expression systems. Viral expression systems include, without limitation, the ViraPower™ Lentiviral (Invitrogen, Inc., Carlsbad, Calif.), the Adenoviral Expression Systems (Invitrogen, Inc., Carlsbad, Calif.), the AdEasy™ XL Adenoviral Vector System (Stratagene, La Jolla, Calif.) and the VirePort® Retroviral Gene Expression System (Stratagene, La Jolla, Calif.). Non-limiting examples of prokaryotic expression systems include the Champion™ pET Expression System (EMD Biosciences-Novagen, Madison, Wis.), the TriEx™ Bacterial Expression Systems (EMD Biosciences-Novagen, Madison, Wis.), the QIAexpress® Expression System (QIAGEN, Inc.), and the Affinity® Protein Expression and Purification System (Stratagene, La Jolla, Calif.). Yeast expression systems include, without limitation, the EasySelect™ *Pichia* Expression Kit (Invitrogen, Inc., Carlsbad, Calif.), the YES-Echo™ Expression Vector Kits (Invitrogen, Inc., Carlsbad, Calif.) and the SpECTRA™ *S. pombe* Expression System (Invitrogen, Inc., Carlsbad, Calif.). Non-limiting examples of baculoviral expression systems include the BaculoDirect™ (Invitrogen, Inc., Carlsbad, Calif.), the Bac-to-Bac® (Invitrogen, Inc., Carlsbad, Calif.), and the BD BaculoGold™ (BD Biosciences-Pharmigen, San Diego, Calif.). Insect expression systems include, without limitation, the Drosophila Expression System (DES®) (Invitrogen, Inc., Carlsbad, Calif.), InsectSelect™ System (Invitrogen, Inc., Carlsbad, Calif.) and InsectDirect™ System (EMD Biosciences-Novagen, Madison, Wis.). Non-limiting examples of mammalian expression systems include the T-REx™ (Tetracycline-Regulated Expression) System (Invitrogen, Inc., Carlsbad, Calif.), the Flp-In™ T-REx™ System (Invitrogen, Inc., Carlsbad, Calif.), the pcDNA™ system (Invitrogen, Inc., Carlsbad, Calif.), the pSecTag2 system (Invitrogen, Inc., Carlsbad, Calif.), the Exchanger® System, InterPlay™ Mammalian TAP System (Stratagene, La Jolla, Calif.), Complete Control® Inducible Mammalian Expression System (Stratagene, La Jolla, Calif.) and LacSwitch® II Inducible Mammalian Expression System (Stratagene, La Jolla, Calif.).

Another procedure of expressing a modified Clostridial toxin encoded by polynucleotide molecule disclosed in the present specification employs a cell-free expression system such as, without limitation, prokaryotic extracts and eukaryotic extracts. Non-limiting examples of prokaryotic cell extracts include the RTS 100 *E. coli* HY Kit (Roche Applied Science, Indianapolis, Ind.), the ActivePro In Vitro Translation Kit (Ambion, Inc., Austin, Tex.), the EcoPro™ System (EMD Biosciences-Novagen, Madison, Wis.) and the Expressway™ Plus Expression System (Invitrogen, Inc., Carlsbad, Calif.). Eukaryotic cell extract include, without limitation, the RTS 100 Wheat Germ CECF Kit (Roche Applied Science, Indianapolis, Ind.), the TnT® Coupled Wheat Germ Extract Systems (Promega Corp., Madison, Wis.), the Wheat Germ IVT™ Kit (Ambion, Inc., Austin, Tex.), the Retic Lysate IVT™ Kit (Ambion, Inc., Austin, Tex.), the PROTEINscript® II System (Ambion, Inc., Austin, Tex.) and the TnT® Coupled Reticulocyte Lysate Systems (Promega Corp., Madison, Wis.).

Another aspect of the present invention provides a method of activating a modified Clostridial toxin comprising an exogenous Clostridial toxin di-chain loop region including a Clostridial toxin di-chain loop protease cleavage site from a different Clostridial toxin, such method comprising the step of incubating the modified Clostridial toxin with a Clostridial toxin di-chain loop protease under physiological conditions, wherein the Clostridial toxin di-chain loop protease is capable of cleaving the Clostridial toxin di-chain loop protease cleavage site present in the exogenous Clostridial toxin di-chain loop region and wherein cleavage of the modified Clostridial toxin by the Clostridial toxin di-chain loop protease converts the modified Clostridial toxin from its single-chain polypeptide form into its di-chain form, thereby activating the modified Clostridial toxin.

Another aspect of the present invention provides a method of activating a recombinantly-expressed Clostridial toxin, such method comprising the step of incubating the Clostridial toxin with a Clostridial toxin di-chain loop protease under physiological conditions, wherein the Clostridial toxin di-chain loop protease is capable of cleaving the Clostridial toxin di-chain loop protease cleavage site present in the Clostridial toxin di-chain loop region and wherein cleavage of the Clostridial toxin by the Clostridial toxin di-chain loop protease converts the Clostridial toxin from its single-chain polypeptide form into its di-chain form, thereby activating the recombinantly-expressed Clostridial toxin.

Aspects of the present invention provide, in part, a Clostridial toxin di-chain loop protease. As used herein, the term "Clostridial toxin di-chain loop protease" means any protease capable of selectively cleaving the $P_1$-$P_{1'}$ scissile bond comprising the di-chain loop protease cleavage site. As used herein, the term "selectively" means having a highly preferred activity or effect. Thus, with reference to a Clostridial toxin di-chain loop protease, there is a discriminatory proteolytic cleavage of the $P_1$-$P_{1'}$ scissile bond comprising the di-chain loop protease cleavage site. It is envisioned that any and all proteases capable of selectively cleaving the $P_1$-$P_{1'}$ scissile bond comprising the di-chain loop protease cleavage site can be useful in the disclosed methods, including, without exception, a sulfhydryl proteinase. One example of a sulfhydryl proteinase is clostripain, also known as clostridiopeptidase B, endoproteinase-Arg-C, or γ-protease. See, e.g., William M. Mitchell & William F. Harrington, Purification and Properties of *Clostridiopeptidase B (Clostripain)*, 243(18) J. Biol. Chem. 4683-4692. (1968); William M. Mitchell & William F. Harrington, *Clostripain*, 19 Methods Enzymol. 635-642 (1970); and Ashu A. Kembhavi, et al., *Clostripain: Characterization of the Active Site*, 283(2) FEBS Lett. 277-280 (1991), each of which is hereby incorporated by reference in its entirety. This two chain cysteine proteinase is highly specific for the carboxyl peptide bond of arginine. Non-limiting examples of clostripain include SEQ ID NO: 33, SEQ ID NO; 34, SEQ ID NO: 35, SEQ ID NO: 36, SEQ ID NO: 37 and SEQ ID NO: 38. Clostripain selectively hydrolysis of arginyl bonds, although lysyl bonds are cleaved at a lower rate.

A clostripain useful in aspects of the invention includes, without limitation, naturally occurring clostripain; naturally occurring clostripain variants; and non-naturally-occurring clostripain variants, such as, e.g., conservative clostripain variants, non-conservative clostripain variants and clostripain peptidomimetics. As used herein, the term "clostripain variant," whether naturally-occurring or non-naturally-occurring, means a clostripain that has at least one amino acid change from the corresponding region of the disclosed reference sequences and can be described in percent identity to the corresponding region of that reference sequence. Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

As used herein, the term "naturally occurring clostripain variant" means any clostripain produced without the aid of any human manipulation, including, without limitation, clostripain isoforms produced from alternatively-spliced transcripts, clostripain isoforms produced by spontaneous mutation and clostripain subtypes. Non-limiting examples of a clostripain isoform include, e.g., BoNT/A di-chain loop region isoforms, BoNT/B di-chain loop region isoforms, BoNT/C1 di-chain loop region isoforms, BoNT/D di-chain loop region isoforms, BoNT/E di-chain loop region isoforms, BoNT/F di-chain loop region isoforms, BoNT/G di-chain loop region isoforms, TeNT di-chain loop region isoforms, BaNT di-chain loop region isoforms, and BuNT di-chain loop region isoforms. Non-limiting examples of a Clostridial toxin subtype include, e.g., BoNT/A di-chain loop region subtypes such as, e.g., a BoNT/A1 di-chain loop region, a BoNT/A2 di-chain loop region, a BoNT/A3 di-chain loop region and a BoNT/A4 di-chain loop region; BoNT/B di-chain loop region subtypes, such as, e.g., a BoNT/B1 di-chain loop region, a BoNT/B2 di-chain loop region, a BoNT/B bivalent di-chain loop region and a BoNT/B nonproteolytic di-chain loop region; BoNT/C1 di-chain loop region subtypes, such as, e.g., a BoNT/C1-1 di-chain loop region and a BoNT/C1-2 di-chain loop region; BoNT/E di-chain loop region subtypes, such as, e.g., a BoNT/E1 di-chain loop region, a BoNT/E2 di-chain loop region and a BoNT/E3 di-chain loop region; and BoNT/F di-chain loop region subtypes, such as, e.g., a BoNT/F1 di-chain loop region, a BoNT/F2 di-chain loop region, a BoNT/F3 di-chain loop region and a BoNT/F4 di-chain loop region.

As used herein, the term "non-naturally occurring clostripain variant" means any clostripain produced with the aid of human manipulation, including, without limitation, clostripain variants produced by genetic engineering using random mutagenesis or rational design and clostripain variants produced by chemical synthesis. Non-limiting examples of non-naturally occurring clostripain variants include, e.g., conservative clostripain variants, non-conservative clostripain variants and clostripain peptidomimetics.

As used herein, the term "conservative clostripain variant" means a clostripain that has at least one amino acid substituted by another amino acid or an amino acid analog that has at least one property similar to that of the original amino acid from the reference clostripain sequence. Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative clostripain variant can function in substantially the same manner as the reference clostripain on which the conservative clostripain variant is based, and can be substituted for the reference clostripain in any aspect of the present invention. A conservative clostripain variant may substitute one or more amino acids, two or more amino acids, three or more amino acids, four or more amino acids or five or more amino acids from the reference clostripain on which the conservative clostripain variant is based. A conservative clostripain variant can also possess at least 50% amino acid identity, 65% amino acid identity, 75% amino acid identity, 85% amino acid identity or 95% amino acid identity to the reference clostripain on which the conservative clostripain variant is based. Non-limiting examples of a conservative clostripain variant include, e.g., conservative clostripain variants of SEQ ID NO: 33, conservative clostripain variants of SEQ ID NO: 34, conservative clostripain variants of SEQ ID NO: 35, conservative clostripain variants of SEQ ID NO: 36, conservative clostripain variants of SEQ ID NO: 37, and conservative clostripain variants of SEQ ID NO: 38.

As used herein, the term "non-conservative clostripain variant" means a clostripain in which 1) at least one amino acid is deleted from the reference clostripain on which the non-conservative clostripain variant is based; 2) at least one amino acid added to the reference clostripain on which the non-conservative clostripain is based; or 3) at least one amino acid is substituted by another amino acid or an amino acid analog that does not share any property similar to that of the original amino acid from the reference clostripain sequence. A non-conservative clostripain variant can function in substantially the same manner as the reference clostripain on which the non-conservative clostripain is based, and can be substituted for the reference clostripain in any aspect of the present invention. A non-conservative clostripain variant can add one or more amino acids, two or more amino acids, three or more amino acids, four or more amino acids, five or more amino acids, and ten or more amino acids to the reference clostripain on which the non-conservative clostripain variant is based. A non-conservative clostripain may substitute one or more amino acids, two or more amino acids, three or more amino acids, four or more amino acids or five or more amino acids from the reference clostripain on which the non-conservative clostripain variant is based. A non-conservative clostripain variant can also possess at least 50% amino acid identity, 65% amino acid identity, 75% amino acid identity, 85% amino acid identity or 95% amino acid identity to the reference clostripain on which the non-conservative clostripain variant is based. Non-limiting examples of a non-conservative clostripain variant include, e.g., non-conservative clostripain variants of SEQ ID NO: 33, non-conservative clostripain variants of SEQ ID NO: 34, non-conservative clostripain variants of SEQ ID NO: 35, non-conservative clostripain variants of SEQ ID NO: 36, non-conservative clostripain variants of SEQ ID NO: 37, and non-conservative clostripain variants of SEQ ID NO: 38.

As used herein, the term "clostripain peptidomimetic" means a clostripain that has at least one amino acid substituted by a non-natural oligomer that has at least one property similar to that of the first amino acid. Examples of properties include, without limitation, topography of a peptide primary structural element, functionality of a peptide primary structural element, topology of a peptide secondary structural element, functionality of a peptide secondary structural element, of the like, or any combination thereof. A clostripain peptidomimetic can function in substantially the same manner as the reference clostripain on which the clostripain peptidomimetic is based, and can be substituted for the reference clostripain in any aspect of the present invention. A clostripain peptidomimetic may substitute one or more amino acids, two or more amino acids, three or more amino acids, four or more amino acids or five or more amino acids from the reference clostripain on which the clostripain peptidomimetic is based. A clostripain peptidomimetic can also possess at least 50% amino acid identity, at least 65% amino acid identity, at least 75% amino acid identity, at least 85% amino acid identity or at least 95% amino acid identity to the reference clostripain on which the clostripain peptidomimetic is based. For examples of peptidomimetic methods see, e.g., Amy S. Ripka & Daniel H. Rich, Peptidomimetic design, 2(4) CURR. OPIN. CHEM. BIOL. 441-452 (1998); and M. Angels Estiarte & Daniel H. Rich, *Peptidomimetics for Drug Design*, 803-861 (BURGER'S MEDICINAL CHEMISTRY AND DRUG DISCOVERY Vol. 1 PRINCIPLE AND PRACTICE, Donald J. Abraham ed., Wiley-Interscience, $6^{th}$ ed 2003). Non-limiting examples of a clostripain peptidomimetic include, e.g., clostripain peptidomimetics of SEQ ID NO: 33, clostripain peptidomimetics of SEQ ID NO: 34, clostripain peptidomimetics of SEQ ID NO: 35, clostripain peptidomimetics of SEQ ID NO: 36, clostripain peptidomimetics of SEQ ID NO: 37, and clostripain peptidomimetics of SEQ ID NO: 38.

Thus, in an embodiment, a Clostridial toxin di-chain loop protease comprises a clostripain. In an aspect of this embodiment, a clostripain can be a naturally occurring clostripain, such as, e.g., a clostripain isoform or a clostripain subtype. In another aspect of this embodiment, a clostripain can be a non-naturally occurring clostripain variant, such as, e.g., a conservative clostripain variant, a non-conservative clostripain variant or an active clostripain fragment, or any combination thereof.

In another embodiment, a clostripain comprises a naturally occurring clostripain variant of SEQ ID NO: 33, such as, e.g., a clostripain isoform of SEQ ID NO: 33 or a clostripain subtype of SEQ ID NO: 33. In still another aspect of this embodiment, a clostripain comprises a non-naturally occurring clostripain variant of SEQ ID NO: 33, such as, e.g., a conservative clostripain variant of SEQ ID NO: 33, a non-conservative clostripain variant of SEQ ID NO: 33 or an active clostripain fragment of SEQ ID NO: 33, or any combination thereof. In yet another embodiment, a clostripain comprises a clostripain of SEQ ID NO: 33.

In other aspects of this embodiment, a clostripain comprises a polypeptide having, e.g., at least 70% amino acid identity with SEQ ID NO: 33, at least 75% amino acid identity with SEQ ID NO: 33, at least 80% amino acid identity with SEQ ID NO: 33, at least 85% amino acid identity with SEQ ID NO: 33, at least 90% amino acid identity with SEQ ID NO: 33 or at least 95% amino acid identity with SEQ ID NO: 33. In yet other aspects of this embodiment, a clostripain comprises a polypeptide having, e.g., at most 70% amino acid identity with SEQ ID NO: 33, at most 75% amino acid identity with SEQ ID NO: 33, at most 80% amino acid identity with SEQ ID NO: 33, at most 85% amino acid identity with SEQ ID NO: 33, at most 90% amino acid identity with SEQ ID NO: 33 or at most 95% amino acid identity with SEQ ID NO: 33.

In other aspects of this embodiment, a clostripain comprises a polypeptide having, e.g., at most one, two, three, four, five, six, seven, eight, nine, 10, 20, 30, 40, 50, or 100 non-contiguous amino acid substitutions relative to SEQ ID NO: 33. In other aspects of this embodiment, a clostripain comprises a polypeptide having, e.g., at least one, two, three, four, five, six, seven, eight, nine, 10, 20, 30, 40, 50, or 100 non-contiguous amino acid substitutions relative to SEQ ID NO: 33. In yet other aspects of this embodiment, a clostripain comprises a polypeptide having, e.g., at most one, two, three, four, five, six, seven, eight, nine, 10, 20, 30, 40, 50, or 100 non-contiguous amino acid deletions relative to SEQ ID NO: 33. In other aspects of this embodiment, a clostripain comprises a polypeptide having, e.g., at least one, two, three, four, five, six, seven, eight, nine, 10, 20, 30, 40, 50, or 100 non-contiguous amino acid deletions relative to SEQ ID NO: 33. In still other aspects of this embodiment, a clostripain comprises a polypeptide having, e.g., at most one, two, three, four, five, six, seven, eight, nine, 10, 20, 30, 40, 50, or 100 non-contiguous amino acid additions relative to SEQ ID NO: 33. In other aspects of this embodiment, a clostripain comprises a polypeptide having, e.g., at least one, two, three, four, five, six, seven, eight, nine, 10, 20, 30, 40, 50, or 100 non-contiguous amino acid additions relative to SEQ ID NO: 33.

In other aspects of this embodiment, a clostripain comprises a polypeptide having, e.g., at most one, two, three, four, five, six, seven, eight, nine, 10, 20, 30, 40, 50, or 100 contiguous amino acid substitutions relative to SEQ ID NO: 33. In other aspects of this embodiment, a clostripain comprises a polypeptide having, e.g., at least one, two, three, four, five, six, seven, eight, nine, 10, 20, 30, 40, 50, or 100 contiguous amino acid substitutions relative to SEQ ID NO: 33. In yet other aspects of this embodiment, a clostripain comprises a polypeptide having, e.g., at most one, two, three, four, five, six, seven, eight, nine, 10, 20, 30, 40, 50, or 100 contiguous amino acid deletions relative to SEQ ID NO: 33. In other aspects of this embodiment, a clostripain comprises a polypeptide having, e.g., at least one, two, three, four, five, six, seven, eight, nine, 10, 20, 30, 40, 50, or 100 contiguous amino acid deletions relative to SEQ ID NO: 33. In still other aspects of this embodiment, a clostripain comprises a polypeptide having, e.g., at most one, two, three, four, five, six, seven, eight, nine, 10, 20, 30, 40, 50, or 100 contiguous amino acid additions relative to SEQ ID NO: 33. In other aspects of this embodiment, a clostripain comprises a polypeptide having, e.g., at least one, two, three, four, five, six, seven, eight, nine, 10, 20, 30, 40, 50, or 100 contiguous amino acid additions relative to SEQ ID NO: 33.

In another embodiment, a clostripain comprises a naturally occurring clostripain variant of SEQ ID NO: 34, such as, e.g., a clostripain isoform of SEQ ID NO: 34 or a clostripain subtype of SEQ ID NO: 34. In still another aspect of this embodiment, a clostripain comprises a non-naturally occurring clostripain variant of SEQ ID NO: 34, such as, e.g., a conservative clostripain variant of SEQ ID NO: 34, a non-conservative clostripain variant of SEQ ID NO: 34 or an active clostripain fragment of SEQ ID NO: 34, or any combination thereof. In yet another embodiment, a clostripain comprises a clostripain of SEQ ID NO: 34.

In other aspects of this embodiment, a clostripain comprises a polypeptide having, e.g., at least 70% amino acid identity with SEQ ID NO: 34, at least 75% amino acid identity with SEQ ID NO: 34, at least 80% amino acid identity with SEQ ID NO: 34, at least 85% amino acid identity with SEQ ID NO: 34, at least 90% amino acid identity with SEQ ID NO: 34 or at least 95% amino acid identity with SEQ ID NO: 34. In yet other aspects of this embodiment, a clostripain comprises a polypeptide having, e.g., at most 70% amino acid identity with SEQ ID NO: 34, at most 75% amino acid identity with SEQ ID NO: 34, at most 80% amino acid identity with SEQ ID NO: 34, at most 85% amino acid identity with SEQ ID NO: 34, at most 90% amino acid identity with SEQ ID NO: 34 or at most 95% amino acid identity with SEQ ID NO: 34.

In other aspects of this embodiment, a clostripain comprises a polypeptide having, e.g., at most one, two, three, four, five, six, seven, eight, nine, 10, 20, 30, 40, 50, or 100 non-contiguous amino acid substitutions relative to SEQ ID NO: 34. In other aspects of this embodiment, a clostripain comprises a polypeptide having, e.g., at least one, two, three, four, five, six, seven, eight, nine, 10, 20, 30, 40, 50, or 100 non-contiguous amino acid substitutions relative to SEQ ID NO: 34. In yet other aspects of this embodiment, a clostripain comprises a polypeptide having, e.g., at most one, two, three, four, five, six, seven, eight, nine, 10, 20, 30, 40, 50, or 100 non-contiguous amino acid deletions relative to SEQ ID NO: 34. In other aspects of this embodiment, a clostripain comprises a polypeptide having, e.g., at least one, two, three, four, five, six, seven, eight, nine, 10, 20, 30, 40, 50, or 100 non-contiguous amino acid deletions relative to SEQ ID NO: 34. In still other aspects of this embodiment, a clostripain comprises a polypeptide having, e.g., at most one, two, three, four, five, six, seven, eight, nine, 10, 20, 30, 40, 50, or 100 non-contiguous amino acid additions relative to SEQ ID NO: 34. In other aspects of this embodiment, a clostripain comprises a polypeptide having, e.g., at least one, two, three, four, five, six, seven, eight, nine, 10, 20, 30, 40, 50, or 100 non-contiguous amino acid additions relative to SEQ ID NO: 34.

In other aspects of this embodiment, a clostripain comprises a polypeptide having, e.g., at most one, two, three, four, five, six, seven, eight, nine, 10, 20, 30, 40, 50, or 100 contiguous amino acid substitutions relative to SEQ ID NO: 34. In other aspects of this embodiment, a clostripain comprises a polypeptide having, e.g., at least one, two, three, four, five, six, seven, eight, nine, 10, 20, 30, 40, 50, or 100 contiguous amino acid substitutions relative to SEQ ID NO: 34. In yet other aspects of this embodiment, a clostripain comprises a polypeptide having, e.g., at most one, two, three, four, five, six, seven, eight, nine, 10, 20, 30, 40, 50, or 100 contiguous amino acid deletions relative to SEQ ID NO: 34. In other aspects of this embodiment, a clostripain comprises a polypeptide having, e.g., at least one, two, three, four, five, six, seven, eight, nine, 10, 20, 30, 40, 50, or 100 contiguous amino acid deletions relative to SEQ ID NO: 34. In still other aspects of this embodiment, a clostripain comprises a polypeptide having, e.g., at most one, two, three, four, five, six, seven, eight, nine, 10, 20, 30, 40, 50, or 100 contiguous amino acid additions relative to SEQ ID NO: 34. In other aspects of this embodiment, a clostripain comprises a polypeptide having, e.g., at least one, two, three, four, five, six, seven, eight, nine, 10, 20, 30, 40, 50, or 100 contiguous amino acid additions relative to SEQ ID NO: 34.

In another embodiment, a clostripain comprises a naturally occurring clostripain variant of SEQ ID NO: 35, such as, e.g., a clostripain isoform of SEQ ID NO: 35 or a clostripain subtype of SEQ ID NO: 35. In still another aspect of this embodiment, a clostripain comprises a non-naturally occurring clostripain variant of SEQ ID NO: 35, such as, e.g., a conservative clostripain variant of SEQ ID NO: 35, a non-conservative clostripain variant of SEQ ID NO: 35 or an active clostripain fragment of SEQ ID NO: 35, or any combination thereof. In yet another embodiment, a clostripain comprises a clostripain of SEQ ID NO: 35.

In other aspects of this embodiment, a clostripain comprises a polypeptide having, e.g., at least 70% amino acid identity with SEQ ID NO: 35, at least 75% amino acid identity with SEQ ID NO: 35, at least 80% amino acid identity with SEQ ID NO: 35, at least 85% amino acid identity with SEQ ID NO: 35, at least 90% amino acid identity with SEQ ID NO: 35 or at least 95% amino acid identity with SEQ ID NO: 35. In yet other aspects of this embodiment, a clostripain comprises a polypeptide having, e.g., at most 70% amino acid identity with SEQ ID NO: 35, at most 75% amino acid identity with SEQ ID NO: 35, at most 80% amino acid identity with SEQ ID NO: 35, at most 85% amino acid identity with SEQ ID NO: 35, at most 90% amino acid identity with SEQ ID NO: 35 or at most 95% amino acid identity with SEQ ID NO: 35.

In other aspects of this embodiment, a clostripain comprises a polypeptide having, e.g., at most one, two, three, four, five, six, seven, eight, nine, 10, 20, 30, 40, 50, or 100 non-contiguous amino acid substitutions relative to SEQ ID NO: 35. In other aspects of this embodiment, a clostripain comprises a polypeptide having, e.g., at least one, two, three, four, five, six, seven, eight, nine, 10, 20, 30, 40, 50, or 100 non-contiguous amino acid substitutions relative to SEQ ID NO: 35. In yet other aspects of this embodiment, a clostripain comprises a polypeptide having, e.g., at most one, two, three, four, five, six, seven, eight, nine, 10, 20, 30, 40, 50, or 100 non-contiguous amino acid deletions relative to SEQ ID NO: 35. In other aspects of this embodiment, a clostripain comprises a polypeptide having, e.g., at least one, two, three, four, five, six, seven, eight, nine, 10, 20, 30, 40, 50, or 100 non-contiguous amino acid deletions relative to SEQ ID NO: 35. In still other aspects of this embodiment, a clostripain comprises a polypeptide having, e.g., at most one, two, three, four, five, six, seven, eight, nine, 10, 20, 30, 40, 50, or 100 non-contiguous amino acid additions relative to SEQ ID NO: 35. In other aspects of this embodiment, a clostripain comprises a polypeptide having, e.g., at least one, two, three, four, five, six, seven, eight, nine, 10, 20, 30, 40, 50, or 100 non-contiguous amino acid additions relative to SEQ ID NO: 35.

In other aspects of this embodiment, a clostripain comprises a polypeptide having, e.g., at most one, two, three, four, five, six, seven, eight, nine, 10, 20, 30, 40, 50, or 100 contiguous amino acid substitutions relative to SEQ ID NO: 35. In other aspects of this embodiment, a clostripain comprises a polypeptide having, e.g., at least one, two, three, four, five, six, seven, eight, nine, 10, 20, 30, 40, 50, or 100 contiguous amino acid substitutions relative to SEQ ID NO: 35. In yet other aspects of this embodiment, a clostripain comprises a polypeptide having, e.g., at most one, two, three, four, five, six, seven, eight, nine, 10, 20, 30, 40, 50, or 100 contiguous amino acid deletions relative to SEQ ID NO: 35. In other aspects of this embodiment, a clostripain comprises a polypeptide having, e.g., at least one, two, three, four, five, six, seven, eight, nine, 10, 20, 30, 40, 50, or 100 contiguous amino acid deletions relative to SEQ ID NO: 35. In still other aspects of this embodiment, a clostripain comprises a polypeptide having, e.g., at most one, two, three, four, five, six, seven, eight, nine, 10, 20, 30, 40, 50, or 100 contiguous amino acid additions relative to SEQ ID NO: 35. In other aspects of this embodiment, a clostripain comprises a polypeptide having, e.g., at least one, two, three, four, five, six, seven, eight, nine, 10, 20, 30, 40, 50, or 100 contiguous amino acid additions relative to SEQ ID NO: 35.

In another embodiment, a clostripain comprises a naturally occurring clostripain variant of SEQ ID NO: 36, such as, e.g., a clostripain isoform of SEQ ID NO: 36 or a clostripain subtype of SEQ ID NO: 36. In still another aspect of this embodiment, a clostripain comprises a non-naturally occurring clostripain variant of SEQ ID NO: 36, such as, e.g., a conservative clostripain variant of SEQ ID NO: 36, a non-conservative clostripain variant of SEQ ID NO: 36 or an active clostripain fragment of SEQ ID NO: 36, or any combination thereof. In yet another embodiment, a clostripain comprises a clostripain of SEQ ID NO: 36.

In other aspects of this embodiment, a clostripain comprises a polypeptide having, e.g., at least 70% amino acid identity with SEQ ID NO: 36, at least 75% amino acid identity with SEQ ID NO: 36, at least 80% amino acid identity with SEQ ID NO: 36, at least 85% amino acid identity with SEQ ID NO: 36, at least 90% amino acid identity with SEQ ID NO: 36 or at least 95% amino acid identity with SEQ ID NO: 36. In yet other aspects of this embodiment, a clostripain comprises a polypeptide having, e.g., at most 70% amino acid identity with SEQ ID NO: 36, at most 75% amino acid identity with SEQ ID NO: 36, at most 80% amino acid identity with SEQ ID NO: 36, at most 85% amino acid identity with SEQ ID NO: 36, at most 90% amino acid identity with SEQ ID NO: 36 or at most 95% amino acid identity with SEQ ID NO: 36.

In other aspects of this embodiment, a clostripain comprises a polypeptide having, e.g., at most one, two, three, four, five, six, seven, eight, nine, 10, 20, 30, 40, 50, or 100 non-contiguous amino acid substitutions relative to SEQ ID NO: 36. In other aspects of this embodiment, a clostripain comprises a polypeptide having, e.g., at least one, two, three, four, five, six, seven, eight, nine, 10, 20, 30, 40, 50, or 100 non-contiguous amino acid substitutions relative to SEQ ID NO: 36. In yet other aspects of this embodiment, a clostripain comprises a polypeptide having, e.g., at most one, two, three, four, five, six, seven, eight, nine, 10, 20, 30, 40, 50, or 100 non-contiguous amino acid deletions relative to SEQ ID NO: 36. In other aspects of this embodiment, a clostripain comprises a polypeptide having, e.g., at least one, two, three, four, five, six, seven, eight, nine, 10, 20, 30, 40, 50, or 100 non-contiguous amino acid deletions relative to SEQ ID NO: 36. In still other aspects of this embodiment, a clostripain comprises a polypeptide having, e.g., at most one, two, three, four, five, six, seven, eight, nine, 10, 20, 30, 40, 50, or 100 non-contiguous amino acid additions relative to SEQ ID NO: 36. In other aspects of this embodiment, a clostripain comprises a polypeptide having, e.g., at least one, two, three, four, five, six, seven, eight, nine, 10, 20, 30, 40, 50, or 100 non-contiguous amino acid additions relative to SEQ ID NO: 36.

In other aspects of this embodiment, a clostripain comprises a polypeptide having, e.g., at most one, two, three, four, five, six, seven, eight, nine, 10, 20, 30, 40, 50, or 100 contiguous amino acid substitutions relative to SEQ ID NO: 36. In other aspects of this embodiment, a clostripain comprises a polypeptide having, e.g., at least one, two, three, four, five, six, seven, eight, nine, 10, 20, 30, 40, 50, or 100 contiguous amino acid substitutions relative to SEQ ID NO: 36. In yet other aspects of this embodiment, a clostripain comprises a polypeptide having, e.g., at most one, two, three, four, five, six, seven, eight, nine, 10, 20, 30, 40, 50, or 100 contiguous amino acid deletions relative to SEQ ID NO: 36. In other aspects of this embodiment, a clostripain comprises a polypeptide having, e.g., at least one, two, three, four, five, six, seven, eight, nine, 10, 20, 30, 40, 50, or 100 contiguous amino acid deletions relative to SEQ ID NO: 36. In still other aspects of this embodiment, a clostripain comprises a polypeptide having, e.g., at most one, two, three, four, five, six, seven, eight, nine, 10, 20, 30, 40, 50, or 100 contiguous amino acid additions relative to SEQ ID NO: 36. In other aspects of this embodiment, a clostripain comprises a polypeptide having, e.g., at least one, two, three, four, five, six, seven, eight, nine, 10, 20, 30, 40, 50, or 100 contiguous amino acid additions relative to SEQ ID NO: 36.

In another embodiment, a clostripain comprises a naturally occurring clostripain variant of SEQ ID NO: 37, such as, e.g., a clostripain isoform of SEQ ID NO: 37 or a clostripain subtype of SEQ ID NO: 37. In still another aspect of this embodiment, a clostripain comprises a non-naturally occurring clostripain variant of SEQ ID NO: 37, such as, e.g., a conservative clostripain variant of SEQ ID NO: 37, a non-conservative clostripain variant of SEQ ID NO: 37 or an active clostripain fragment of SEQ ID NO: 37, or any combination thereof. In yet another embodiment, a clostripain comprises a clostripain of SEQ ID NO: 37.

In other aspects of this embodiment, a clostripain comprises a polypeptide having, e.g., at least 70% amino acid identity with SEQ ID NO: 37, at least 75% amino acid identity with SEQ ID NO: 37, at least 80% amino acid identity with SEQ ID NO: 37, at least 85% amino acid identity with SEQ ID NO: 37, at least 90% amino acid identity with SEQ ID NO: 37 or at least 95% amino acid identity with SEQ ID NO: 37. In yet other aspects of this embodiment, a clostripain comprises a polypeptide having, e.g., at most 70% amino acid identity with SEQ ID NO: 37, at most 75% amino acid identity with SEQ ID NO: 37, at most 80% amino acid identity with SEQ ID NO: 37, at most 85% amino acid identity with SEQ ID NO: 37, at most 90% amino acid identity with SEQ ID NO: 37 or at most 95% amino acid identity with SEQ ID NO: 37.

In other aspects of this embodiment, a clostripain comprises a polypeptide having, e.g., at most one, two, three, four, five, six, seven, eight, nine, 10, 20, 30, 40, 50, or 100 non-contiguous amino acid substitutions relative to SEQ ID NO: 37. In other aspects of this embodiment, a clostripain comprises a polypeptide having, e.g., at least one, two, three, four, five, six, seven, eight, nine, 10, 20, 30, 40, 50, or 100 non-contiguous amino acid substitutions relative to SEQ ID NO: 37. In yet other aspects of this embodiment, a clostripain comprises a polypeptide having, e.g., at most one, two, three, four, five, six, seven, eight, nine, 10, 20, 30, 40, 50, or 100 non-contiguous amino acid deletions relative to SEQ ID NO: 37. In other aspects of this embodiment, a clostripain comprises a polypeptide having, e.g., at least one, two, three, four, five, six, seven, eight, nine, 10, 20, 30, 40, 50, or 100 non-contiguous amino acid deletions relative to SEQ ID NO: 37. In still other aspects of this embodiment, a clostripain comprises a polypeptide having, e.g., at most one, two, three, four, five, six, seven, eight, nine, 10, 20, 30, 40, 50, or 100 non-contiguous amino acid additions relative to SEQ ID NO: 37. In other aspects of this embodiment, a clostripain comprises a polypeptide having, e.g., at least one, two, three, four, five, six, seven, eight, nine, 10, 20, 30, 40, 50, or 100 non-contiguous amino acid additions relative to SEQ ID NO: 37.

In other aspects of this embodiment, a clostripain comprises a polypeptide having, e.g., at most one, two, three, four, five, six, seven, eight, nine, 10, 20, 30, 40, 50, or 100 contiguous amino acid substitutions relative to SEQ ID NO: 37. In other aspects of this embodiment, a clostripain comprises a polypeptide having, e.g., at least one, two, three, four, five, six, seven, eight, nine, 10, 20, 30, 40, 50, or 100 contiguous amino acid substitutions relative to SEQ ID NO: 37. In yet other aspects of this embodiment, a clostripain comprises a polypeptide having, e.g., at most one, two, three, four, five, six, seven, eight, nine, 10, 20, 30, 40, 50, or 100 contiguous amino acid deletions relative to SEQ ID NO: 37. In other aspects of this embodiment, a clostripain comprises a polypeptide having, e.g., at least one, two, three, four, five, six, seven, eight, nine, 10, 20, 30, 40, 50, or 100 contiguous amino acid deletions relative to SEQ ID NO: 37. In still other aspects of this embodiment, a clostripain comprises a polypeptide having, e.g., at most one, two, three, four, five, six, seven, eight, nine, 10, 20, 30, 40, 50, or 100 contiguous amino acid additions relative to SEQ ID NO: 37. In other aspects of this embodiment, a clostripain comprises a polypeptide having, e.g., at least one, two, three, four, five, six, seven, eight, nine, 10, 20, 30, 40, 50, or 100 contiguous amino acid additions relative to SEQ ID NO: 37.

In another embodiment, a clostripain comprises a naturally occurring clostripain variant of SEQ ID NO: 38, such as, e.g., a clostripain isoform of SEQ ID NO: 38 or a clostripain subtype of SEQ ID NO: 38. In still another aspect of this embodiment, a clostripain comprises a non-naturally occurring clostripain variant of SEQ ID NO: 38, such as, e.g., a conservative clostripain variant of SEQ ID NO: 38, a non-conservative clostripain variant of SEQ ID NO: 38 or an active clostripain fragment of SEQ ID NO: 38, or any combination thereof. In yet another embodiment, a clostripain comprises a clostripain of SEQ ID NO: 38.

In other aspects of this embodiment, a clostripain comprises a polypeptide having, e.g., at least 70% amino acid identity with SEQ ID NO: 38, at least 75% amino acid identity with SEQ ID NO: 38, at least 80% amino acid identity with SEQ ID NO: 38, at least 85% amino acid identity with SEQ ID NO: 38, at least 90% amino acid identity with SEQ ID NO: 38 or at least 95% amino acid identity with SEQ ID NO: 38. In yet other aspects of this embodiment, a clostripain comprises a polypeptide having, e.g., at most 70% amino acid identity with SEQ ID NO: 38, at most 75% amino acid identity with SEQ ID NO: 38, at most 80% amino acid identity with SEQ ID NO: 38, at most 85% amino acid identity with SEQ ID NO: 38, at most 90% amino acid identity with SEQ ID NO: 38 or at most 95% amino acid identity with SEQ ID NO: 38.

In other aspects of this embodiment, a clostripain comprises a polypeptide having, e.g., at most one, two, three, four, five, six, seven, eight, nine, 10, 20, 30, 40, 50, or 100 non-contiguous amino acid substitutions relative to SEQ ID NO: 38. In other aspects of this embodiment, a clostripain comprises a polypeptide having, e.g., at least one, two, three, four, five, six, seven, eight, nine, 10, 20, 30, 40, 50, or 100 non-contiguous amino acid substitutions relative to SEQ ID NO: 38. In yet other aspects of this embodiment, a clostripain comprises a polypeptide having, e.g., at most one, two, three, four, five, six, seven, eight, nine, 10, 20, 30, 40, 50, or 100 non-contiguous amino acid deletions relative to SEQ ID NO: 38. In other aspects of this embodiment, a clostripain comprises a polypeptide having, e.g., at least one, two, three, four, five, six, seven, eight, nine, 10, 20, 30, 40, 50, or 100 non-contiguous amino acid deletions relative to SEQ ID NO: 38. In still other aspects of this embodiment, a clostripain comprises a polypeptide having, e.g., at most one, two, three, four, five, six, seven, eight, nine, 10, 20, 30, 40, 50, or 100 non-contiguous amino acid additions relative to SEQ ID NO: 38. In other aspects of this embodiment, a clostripain comprises a polypeptide having, e.g., at least one, two, three, four, five, six, seven, eight, nine, 10, 20, 30, 40, 50, or 100 non-contiguous amino acid additions relative to SEQ ID NO: 38.

In other aspects of this embodiment, a clostripain comprises a polypeptide having, e.g., at most one, two, three, four, five, six, seven, eight, nine, 10, 20, 30, 40, 50, or 100 contiguous amino acid substitutions relative to SEQ ID NO: 38. In other aspects of this embodiment, a clostripain comprises a polypeptide having, e.g., at least one, two, three, four, five, six, seven, eight, nine, 10, 20, 30, 40, 50, or 100 contiguous amino acid substitutions relative to SEQ ID NO: 38. In yet other aspects of this embodiment, a clostripain comprises a polypeptide having, e.g., at most one, two, three, four, five, six, seven, eight, nine, 10, 20, 30, 40, 50, or 100 contiguous amino acid deletions relative to SEQ ID NO: 38. In other aspects of this embodiment, a clostripain comprises a polypeptide having, e.g., at least one, two, three, four, five, six, seven, eight, nine, 10, 20, 30, 40, 50, or 100 contiguous amino acid deletions relative to SEQ ID NO: 38. In still other aspects of this embodiment, a clostripain comprises a polypeptide having, e.g., at most one, two, three, four, five, six, seven, eight, nine, 10, 20, 30, 40, 50, or 100 contiguous amino acid additions relative to SEQ ID NO: 38. In other aspects of this embodiment, a clostripain comprises a polypeptide having, e.g., at least one, two, three, four, five, six, seven, eight, nine, 10, 20, 30, 40, 50, or 100 contiguous amino acid additions relative to SEQ ID NO: 38.

Other examples of a di-chain loop protease include SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, and SEQ ID NO: 49, or a naturally-occurring of non-naturally occurring variant.

It is envisioned that any and all assay conditions suitable for proteolytic cleavage of the scissile bond comprising a di-chain protease cleavage site by a di-chain loop protease are useful in the methods disclosed in the present specification, such as, e.g., linear assay conditions and non-linear assay conditions. In an embodiment of the present invention, the assay conditions are linear. In an aspect of this embodiment, the assay amount of a recombinantly-expressed or a modified Clostridial toxin is in excess. In an aspect of this embodiment, the assay amount of a di-chain loop protease is in excess. In another aspect of this embodiment, the assay amount of a recombinantly-expressed or a modified Clostridial toxin is rate-limiting. In another aspect of this embodiment, the assay amount of a di-chain loop protease is rate-limiting.

In other aspects of this embodiment, assay conditions suitable for activating a recombinantly-expressed or modified Clostridial toxin can be provided such that, e.g., at least 10% of the recombinantly-expressed or modified Clostridial toxin is cleaved, at least 20% of the recombinantly-expressed or modified Clostridial toxin is cleaved, at least 30% of the recombinantly-expressed or modified Clostridial toxin is cleaved, at least 40% of the recombinantly-expressed or modified Clostridial toxin is cleaved, at least 50% of the recombinantly-expressed or modified Clostridial toxin is cleaved, at least 60% of the recombinantly-expressed or modified Clostridial toxin is cleaved, at least 70% of the recombinantly-expressed or modified Clostridial toxin is cleaved, at least 80% of the recombinantly-expressed or modified Clostridial toxin is cleaved or at least 90% of the recombinantly-expressed or modified Clostridial toxin is cleaved. In other aspects of this embodiment, conditions suitable for activating a recombinantly-expressed or modified Clostridial toxin can be provided such that, e.g., at most 10% of the recombinantly-expressed or modified Clostridial toxin is cleaved, at most 20% of the recombinantly-expressed or modified Clostridial toxin is cleaved, at most 30% of the recombinantly-expressed or modified Clostridial toxin is cleaved, at most 40% of the recombinantly-expressed or modified Clostridial toxin is cleaved, at most 50% of the recombinantly-expressed or modified Clostridial toxin is cleaved, at most 60% of the recombinantly-expressed or modified Clostridial toxin is cleaved, at most 70% of the recombinantly-expressed or modified Clostridial toxin is cleaved, at most 80% of the recombinantly-expressed or modified Clostridial toxin is cleaved or at most 90% of the recombinantly-expressed or modified Clostridial toxin is cleaved. In another aspect of this embodiment, conditions suitable for activating a recombinantly-expressed or a modified Clostridial toxin can be provided such that 100% of the recombinantly-expressed or modified Clostridial toxin is cleaved. In another aspect of this embodiment, the conditions suitable for activating a recombinantly-expressed or a modified Clostridial toxin are provided such that the assay is linear. In another aspect of this embodiment, the conditions suitable for activating a recombinantly-expressed or a modified Clostridial toxin are provided such that the assay is non-linear.

The presence of calcium ions is essential for Clostripain proteolytic activity. Thus, in another embodiment, assay conditions suitable for activating a recombinantly-expressed or modified Clostridial toxin include a source of calcium, such as calcium chloride or calcium acetate. In aspects of this embodiment, assay conditions include calcium in the range of about 0.1 μM to about 500 μM, for example, about 0.1 μM to about 50 μM, about 0.1 μM to about 5 μM, about 1 μM to about 500 μM, about 1 μM to about 50 μM, about 1 μM to about 5 μM, about 5 μM to about 15 μM, and about 5 μM to about 10 μM. One skilled in the art understands that calcium chelators such as EGTA generally are excluded from an assay condition used to activate a recombinantly-expressed or modified Clostridial toxin. Potent inhibitors of clostripain activity include, e.g., oxidizing agents, thiol-blocking agents, $Co^{2+}$, $Cu^{2+}$, $Cd^{2+}$ and heavy metal ions. Citrate, borate and Tris partially inhibit Clostripain proteolytic activity.

In addition, the activity of clostripain depends upon a cysteine thiol group, so a reducing agent such as, e.g., dithiothreitol (DTT), cysteine, β-mercaptoethanol, dimethylsulfoxide (DMSO), or other sulfhydryl containing reagents is included in the assay buffer. In aspect of this embodiment, concentrations for a reducing agent may include, e.g., at least 10 nM, at least 50 nM, at least 100 nM, at least 500 nM, at least 1 mM, at least 10 mM or at least 100 mM. In another aspect of this embodiment, concentrations for a reducing agent may include, e.g., at most 10 nM, at most 50 nM, at most 100 nM, at most 500 nM, at most 1 mM, at most 10 mM or at most 100 mM. Non-limiting examples of how to make and use specific reducing agents are described in, e.g., MOLECULAR CLONING, A LABORATORY MANUAL, supra, (2001); and CURRENT PROTOCOLS IN MOLECULAR BIOLOGY, supra, (2004).

In another embodiment, the amount of di-chain loop protease used to activate a recombinantly-expressed or a modified Clostridial toxin can be in the range of about 0.001 μg to about 500 μg, for example, from about 0.001 μg to about 05 μg, about 0.001 μg to about 5 μg, about 0.001 μg to about 50 μg, about 0.01 μg to about 05 μg, 0.01 μg to about 5 μg, about 0.01 μg to about 50 μg, about 0.01 μg to about 500 μg, about 0.1 μg to about 05 μg, 0.1 μg to about 5 μg, about 0.1 μg to about 50 μg, about 0.1 μg to about 500 μg, about 1 μg to about 05 μg, about 1 μg to about 5 μg, about 1 μg to about 50 μg, or about 1 μg to about 500 μg.

In another embodiment, the pH of the buffer used in the method to activate a recombinantly-expressed or a modified Clostridial toxin can be in the range of about pH 6.0 to about about pH 9.5, for example, from about pH 6.0 to about pH 9.0, about pH 6.0 to about pH 8.5, about pH 6.0 to about pH 8.0, about pH 6.0 to about pH 7.5, about pH 7.0 to about pH 9.0, about pH 7.0 to about pH 8.5, about pH 7.0 to about pH 8.0, about pH 7.2 to about pH 8.0, about pH 7.2 to about pH 7.8, about pH 7.2 to about pH 7.6, about pH 7.2 to about pH 7.4, about pH 7.4 to about pH 8.0, about pH 7.4 to about pH 7.8, about pH 7.4 to about pH 7.6, about pH 7.4 to about pH 8.0, about pH 7.4 to about pH 7.8, or about pH 7.4 to about pH 7.6.

In a further embodiment, it is also envisioned that any and all buffers that allow the cleavage of the di-chain loop protease cleavage site by a di-chain loop protease can optionally be used in the activation methods disclosed in the present specification. Assay buffers can be varied as appropriate by one skilled in the art and generally depend, in part, on the pH value desired for the assay and the detection means employed. Therefore, aspects of this embodiment may optionally include, e.g., 2-amino-2-hydroxymethyl-1,3-propanediol (Tris) buffers; Phosphate buffers, such as, e.g., potassium phosphate buffers and sodium phosphate buffers; Good buffers, such as, e.g., 2-(N-morpholino) ethanesulfonic acid (MES), piperazine-N,N'-bis(2-ethanesulfonic acid)(PIPES), N,N'-bis(2-hydroxyethyl)-2-aminoethanesulfonic acid (BES), 3-(N-morpholino) propanesulfonic acid (MOPS), N-(2-hydroxyethyl)piperazine-N'-(2-ethanesulfonic acid) (HEPES), piperazine-N,N'-bis(2-hydroxypropanesulfonic acid) (POPSO), N-tris(hydroxymethyl)methylglycine (Tricine), N-tris(hydroxymethyl)methyl-3-aminopropanesulfonic acid (TAPS), 3-[(1,1-dimethyl-2-hydroxyethyl) amino]-2-hydroxypropanesulfonic acid (AMPSO), 3-(cyclohexylamino)-2-hydroxy-1-propanesulfonic acid (CAPSO), and 3-(cyclohexylamino)-1-propanesulfonic acid (CAPS); saline buffers, such as, e.g., Phosphate-buffered saline (PBS), HEPES-buffered saline, and Tris-buffered saline (TBS); Acetate buffers, such as, e.g., magnesium acetate, potassium actetate, and Tris acetate; and the like, or any combination thereof. In addition, the buffer concentration in a method disclosed in the present specification can be varied as appropriate by one skilled in the art and generally depend, in part, on the buffering capacity of a particular buffer being used and the detection means employed. Thus, aspects of this embodiment may include a buffer concentration of, e.g., at least 1 mM, at least 5 mM, at least 10 mM, at least 20 mM, at least 30 mM, at least 40 mM, at least 50 mM, at least 60 mM, at least 70 mM, at least 80 mM, at least 90 mM, or at least 100 mM. Non-limiting examples of how to make and use specific buffers are described in, e.g., MOLECULAR CLONING, A LABORATORY MANUAL, supra, (2001); and CURRENT PROTOCOLS IN MOLECULAR BIOLOGY, supra, (2004).

In a further embodiment, it is also envisioned that any and all salts that allow the cleavage of the di-chain loop protease cleavage site by a di-chain loop protease can optionally be used in the activation methods disclosed in the present specification. Assay salts can be varied as appropriate by one skilled in the art and generally depend, in part, on the physiological conditions desired for the assay and the detection means employed. Therefore, aspects of this embodiment may optionally include, e.g., sodium chloride, potassium chloride, calcium chloride, magnesium chloride, manganese chloride, zinc chloride, magnesium sulfate, zinc sulfate, and the like, or any combination thereof. In addition, the salt concentration in a method disclosed in the present specification can be varied as appropriate by one skilled in the art and generally depend, in part, on the buffering capacity of a particular buffer being used and the detection means employed. Thus, aspects of this embodiment may include a salt concentration of, e.g., at least 1 mM, at least 5 mM, at least 10 mM, at least 20 mM, at least 30 mM, at least 40 mM, at least 50 mM, at least 60 mM, at least 70 mM, at least 80 mM, at least 90 mM, or at least 100 mM. Non-limiting examples of how to make and use specific salts are described in, e.g., MOLECULAR CLONING, A LABORATORY MANUAL, supra, (2001); and CURRENT PROTOCOLS IN MOLECULAR BIOLOGY, supra, (2004).

In another embodiment, the concentration of a recombinantly-expressed or a modified Clostridial toxin to be activated can be in the range of about 0.0001 ng/ml to 500 μg/ml toxin, for example, about 0.0001 ng/ml to 50 μg/ml toxin, 0.001 ng/ml to 500 μg/ml toxin, 0.001 ng/ml to 50 μg/ml toxin, 0.0001 ng/ml to 5000 ng/ml toxin, 0.001 ng/ml to 5000 ng/ml, 0.01 ng/ml to 5000 ng/ml, 0.1 ng/ml to 5000 ng/ml, 0.1 ng/ml to 500 ng/ml, 0.1 ng/ml to 50 ng/ml, 1 ng/ml to 5000 ng/ml, 1 ng/ml to 500 ng/ml, 1 ng/ml to 50 ng/ml, 10 ng/ml to 5000 ng/ml, 10 ng/ml to 500 ng/ml, 50 ng/ml to 5000 ng/ml, 50 ng/ml to 500 ng/ml or 100 ng/ml to 5000 ng/ml toxin. In another embodiment, the concentration of a recombinantly-expressed or a modified Clostridial toxin to be activated can be in the range of about 0.1 pM to 500 μM, 0.1 pM to 100 μM, 0.1 pM to 10 μM, 0.1 pM to 1 μM, 0.1 pM to 500 nM, 0.1 pM to 100 nM, 0.1 pM to 10 nM, 0.1 pM to 1 nM, 0.1 pM to 500 pM, 0.1 pM to 100 pM, 0.1 pM to 50 pM, 0.1 pM to 10 pM, 1 pM to 500 μM, 1 pM to 100 μM, 1 pM to 10 μM, 1 pM to 1 μM, 1 pM to 500 nM, 1 pM to 100 nM, 1 pM to 10 nM, 1 pM to 1 nM, 1 pM to 500 pM, 1 pM to 100 pM, 1 pM to 50 pM, 1 pM to 10 pM, 10 pM to 500 μM, 10 pM to 100 μM, 10 pM to 10 μM, 10 pM to 1 μM, 10 pM to 500 nM, 10 pM to 100 nM, 10 pM to 10 nM, 10 pM to 1 nM, 10 pM to 500 pM, 10 pM to 100 pM, 10 pM to 50 pM, 100 pM to 500 μM, 100 pM to 100 μM, 100 pM to 10 μM, 100 pM to 1 μM, 100 pM to 500 nM, 100 pM to 100 nM, 100 pM to 10 nM, 100 pM to 1 nM, 100 pM to 500 pM 1 nM to 500 μM, 1 nM to 100 μM, 1 nM to 10 μM, 1 nM to 1 μM, 1 nM to 500 nM, 1 nM to 100 nM, 1 nM to 50 nM, 1 nM to 10 nM, 3 nM to 100 nM toxin. One skilled in the art understands that the concentration of a recombinantly-expressed or a modified Clostridial toxin to be activated will depend on the particular recombinantly-expressed or modified Clostridial toxin to be activated, as well as, the particular di-chain loop protease used, the presence of inhibitory components, and the assay conditions.

In still another embodiment, it is envisioned that any and all temperatures that allow activation of a recombinantly-expressed or a modified Clostridial toxin by a di-chain loop protease can be used in methods disclosed in the present specification. Assay temperatures can be varied as appropriate by one skilled in the art and generally depend, in part, on the concentration, purity of the recombinantly-expressed or modified Clostridial toxin, the activity of the di-chain loop protease, the assay time or the convenience of the artisan. Thus, an assay temperature should not be as low as to cause the solution to freeze and should not be as high as to denature a recombinantly-expressed or a modified Clostridial toxin or a di-chain loop protease disclosed in the present specification. In an aspect of this embodiment, the activation method is performed within a temperature range above 0° C., but below 40° C. In another aspect of this embodiment, the activation method is performed within a temperature range of about 4° C. to about 37° C. In yet another aspect of this embodiment, the activation method is performed within a temperature range of about 2° C. to 10° C. In yet another aspect of this embodiment, the activation method is performed at about 4° C. In still another aspect of this embodiment, the activation method is performed within a temperature range of about 10° C. to about 18° C. In still another aspect of this embodiment, the activation method is performed at about 16° C. In yet another aspect of this embodiment, the activation method is performed within a temperature range of about 18° C. to about 32° C. In yet another aspect of this embodiment, the activation method is performed at about 20° C. In another aspect of this embodiment, the activation method is performed within a temperature range of about 32° C. to about 40° C. In another aspect of this embodiment, the activation method is performed at about 37° C.

In still another embodiment, it is envisioned that any and all times sufficient for activating a recombinantly-expressed or a modified Clostridial toxin can be used in methods disclosed in the present specification. Assay times can be varied as appropriate by the skilled artisan and generally depend, in part, on the concentration and purity of the recombinantly-expressed or a modified Clostridial toxin, activity of the di-chain loop protease, incubation temperature or the convenience of the artisan. Assay times generally vary, without limitation, in the range of about 15 minutes to about 4 hours, 30 minutes to 8 hours, 1 hour to 12 hours, 2 hours to 24 hours, 4 hours to 48 hours, 6 hours to 72 hours. It is understood that assays can be terminated at any time.

Aspects of the present invention can also be described as follows:

1. A modified Clostridial toxin comprising an exogenous Clostridial toxin di-chain loop region including a di-chain protease cleavage site; wherein the Clostridial toxin di-chain loop region replaces an endogenous Clostridial toxin di-chain loop region.
2. The modified Clostridial toxin of 1, wherein the Clostridial toxin being modified is BoNT/B, BoNT/C1, BoNT/D, BoNT/E, BoNT/F, BoNT/G, TeNT, BaNT, or BuNT and the exogenous Clostridial toxin di-chain loop region is BoNT/A.
3. The modified Clostridial toxin of 2, wherein the modified Clostridial toxin is SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, or SEQ ID NO: 58.
4. The modified Clostridial toxin of 1, wherein the Clostridial toxin being modified is BoNT/A, BoNT/C1, BoNT/D, BoNT/E, BoNT/F, BoNT/G, TeNT, BaNT, or BuNT and the exogenous Clostridial toxin di-chain loop region is BoNT/B.
5. The modified Clostridial toxin of 1, wherein the Clostridial toxin being modified is BoNT/A, BoNT/B, BoNT/C1, BoNT/D, BoNT/E, BoNT/G, TeNT, BaNT, or BuNT and the exogenous Clostridial toxin di-chain loop region is BoNT/F.
6. The modified Clostridial toxin of 1, wherein the Clostridial toxin being modified is BoNT/A, BoNT/B, BoNT/C1, BoNT/D, BoNT/E, BoNT/G, BaNT, or BuNT and the exogenous Clostridial toxin di-chain loop region is TeNT.
7. The modified Clostridial toxin of 1, wherein the Clostridial toxin being modified is BoNT/A, BoNT/B, BoNT/C1, BoNT/D, BoNT/E, BoNT/G, TeNT, or BuNT and the exogenous Clostridial toxin di-chain loop region is BaNT.
8. A polynucleotide molecule encoding a modified Clostridial toxin according to any one of 1-7.
9. The polynucleotide molecule of 8, further comprising an expression vector.
10. A method of producing a modified Clostridial toxin comprising the step of expressing in a cell a polynucleotide molecule according to 9, wherein expression from the polynucleotide molecule produces the encoded modified Clostridial toxin.
11. A method of producing a modified Clostridial toxin comprising the steps of:
   a. introducing into a cell a polynucleotide molecule as defined in 9; and
   b. expressing the polynucleotide molecule, wherein expression from the polynucleotide molecule produces the encoded modified Clostridial toxin.
12. A method of activating a modified Clostridial toxin, the method comprising the step of incubating a modified Clostridial toxin according to any one of 1-7 with a di-chain loop protease, wherein cleavage of the modified Clostridial toxin by the di-chain loop protease converts the modified Clostridial toxin from its single-chain polypeptide form into its di-chain form, thereby activating the modified Clostridial toxin.
13. A method of activating a modified Clostridial toxin, the method comprising the step of incubating a modified Clostridial toxin according to any one of 2 with a BoNT/A di-chain loop protease under physiological conditions; wherein cleavage of the modified Clostridial toxin by the BoNT/A di-chain loop protease converts the modified Clostridial toxin from its single-chain polypeptide form into its di-chain form, thereby activating the modified Clostridial toxin.
14. A method of either 13 Or 14, wherein the BoNT/A toxin di-chain loop protease is SEQ ID NO: 33, SEQ ID NO: 34, SEQ ID NO: 35, SEQ ID NO: 36, SEQ ID NO: 37, or SEQ ID NO: 38; and
15. A method of activating a recombinatly-expressed Clostridial toxin, the method comprising the steps of:
   a. expressing in an aerobic bacterial cell a polynucleotide molecule encoding a Clostridial toxin;
   b. purifying the Clostridial toxin; and
   c. incubating the purified Clostridial toxin with a Clostridial toxin di-chain loop protease under physiological conditions;
   wherein cleavage of the purified Clostridial toxin by the Clostridial toxin di-chain loop protease converts the purified Clostridial toxin from its single-chain polypeptide form into its di-chain form, thereby activating the recombinatly-expressed Clostridial toxin.
16. A method of activating a recombinatly-expressed BoNT/A, the method comprising the steps of:
   a. expressing in an aerobic bacterial cell a polynucleotide molecule encoding a BoNT/A;
   b. purifying the BoNT/A; and
   c. incubating the purified BoNT/A with a BoNT/A di-chain loop protease under physiological conditions;
   wherein the BoNT/A toxin di-chain loop protease is SEQ ID NO: 33, SEQ ID NO: 34, SEQ ID NO: 35, SEQ ID NO: 36, SEQ ID NO: 37, or SEQ ID NO: 38; and
   wherein cleavage of the purified BoNT/A by the BoNT/A di-chain loop protease converts the purified BoNT/A from its single-chain polypeptide form into its di-chain form, thereby activating the recombinatly-expressed BoNT/A.
17. A modified Clostridial toxin comprising:
   a) a Clostridial toxin enzymatic domain;
   b) a Clostridial toxin translocation domain;
   c) a targeting moiety;
   d) an exogenous Clostridial toxin di-chain loop region including a di-chain protease cleavage site; wherein the Clostridial toxin di-chain loop region replaces an endogenous Clostridial toxin di-chain loop region.
18. The modified Clostridial toxin of 17, wherein the targeting moiety is one disclosed in Steward, supra, International Patent Publication No. 2006/008956; Steward, supra, U.S. patent application Ser. No. 11/776,043; Steward, supra, International Patent Publication No. 2006/009831; Steward, supra, U.S. Patent Publication No. 2006/0211619; Steward, supra, U.S. patent application Ser. No. 11/776, 052; Foster, supra, U.S. Pat. No. 5,989,545; Shone, supra, U.S. Pat. No. 6,461,617; Quinn, supra, U.S. Pat. No. 6,632, 440; Steward, supra, U.S. Pat. No. 6,843,998; Donovan, supra, U.S. Pat. No. 7,138,127; Foster, supra, U.S. Patent Publication 2003/0180289; Dolly, supra, U.S. Pat. No. 7,132,259; Foster, supra, International Patent Publication WO 2005/023309; Steward, supra, U.S. patent application Ser. No. 11/376,696; Foster, supra, International Patent Publication WO 2006/059093; Foster, supra, International Patent Publication WO 2006/059105; or Steward, supra, U.S. patent application Ser. No. 11/776,075.

EXAMPLES

The following non-limiting examples are provided for illustrative purposes only in order to facilitate a more complete understanding of disclosed embodiments and are in no way intended to limit any of the embodiments disclosed in the present specification.

Example 1

Construction of Modified Clostridial Toxins Comprising a Di-Chain Loop Protease Cleavage Site from a Different Clostridial Toxin This example illustrates how to make a modified Clostridial toxin comprising a di-chain loop protease cleavage site from a different Clostridial toxin located in the di-chain loop region of the modified toxin.

A polynucleotide molecule based on BoNT/E-DiA (SEQ ID NO: 50) will be synthesized using standard procedures (BlueHeron® Biotechnology, Bothell, Wash.). BoNT/E-DiA is a toxin which is modified to replace the endogenous di-chain loop region of BoNT/E (SEQ ID NO: 15) with the BoNT/A di-chain loop region of SEQ ID NO: 11. Oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/E-DiA. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule based on BoNT/E-DiA (SEQ ID NO: 50) can be synthesized in order to improve expression in an *Escherichia coli* strain. The polynucleotide molecule encoding the BoNT/E-DiA can be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al. Optimizing Expression of Active Botulinum Toxin Type E, International Patent Publication No. WO 2006/011966 (Feb. 2, 2006); Lance E. Steward et al. Optimizing Expression of Active Botulinum Toxin Type A, International Patent Publication No. WO 2006/017749 (Feb. 16, 2006), each of which is hereby incorporated by reference in its entirety. Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/E-DiA. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). If so desired, optimization to a different organism, such as, e.g., a yeast strain, an insect cell-line or a mammalian cell line, can be done, see, e.g., Steward, supra, International Patent Publication No. WO 2006/011966 (Feb. 2, 2006); and Steward, supra, International Patent Publication No. WO 2006/017749 (Feb. 16, 2006).

A similar cloning strategy is used to make pUCBHB1 cloning constructs for BoNT/E-DiB, a modified BoNT/E where SEQ ID NO: 15 is replaced with SEQ ID NO: 12, a BoNT/B di-chain loop region; BoNT/E-DiF, a modified BoNT/E where SEQ ID NO: 15 is replaced with SEQ ID NO: 16, a BoNT/F di-chain loop region; BoNT/E-DiBa, a modified BoNT/E where SEQ ID NO: 15 is replaced with SEQ ID NO: 19, a BaNT di-chain loop region; and BoNT/E-DiT, a modified BoNT/E where SEQ ID NO: 15 is replaced with SEQ ID NO: 18, a TeNT di-chain loop region. In addition, using a similar strategy one skilled in the art can, e.g., modify BoNT/B by replacing the BoNT/B di-chain loop region of SEQ ID NO: 12 with SEQ ID NO: 11, a BoNT/A di-chain loop region, to construct BoNT/B-Di-A (SEQ ID NO: 51); modify BoNT/C1 by replacing the BoNT/C1 di-chain loop region of SEQ ID NO: 13 with SEQ ID NO: 11, a BoNT/A di-chain loop region, to construct BoNT/C1-Di-A (SEQ ID NO: 52); modify BoNT/D by replacing the BoNT/D di-chain loop region of SEQ ID NO: 14 with SEQ ID NO: 11, a BoNT/A di-chain loop region, to construct BoNT/D-Di-A (SEQ ID NO: 53); modify BoNT/F by replacing the BoNT/F di-chain loop region of SEQ ID NO: 16 with SEQ ID NO: 11, a BoNT/A di-chain loop region, to construct BoNT/F-Di-A (SEQ ID NO: 54); modify BoNT/G by replacing the BoNT/G di-chain loop region of SEQ ID NO: 17 with SEQ ID NO: 11, a BoNT/A di-chain loop region, to construct BoNT/G-Di-A (SEQ ID NO: 55); modify TeNT by replacing the TeNT di-chain loop region of SEQ ID NO: 18 with SEQ ID NO: 11, a BoNT/A di-chain loop region, to construct TeNT-Di-A (SEQ ID NO: 56); modify BaNT by replacing the BaNT di-chain loop region of SEQ ID NO: 19 with SEQ ID NO: 11, a BoNT/A di-chain loop region, to construct BaNT-Di-A (SEQ ID NO: 57); and modify BuNT by replacing the BuNT di-chain loop region of SEQ ID NO: 20 with SEQ ID NO: 11, a BoNT/A di-chain loop region, to construct BuNT-Di-A (SEQ ID NO: 58).

To construct pET29/BoNT/E-DiA, a pUCBHB1/BoNT/E-DiA construct is digested with restriction endonucleases that 1) will excise the polynucleotide molecule encoding BoNT/E-DiA; and 2) will enable this polynucleotide molecule to be operably-linked to a pET29 vector (EMD Biosciences-Novagen, Madison, Wis.). This insert will be subcloned using a T4 DNA ligase procedure into a pET29 vector that is digested with appropriate restriction endonucleases to yield pET29/BoNT/E-DiA. The ligation mixture will be transformed into chemically competent *E. coli* DH5α cells (Invitrogen, Inc, Carlsbad, Calif.) using a heat shock method, will be plated on 1.5% Luria-Bertani agar plates (pH 7.0) containing 50 μg/mL of Kanamycin, and will be placed in a 37° C. incubator for overnight growth. Bacteria containing expression constructs will be identified as Kanamycin resistant colonies. Candidate constructs will be isolated using an alkaline lysis plasmid mini-preparation procedure and will be analyzed by restriction endonuclease digest mapping to determine the presence and orientation of the insert. This cloning strategy will yield a pET29 expression construct comprising the polynucleotide molecule encoding the BoNT/E-DiA operably-linked to a carboxyl terminal polyhistidine affinity binding peptide.

A similar cloning strategy can be used to make pET29 expression constructs comprising the polynucleotide molecule encoding BoNT/E-DiB, BoNT/E-DiF, BoNT/E-Ba and BoNT/E-DiT. Likewise, a similar cloning strategy will be used to make pET29 expression constructs comprising a polynucleotide molecule encoding BoNT/B-DiA, BoNT/C1-DiA, BoNT/D-DiA, BoNT/F-DiA, BoNT/G-DiA, TeNT-DiA, BaNT-DiA, and BuNT-DiA.

Example 2

Expression of Modified Clostridial Toxins in a Bacterial Cell

The following example illustrates a procedure useful for expressing any of the modified Clostridial toxins disclosed in the present specification in a bacterial cell.

An expression construct, such as, e.g., pET29/BoNT/E-DiA, see, e.g., Example 1 is introduced into chemically competent E. coli BL21 (DE3) cells (Invitrogen, Inc, Carlsbad, Calif.) using a heat-shock transformation protocol. The heat-shock reaction is plated onto 1.5% Luria-Bertani agar plates (pH 7.0) containing 50 µg/mL of Kanamycin and is placed in a 37° C. incubator for overnight growth. Kanamycin-resistant colonies of transformed E. coli containing the expression construct, such as, e.g., pET29/BoNT/E-DiA are used to inoculate a baffled flask containing 3.0 mL of PA-0.5G media containing 50 µg/mL of Kanamycin which is then placed in a 37° C. incubator, shaking at 250 rpm, for overnight growth. The resulting overnight starter culture is in turn used to inoculate a 3 L baffled flask containing ZYP-5052 autoinducing media containing 50 µg/mL of Kanamycin at a dilution of 1:1000. Culture volumes ranged from about 600 mL (20% flask volume) to about 750 mL (25% flask volume). These cultures are grown in a 37° C. incubator shaking at 250 rpm for approximately 5.5 hours and are then transferred to a 16° C. incubator shaking at 250 rpm for overnight expression. Cells are harvested by centrifugation (4,000 rpm at 4° C. for 20-30 minutes) and are used immediately, or stored dry at −80° C. until needed.

Example 3

Purification and Quantification of Modified Clostridial Toxins

The following example illustrates methods useful for purification and quantification of any modified Clostridial toxins disclosed in the present specification.

For immobilized metal affinity chromatography (IMAC) protein purification, E. coli BL21 (DE3) cell pellets used to express a modified Clostridial toxin, as described in Example 2, are resuspended in Column Binding Buffer (25 mM N-(2-hydroxyethyl) piperazine-N'-(2-ethanesulfonic acid) (HEPES), pH 7.8; 500 mM sodium chloride; 10 mM imidazole; 2× Protease Inhibitor Cocktail Set III (EMD Biosciences-Calbiochem, San Diego Calif.); 5 units/mL of Benzonase (EMD Biosciences-Novagen, Madison, Wis.); 0.1% (v/v) Triton-X® 100, 4-octylphenol polyethoxylate; 10% (v/v) glycerol), and then are transferred to a cold Oakridge centrifuge tube. The cell suspension is sonicated on ice (10-12 pulses of 10 seconds at 40% amplitude with 60 seconds cooling intervals on a Branson Digital Sonifier) in order to lyse the cells and then is centrifuged (16,000 rpm at 4° C. for 20 minutes) to clarify the lysate. An immobilized metal affinity chromatography column is prepared using a 20 mL Econo-Pac column support (Bio-Rad Laboratories, Hercules, Calif.) packed with 2.5-5.0 mL of TALON™ SuperFlow $Co^{2+}$ affinity resin (BD Biosciences-Clontech, Palo Alto, Calif.), which is then equilibrated by rinsing with 5 column volumes of deionized, distilled water, followed by 5 column volumes of Column Binding Buffer. The clarified lysate is applied slowly to the equilibrated column by gravity flow (approximately 0.25-0.3 mL/minute). The column is then washed with 5 column volumes of Column Wash Buffer (N-(2-hydroxyethyl) piperazine-N'-(2-ethanesulfonic acid) (HEPES), pH 7.8; 500 mM sodium chloride; 10 mM imidazole; 0.1% (v/v) Triton-X® 100, 4-octylphenol polyethoxylate; 10% (v/v) glycerol). The Clostridial toxin is eluted with 20-30 mL of Column Elution Buffer (25 mM N-(2-hydroxyethyl)piperazine-N'-(2-ethanesulfonic acid) (HEPES), pH 7.8; 500 mM sodium chloride; 500 mM imidazole; 0.1% (v/v) Triton-X® 100, 4-octylphenol polyethoxylate; 10% (v/v) glycerol) and is collected in approximately twelve 1 mL fractions. The amount of Clostridial toxin contained in each elution fraction is determined by a Bradford dye assay. In this procedure, 20 µL aliquots of each 1.0 mL fraction is combined with 200 µL of Bio-Rad Protein Reagent (Bio-Rad Laboratories, Hercules, Calif.), diluted 1 to 4 with deionized, distilled water, and then the intensity of the colorimetric signal is measured using a spectrophotometer. The five fractions with the strongest signal are considered the elution peak and are combined together. Total protein yield is determined by estimating the total protein concentration of the pooled peak elution fractions using bovine gamma globulin as a standard (Bio-Rad Laboratories, Hercules, Calif.).

For purification of a modified Clostridial toxin using a FPLC desalting column, a HiPrep™ 26/10 size exclusion column (Amersham Biosciences, Piscataway, N.J.) is pre-equilibrated with 80 mL of 4° C. Column Buffer (50 mM sodium phosphate, pH 6.5). After the column is equilibrated, a Clostridial toxin sample is applied to the size exclusion column with an isocratic mobile phase of 4° C. Column Buffer and at a flow rate of 10 mL/minute using a BioLogic DuoFlow chromatography system (Bio-Rad Laboratories, Hercules, Calif.). The desalted modified Clostridial toxin sample is collected as a single fraction of approximately 7-12 mL.

For purification of a modified Clostridial toxin using a FPLC ion exchange column, a Clostridial toxin sample that has been desalted following elution from an IMAC column is applied to a 1 mL Q1™ anion exchange column (Bio-Rad Laboratories, Hercules, Calif.) using a BioLogic DuoFlow chromatography system (Bio-Rad Laboratories, Hercules, Calif.). The sample is applied to the column in 4° C. Column Buffer (50 mM sodium phosphate, pH 6.5) and is eluted by linear gradient with 4° C. Elution Buffer (50 mM sodium phosphate, 1 M sodium chloride, pH 6.5) as follows: step 1, 5.0 mL of 5% Elution Buffer at a flow rate of 1 mL/minute; step 2, 20.0 mL of 5-30% Elution Buffer at a flow rate of 1 mL/minute; step 3, 2.0 mL of 50% Elution Buffer at a flow rate of 1.0 mL/minute; step 4, 4.0 mL of 100% Elution Buffer at a flow rate of 1.0 mL/minute; and step 5, 5.0 mL of 0% Elution Buffer at a flow rate of 1.0 mL/minute. Elution of Clostridial toxin from the column is monitored at 280, 260, and 214 nm, and peaks absorbing above a minimum threshold (0.01 au) at 280 nm are collected. Most of the Clostridial toxin will elute at a sodium chloride concentration of approximately 100 to 200 mM. Average total yields of Clostridial toxin will be determined by a Bradford assay.

Expression of a modified Clostridial toxin is analyzed by polyacrylamide gel electrophoresis. Samples purified using the procedure described above are added to 2×LDS Sample Buffer (Invitrogen, Inc, Carlsbad, Calif.) and are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Gels are stained with SYPRO® Ruby (Bio-Rad Laboratories, Hercules, Calif.) and the separated polypeptides are imaged using a Fluor-S MAX MultiImager (Bio-Rad Laboratories, Hercules, Calif.) for quantification of Clostridial toxin expression levels. The size and amount of the Clostridial toxin is determined by comparison to Magic-Mark™ protein molecular weight standards (Invitrogen, Inc, Carlsbad, Calif.).

Expression of modified Clostridial toxin is also analyzed by Western blot analysis. Protein samples purified using the procedure described above are added to 2×LDS Sample Buffer (Invitrogen, Inc, Carlsbad, Calif.) and are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated polypeptides are transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes are blocked by incubating at room temperature for 2 hours in a solution containing 25 mM Tris-Buffered Saline (25 mM 2-amino-2-hydroxymethyl-1,3-propanediol hydrochloric acid (Tris-HCl)(pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes are incubated at 4° C. for overnight in Tris-Buffered Saline TWEEN-20® (25 mM Tris-Buffered Saline, 0.1% TWEEN-20®, polyoxyethylene (20) sorbitan monolaureate) containing appropriate primary antibodies as a probe. Primary antibody probed blots are washed three times for 15 minutes each time in Tris-Buffered Saline TWEEN-20®. Washed membranes are incubated at room temperature for 2 hours in Tris-Buffered Saline TWEEN-20® containing an appropriate immunoglobulin G antibody conjugated to horseradish peroxidase as a secondary antibody. Secondary antibody-probed blots are washed three times for 15 minutes each time in Tris-Buffered Saline TWEEN-20®. Signal detection of the labeled Clostridial toxin are visualized using the ECL Plus™ Western Blot Detection System (Amersham Biosciences, Piscataway, N.J.) and are imaged with a Typhoon 9410 Variable Mode Imager (Amersham Biosciences, Piscataway, N.J.) for quantification of modified Clostridial toxin expression levels.

Example 4

Expression of Modified Clostridial Toxins in a Yeast Cell

The following example illustrates a procedure useful for expressing any of the modified Clostridial toxins disclosed in the present specification in a yeast cell.

To construct a suitable yeast expression construct encoding a modified Clostridial toxin, restriction endonuclease sites suitable for cloning an operably linked polynucleotide molecule into a pPIC A vector (Invitrogen, Inc, Carlsbad, Calif.) are incorporated into the 5'- and 3' ends of the polynucleotide molecule encoding BoNT/E-DiA of SEQ ID NO: 50. This polynucleotide molecule is synthesized and a pUCBHB1/BoNT/E-DiA construct is obtained as described in Example 1. This construct is digested with restriction enzymes that 1) will excise the insert containing the open reading frame encoding BoNT/E-DiA; and 2) enable this insert to be operably-linked to a pPIC A vector. This insert is subcloned using a T4 DNA ligase procedure into a pPIC A vector that is digested with appropriate restriction endonucleases to yield pPIC A/BoNT/E-DiA. The ligation mixture is transformed into chemically competent E. coli DH5α cells (Invitrogen, Inc, Carlsbad, Calif.) using a heat shock method, plated on 1.5% low salt Luria-Bertani agar plates (pH 7.5) containing 25 μg/mL of Zeocin™, and placed in a 37° C. incubator for overnight growth. Bacteria containing expression constructs are identified as Zeocin™ resistant colonies. Candidate constructs are isolated using an alkaline lysis plasmid mini-preparation procedure and analyzed by restriction endonuclease digest mapping to determine the presence and orientation of the insert. This cloning strategy yielded a pPIC A expression construct comprising the polynucleotide molecule encoding the BoNT/E-DiA of SEQ ID NO: 50 operably-linked to a carboxyl-terminal c-myc and polyhistidine binding peptides.

A similar cloning strategy is used to make pPIC A expression constructs encoding BoNT/E-DiB, BoNT/E-DiF, BoNT/E-Ba, BoNT/E-DiT, BoNT/B-DiA, BoNT/C1-DiA, BoNT/D-DiA, BoNT/F-DiA, BoNT/G-DiA, TeNT-DiA, BaNT-DiA, and BuNT-DiA.

To construct a yeast cell line expressing a modified Clostridial toxin, pPICZ A/BoNT/E-DiA is digested with a suitable restriction endonuclease (i.e., SacI, PmeI or BstXI) and the resulting linearized expression construct is transformed into an appropriate P. pastoris Mut$^s$ strain KM71 H using an electroporation method. The transformation mixture is plated on 1.5% YPDS agar plates (pH 7.5) containing 100 μg/mL of Zeocin™ and placed in a 28-30° C. incubator for 1-3 days of growth. Selection of transformants integrating the pPICZ A/BoNT/E-DiA at the 5' AOX1 locus is determined by colony resistance to Zeocin™. Cell lines integrating a pPICZ A/BoNT/E-DiA construct is tested for BoNT/E-DiA expression using a small-scale expression test. Isolated colonies from test cell lines that have integrated pPICZ A/BoNT/E-DiA are used to inoculate 1.0 L baffled flasks containing 100 mL of MGYH media and grown at about 28-30° C. in a shaker incubator (250 rpm) until the culture reaches an $OD_{600}$=2-6 (approximately 16-18 hours). Cells are harvested by centrifugation (3,000×g at 22° C. for 5 minutes). To induce expression, the cell pellet is resuspended in 15 mL of MMH media and 100% methanol is added to a final concentration of 0.5%. Cultures are grown at about 28-30° C. in a shaker incubator (250 rpm) for six days. Additional 100% methanol is added to the culture every 24 hours to a final concentration of 0.5%. A 1.0 mL test aliquot is taken from the culture every 24 hours starting at time zero and ending at time 144 hours. Cells are harvested from the aliquots by microcentrifugation to pellet the cells and lysed using three freeze-thaw rounds consisting of −80° C. for 5 minutes, then 37° C. for 5 minutes. Lysis samples are added to 2×LDS Sample Buffer (Invitrogen, Inc, Carlsbad, Calif.) and expression from established cell lines is measured by Western blot analysis (as described in Example 8) using either anti-BoNT/E, anti-myc or anti-His antibodies in order to identify lines expressing BoNT/E-DiA. The P. pastoris Mut$^s$ KM71H cell line showing the highest expression level of BoNT/E-DiA is selected for large-scale expression using commercial fermentation procedures. Procedures for large-scale expression are as outlined above except the culture volume is approximately 2.5 L MGYH media grown in a 5 L BioFlo 3000 fermentor and concentrations of all reagents will be proportionally increased for this volume. A similar procedure can be used to express a pPICZ A construct encoding BoNT/E-DiB, BoNT/E-DiF, BoNT/E-Ba, BoNT/E-DiT, BoNT/B-DiA, BoNT/C1-DiA, BoNT/D-DiA, BoNT/F-DiA, BoNT/G-DiA, TeNT-DiA, BaNT-DiA, and BuNT-DiA.

BoNT/E-DiA is purified using the IMAC procedure, as described in Example 3. Expression from each culture is evaluated by a Bradford dye assay, polyacrylamide gel electrophoresis and Western blot analysis (as described in Example 3) in order to determine the amounts of BoNT/E-DiA produced.

Example 5

Expression of Modified Clostridial Toxins in an Insect Cell

The following example illustrates a procedure useful for expressing any of the modified Clostridial toxins disclosed in the present specification in an insect cell.

To construct suitable an insect expression construct encoding a modified Clostridial toxin, restriction endonuclease sites suitable for cloning an operably linked polynucleotide molecule into a pBACgus3 vector (EMD Biosciences-Novagen, Madison, Wis.) are incorporated into the 5'- and 3' ends of the polynucleotide molecule encoding BoNT/E-DiA of SEQ ID NO: 50. This polynucleotide molecule is synthesized and a pUCBHB1/BoNT/E-DiA construct is obtained as described in Example 1. This construct is digested with restriction enzymes that 1) will excise the insert containing the open reading frame encoding BoNT/E-DiA; and 2) enable this insert to be operably-linked to a pBACgus3 vector. This insert is subcloned using a T4 DNA ligase procedure into a pBACgus3 vector that is digested with appropriate restriction endonucleases to yield pBACgus3/BoNT/E-DiA. The ligation mixture is transformed into chemically competent E. coli DH5α cells (Invitrogen, Inc, Carlsbad, Calif.) using a heat shock method, plated on 1.5% Luria-Bertani agar plates (pH 7.0) containing 100 µg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yielded a pBACgus3 expression construct comprising the polynucleotide molecule encoding the BoNT/E-DiA of SEQ ID NO: 50 operably linked to an amino-terminal gp64 signal peptide and a carboxyl-terminal, Thrombin cleavable, polyhistidine affinity binding peptide.

A similar cloning strategy is used to make pBACgus3 expression constructs encoding BoNT/E-DiB, BoNT/E-DiF, BoNT/E-Ba, BoNT/E-DiT, BoNT/B-DiA, BoNT/C1-DiA, BoNT/D-DiA, BoNT/F-DiA, BoNT/G-DiA, TeNT-DiA, BaNT-DiA, and BuNT-DiA.

To express a modified Clostridial toxin using a baculoviral expression system, about $2.5 \times 10^6$ Sf9 cells are plated in four 60 mm culture dishes containing 2 mL of BacVector® Insect media (EMD Biosciences-Novagen, Madison, Wis.) and incubated for approximately 20 minutes in a 28° C. incubator. For each transfection, a 50 µL transfection solution is prepared in a 6 mL polystyrene tube by adding 25 µL of BacVector® Insect media containing 100 ng of a pBACgus3 construct encoding a modified Clostridial toxin, such as, e.g., pBACgus3/BoNT/E-DiA, and 500 ng TlowE transfer plasmid to 25 µL of diluted Insect GeneJuice® containing 5 µL Insect GeneJuice® (EMD Biosciences-Novagen, Madison, Wis.) and 20 µL nuclease-free water and this solution is incubated for approximately 15 minutes. After the 15 minute incubation, add 450 µL BacVector® media to the transfection solution and mix gently. Using this stock transfection solution as the ⅒ dilution make additional transfection solutions of ⅕₀, ¹⁄₂₅₀ and ¹⁄₁₂₅₀ dilutions. Add 100 µL of a transfection solution to the Sf9 cells from one of the four 60 mm culture dishes, twice washed with antibiotic-free, serum-free BacVector® Insect media and incubate at 22° C. After one hour, add 6 mL of 1% BacPlaque agarose-BacVector® Insect media containing 5% bovine serum albumin. After the agarose is solidified, add 2 mL BacVector® Insect media containing 5% bovine serum albumin to the transfected cells and transfer the cells to a 28° C. incubator for 3-5 days until plaques are visible. After 3-5 days post-transfection, plaques in the monolayer will be stained for R-glucuronidase reporter gene activity to test for the presence of recombinant virus plaques containing pBACgus3/BoNT/E-DiA by incubating the washed monolayer with 2 mL of BacVector® Insect media containing 30 µL of 20 mg/mL X-Gluc Solution (EMD Biosciences-Novagen, Madison, Wis.) for approximately 2 hours in a 28° C. incubator.

After identifying candidate recombinant virus plaques, several candidate virus plaques are eluted and plaque purified. To elute a recombinant virus, transfer a plug containing a recombinant virus plaque with a sterile Pasteur pipet to 1 mL BacVector® Insect media (EMD Biosciences-Novagen, Madison, Wis.) in a sterile screw-cap vial. Incubate the vial for approximately 2 hours at 22° C. or for approximately 16 hours at 4° C. For each recombinant virus plaque, $2.5 \times 10^5$ Sf9 cells are plated in 35 mm culture dishes containing 2 mL of BacVector® Insect media (EMD Biosciences-Novagen, Madison, Wis.) and incubated for approximately 20 minutes in a 28° C. incubator. Remove the media and add 200 µL of eluted recombinant virus. After one hour, add 2 mL of 1% BacPlaque agarose-BacVector® Insect media containing 5% bovine serum albumin. After the agarose is solidified, add 1 mL BacVector® Insect media containing 5% bovine serum albumin to the transfected cells and transfer the cells to a 28° C. incubator for 3-5 days until plaques are visible. After 3-5 days post-transfection, plaques in the monolayer will be stained for R-glucuronidase reporter gene activity to test for the presence of recombinant virus plaques containing pBACgus3/BoNT/E-DiA by incubating the washed monolayer with 2 mL of BacVector® Insect media containing 30 µL of 20 mg/mL X-Gluc Solution (EMD Biosciences-Novagen, Madison, Wis.) for approximately 2 hours in a 28° C. incubator.

To prepare a seed stock of virus, elute a recombinant virus by transferring a plug containing a recombinant virus plaque with a sterile Pasteur pipet to 1 mL BacVector® Insect media (EMD Biosciences-Novagen, Madison, Wis.) in a sterile screw-cap vial. Incubate the vial for approximately 16 hours at 4° C. Approximately $5 \times 10^5$ Sf9 cells are plated in T-25 flask containing 5 mL of BacVector® Insect media (EMD Biosciences-Novagen, Madison, Wis.) and are incubated for approximately 20 minutes in a 28° C. incubator. Remove the media and add 300 µL of eluted recombinant virus. After one hour, add 5 mL BacVector® Insect media containing 5% bovine serum albumin to the transfected cells and transfer the cells to a 28° C. incubator for 3-5 days until the majority of cells become unattached and unhealthy. The virus is harvested by transferring the media to 15 mL snap-cap tubes and centrifuging tubes at 1000×g for 5 minutes to remove debris. The clarified supernatant is transferred to fresh 15 mL snap-cap tubes and are stored at 4° C.

To prepare a high titer stock of virus, approximately $2 \times 10^7$ Sf9 cells are plated in T-75 flask containing 10 mL of BacVector® Insect media (EMD Biosciences-Novagen, Madison, Wis.) and are incubated for approximately 20 minutes in a 28° C. incubator. Remove the media and add 500 µL of virus seed stock. After one hour, add 10 mL BacVector® Insect media containing 5% bovine serum albumin to the transfected cells and transfer the cells to a 28° C. incubator for 3-5 days until the majority of cells become unattached and unhealthy. The virus is harvested by transferring the media to 15 mL snap-cap tubes and centrifuging tubes at 1000×g for 5 minutes to remove debris. The clarified supernatant is transferred to fresh 15 mL snap-cap tubes and are stored at 4° C. High titer virus stocks should contain approximately $2 \times 10^8$ to $3 \times 10^9$ pfu of baculovirus.

To express gp64-BoNT/E-DiA using a baculoviral expression system, about $1.25 \times 10^8$ Sf9 cells are seeded in a 1 L flask containing 250 mL of BacVector® Insect media and are grown in an orbital shaker (150 rpm) to a cell density of approximately $5 \times 10^8$. The culture is inoculated with approximately $2.5 \times 10^9$ of high titer stock recombinant baculovirus and incubated for approximately 48 hours in a 28° C. orbital shaker (150 rpm). Media is harvested by transferring the media to tubes and centrifuging tubes at 500×g for 5 minutes to remove debris. Media samples are added to 2×LDS Sample Buffer (Invitrogen, Inc, Carlsbad, Calif.) and expression is measured by Western blot analysis (as described in Example 8) using either anti-BoNT/A or anti-His antibodies in order to identify baculoviral stocks expressing BoNT/E-DiA. A similar procedure can be used to express a pBACgus3 construct encoding BoNT/E-DiB, BoNT/E-DiF, BoNT/E-Ba, BoNT/E-DiT, BoNT/B-DiA, BoNT/C1-DiA, BoNT/D-DiA, BoNT/F-DiA, BoNT/G-DiA, TeNT-DiA, BaNT-DiA, and BuNT-DiA.

BoNT/E-DiA is purified using the IMAC procedure, as described in Example 3. Expression from each culture is evaluated by a Bradford dye assay, polyacrylamide gel electrophoresis and Western blot analysis (as described in Example 3) in order to determine the amounts of BoNT/E-DiA produced.

Example 6

Expression of Modified Clostridial Toxins in a Mammalian Cell

The following example illustrates a procedure useful for expressing any of the modified Clostridial toxins disclosed in the present specification in a mammalian cell.

To construct a suitable mammalian expression construct encoding a modified Clostridial toxin, restriction endonuclease sites suitable for cloning an operably linked polynucleotide molecule into a pSecTag2 vector (Invitrogen, Inc, Carlsbad, Calif.) are incorporated into the 5'- and 3' ends of the polynucleotide molecule encoding BoNT/E-DiA of SEQ ID NO: 50. This polynucleotide molecule is synthesized and a pUCBHB1/BoNT/E-DiA construct is obtained as described in Example 1. This construct is digested with restriction enzymes that 1) will excise the insert containing the open reading frame encoding BoNT/E-DiA; and 2) enable this insert to be operably-linked to a pSecTag2 vector. This insert is subcloned using a T4 DNA ligase procedure into a pSecTag2 vector that is digested with appropriate restriction endonucleases to yield pSecTag2/BoNT/E-DiA. The ligation mixture is transformed into chemically competent E. coli DH5α cells (Invitrogen, Inc, Carlsbad, Calif.) using a heat shock method, plated on 1.5% Luria-Bertani agar plates (pH 7.0) containing 100 µg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the insert. This cloning strategy yielded a pSecTag2 expression construct comprising the polynucleotide molecule encoding the BoNT/E-DiA of SEQ ID NO: 50 operably-linked to a carboxyl-terminal c-myc and polyhistidine binding peptides.

A similar cloning strategy is used to make pSecTag2 expression constructs encoding BoNT/E-DiB, BoNT/E-DiF, BoNT/E-Ba, BoNT/E-DiT, BoNT/B-DiA, BoNT/C1-DiA, BoNT/D-DiA, BoNT/F-DiA, BoNT/G-DiA, TeNT-DiA, BaNT-DiA, and BuNT-DiA.

To transiently express modified Clostridial toxin in a cell line, about $1.5 \times 10^5$ SH-SY5Y cells are plated in a 35 mm tissue culture dish containing 3 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until cells reach a density of about $5 \times 10^5$ cells/ml (6-16 hours). A 500 µL transfection solution is prepared by adding 250 µL of OPTI-MEM Reduced Serum Medium containing 15 µL of LipofectAmine 2000 (Invitrogen, Carlsbad, Calif.) incubated at room temperature for 5 minutes to 250 µL of OPTI-MEM Reduced Serum Medium containing 5 µg of a pSecTag2 expression construct encoding a modified Clostridial toxin, such as, e.g., pSecTag2/BoNT/E-DiA. This transfection is incubated at room temperature for approximately 20 minutes. The complete, supplemented DMEM media is replaced with 2 mL of OPTI-MEM Reduced Serum Medium and the 500 µL transfection solution is added to the SH-SY5Y cells and the cells are incubated in a 37° C. incubator under 5% carbon dioxide for approximately 6 to 18 hours. Transfection media is replaced with 3 mL of fresh complete, supplemented DMEM and the cells are incubated in a 37° C. incubator under 5% carbon dioxide for 48 hours. Both media and cells are collected for expression analysis of BoNT/E-DiA. Media is harvested by transferring the media to 15 mL snap-cap tubes and centrifuging tubes at 500×g for 5 minutes to remove debris. Cells are harvested by rinsing cells once with 3.0 mL of 100 mM phosphate-buffered saline, pH 7.4 and lysing cells with a buffer containing 62.6 mM 2-amino-2-hydroxymethyl-1,3-propanediol hydrochloric acid (Tris-HCl), pH 6.8 and 2% sodium lauryl sulfate (SDS). Both media and cell samples are added to 2×LDS Sample Buffer (Invitrogen, Inc, Carlsbad, Calif.) and expression is measured by Western blot analysis (as described in Example 5) using either anti-BoNT/E, anti-c-myc or anti-His antibodies in order to identify pSecTag2 constructs expressing BoNT/E-DiA. A similar procedure can be used to transiently express a pSecTag2 construct encoding BoNT/E-DiB, BoNT/E-DiF, BoNT/E-Ba, BoNT/E-DiT, BoNT/B-DiA, BoNT/C1-DiA, BoNT/D-DiA, BoNT/F-DiA, BoNT/G-DiA, TeNT-DiA, BaNT-DiA, and BuNT-DiA.

To generate a stably-integrated cell line expressing a modified Clostridial toxin, approximately $1.5 \times 10^5$ SH-SY5Y cells are plated in a 35 mm tissue culture dish containing 3 mL of complete DMEM, supplemented with 10% FBS, 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until cells reach a density of about $5 \times 10^5$ cells/ml (6-16 hours). A 500 µL transfection solution is prepared by adding 250 µL of OPTI-MEM Reduced Serum Medium containing 15 µL of LipofectAmine 2000 (Invitrogen, Carlsbad, Calif.) incubated at room temperature for 5 minutes to 250 µL of OPTI-MEM Reduced Serum Medium containing 5 µg of a pSecTag2 expression construct encoding a modified Clostridial toxin, such as, e.g., pSecTag2/BoNT/E-DiA. This transfection solution is incubated at room temperature for approximately 20 minutes. The complete, supplemented DMEM media is replaced with 2 mL of OPTI-MEM Reduced Serum Medium and the 500 µL transfection solution is added to the SH-SY5Y cells and the cells are incubated in a 37° C. incubator under 5% carbon dioxide for approximately 6 to 18 hours. Transfection media is replaced with 3 mL of fresh complete, supplemented DMEM and cells are incubated in a 37° C. incubator under 5% carbon dioxide for approximately 48 hours. Media is replaced with 3 mL of fresh complete DMEM, containing approximately 5 µg/mL of Zeocin™, 10% FBS, 1× penicillin/streptomycin solution (Invitrogen, Inc, Carlsbad, Calif.) and 1×MEM non-essential amino acids solution (Invitrogen, Inc, Carlsbad, Calif.). Cells are incubated in a 37° C. incubator under 5% carbon dioxide for approximately 3-4 weeks, with old media being replaced with fresh Zeocin™-selective, complete, supplemented DMEM every 4 to 5 days. Once Zeocin™-resistant colonies are established, resistant clones are replated to new 35 mm culture plates containing fresh complete DMEM, supplemented with approximately 5 µg/mL of Zeocin™, 10% FBS, 1× penicillin/streptomycin solution (Invitrogen, Inc, Carlsbad, Calif.) and 1×MEM non-essential amino acids solution (Invitrogen, Inc, Carlsbad, Calif.), until these cells reach a density of 6 to 20×$10^5$ cells/mL. To test for expression of BoNT/E-DiA from SH-SY5Y cell lines that have stably-integrated a pSecTag2/BoNT/E-DiA, approximately 1.5×$10^5$ SH-SY5Y cells from each cell line are plated in a 35 mm tissue culture dish containing 3 mL of Zeocin™-selective, complete, supplemented DMEM and grown in a 37° C. incubator under 5% carbon dioxide until cells reach a density of about 5×$10^5$ cells/ml (6-16 hours). Media is replaced with 3 mL of fresh Zeocin™-selective, complete, supplemented DMEM and cells are incubated in a 37° C. incubator under 5% carbon dioxide for 48 hours. Both media and cells are collected for expression analysis of BoNT/E-DiA-c-myc-His. Media is harvested by transferring the media to 15 mL snap-cap tubes and centrifuging tubes at 500×g for 5 minutes to remove debris. Cells are harvest by rinsing cells once with 3.0 mL of 100 mM phosphate-buffered saline, pH 7.4 and lysing cells with a buffer containing 62.6 mM 2-amino-2-hydroxymethyl-1,3-propanediol hydrochloric acid (Tris-HCl), pH 6.8 and 2% sodium lauryl sulfate (SDS). Both media and cell samples are added to 2×LDS Sample Buffer (Invitrogen, Inc, Carlsbad, Calif.) and expression is measured by Western blot analysis (as described in Example 5) using either anti-BoNT/A, anti-c-myc or anti-His antibodies in order to identify SH-SY5Y cell lines expressing BoNT/E-DiA. The established SH-SY5Y cell line showing the highest expression level of BoNT/E-DiA is selected for large-scale expression using 3 L flasks. Procedures for large-scale expression are as outlined above except the starting volume is approximately 800-1000 mL of complete DMEM and concentrations of all reagents are proportionally increased for this volume. A similar procedure can be used to stably express a pSecTag2 construct encoding BoNT/E-DiB, BoNT/E-DiF, BoNT/E-Ba, BoNT/E-DiT, BoNT/B-DiA, BoNT/C1-DiA, BoNT/D-DiA, BoNT/F-DiA, BoNT/G-DiA, TeNT-DiA, BaNT-DiA, and BuNT-DiA.

BoNT/E-DiA is purified using the IMAC procedure, as described in Example 3. Expression from each culture is evaluated by a Bradford dye assay, polyacrylamide gel electrophoresis and Western blot analysis (as described in Example 3) in order to determine whether the amounts of BoNT/E-DiA produced.

Example 7

Construction of Clostridial Toxins for Recombinant Expression

A polynucleotide molecule based on BoNT/A (SEQ ID NO: 1) will be synthesized and cloned into a pUCBHB1 vector as described in Example 1. If so desired, expression optimization to a different organism, such as, e.g., a bacteria, a yeast strain, an insect cell-line or a mammalian cell line, can be done as described above, see, e.g., Steward, supra, (Feb. 2, 2006); and Steward, supra, (Feb. 16, 2006). A similar cloning strategy will be used to make pUCBHB1 cloning constructs BoNT/B (SEQ ID NO: 2), BoNT/C1 (SEQ ID NO: 3), BoNT/D (SEQ ID NO: 4), BoNT/E (SEQ ID NO: 5), BoNT/F (SEQ ID NO: 6), BoNT/G (SEQ ID NO: 7), TeNT (SEQ ID NO: 8), BaNT (SEQ ID NO: 9), and BuNT (SEQ ID NO: 10).

To construct pET29/BoNT/A, a pUCBHB1/BoNT/A construct will be digested with restriction endonucleases that 1) will excise the polynucleotide molecule encoding the open reading frame of BoNT/A; and 2) will enable this polynucleotide molecule to be operably-linked to a pET29 vector (EMD Biosciences-Novagen, Madison, Wis.). This insert will be subcloned using a T4 DNA ligase procedure into a pET29 vector that is digested with appropriate restriction endonucleases to yield pET29/BoNT/A. The ligation mixture will be transformed into chemically competent E. coli DH5α cells (Invitrogen, Inc, Carlsbad, Calif.) using a heat shock method, will be plated on 1.5% Luria-Bertani agar plates (pH 7.0) containing 50 µg/mL of Kanamycin, and will be placed in a 37° C. incubator for overnight growth. Bacteria containing expression constructs will be identified as Kanamycin resistant colonies. Candidate constructs will be isolated using an alkaline lysis plasmid mini-preparation procedure and will be analyzed by restriction endonuclease digest mapping to determine the presence and orientation of the insert. This cloning strategy will yield a pET29 expression construct comprising the polynucleotide molecule encoding the BoNT/A operably-linked to a carboxyl terminal polyhistidine affinity binding peptide. A similar cloning strategy will be used to make pET29 expression constructs for other modified BoNT/B, BoNT/C1, BoNT/D, BoNT/E, BoNT/F, BoNT/G-TEV, TeNT-TEV, BaNT, or BuNT.

Example 8

Expression and Purification of Recombinant Clostridial Toxins in a Bacterial Cell The following example illustrates a procedure useful for recombinantly expressing any of the Clostridial toxins disclosed in the present specification in a bacterial cell.

An expression construct, such as, e.g., pET29/BoNT/A, see, e.g., Example 7 is introduced into chemically competent E. coli BL21 (DE3) cells (Invitrogen, Inc, Carlsbad, Calif.) using a heat-shock transformation protocol. The heat-shock reaction is plated onto 1.5% Luria-Bertani agar plates (pH 7.0) containing 50 µg/mL of Kanamycin and is placed in a 37° C. incubator for overnight growth. Kanamycin-resistant colonies of transformed E. coli containing the expression construct, such as, e.g., pET29/BoNT/iA are used to inoculate a baffled flask containing 3.0 mL of PA-0.5G media containing 50 µg/mL of Kanamycin which is then placed in a 37° C. incubator, shaking at 250 rpm, for overnight growth. The resulting overnight starter culture is in turn used to inoculate a 3 L baffled flask containing ZYP-5052 autoinducing media containing 50 µg/mL of Kanamycin at a dilution of 1:1000. Culture volumes ranged from about 600 mL (20% flask volume) to about 750 mL (25% flask volume). These cultures are grown in a 37° C. incubator shaking at 250 rpm for approximately 5.5 hours and are then transferred to a 16° C. incubator shaking at 250 rpm for overnight expression. Cells are harvested by centrifugation (4,000 rpm at 4° C. for 20-30 minutes) and are used immediately, or stored dry at −80° C. until needed.

Recombinantly-expressed BoNT/A is purified using the IMAC procedure, as described in Example 3. Expression from each culture is evaluated by a Bradford dye assay, polyacrylamide gel electrophoresis and Western blot analysis (as described in Example 3) in order to determine the amounts of recombinantly-expressed BoNT/A produced.

To activate purified, recombinantly-expressed BoNT/A, approximately 30 μg of purified, recombinantly-expressed BoNT/A will be incubated with 3 μg of di-chain loop protease of SEQ ID NO: 33 in 20 mM Tris-HCl, pH 8.0 with 200 mM NaCl. Following incubation at 23° C. for 2 hours, the nicking reaction will be quenched by addition of 1× Protease Inhibitor Cocktail Set III (CalBiochem; 1× inhibitor contains 1 mM AEBSF, 0.8 μM Aprotinin, 50 μM Bestatin, 15 μM E-64, 20 μM Leupeptin, and 10 μM Pepstatin A). The samples may be flash frozen in liquid nitrogen and immediately stored at −80° C.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention.

What is claimed:

1. A method of activating a modified Clostridial toxin, the method comprising the step of incubating a modified Clostridial toxin with a BoNT/A di-chain loop protease under physiological conditions;
   wherein the BoNT/A toxin di-chain loop protease is SEQ ID NO: 33, SEQ ID NO: 34, SEQ ID NO: 35, SEQ ID NO: 36, SEQ ID NO: 37 or SEQ ID NO: 38; and
   wherein cleavage of the modified Clostridial toxin by the BoNT/A di-chain loop protease converts the modified Clostridial toxin from its single-chain polypeptide form into its di-chain form, thereby activating the modified Clostridial toxin.

2. A method of activating a recombinantly expressed BoNT/A, the method comprising the steps of:
   a. expressing in an aerobic bacterial cell a polynucleotide molecule encoding a BoNT/A;
   b. purifying the BoNT/A; and
   c. incubating the purified BoNT/A with a BoNT/A di-chain loop protease under physiological conditions;
   wherein the BoNT/A toxin di-chain loop protease is SEQ ID NO: 33, SEQ ID NO: 34, SEQ ID NO: 35, SEQ ID NO: 36, SEQ ID NO: 37, or SEQ ID NO: 38; and
   wherein cleavage of the purified BoNT/A by the BoNT/A di-chain loop protease converts the purified BoNT/A from its single-chain polypeptide form into its di-chain form, thereby activating the recombinantly expressed BoNT/A.

* * * * *

SEQUENCE LISTING

<160> NUMBER OF SEQ ID NOS: 58

<210> SEQ ID NO 1
<211> LENGTH: 1296
<212> TYPE: PRT
<213> ORGANISM: Clostridium botulinum serotype A

<400> SEQUENCE: 1

```
Met Pro Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
                 20                  25                  30

Val Lys Ala Phe Lys Ile His Asn Lys Ile Trp Val Ile Pro Glu Arg
             35                  40                  45

Asp Thr Phe Thr Asn Pro Glu Glu Gly Asp Leu Asn Pro Pro Pro Glu
         50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270
```

```
Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
        290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
                435                 440                 445

Ala Leu Asn Asp Leu Cys Ile Lys Val Asn Asn Trp Asp Leu Phe Phe
        450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
                595                 600                 605

Gln Leu Val Tyr Asp Phe Thr Asp Glu Thr Ser Glu Val Ser Thr Thr
        610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
```

```
            690                 695                 700
Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
                755                 760                 765

Leu Ser Ser Lys Leu Asn Glu Ser Ile Asn Lys Ala Met Ile Asn Ile
            770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
                835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
                915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
                995                 1000                1005

Asp Tyr Ile Asn Arg Trp Ile Phe Val Thr Ile Thr Asn Asn Arg Leu
            1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
                1060                1065                1070

Asn Leu Phe Asp Lys Glu Leu Asn Glu Lys Glu Ile Lys Asp Leu Tyr
            1075                1080                1085

Asp Asn Gln Ser Asn Ser Gly Ile Leu Lys Asp Phe Trp Gly Asp Tyr
            1090                1095                1100

Leu Gln Tyr Asp Lys Pro Tyr Tyr Met Leu Asn Leu Tyr Asp Pro Asn
1105                1110                1115                1120
```

```
Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
        1140                1145                1150

Ser Leu Tyr Arg Gly Thr Lys Phe Ile Ile Lys Lys Tyr Ala Ser Gly
            1155                1160                1165

Asn Lys Asp Asn Ile Val Arg Asn Asn Asp Arg Val Tyr Ile Asn Val
        1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295

<210> SEQ ID NO 2
<211> LENGTH: 1291
<212> TYPE: PRT
<213> ORGANISM: Clostridium botulinum serotype B

<400> SEQUENCE: 2

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205
```

-continued

```
Asn Lys Gly Ala Ser Ile Phe Asn Arg Arg Gly Tyr Phe Ser Asp Pro
    210                 215                 220
Ala Leu Ile Leu Met His Glu Leu Ile His Val Leu His Gly Leu Tyr
225                 230                 235                 240
Gly Ile Lys Val Asp Asp Leu Pro Ile Val Pro Asn Glu Lys Lys Phe
                245                 250                 255
Phe Met Gln Ser Thr Asp Ala Ile Gln Ala Glu Glu Leu Tyr Thr Phe
            260                 265                 270
Gly Gly Gln Asp Pro Ser Ile Ile Thr Pro Ser Thr Asp Lys Ser Ile
        275                 280                 285
Tyr Asp Lys Val Leu Gln Asn Phe Arg Gly Ile Val Asp Arg Leu Asn
    290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
                325                 330                 335
Lys Tyr Ser Ile Asp Val Glu Ser Phe Asp Lys Leu Tyr Lys Ser Leu
            340                 345                 350
Met Phe Gly Phe Thr Glu Thr Asn Ile Ala Glu Asn Tyr Lys Ile Lys
        355                 360                 365
Thr Arg Ala Ser Tyr Phe Ser Asp Ser Leu Pro Pro Val Lys Ile Lys
    370                 375                 380
Asn Leu Leu Asp Asn Glu Ile Tyr Thr Ile Glu Glu Gly Phe Asn Ile
385                 390                 395                 400
Ser Asp Lys Asp Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
            420                 425                 430
Lys Ile Gln Met Cys Lys Ser Val Lys Ala Pro Gly Ile Cys Ile Asp
        435                 440                 445
Val Asp Asn Glu Asp Leu Phe Phe Ile Ala Asp Lys Asn Ser Phe Ser
    450                 455                 460
Asp Asp Leu Ser Lys Asn Glu Arg Ile Glu Tyr Asn Thr Gln Ser Asn
465                 470                 475                 480
Tyr Ile Glu Asn Asp Phe Pro Ile Asn Glu Leu Ile Leu Asp Thr Asp
                485                 490                 495
Leu Ile Ser Lys Ile Glu Leu Pro Ser Glu Asn Thr Glu Ser Leu Thr
            500                 505                 510
Asp Phe Asn Val Asp Val Pro Val Tyr Glu Lys Gln Pro Ala Ile Lys
        515                 520                 525
Lys Ile Phe Thr Asp Glu Asn Thr Ile Phe Gln Tyr Leu Tyr Ser Gln
    530                 535                 540
Thr Phe Pro Leu Asp Ile Arg Asp Ile Ser Leu Thr Ser Ser Phe Asp
545                 550                 555                 560
Asp Ala Leu Leu Phe Ser Asn Lys Val Tyr Ser Phe Ser Met Asp
                565                 570                 575
Tyr Ile Lys Thr Ala Asn Lys Val Val Glu Ala Gly Leu Phe Ala Gly
            580                 585                 590
Trp Val Lys Gln Ile Val Asn Asp Phe Val Ile Glu Ala Asn Lys Ser
        595                 600                 605
Asn Thr Met Asp Lys Ile Ala Asp Ile Ser Leu Ile Val Pro Tyr Ile
    610                 615                 620
Gly Leu Ala Leu Asn Val Gly Asn Glu Thr Ala Lys Gly Asn Phe Glu
625                 630                 635                 640
```

-continued

```
Asn Ala Phe Glu Ile Ala Gly Ala Ser Ile Leu Leu Glu Phe Ile Pro
                645                 650                 655
Glu Leu Leu Ile Pro Val Val Gly Ala Phe Leu Leu Glu Ser Tyr Ile
                660                 665                 670
Asp Asn Lys Asn Lys Ile Ile Lys Thr Ile Asp Asn Ala Leu Thr Lys
                675                 680                 685
Arg Asn Glu Lys Trp Ser Asp Met Tyr Gly Leu Ile Val Ala Gln Trp
                690                 695                 700
Leu Ser Thr Val Asn Thr Gln Phe Tyr Thr Ile Lys Glu Gly Met Tyr
705                 710                 715                 720
Lys Ala Leu Asn Tyr Gln Ala Gln Ala Leu Glu Glu Ile Ile Lys Tyr
                725                 730                 735
Arg Tyr Asn Ile Tyr Ser Glu Lys Glu Lys Ser Asn Ile Asn Ile Asp
                740                 745                 750
Phe Asn Asp Ile Asn Ser Lys Leu Asn Glu Gly Ile Asn Gln Ala Ile
                755                 760                 765
Asp Asn Ile Asn Asn Phe Ile Asn Gly Cys Ser Val Ser Tyr Leu Met
770                 775                 780
Lys Lys Met Ile Pro Leu Ala Val Glu Lys Leu Leu Asp Phe Asp Asn
785                 790                 795                 800
Thr Leu Lys Lys Asn Leu Leu Asn Tyr Ile Asp Glu Asn Lys Leu Tyr
                805                 810                 815
Leu Ile Gly Ser Ala Glu Tyr Glu Lys Ser Lys Val Asn Lys Tyr Leu
                820                 825                 830
Lys Thr Ile Met Pro Phe Asp Leu Ser Ile Tyr Thr Asn Asp Thr Ile
                835                 840                 845
Leu Ile Glu Met Phe Asn Lys Tyr Asn Ser Glu Ile Leu Asn Asn Ile
                850                 855                 860
Ile Leu Asn Leu Arg Tyr Lys Asp Asn Asn Leu Ile Asp Leu Ser Gly
865                 870                 875                 880
Tyr Gly Ala Lys Val Glu Val Tyr Asp Gly Val Glu Leu Asn Asp Lys
                885                 890                 895
Asn Gln Phe Lys Leu Thr Ser Ser Ala Asn Ser Lys Ile Arg Val Thr
                900                 905                 910
Gln Asn Gln Asn Ile Ile Phe Asn Ser Val Phe Leu Asp Phe Ser Val
                915                 920                 925
Ser Phe Trp Ile Arg Ile Pro Lys Tyr Lys Asn Asp Gly Ile Gln Asn
930                 935                 940
Tyr Ile His Asn Glu Tyr Thr Ile Ile Asn Cys Met Lys Asn Asn Ser
945                 950                 955                 960
Gly Trp Lys Ile Ser Ile Arg Gly Asn Arg Ile Ile Trp Thr Leu Ile
                965                 970                 975
Asp Ile Asn Gly Lys Thr Lys Ser Val Phe Phe Glu Tyr Asn Ile Arg
                980                 985                 990
Glu Asp Ile Ser Glu Tyr Ile Asn Arg Trp Phe Phe Val Thr Ile Thr
                995                 1000                1005
Asn Asn Leu Asn Asn Ala Lys Ile Tyr Ile Asn Gly Lys Leu Glu Ser
            1010                1015                1020
Asn Thr Asp Ile Lys Asp Ile Arg Glu Val Ile Ala Asn Gly Glu Ile
1025                1030                1035                1040
Ile Phe Lys Leu Asp Gly Asp Ile Asp Arg Thr Gln Phe Ile Trp Met
                1045                1050                1055
Lys Tyr Phe Ser Ile Phe Asn Thr Glu Leu Ser Gln Ser Asn Ile Glu
```

```
                    1060           1065             1070
Glu Arg Tyr Lys Ile Gln Ser Tyr Ser Glu Tyr Leu Lys Asp Phe Trp
            1075             1080            1085
Gly Asn Pro Leu Met Tyr Asn Lys Glu Tyr Tyr Met Phe Asn Ala Gly
        1090            1095            1100
Asn Lys Asn Ser Tyr Ile Lys Leu Lys Lys Asp Ser Pro Val Gly Glu
1105            1110            1115            1120
Ile Leu Thr Arg Ser Lys Tyr Asn Gln Asn Ser Lys Tyr Ile Asn Tyr
            1125            1130            1135
Arg Asp Leu Tyr Ile Gly Glu Lys Phe Ile Ile Arg Arg Lys Ser Asn
            1140            1145            1150
Ser Gln Ser Ile Asn Asp Asp Ile Val Arg Lys Glu Asp Tyr Ile Tyr
            1155            1160            1165
Leu Asp Phe Phe Asn Leu Asn Gln Glu Trp Arg Val Tyr Thr Tyr Lys
            1170            1175            1180
Tyr Phe Lys Lys Glu Glu Glu Lys Leu Phe Leu Ala Pro Ile Ser Asp
1185            1190            1195            1200
Ser Asp Glu Phe Tyr Asn Thr Ile Gln Ile Lys Glu Tyr Asp Glu Gln
            1205            1210            1215
Pro Thr Tyr Ser Cys Gln Leu Leu Phe Lys Lys Asp Glu Glu Ser Thr
            1220            1225            1230
Asp Glu Ile Gly Leu Ile Gly Ile His Arg Phe Tyr Glu Ser Gly Ile
            1235            1240            1245
Val Phe Glu Glu Tyr Lys Asp Tyr Phe Cys Ile Ser Lys Trp Tyr Leu
            1250            1255            1260
Lys Glu Val Lys Arg Lys Pro Tyr Asn Leu Lys Leu Gly Cys Asn Trp
1265            1270            1275            1280
Gln Phe Ile Pro Lys Asp Glu Gly Trp Thr Glu
            1285            1290

<210> SEQ ID NO 3
<211> LENGTH: 1291
<212> TYPE: PRT
<213> ORGANISM: Clostridium botulinum serotype C1

<400> SEQUENCE: 3

Met Pro Ile Thr Ile Asn Asn Phe Asn Tyr Ser Asp Pro Val Asp Asn
1               5                   10                  15
Lys Asn Ile Leu Tyr Leu Asp Thr His Leu Asn Thr Leu Ala Asn Glu
            20                  25                  30
Pro Glu Lys Ala Phe Arg Ile Thr Gly Asn Ile Trp Val Ile Pro Asp
        35                  40                  45
Arg Phe Ser Arg Asn Ser Asn Pro Asn Leu Asn Lys Pro Pro Arg Val
    50                  55                  60
Thr Ser Pro Lys Ser Gly Tyr Tyr Asp Pro Asn Tyr Leu Ser Thr Asp
65                  70                  75                  80
Ser Asp Lys Asp Pro Phe Leu Lys Glu Ile Ile Lys Leu Phe Lys Arg
                85                  90                  95
Ile Asn Ser Arg Glu Ile Gly Glu Glu Leu Ile Tyr Arg Leu Ser Thr
            100                 105                 110
Asp Ile Pro Phe Pro Gly Asn Asn Asn Thr Pro Ile Asn Thr Phe Asp
        115                 120                 125
Phe Asp Val Asp Phe Asn Ser Val Asp Val Lys Thr Arg Gln Gly Asn
    130                 135                 140
Asn Trp Val Lys Thr Gly Ser Ile Asn Pro Ser Val Ile Ile Thr Gly
```

```
                145                 150                 155                 160
Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
    450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575
```

-continued

```
Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Glu Asp
        595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
            645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
        690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
            725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
        770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
            805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
        850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
            885                 890                 895

Gly Asp Val Gln Leu Asn Pro Ile Phe Pro Phe Asp Phe Lys Leu Gly
            900                 905                 910

Ser Ser Gly Glu Asp Arg Gly Lys Val Ile Val Thr Gln Asn Glu Asn
        915                 920                 925

Ile Val Tyr Asn Ser Met Tyr Glu Ser Phe Ser Ile Ser Phe Trp Ile
        930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
            965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn Ala Pro Gly Tyr Asn Lys Trp Phe
        995                 1000                1005
```

-continued

Phe Val Thr Val Thr Asn Asn Met Met Gly Asn Met Lys Ile Tyr Ile
        1010                1015                1020

Asn Gly Lys Leu Ile Asp Thr Ile Lys Val Lys Glu Leu Thr Gly Ile
1025                1030                1035                1040

Asn Phe Ser Lys Thr Ile Thr Phe Glu Ile Asn Lys Ile Pro Asp Thr
            1045                1050                1055

Gly Leu Ile Thr Ser Asp Ser Asp Asn Ile Asn Met Trp Ile Arg Asp
            1060                1065                1070

Phe Tyr Ile Phe Ala Lys Glu Leu Asp Gly Lys Asp Ile Asn Ile Leu
            1075                1080                1085

Phe Asn Ser Leu Gln Tyr Thr Asn Val Val Lys Asp Tyr Trp Gly Asn
        1090                1095                1100

Asp Leu Arg Tyr Asn Lys Glu Tyr Tyr Met Val Asn Ile Asp Tyr Leu
1105                1110                1115                1120

Asn Arg Tyr Met Tyr Ala Asn Ser Arg Gln Ile Val Phe Asn Thr Arg
            1125                1130                1135

Arg Asn Asn Asn Asp Phe Asn Glu Gly Tyr Lys Ile Ile Lys Arg
        1140                1145                1150

Ile Arg Gly Asn Thr Asn Asp Thr Arg Val Arg Gly Gly Asp Ile Leu
            1155                1160                1165

Tyr Phe Asp Met Thr Ile Asn Asn Lys Ala Tyr Asn Leu Phe Met Lys
            1170                1175                1180

Asn Glu Thr Met Tyr Ala Asp Asn His Ser Thr Glu Asp Ile Tyr Ala
1185                1190                1195                1200

Ile Gly Leu Arg Glu Gln Thr Lys Asp Ile Asn Asp Asn Ile Ile Phe
            1205                1210                1215

Gln Ile Gln Pro Met Asn Asn Thr Tyr Tyr Tyr Ala Ser Gln Ile Phe
            1220                1225                1230

Lys Ser Asn Phe Asn Gly Glu Asn Ile Ser Gly Ile Cys Ser Ile Gly
            1235                1240                1245

Thr Tyr Arg Phe Arg Leu Gly Gly Asp Trp Tyr Arg His Asn Tyr Leu
        1250                1255                1260

Val Pro Thr Val Lys Gln Gly Asn Tyr Ala Ser Leu Leu Glu Ser Thr
1265                1270                1275                1280

Ser Thr His Trp Gly Phe Val Pro Val Ser Glu
            1285                1290

<210> SEQ ID NO 4
<211> LENGTH: 1276
<212> TYPE: PRT
<213> ORGANISM: Clostridium botulinum serotype D

<400> SEQUENCE: 4

Met Thr Trp Pro Val Lys Asp Phe Asn Tyr Ser Asp Pro Val Asn Asp
  1               5                  10                  15

Asn Asp Ile Leu Tyr Leu Arg Ile Pro Gln Asn Lys Leu Ile Thr Thr
                20                  25                  30

Pro Val Lys Ala Phe Met Ile Thr Gln Asn Ile Trp Val Ile Pro Glu
            35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

```
Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
        435                 440                 445

Thr Cys Ile Lys Val Lys Asn Asn Arg Leu Pro Tyr Val Ala Asp Lys
    450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
                485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
```

-continued

```
            515                 520                 525
Phe Tyr Asp Asp Ile Thr Lys Tyr Val Asp Tyr Leu Asn Ser Tyr Tyr
530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                    565                 570                 575

Phe Leu Pro Ser Leu Ala Glu Lys Val Asn Lys Gly Val Gln Ala Gly
                    580                 585                 590

Leu Phe Leu Asn Trp Ala Asn Glu Val Val Glu Asp Phe Thr Thr Asn
    595                 600                 605

Ile Met Lys Lys Asp Thr Leu Asp Lys Ile Ser Asp Val Ser Val Ile
    610                 615                 620

Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
                    645                 650                 655

Glu Gly Phe Pro Glu Phe Thr Ile Pro Ala Leu Gly Val Phe Thr Phe
                    660                 665                 670

Tyr Ser Ser Ile Gln Glu Arg Glu Lys Ile Ile Lys Thr Ile Glu Asn
                    675                 680                 685

Cys Leu Glu Gln Arg Val Lys Arg Trp Lys Asp Ser Tyr Gln Trp Met
690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                    725                 730                 735

Lys Ile Asp Leu Glu Tyr Lys Lys Tyr Ser Gly Ser Asp Lys Glu Asn
                    740                 745                 750

Ile Lys Ser Gln Val Glu Asn Leu Lys Asn Ser Leu Asp Val Lys Ile
                    755                 760                 765

Ser Glu Ala Met Asn Asn Ile Asn Lys Phe Ile Arg Glu Cys Ser Val
770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                    805                 810                 815

His Asn Ile Ile Leu Val Gly Glu Val Asp Arg Leu Lys Ala Lys Val
                    820                 825                 830

Asn Glu Ser Phe Glu Asn Thr Met Pro Phe Asn Ile Phe Ser Tyr Thr
                    835                 840                 845

Asn Asn Ser Leu Leu Lys Asp Ile Ile Asn Glu Tyr Phe Asn Ser Ile
850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                    885                 890                 895

Leu Asn Thr Ile Tyr Thr Asn Asp Phe Lys Leu Ser Ser Ser Gly Asp
                    900                 905                 910

Lys Ile Ile Val Asn Leu Asn Asn Asn Ile Leu Tyr Ser Ala Ile Tyr
                    915                 920                 925

Glu Asn Ser Ser Val Ser Phe Trp Ile Lys Ile Ser Lys Asp Leu Thr
930                 935                 940
```

-continued

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
            965                 970                 975

Asp Val Asn Arg Lys Tyr Lys Ser Leu Ile Phe Asp Tyr Ser Glu Ser
        980                 985                 990

Leu Ser His Thr Gly Tyr Thr Asn Lys Trp Phe Phe Val Thr Ile Thr
    995                 1000                1005

Asn Asn Ile Met Gly Tyr Met Lys Leu Tyr Ile Asn Gly Glu Leu Lys
1010                1015                1020

Gln Ser Gln Lys Ile Glu Asp Leu Asp Glu Val Lys Leu Asp Lys Thr
1025                1030                1035                1040

Ile Val Phe Gly Ile Asp Glu Asn Ile Asp Glu Asn Gln Met Leu Trp
            1045                1050                1055

Ile Arg Asp Phe Asn Ile Phe Ser Lys Glu Leu Ser Asn Glu Asp Ile
        1060                1065                1070

Asn Ile Val Tyr Glu Gly Gln Ile Leu Arg Asn Val Ile Lys Asp Tyr
    1075                1080                1085

Trp Gly Asn Pro Leu Lys Phe Asp Thr Glu Tyr Tyr Ile Ile Asn Asp
1090                1095                1100

Asn Tyr Ile Asp Arg Tyr Ile Ala Pro Glu Ser Asn Val Leu Val Leu
1105                1110                1115                1120

Val Gln Tyr Pro Asp Arg Ser Lys Leu Tyr Thr Gly Asn Pro Ile Thr
            1125                1130                1135

Ile Lys Ser Val Ser Asp Lys Asn Pro Tyr Ser Arg Ile Leu Asn Gly
        1140                1145                1150

Asp Asn Ile Ile Leu His Met Leu Tyr Asn Ser Arg Lys Tyr Met Ile
    1155                1160                1165

Ile Arg Asp Thr Asp Thr Ile Tyr Ala Thr Gln Gly Gly Glu Cys Ser
1170                1175                1180

Gln Asn Cys Val Tyr Ala Leu Lys Leu Gln Ser Asn Leu Gly Asn Tyr
1185                1190                1195                1200

Gly Ile Gly Ile Phe Ser Ile Lys Asn Ile Val Ser Lys Asn Lys Tyr
            1205                1210                1215

Cys Ser Gln Ile Phe Ser Ser Phe Arg Glu Asn Thr Met Leu Leu Ala
        1220                1225                1230

Asp Ile Tyr Lys Pro Trp Arg Phe Ser Phe Lys Asn Ala Tyr Thr Pro
    1235                1240                1245

Val Ala Val Thr Asn Tyr Glu Thr Lys Leu Leu Ser Thr Ser Ser Phe
1250                1255                1260

Trp Lys Phe Ile Ser Arg Asp Pro Gly Trp Val Glu
1265                1270                1275

<210> SEQ ID NO 5
<211> LENGTH: 1252
<212> TYPE: PRT
<213> ORGANISM: Clostridium botulinum serotype E

<400> SEQUENCE: 5

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

```
Gly Thr Thr Pro Gln Asp Phe His Pro Pro Thr Ser Leu Lys Asn Gly
     50                  55                  60

Asp Ser Ser Tyr Tyr Asp Pro Asn Tyr Leu Gln Ser Asp Glu Glu Lys
 65                  70                  75                  80

Asp Arg Phe Leu Lys Ile Val Thr Lys Ile Phe Asn Arg Ile Asn Asn
                 85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480
```

```
Pro Gly Leu Ser Asp Glu Lys Leu Asn Leu Thr Ile Gln Asn Asp Ala
            485                 490                 495

Tyr Ile Pro Lys Tyr Asp Ser Asn Gly Thr Ser Asp Ile Glu Gln His
        500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
        530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Pro Tyr Ile Gly Leu
        595                 600                 605

Ala Leu Asn Ile Gly Asn Glu Ala Gln Lys Gly Asn Phe Lys Asp Ala
        610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
        690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
        850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
```

```
                900             905             910
Lys Asn Phe Ser Ile Ser Phe Trp Val Arg Ile Pro Asn Tyr Asp Asn
            915                 920                 925
Lys Ile Val Asn Val Asn Asn Glu Tyr Thr Ile Ile Asn Cys Met Arg
        930                 935                 940
Asp Asn Asn Ser Gly Trp Lys Val Ser Leu Asn His Asn Glu Ile Ile
945                 950                 955                 960
Trp Thr Leu Gln Asp Asn Ala Gly Ile Asn Gln Lys Leu Ala Phe Asn
                965                 970                 975
Tyr Gly Asn Ala Asn Gly Ile Ser Asp Tyr Ile Asn Lys Trp Ile Phe
            980                 985                 990
Val Thr Ile Thr Asn Asp Arg Leu Gly Asp Ser Lys Leu Tyr Ile Asn
        995                 1000                1005
Gly Asn Leu Ile Asp Gln Lys Ser Ile Leu Asn Leu Gly Asn Ile His
    1010                1015                1020
Val Ser Asp Asn Ile Leu Phe Lys Ile Val Asn Cys Ser Tyr Thr Arg
1025                1030                1035                1040
Tyr Ile Gly Ile Arg Tyr Phe Asn Ile Phe Asp Lys Glu Leu Asp Glu
                1045                1050                1055
Thr Glu Ile Gln Thr Leu Tyr Ser Asn Glu Pro Asn Thr Asn Ile Leu
            1060                1065                1070
Lys Asp Phe Trp Gly Asn Tyr Leu Leu Tyr Asp Lys Glu Tyr Tyr Leu
        1075                1080                1085
Leu Asn Val Leu Lys Pro Asn Asn Phe Ile Asp Arg Arg Lys Asp Ser
    1090                1095                1100
Thr Leu Ser Ile Asn Asn Ile Arg Ser Thr Ile Leu Leu Ala Asn Arg
1105                1110                1115                1120
Leu Tyr Ser Gly Ile Lys Val Lys Ile Gln Arg Val Asn Asn Ser Ser
                1125                1130                1135
Thr Asn Asp Asn Leu Val Arg Lys Asn Asp Gln Val Tyr Ile Asn Phe
            1140                1145                1150
Val Ala Ser Lys Thr His Leu Phe Pro Leu Tyr Ala Asp Thr Ala Thr
        1155                1160                1165
Thr Asn Lys Glu Lys Thr Ile Lys Ile Ser Ser Ser Gly Asn Arg Phe
    1170                1175                1180
Asn Gln Val Val Val Met Asn Ser Val Gly Asn Asn Cys Thr Met Asn
1185                1190                1195                1200
Phe Lys Asn Asn Asn Gly Asn Asn Ile Gly Leu Leu Gly Phe Lys Ala
                1205                1210                1215
Asp Thr Val Val Ala Ser Thr Trp Tyr Tyr Thr His Met Arg Asp His
            1220                1225                1230
Thr Asn Ser Asn Gly Cys Phe Trp Asn Phe Ile Ser Glu Glu His Gly
        1235                1240                1245
Trp Gln Glu Lys
    1250

<210> SEQ ID NO 6
<211> LENGTH: 1274
<212> TYPE: PRT
<213> ORGANISM: Clostridium botulinum serotype F

<400> SEQUENCE: 6

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
```

-continued

```
                    20                  25                  30
Tyr Tyr Lys Ala Phe Glu Ile Met Arg Asn Val Trp Ile Ile Pro Glu
             35                  40                  45
Arg Asn Thr Ile Gly Thr Asn Pro Ser Asp Phe Asp Pro Pro Ala Ser
         50                  55                  60
Leu Lys Asn Gly Ser Ser Ala Tyr Tyr Asp Pro Asn Tyr Leu Thr Thr
 65                  70                  75                  80
Asp Ala Glu Lys Asp Arg Tyr Leu Lys Thr Thr Ile Lys Leu Phe Lys
                 85                  90                  95
Arg Ile Asn Ser Asn Pro Ala Gly Lys Val Leu Leu Gln Glu Ile Ser
             100                 105                 110
Tyr Ala Lys Pro Tyr Leu Gly Asn Asp His Thr Pro Ile Asp Glu Phe
         115                 120                 125
Ser Pro Val Thr Arg Thr Thr Ser Val Asn Ile Lys Leu Ser Thr Asn
     130                 135                 140
Val Glu Ser Ser Met Leu Leu Asn Leu Val Leu Gly Ala Gly Pro
145                 150                 155                 160
Asp Ile Phe Glu Ser Cys Cys Tyr Pro Val Arg Lys Leu Ile Asp Pro
                 165                 170                 175
Asp Val Val Tyr Asp Pro Ser Asn Tyr Gly Phe Gly Ser Ile Asn Ile
             180                 185                 190
Val Thr Phe Ser Pro Glu Tyr Glu Tyr Thr Phe Asn Asp Ile Ser Gly
         195                 200                 205
Gly His Asn Ser Ser Thr Glu Ser Phe Ile Ala Asp Pro Ala Ile Ser
     210                 215                 220
Leu Ala His Glu Leu Ile His Ala Leu His Gly Leu Tyr Gly Ala Arg
225                 230                 235                 240
Gly Val Thr Tyr Glu Glu Thr Ile Glu Val Lys Gln Ala Pro Leu Met
                 245                 250                 255
Ile Ala Glu Lys Pro Ile Arg Leu Glu Glu Phe Leu Thr Phe Gly Gly
             260                 265                 270
Gln Asp Leu Asn Ile Ile Thr Ser Ala Met Lys Glu Lys Ile Tyr Asn
         275                 280                 285
Asn Leu Leu Ala Asn Tyr Glu Lys Ile Ala Thr Arg Leu Ser Glu Val
     290                 295                 300
Asn Ser Ala Pro Pro Glu Tyr Asp Ile Asn Glu Tyr Lys Asp Tyr Phe
305                 310                 315                 320
Gln Trp Lys Tyr Gly Leu Asp Lys Asn Ala Asp Gly Ser Tyr Thr Val
                 325                 330                 335
Asn Glu Asn Lys Phe Asn Glu Ile Tyr Lys Lys Leu Tyr Ser Phe Thr
             340                 345                 350
Glu Ser Asp Leu Ala Asn Lys Phe Lys Val Lys Cys Arg Asn Thr Tyr
         355                 360                 365
Phe Ile Lys Tyr Glu Phe Leu Lys Val Pro Asn Leu Leu Asp Asp Asp
     370                 375                 380
Ile Tyr Thr Val Ser Glu Gly Phe Asn Ile Gly Asn Leu Ala Val Asn
385                 390                 395                 400
Asn Arg Gly Gln Ser Ile Lys Leu Asn Pro Lys Ile Ile Asp Ser Ile
                 405                 410                 415
Pro Asp Lys Gly Leu Val Glu Lys Ile Val Lys Phe Cys Lys Ser Val
             420                 425                 430
Ile Pro Arg Lys Gly Thr Lys Ala Pro Pro Arg Leu Cys Ile Arg Val
         435                 440                 445
```

```
Asn Asn Ser Glu Leu Phe Phe Val Ala Ser Glu Ser Ser Tyr Asn Glu
450                 455                 460

Asn Asp Ile Asn Thr Pro Lys Glu Ile Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Gln Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
        515                 520                 525

Glu Glu Tyr Asp Val Val Asp Phe Asn Val Phe Phe Tyr Leu His Ala
530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
                565                 570                 575

Phe Ile Asp Thr Ile Asn Lys Pro Val Asn Ala Ala Leu Phe Ile Asp
            580                 585                 590

Trp Ile Ser Lys Val Ile Arg Asp Phe Thr Thr Glu Ala Thr Gln Lys
        595                 600                 605

Ser Thr Val Asp Lys Ile Ala Asp Ile Ser Leu Ile Val Pro Tyr Val
    610                 615                 620

Gly Leu Ala Leu Asn Ile Ile Glu Ala Glu Lys Gly Asn Phe Glu
625                 630                 635                 640

Glu Ala Phe Glu Leu Leu Gly Val Gly Ile Leu Leu Glu Phe Val Pro
                645                 650                 655

Glu Leu Thr Ile Pro Val Ile Leu Val Phe Thr Ile Lys Ser Tyr Ile
            660                 665                 670

Asp Ser Tyr Glu Asn Lys Asn Lys Ala Ile Lys Ala Ile Asn Asn Ser
        675                 680                 685

Leu Ile Glu Arg Glu Ala Lys Trp Lys Glu Ile Tyr Ser Trp Ile Val
    690                 695                 700

Ser Asn Trp Leu Thr Arg Ile Asn Thr Gln Phe Asn Lys Arg Lys Glu
705                 710                 715                 720

Gln Met Tyr Gln Ala Leu Gln Asn Gln Val Asp Ala Ile Lys Thr Ala
                725                 730                 735

Ile Glu Tyr Lys Tyr Asn Asn Tyr Thr Ser Asp Glu Lys Asn Arg Leu
            740                 745                 750

Glu Ser Glu Tyr Asn Ile Asn Asn Ile Glu Glu Glu Leu Asn Lys Lys
        755                 760                 765

Val Ser Leu Ala Met Lys Asn Ile Glu Arg Phe Met Thr Glu Ser Ser
770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
                805                 810                 815

Asp His Arg Ser Ile Leu Gly Glu Gln Thr Asn Glu Leu Ser Asp Leu
            820                 825                 830

Val Thr Ser Thr Leu Asn Ser Ser Ile Pro Phe Glu Leu Ser Ser Tyr
        835                 840                 845

Thr Asn Asp Lys Ile Leu Ile Ile Tyr Phe Asn Arg Leu Tyr Lys Lys
    850                 855                 860

Ile Lys Asp Ser Ser Ile Leu Asp Met Arg Tyr Glu Asn Asn Lys Phe
865                 870                 875                 880
```

Ile Asp Ile Ser Gly Tyr Gly Ser Asn Ile Ser Ile Asn Gly Asn Val
            885                 890                 895

Tyr Ile Tyr Ser Thr Asn Arg Asn Gln Phe Gly Ile Tyr Asn Ser Arg
            900                 905                 910

Leu Ser Glu Val Asn Ile Ala Gln Asn Asn Asp Ile Ile Tyr Asn Ser
            915                 920                 925

Arg Tyr Gln Asn Phe Ser Ile Ser Phe Trp Val Arg Ile Pro Lys His
            930                 935                 940

Tyr Lys Pro Met Asn His Asn Arg Glu Tyr Thr Ile Ile Asn Cys Met
945                 950                 955                 960

Gly Asn Asn Asn Ser Gly Trp Lys Ile Ser Leu Arg Thr Val Arg Asp
                965                 970                 975

Cys Glu Ile Ile Trp Thr Leu Gln Asp Thr Ser Gly Asn Lys Glu Asn
            980                 985                 990

Leu Ile Phe Arg Tyr Glu Glu Leu Asn Arg Ile Ser Asn Tyr Ile Asn
            995                 1000                1005

Lys Trp Ile Phe Val Thr Ile Thr Asn Asn Arg Leu Gly Asn Ser Arg
            1010                1015                1020

Ile Tyr Ile Asn Gly Asn Leu Ile Val Glu Lys Ser Ile Ser Asn Leu
1025                1030                1035                1040

Gly Asp Ile His Val Ser Asp Asn Ile Leu Phe Lys Ile Val Gly Cys
                1045                1050                1055

Asp Asp Glu Thr Tyr Val Gly Ile Arg Tyr Phe Lys Val Phe Asn Thr
            1060                1065                1070

Glu Leu Asp Lys Thr Glu Ile Glu Thr Leu Tyr Ser Asn Glu Pro Asp
            1075                1080                1085

Pro Ser Ile Leu Lys Asn Tyr Trp Gly Asn Tyr Leu Leu Tyr Asn Lys
            1090                1095                1100

Lys Tyr Tyr Leu Phe Asn Leu Leu Arg Lys Asp Lys Tyr Ile Thr Leu
1105                1110                1115                1120

Asn Ser Gly Ile Leu Asn Ile Asn Gln Gln Arg Gly Val Thr Glu Gly
            1125                1130                1135

Ser Val Phe Leu Asn Tyr Lys Leu Tyr Glu Gly Val Glu Val Ile Ile
            1140                1145                1150

Arg Lys Asn Gly Pro Ile Asp Ile Ser Asn Thr Asp Asn Phe Val Arg
            1155                1160                1165

Lys Asn Asp Leu Ala Tyr Ile Asn Val Val Asp Arg Gly Val Glu Tyr
            1170                1175                1180

Arg Leu Tyr Ala Asp Thr Lys Ser Glu Lys Glu Lys Ile Ile Arg Thr
1185                1190                1195                1200

Ser Asn Leu Asn Asp Ser Leu Gly Gln Ile Ile Val Met Asp Ser Ile
            1205                1210                1215

Gly Asn Asn Cys Thr Met Asn Phe Gln Asn Asn Asn Gly Ser Asn Ile
            1220                1225                1230

Gly Leu Leu Gly Phe His Ser Asn Asn Leu Val Ala Ser Ser Trp Tyr
            1235                1240                1245

Tyr Asn Asn Ile Arg Arg Asn Thr Ser Ser Asn Gly Cys Phe Trp Ser
            1250                1255                1260

Ser Ile Ser Lys Glu Asn Gly Trp Lys Glu
1265                1270

<210> SEQ ID NO 7
<211> LENGTH: 1297
<212> TYPE: PRT

<213> ORGANISM: Clostridium botulinum serotype G

<400> SEQUENCE: 7

```
Met Pro Val Asn Ile Lys Asn Phe Asn Tyr Asn Asp Pro Ile Asn Asn
1               5                   10                  15
Asp Asp Ile Ile Met Met Glu Pro Phe Asn Asp Pro Gly Pro Gly Thr
            20                  25                  30
Tyr Tyr Lys Ala Phe Arg Ile Ile Asp Arg Ile Trp Ile Val Pro Glu
        35                  40                  45
Arg Phe Thr Tyr Gly Phe Gln Pro Asp Gln Phe Asn Ala Ser Thr Gly
    50                  55                  60
Val Phe Ser Lys Asp Val Tyr Glu Tyr Tyr Asp Pro Thr Tyr Leu Lys
65                  70                  75                  80
Thr Asp Ala Glu Lys Asp Lys Phe Leu Lys Thr Met Ile Lys Leu Phe
                85                  90                  95
Asn Arg Ile Asn Ser Lys Pro Ser Gly Gln Arg Leu Leu Asp Met Ile
            100                 105                 110
Val Asp Ala Ile Pro Tyr Leu Gly Asn Ala Ser Thr Pro Pro Asp Lys
        115                 120                 125
Phe Ala Ala Asn Val Ala Asn Val Ser Ile Asn Lys Lys Ile Ile Gln
    130                 135                 140
Pro Gly Ala Glu Asp Gln Ile Lys Gly Leu Met Thr Asn Leu Ile Ile
145                 150                 155                 160
Phe Gly Pro Gly Pro Val Leu Ser Asp Asn Phe Thr Asp Ser Met Ile
                165                 170                 175
Met Asn Gly His Ser Pro Ile Ser Glu Gly Phe Gly Ala Arg Met Met
            180                 185                 190
Ile Arg Phe Cys Pro Ser Cys Leu Asn Val Phe Asn Asn Val Gln Glu
        195                 200                 205
Asn Lys Asp Thr Ser Ile Phe Ser Arg Arg Ala Tyr Phe Ala Asp Pro
    210                 215                 220
Ala Leu Thr Leu Met His Glu Leu Ile His Val Leu His Gly Leu Tyr
225                 230                 235                 240
Gly Ile Lys Ile Ser Asn Leu Pro Ile Thr Pro Asn Thr Lys Glu Phe
                245                 250                 255
Phe Met Gln His Ser Asp Pro Val Gln Ala Glu Glu Leu Tyr Thr Phe
            260                 265                 270
Gly Gly His Asp Pro Ser Val Ile Ser Pro Ser Thr Asp Met Asn Ile
        275                 280                 285
Tyr Asn Lys Ala Leu Gln Asn Phe Gln Asp Ile Ala Asn Arg Leu Asn
    290                 295                 300
Ile Val Ser Ser Ala Gln Gly Ser Gly Ile Asp Ile Ser Leu Tyr Lys
305                 310                 315                 320
Gln Ile Tyr Lys Asn Lys Tyr Asp Phe Val Glu Asp Pro Asn Gly Lys
                325                 330                 335
Tyr Ser Val Asp Lys Asp Lys Phe Asp Lys Leu Tyr Lys Ala Leu Met
            340                 345                 350
Phe Gly Phe Thr Glu Thr Asn Leu Ala Gly Glu Tyr Gly Ile Lys Thr
        355                 360                 365
Arg Tyr Ser Tyr Phe Ser Glu Tyr Leu Pro Pro Ile Lys Thr Glu Lys
    370                 375                 380
Leu Leu Asp Asn Thr Ile Tyr Thr Gln Asn Glu Gly Phe Asn Ile Ala
385                 390                 395                 400
Ser Lys Asn Leu Lys Thr Glu Phe Asn Gly Gln Asn Lys Ala Val Asn
```

```
                    405                 410                 415
Lys Glu Ala Tyr Glu Glu Ile Ser Leu Glu His Leu Val Ile Tyr Arg
                420                 425                 430

Ile Ala Met Cys Lys Pro Val Met Tyr Lys Asn Thr Gly Lys Ser Glu
            435                 440                 445

Gln Cys Ile Ile Val Asn Asn Glu Asp Leu Phe Phe Ile Ala Asn Lys
        450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
        515                 520                 525

Gln Ser Ala Leu Lys Lys Ile Phe Val Asp Gly Asp Ser Leu Phe Glu
    530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Lys Val Tyr Thr
                565                 570                 575

Phe Phe Ser Thr Asn Leu Val Glu Lys Ala Asn Thr Val Gly Ala
            580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
    610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
        675                 680                 685

Asn Ala Leu Lys Lys Arg Asp Gln Lys Trp Thr Asp Met Tyr Gly Leu
    690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
            740                 745                 750

Asn Ile Asn Ile Asp Phe Asn Asp Ile Asp Phe Lys Leu Asn Gln Ser
        755                 760                 765

Ile Asn Leu Ala Ile Asn Asn Ile Asp Asp Phe Ile Asn Gln Cys Ser
    770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
            820                 825                 830
```

```
Val Asn Arg His Leu Lys Asp Ser Ile Pro Phe Asp Leu Ser Leu Tyr
        835                 840                 845

Thr Lys Asp Thr Ile Leu Ile Gln Val Phe Asn Asn Tyr Ile Ser Asn
    850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
            885                 890                 895

Ile Phe Asn Asp Ile Gly Asn Gly Gln Phe Lys Leu Asn Asn Ser Glu
                900                 905                 910

Asn Ser Asn Ile Thr Ala His Gln Ser Lys Phe Val Val Tyr Asp Ser
            915                 920                 925

Met Phe Asp Asn Phe Ser Ile Asn Phe Trp Val Arg Thr Pro Lys Tyr
    930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp Asn Ile Ser Asp Tyr Ile Asn Lys
                995                 1000                1005

Trp Phe Ser Ile Thr Ile Thr Asn Asp Arg Leu Gly Asn Ala Asn Ile
    1010                1015                1020

Tyr Ile Asn Gly Ser Leu Lys Lys Ser Glu Lys Ile Leu Asn Leu Asp
1025                1030                1035                1040

Arg Ile Asn Ser Ser Asn Asp Ile Asp Phe Lys Leu Ile Asn Cys Thr
            1045                1050                1055

Asp Thr Thr Lys Phe Val Trp Ile Lys Asp Phe Asn Ile Phe Gly Arg
            1060                1065                1070

Glu Leu Asn Ala Thr Glu Val Ser Ser Leu Tyr Trp Ile Gln Ser Ser
    1075                1080                1085

Thr Asn Thr Leu Lys Asp Phe Trp Gly Asn Pro Leu Arg Tyr Asp Thr
    1090                1095                1100

Gln Tyr Tyr Leu Phe Asn Gln Gly Met Gln Asn Ile Tyr Ile Lys Tyr
1105                1110                1115                1120

Phe Ser Lys Ala Ser Met Gly Glu Thr Ala Pro Arg Thr Asn Phe Asn
            1125                1130                1135

Asn Ala Ala Ile Asn Tyr Gln Asn Leu Tyr Leu Gly Leu Arg Phe Ile
            1140                1145                1150

Ile Lys Lys Ala Ser Asn Ser Arg Asn Ile Asn Asn Asp Asn Ile Val
            1155                1160                1165

Arg Glu Gly Asp Tyr Ile Tyr Leu Asn Ile Asp Asn Ile Ser Asp Glu
    1170                1175                1180

Ser Tyr Arg Val Tyr Val Leu Val Asn Ser Lys Glu Ile Gln Thr Gln
1185                1190                1195                1200

Leu Phe Leu Ala Pro Ile Asn Asp Asp Pro Thr Phe Tyr Asp Val Leu
            1205                1210                1215

Gln Ile Lys Lys Tyr Tyr Glu Lys Thr Thr Tyr Asn Cys Gln Ile Leu
            1220                1225                1230

Cys Glu Lys Asp Thr Lys Thr Phe Gly Leu Phe Gly Ile Gly Lys Phe
            1235                1240                1245

Val Lys Asp Tyr Gly Tyr Val Trp Asp Thr Tyr Asp Asn Tyr Phe Cys
1250                1255                1260
```

```
Ile Ser Gln Trp Tyr Leu Arg Arg Ile Ser Glu Asn Ile Asn Lys Leu
1265                1270                1275                1280

Arg Leu Gly Cys Asn Trp Gln Phe Ile Pro Val Asp Glu Gly Trp Thr
                1285                1290                1295

Glu

<210> SEQ ID NO 8
<211> LENGTH: 1315
<212> TYPE: PRT
<213> ORGANISM: Clostridium teteni

<400> SEQUENCE: 8

Met Pro Ile Thr Ile Asn Asn Phe Arg Tyr Ser Asp Pro Val Asn Asn
 1               5                  10                  15

Asp Thr Ile Ile Met Met Glu Pro Pro Tyr Cys Lys Gly Leu Asp Ile
                20                  25                  30

Tyr Tyr Lys Ala Phe Lys Ile Thr Asp Arg Ile Trp Ile Val Pro Glu
            35                  40                  45

Arg Tyr Glu Phe Gly Thr Lys Pro Glu Asp Phe Asn Pro Pro Ser Ser
 50                  55                  60

Leu Ile Glu Gly Ala Ser Glu Tyr Tyr Asp Pro Asn Tyr Leu Arg Thr
 65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335
```

```
Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
            355                 360                 365

Ile Lys Thr Arg Leu Ser Tyr Phe Ser Met Asn His Asp Pro Val Lys
            370                 375             380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
            450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
            530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
            595                 600                 605

Gly Ile Leu Phe Leu Gln Trp Val Arg Asp Ile Ile Asp Asp Phe Thr
            610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
            675                 680                 685

Ser Ile Ala Glu Ser Ser Thr Gln Lys Glu Lys Ile Ile Lys Thr Ile
            690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
            755                 760                 765
```

```
Glu Gln Ile Ala Asp Glu Ile Asn Asn Leu Lys Asn Lys Leu Glu Glu
            770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
            835                 840                 845

Ser Lys Ile Asn Lys Val Phe Ser Thr Pro Ile Pro Phe Ser Tyr Ser
    850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
            915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu Ile Trp Thr Leu Lys Asp Ser Ala
            995                 1000                1005

Gly Glu Val Arg Gln Ile Thr Phe Arg Asp Leu Pro Asp Lys Phe Asn
    1010                1015                1020

Ala Tyr Leu Ala Asn Lys Trp Val Phe Ile Thr Ile Thr Asn Asp Arg
1025                1030                1035                1040

Leu Ser Ser Ala Asn Leu Tyr Ile Asn Gly Val Leu Met Gly Ser Ala
                1045                1050                1055

Glu Ile Thr Gly Leu Gly Ala Ile Arg Glu Asp Asn Asn Ile Thr Leu
            1060                1065                1070

Lys Leu Asp Arg Cys Asn Asn Asn Asn Gln Tyr Val Ser Ile Asp Lys
            1075                1080                1085

Phe Arg Ile Phe Cys Lys Ala Leu Asn Pro Lys Glu Ile Glu Lys Leu
    1090                1095                1100

Tyr Thr Ser Tyr Leu Ser Ile Thr Phe Leu Arg Asp Phe Trp Gly Asn
1105                1110                1115                1120

Pro Leu Arg Tyr Asp Thr Glu Tyr Tyr Leu Ile Pro Val Ala Ser Ser
                1125                1130                1135

Ser Lys Asp Val Gln Leu Lys Asn Ile Thr Asp Tyr Met Tyr Leu Thr
            1140                1145                1150

Asn Ala Pro Ser Tyr Thr Asn Gly Lys Leu Asn Ile Tyr Tyr Arg Arg
            1155                1160                1165

Leu Tyr Asn Gly Leu Lys Phe Ile Ile Lys Arg Tyr Thr Pro Asn Asn
    1170                1175                1180

Glu Ile Asp Ser Phe Val Lys Ser Gly Asp Phe Ile Lys Leu Tyr Val
```

```
                  1185                1190                1195                1200
Ser Tyr Asn Asn Glu His Ile Val Gly Tyr Pro Lys Asp Gly Asn
                1205                1210                1215

Ala Phe Asn Asn Leu Asp Arg Ile Leu Arg Val Gly Tyr Asn Ala Pro
            1220                1225                1230

Gly Ile Pro Leu Tyr Lys Lys Met Glu Ala Val Lys Leu Arg Asp Leu
        1235                1240                1245

Lys Thr Tyr Ser Val Gln Leu Lys Leu Tyr Asp Lys Asn Ala Ser
    1250                1255                1260

Leu Gly Leu Val Gly Thr His Asn Gly Gln Ile Gly Asn Asp Pro Asn
1265                1270                1275                1280

Arg Asp Ile Leu Ile Ala Ser Asn Trp Tyr Phe Asn His Leu Lys Asp
                1285                1290                1295

Lys Ile Leu Gly Cys Asp Trp Tyr Phe Val Pro Thr Asp Glu Gly Trp
            1300                1305                1310

Thr Asn Asp
        1315
```

<210> SEQ ID NO 9
<211> LENGTH: 1268
<212> TYPE: PRT
<213> ORGANISM: Clostridium baratii

<400> SEQUENCE: 9

```
Met Pro Val Asn Ile Asn Asn Phe Asn Tyr Asn Asp Pro Ile Asn Asn
 1                5                  10                  15

Thr Thr Ile Leu Tyr Met Lys Met Pro Tyr Tyr Glu Asp Ser Asn Lys
                20                  25                  30

Tyr Tyr Lys Ala Phe Glu Ile Met Asp Asn Val Trp Ile Ile Pro Glu
            35                  40                  45

Arg Asn Ile Ile Gly Lys Lys Pro Ser Asp Phe Tyr Pro Pro Ile Ser
        50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95

Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
        115                 120                 125

Cys Ala Asn Asn Arg Ser Thr Ser Val Glu Ile Lys Glu Ser Asn Gly
    130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
        195                 200                 205

Phe Ile Ala Asp Pro Ala Ile Ser Leu Ala His Glu Leu Ile His Val
    210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
```

```
            245                 250                 255
Glu Glu Phe Ile Thr Phe Gly Gly Gln Asp Leu Asn Ile Ile Thr Asn
            260                 265                 270

Ser Thr Asn Gln Lys Ile Tyr Val Ile Leu Leu Ser Asn Tyr Thr Ala
        275                 280                 285

Ile Ala Ser Arg Leu Ser Gln Val Asn Arg Asn Asn Ser Ala Leu Asn
    290                 295                 300

Thr Thr Tyr Tyr Lys Asn Phe Phe Gln Trp Lys Tyr Gly Leu Asp Gln
305                 310                 315                 320

Asp Ser Asn Gly Asn Tyr Thr Val Asn Ile Ser Lys Phe Asn Ala Ile
                325                 330                 335

Tyr Lys Lys Leu Phe Ser Phe Thr Glu Cys Asp Leu Ala Gln Lys Phe
                    340                 345                 350

Gln Val Lys Asn Arg Ser Asn Tyr Leu Phe His Phe Lys Pro Phe Arg
                355                 360                 365

Leu Leu Asp Leu Asp Asp Asn Ile Tyr Ser Ile Ser Glu Gly Phe
            370                 375                 380

Asn Ile Gly Ser Leu Arg Val Asn Asn Asn Gly Gln Asn Ile Asn Leu
385                 390                 395                 400

Asn Ser Arg Ile Val Gly Pro Ile Pro Asp Asn Gly Leu Val Glu Arg
                    405                 410                 415

Phe Val Gly Leu Cys Lys Ser Ile Val Ser Lys Lys Gly Thr Lys Asn
                420                 425                 430

Ser Leu Cys Ile Lys Val Asn Asn Arg Asp Leu Phe Phe Val Ala Ser
            435                 440                 445

Glu Ser Ser Tyr Asn Glu Asn Gly Ile Asn Ser Pro Lys Glu Ile Asp
        450                 455                 460

Asp Thr Thr Ile Thr Asn Asn Tyr Lys Lys Asn Leu Asp Glu Val
465                 470                 475                 480

Ile Leu Asp Tyr Asn Ser Asp Ala Ile Pro Asn Leu Ser Ser Arg Leu
                485                 490                 495

Leu Asn Thr Thr Ala Gln Asn Asp Ser Tyr Val Pro Lys Tyr Asp Ser
            500                 505                 510

Asn Gly Thr Ser Glu Ile Lys Glu Tyr Thr Val Asp Lys Leu Asn Val
        515                 520                 525

Phe Phe Tyr Leu Tyr Ala Gln Lys Ala Pro Glu Gly Glu Ser Ala Ile
    530                 535                 540

Ser Leu Thr Ser Ser Val Asn Thr Ala Leu Leu Asp Ala Ser Lys Val
545                 550                 555                 560

Tyr Thr Phe Phe Ser Ser Asp Phe Ile Asn Thr Val Asn Lys Pro Val
                565                 570                 575

Gln Ala Ala Leu Phe Ile Ser Trp Ile Gln Gln Val Ile Asn Asp Phe
                580                 585                 590

Thr Thr Glu Ala Thr Gln Lys Ser Thr Ile Asp Lys Ile Ala Asp Ile
            595                 600                 605

Ser Leu Ile Val Pro Tyr Val Gly Leu Ala Leu Asn Ile Gly Asn Glu
        610                 615                 620

Val Gln Lys Gly Asn Phe Lys Glu Ala Ile Glu Leu Leu Gly Ala Gly
625                 630                 635                 640

Ile Leu Leu Glu Phe Val Pro Glu Leu Leu Ile Pro Thr Ile Leu Val
                645                 650                 655

Phe Thr Ile Lys Ser Phe Ile Asn Ser Asp Asp Ser Lys Asn Lys Ile
            660                 665                 670
```

```
Ile Lys Ala Ile Asn Asn Ala Leu Arg Glu Arg Glu Leu Lys Trp Lys
    675                 680                 685

Glu Val Tyr Ser Trp Ile Val Ser Asn Trp Leu Thr Arg Ile Asn Thr
    690                 695                 700

Gln Phe Asn Lys Arg Lys Glu Gln Met Tyr Gln Ala Leu Gln Asn Gln
705                 710                 715                 720

Val Asp Gly Ile Lys Lys Ile Glu Tyr Lys Tyr Asn Asn Tyr Thr
                725                 730                 735

Leu Asp Glu Lys Asn Arg Leu Arg Ala Glu Tyr Asn Ile Tyr Ser Ile
                740                 745                 750

Lys Glu Glu Leu Asn Lys Lys Val Ser Leu Ala Met Gln Asn Ile Asp
            755                 760                 765

Arg Phe Leu Thr Glu Ser Ser Ile Ser Tyr Leu Met Lys Leu Ile Asn
770                 775                 780

Glu Ala Lys Ile Asn Lys Leu Ser Glu Tyr Asp Lys Arg Val Asn Gln
785                 790                 795                 800

Tyr Leu Leu Asn Tyr Ile Leu Glu Asn Ser Ser Thr Leu Gly Thr Ser
                805                 810                 815

Ser Val Pro Glu Leu Asn Asn Leu Val Ser Asn Thr Leu Asn Asn Ser
            820                 825                 830

Ile Pro Phe Glu Leu Ser Glu Tyr Thr Asn Asp Lys Ile Leu Ile His
        835                 840                 845

Ile Leu Ile Arg Phe Tyr Lys Arg Ile Ile Asp Ser Ser Ile Leu Asn
850                 855                 860

Met Lys Tyr Glu Asn Asn Arg Phe Ile Asp Ser Ser Gly Tyr Gly Ser
865                 870                 875                 880

Asn Ile Ser Ile Asn Gly Asp Ile Tyr Ile Tyr Ser Thr Asn Arg Asn
                885                 890                 895

Gln Phe Gly Ile Tyr Ser Ser Arg Leu Ser Glu Val Asn Ile Thr Gln
                900                 905                 910

Asn Asn Thr Ile Ile Tyr Asn Ser Arg Tyr Gln Asn Phe Ser Val Ser
        915                 920                 925

Phe Trp Val Arg Ile Pro Lys Tyr Asn Asn Leu Lys Asn Leu Asn Asn
    930                 935                 940

Glu Tyr Thr Ile Ile Asn Cys Met Arg Asn Asn Asn Ser Gly Trp Lys
945                 950                 955                 960

Ile Ser Leu Asn Tyr Asn Asn Ile Ile Trp Thr Leu Gln Asp Thr Thr
                965                 970                 975

Gly Asn Asn Gln Lys Leu Val Phe Asn Tyr Thr Gln Met Ile Asp Ile
            980                 985                 990

Ser Asp Tyr Ile Asn Lys Trp Thr Phe Val Thr Ile Thr Asn Asn Arg
            995                 1000                1005

Leu Gly His Ser Lys Leu Tyr Ile Asn Gly Asn Leu Thr Asp Gln Lys
    1010                1015                1020

Ser Ile Leu Asn Leu Gly Asn Ile His Val Asp Asp Asn Ile Leu Phe
1025                1030                1035                1040

Lys Ile Val Gly Cys Asn Asp Thr Arg Tyr Val Gly Ile Arg Tyr Phe
                1045                1050                1055

Lys Ile Phe Asn Met Glu Leu Asp Lys Thr Glu Ile Glu Thr Leu Tyr
            1060                1065                1070

His Ser Glu Pro Asp Ser Thr Ile Leu Lys Asp Phe Trp Gly Asn Tyr
        1075                1080                1085

Leu Leu Tyr Asn Lys Lys Tyr Tyr Leu Leu Asn Leu Leu Lys Pro Asn
    1090                1095                1100
```

```
Met Ser Val Thr Lys Asn Ser Asp Ile Leu Asn Ile Asn Arg Gln Arg
1105                1110                1115                1120

Gly Ile Tyr Ser Lys Thr Asn Ile Phe Ser Asn Ala Arg Leu Tyr Thr
                1125                1130                1135

Gly Val Glu Val Ile Ile Arg Lys Val Gly Ser Thr Thr Ser Asn
            1140                1145                1150

Thr Asp Asn Phe Val Arg Lys Asn Asp Thr Val Tyr Ile Asn Val Val
            1155                1160                1165

Asp Gly Asn Ser Glu Tyr Gln Leu Tyr Ala Asp Val Ser Thr Ser Ala
            1170                1175                1180

Val Glu Lys Thr Ile Lys Leu Arg Arg Ile Ser Asn Ser Asn Tyr Asn
1185                1190                1195                1200

Ser Asn Gln Met Ile Ile Met Asp Ser Ile Gly Asp Asn Cys Thr Met
                1205                1210                1215

Asn Phe Lys Thr Asn Asn Gly Asn Asp Ile Gly Leu Leu Gly Phe His
                1220                1225                1230

Leu Asn Asn Leu Val Ala Ser Ser Trp Tyr Tyr Lys Asn Ile Arg Asn
                1235                1240                1245

Asn Thr Arg Asn Asn Gly Cys Phe Trp Ser Phe Ile Ser Lys Glu His
                1250                1255                1260

Gly Trp Gln Glu
1265

<210> SEQ ID NO 10
<211> LENGTH: 1251
<212> TYPE: PRT
<213> ORGANISM: Clostridium butyricum

<400> SEQUENCE: 10

Met Pro Thr Ile Asn Ser Phe Asn Tyr Asn Asp Pro Val Asn Asn Arg
1               5                   10                  15

Thr Ile Leu Tyr Ile Lys Pro Gly Gly Cys Gln Gln Phe Tyr Lys Ser
            20                  25                  30

Phe Asn Ile Met Lys Asn Ile Trp Ile Ile Pro Glu Arg Asn Val Ile
        35                  40                  45

Gly Thr Ile Pro Gln Asp Phe Leu Pro Pro Thr Ser Leu Lys Asn Gly
    50                  55                  60

Asp Ser Ser Tyr Tyr Asp Pro Asn Tyr Leu Gln Ser Asp Gln Glu Lys
65                  70                  75                  80

Asp Lys Phe Leu Lys Ile Val Thr Lys Ile Phe Asn Arg Ile Asn Asp
                85                  90                  95

Asn Leu Ser Gly Arg Ile Leu Leu Glu Glu Leu Ser Lys Ala Asn Pro
            100                 105                 110

Tyr Leu Gly Asn Asp Asn Thr Pro Asp Gly Asp Phe Ile Ile Asn Asp
        115                 120                 125

Ala Ser Ala Val Pro Ile Gln Phe Ser Asn Gly Ser Gln Ser Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Lys Asp Asn Ser Met Asn Glu Phe Ile Gln Asp Pro Ala Leu
        195                 200                 205
```

```
Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Gly Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
```

-continued

```
            625                 630                 635                 640
Leu Ile Pro Thr Ile Leu Val Phe Thr Ile Lys Ser Phe Leu Gly Ser
                    645                 650                 655
Ser Asp Asn Lys Asn Lys Val Ile Lys Ala Ile Asn Asn Ala Leu Lys
                660                 665                 670
Glu Arg Asp Glu Lys Trp Lys Glu Val Tyr Ser Phe Ile Val Ser Asn
            675                 680                 685
Trp Met Thr Lys Ile Asn Thr Gln Phe Asn Lys Arg Lys Glu Gln Met
        690                 695                 700
Tyr Gln Ala Leu Gln Asn Gln Val Asn Ala Leu Lys Ala Ile Ile Glu
705                 710                 715                 720
Ser Lys Tyr Asn Ser Tyr Thr Leu Glu Glu Lys Asn Glu Leu Thr Asn
                    725                 730                 735
Lys Tyr Asp Ile Glu Gln Ile Glu Asn Glu Leu Asn Gln Lys Val Ser
                740                 745                 750
Ile Ala Met Asn Asn Ile Asp Arg Phe Leu Thr Glu Ser Ser Ile Ser
            755                 760                 765
Tyr Leu Met Lys Leu Ile Asn Glu Val Lys Ile Asn Lys Leu Arg Glu
        770                 775                 780
Tyr Asp Glu Asn Val Lys Thr Tyr Leu Leu Asp Tyr Ile Ile Lys His
785                 790                 795                 800
Gly Ser Ile Leu Gly Glu Ser Gln Gln Glu Leu Asn Ser Met Val Ile
                    805                 810                 815
Asp Thr Leu Asn Asn Ser Ile Pro Phe Lys Leu Ser Ser Tyr Thr Asp
                820                 825                 830
Asp Lys Ile Leu Ile Ser Tyr Phe Asn Lys Phe Phe Lys Arg Ile Lys
            835                 840                 845
Ser Ser Ser Val Leu Asn Met Arg Tyr Lys Asn Asp Lys Tyr Val Asp
        850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
                    885                 890                 895
Glu Val Asn Ile Ser Gln Asn Asp Tyr Ile Ile Tyr Asp Asn Lys Tyr
                900                 905                 910
Lys Asn Phe Ser Ile Ser Phe Trp Val Arg Ile Pro Asn Tyr Asp Asn
            915                 920                 925
Lys Ile Val Asn Val Asn Asn Glu Tyr Thr Ile Ile Asn Cys Met Arg
        930                 935                 940
Asp Asn Asn Ser Gly Trp Lys Val Ser Leu Asn His Asn Glu Ile Ile
945                 950                 955                 960
Trp Thr Leu Gln Asp Asn Ser Gly Ile Asn Gln Lys Leu Ala Phe Asn
                    965                 970                 975
Tyr Gly Asn Ala Asn Gly Ile Ser Asp Tyr Ile Asn Lys Trp Ile Phe
                980                 985                 990
Val Thr Ile Thr Asn Asp Arg Leu Gly Asp Ser Lys Leu Tyr Ile Asn
            995                 1000                1005
Gly Asn Leu Ile Asp Lys Lys Ser Ile Leu Asn Leu Gly Asn Ile His
        1010                1015                1020
Val Ser Asp Asn Ile Leu Phe Lys Ile Val Asn Cys Ser Tyr Thr Arg
1025                1030                1035                1040
Tyr Ile Gly Ile Arg Tyr Phe Asn Ile Phe Asp Lys Glu Leu Asp Glu
                    1045                1050                1055
```

-continued

Thr Glu Ile Gln Thr Leu Tyr Asn Asn Glu Pro Asn Ala Asn Ile Leu
              1060                1065                1070

Lys Asp Phe Trp Gly Asn Tyr Leu Leu Tyr Asp Lys Glu Tyr Tyr Leu
         1075                1080                1085

Leu Asn Val Leu Lys Pro Asn Asn Phe Ile Asn Arg Arg Thr Asp Ser
    1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
             1125                1130                1135

Thr Asn Asp Asn Leu Val Arg Lys Asn Asp Gln Val Tyr Ile Asn Phe
              1140                1145                1150

Val Ala Ser Lys Thr His Leu Leu Pro Leu Tyr Ala Asp Thr Ala Thr
              1155                1160                1165

Thr Asn Lys Glu Lys Thr Ile Lys Ile Ser Ser Ser Gly Asn Arg Phe
    1170                1175                1180

Asn Gln Val Val Val Met Asn Ser Val Gly Asn Cys Thr Met Asn Phe
1185                1190                1195                1200

Lys Asn Asn Asn Gly Asn Asn Ile Gly Leu Leu Gly Phe Lys Ala Asp
             1205                1210                1215

Thr Val Val Ala Ser Thr Trp Tyr Tyr Thr His Met Arg Asp Asn Thr
             1220                1225                1230

Asn Ser Asn Gly Phe Phe Trp Asn Phe Ile Ser Glu Glu His Gly Trp
         1235                1240                1245

Gln Glu Lys
    1250

<210> SEQ ID NO 11
<211> LENGTH: 25
<212> TYPE: PRT
<213> ORGANISM: Artificial Sequence
<220> FEATURE:
<223> OTHER INFORMATION: BoNT/A di-chain loop region

<400> SEQUENCE: 11

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25

<210> SEQ ID NO 12
<211> LENGTH: 10
<212> TYPE: PRT
<213> ORGANISM: Artificial Sequence
<220> FEATURE:
<223> OTHER INFORMATION: BoNT/B di-chain loop region

<400> SEQUENCE: 12

Cys Lys Ser Val Lys Ala Pro Gly Ile Cys
1               5                   10

<210> SEQ ID NO 13
<211> LENGTH: 17
<212> TYPE: PRT
<213> ORGANISM: Artificial Sequence
<220> FEATURE:
<223> OTHER INFORMATION: BoNT/C1 di-chain loop region

<400> SEQUENCE: 13

Cys His Lys Ala Ile Asp Gly Arg Ser Leu Tyr Asn Lys Thr Leu Asp
1               5                   10                  15

Cys

<210> SEQ ID NO 14
<211> LENGTH: 14
<212> TYPE: PRT
<213> ORGANISM: Artificial Sequence
<220> FEATURE:
<223> OTHER INFORMATION: BoNT/D di-chain loop region

<400> SEQUENCE: 14

Cys Leu Arg Leu Thr Lys Asn Ser Arg Asp Asp Ser Thr Cys
1 5 10

<210> SEQ ID NO 15
<211> LENGTH: 15
<212> TYPE: PRT
<213> ORGANISM: Artificial Sequence
<220> FEATURE:
<223> OTHER INFORMATION: BoNT/E di-chain loop region

<400> SEQUENCE: 15

Cys Lys Asn Ile Val Ser Val Lys Gly Ile Arg Lys Ser Ile Cys
1 5 10 15

<210> SEQ ID NO 16
<211> LENGTH: 17
<212> TYPE: PRT
<213> ORGANISM: Artificial Sequence
<220> FEATURE:
<223> OTHER INFORMATION: BoNT/F di-chain loop region

<400> SEQUENCE: 16

Cys Lys Ser Val Ile Pro Arg Lys Gly Thr Lys Ala Pro Pro Arg Leu
1 5 10 15

Cys

<210> SEQ ID NO 17
<211> LENGTH: 15
<212> TYPE: PRT
<213> ORGANISM: Artificial Sequence
<220> FEATURE:
<223> OTHER INFORMATION: BoNT/G di-chain loop region

<400> SEQUENCE: 17

Cys Lys Pro Val Met Tyr Lys Asn Thr Gly Lys Ser Glu Gln Cys
1 5 10 15

<210> SEQ ID NO 18
<211> LENGTH: 29
<212> TYPE: PRT
<213> ORGANISM: Artificial Sequence
<220> FEATURE:
<223> OTHER INFORMATION: TeNT di-chain loop region

<400> SEQUENCE: 18

Cys Lys Lys Ile Ile Pro Pro Thr Asn Ile Arg Glu Asn Leu Tyr Asn
1 5 10 15

Arg Thr Ala Ser Leu Thr Asp Leu Gly Gly Glu Leu Cys
20 25

<210> SEQ ID NO 19
<211> LENGTH: 15
<212> TYPE: PRT
<213> ORGANISM: Artificial Sequence
<220> FEATURE:
<223> OTHER INFORMATION: BaNT di-chain loop region

```
<400> SEQUENCE: 19

Cys Lys Ser Ile Val Ser Lys Gly Thr Lys Asn Ser Leu Cys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: BuNT di-chain loop region

<400> SEQUENCE: 20

Cys Lys Asn Ile Val Ser Val Lys Gly Ile Arg Lys Ser Ile Cys
1               5                   10                  15

<210> SEQ ID NO 21
<211> LENGTH: 5
<212> TYPE: PRT
<213> ORGANISM: Artificial Sequence
<220> FEATURE:
<223> OTHER INFORMATION: G-spacer

<400> SEQUENCE: 21

Gly Gly Gly Gly Ser
1               5

<210> SEQ ID NO 22
<211> LENGTH: 5
<212> TYPE: PRT
<213> ORGANISM: Artificial Sequence
<220> FEATURE:
<223> OTHER INFORMATION: A-spacer

<400> SEQUENCE: 22

Glu Ala Ala Ala Lys
1               5

<210> SEQ ID NO 23
<211> LENGTH: 8
<212> TYPE: PRT
<213> ORGANISM: Artificial Sequence
<220> FEATURE:
<223> OTHER INFORMATION: FLAG epitope-binding region

<400> SEQUENCE: 23

Asp Tyr Lys Asp Asp Asp Asp Lys
1               5

<210> SEQ ID NO 24
<211> LENGTH: 9
<212> TYPE: PRT
<213> ORGANISM: Artificial Sequence
<220> FEATURE:
<223> OTHER INFORMATION: Human Influenza virus hemagluttinin (HA)
      epitope-binding region

<400> SEQUENCE: 24

Tyr Pro Tyr Asp Val Pro Asp Tyr Ala
1               5

<210> SEQ ID NO 25
<211> LENGTH: 10
<212> TYPE: PRT
<213> ORGANISM: Artificial Sequence
<220> FEATURE:
<223> OTHER INFORMATION: Human p62 c-Myc epitope-binding region
```

```
<400> SEQUENCE: 25

Glu Gln Lys Leu Ile Ser Glu Glu Asp Leu
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Vesicular Stomatitis Virus Glycoprotein (VSV-G)
      epitope-binding region

<400> SEQUENCE: 26

Tyr Thr Asp Ile Glu Met Asn Arg Leu Gly Lys
1               5                   10

<210> SEQ ID NO 27
<211> LENGTH: 6
<212> TYPE: PRT
<213> ORGANISM: Artificial Sequence
<220> FEATURE:
<223> OTHER INFORMATION: Substance P epitope-binding region

<400> SEQUENCE: 27

Gln Phe Phe Gly Leu Met
1               5

<210> SEQ ID NO 28
<211> LENGTH: 11
<212> TYPE: PRT
<213> ORGANISM: Artificial Sequence
<220> FEATURE:
<223> OTHER INFORMATION: Glycoprotein-D precursor of Herpes simplex
      virus epitope-binding region

<400> SEQUENCE: 28

Gln Pro Glu Leu Ala Pro Glu Asp Pro Glu Asp
1               5                   10

<210> SEQ ID NO 29
<211> LENGTH: 14
<212> TYPE: PRT
<213> ORGANISM: Artificial Sequence
<220> FEATURE:
<223> OTHER INFORMATION: V5 epitope-binding region

<400> SEQUENCE: 29

Gly Lys Pro Ile Pro Asn Pro Leu Leu Gly Leu Asp Ser Thr
1               5                   10

<210> SEQ ID NO 30
<211> LENGTH: 6
<212> TYPE: PRT
<213> ORGANISM: Artificial Sequence
<220> FEATURE:
<223> OTHER INFORMATION: AU1 epitope-binding region

<400> SEQUENCE: 30

Asp Thr Tyr Arg Tyr Ile
1               5

<210> SEQ ID NO 31
<211> LENGTH: 6
<212> TYPE: PRT
<213> ORGANISM: Artificial Sequence
<220> FEATURE:
<223> OTHER INFORMATION: AU5 epitope-binding region
```

-continued

<400> SEQUENCE: 31

Thr Asp Phe Tyr Leu Lys
1               5

<210> SEQ ID NO 32
<211> LENGTH: 6
<212> TYPE: PRT
<213> ORGANISM: Artificial Sequence
<220> FEATURE:
<223> OTHER INFORMATION: HIS epitope-binding region

<400> SEQUENCE: 32

His His His His His His
1               5

<210> SEQ ID NO 33
<211> LENGTH: 527
<212> TYPE: PRT
<213> ORGANISM: Clostridium botulinum serotype A

<400> SEQUENCE: 33

Met Tyr Ile Met Leu Lys Asn Lys Leu Ser Ile Leu Leu Thr Ser Thr
1               5                   10                  15

Leu Val Ala Ala Ser Leu Leu Ser Phe Lys Pro Val Tyr Ala Asp Ser
                20                  25                  30

Val Asn Asn Ser Asn Lys Thr Asn Leu Asn Asn Val Arg Gln Glu Ile
            35                  40                  45

Gln Lys Ala Lys Asn Asn Asn Gln Lys Val Thr Ile Met Tyr Tyr Cys
        50                  55                  60

Asp Ala Asp Asn Asn Leu Glu Ser Ser Leu Leu Ser Asp Ile Glu Glu
65                  70                  75                  80

Met Lys Lys Gly Tyr Val Asn Pro Asn Leu Asn Leu Val Thr Leu
                85                  90                  95

Ile Asp Arg Ser Ser Arg Tyr Thr Ser Asp Lys Thr Val Phe Gly Glu
            100                 105                 110

Asp Phe Glu Asp Ala Arg Leu Tyr Lys Ile Glu His Asn Lys Thr Lys
        115                 120                 125

Arg Leu Asp Gly Gly Lys Glu Phe Pro Glu Ile Thr Leu Asn Ser Asn
130                 135                 140

Tyr Glu Ala Asn Met Gly Asp Ala Asp Thr Leu Lys Lys Phe Ile Asn
145                 150                 155                 160

Tyr Cys Lys Ala Asn Tyr Lys Ala Asp Lys Tyr Val Leu Ile Met Ala
                165                 170                 175

Asn His Gly Gly Gly Ala Lys Glu Lys Leu Lys Asn Asn Gln Asp Val
            180                 185                 190

Asn Arg Ala Ile Cys Trp Asp Ser His Tyr Asp Gly Asn Ser Pro
        195                 200                 205

Asp Cys Leu Tyr Met Gly Glu Ile Ser Asp Thr Leu Thr Gln Glu Gln
    210                 215                 220

Ser Val Asp Val Leu Ala Phe Asp Ala Cys Leu Met Gly Thr Ala Glu
225                 230                 235                 240

Val Ala Tyr Gln Phe Arg Pro Gly Asn Gly Gly Phe Ser Ala Asp Gly
                245                 250                 255

Ile Val Ala Ser Ser Pro Val Val Trp Gly Pro Gly Phe Gln Tyr Asp
            260                 265                 270

Asn Ile Leu Ser Arg Leu Lys Ser Gly Gly Ser Asn Glu Asp
        275                 280                 285

```
Asp Leu Thr Leu Gly Gly Lys Glu Lys Asn Phe Asp Pro Ala Thr Ile
    290                 295                 300

Thr Asn Glu Gln Leu Gly Ala Leu Phe Val Glu Gln Arg Asp Ser
305                 310                 315                 320

Thr His Ala Arg Gly Ser Tyr Asp Gln His Leu Ser Phe Tyr Asp Ala
                325                 330                 335

Ala Lys Val Glu Asp Val Lys Arg Ser Ile Asp Asn Leu Ala Ile Asn
            340                 345                 350

Leu Ser Asn Glu Asn Lys Lys Asp Gly Ile Glu Lys Leu Arg Gly Ser
        355                 360                 365

Lys Asn Asn Thr Asn Leu Met His Tyr Phe Asp Glu Tyr Asn Glu Gln
    370                 375                 380

Glu Trp Ile Glu Tyr Pro Tyr Phe Asp Ile Tyr Asp Leu Cys Glu Lys
385                 390                 395                 400

Ile Asn Glu Ser Asn Asn Phe Ser Asn Glu Thr Arg Thr Leu Ala Ser
                405                 410                 415

Ile Cys Met Asp Lys Ile Asp Glu Met Val Val Tyr Ser Phe Gly Gly
            420                 425                 430

Pro Ser Lys Glu Phe Lys Glu Gly Lys Asn Gly Leu Ser Ile Phe Leu
        435                 440                 445

Pro Asp Gly Asp Lys Lys Tyr Ser Asn Tyr Tyr Asn Ser Ile Pro His
    450                 455                 460

Trp Thr Ile Gln Ser Trp Tyr Asn Ser Ile Asp Thr Val Gln Asn Gly
465                 470                 475                 480

Leu Pro Pro Tyr Gly Lys Leu Thr Trp Cys Gln Asp Gly Gln Asp Pro
                485                 490                 495

Arg Val Asn Lys Val Gly Asn Trp Phe Glu Leu Leu Asp Ser Trp Phe
            500                 505                 510

Asp Lys Thr Asn Gly Ala Asp Gly Gly Val Asn His Tyr Gln Trp
        515                 520                 525

<210> SEQ ID NO 34
<211> LENGTH: 526
<212> TYPE: PRT
<213> ORGANISM: Clostridium histolyticum

<400> SEQUENCE: 34

Met Leu Arg Arg Lys Val Ser Thr Leu Leu Met Thr Ala Leu Ile Thr
1               5                   10                  15

Thr Ser Phe Leu Asn Ser Lys Pro Val Tyr Ala Asn Pro Val Thr Lys
            20                  25                  30

Ser Lys Asp Asn Asn Leu Lys Glu Val Gln Gln Val Thr Ser Lys Ser
        35                  40                  45

Asn Lys Asn Lys Asn Gln Lys Val Thr Ile Met Tyr Tyr Cys Asp Ala
    50                  55                  60

Asp Asn Asn Leu Glu Gly Ser Leu Leu Asn Asp Ile Glu Glu Met Lys
65                  70                  75                  80

Thr Gly Tyr Lys Asp Ser Pro Asn Leu Asn Leu Ile Ala Leu Val Asp
                85                  90                  95

Arg Ser Pro Arg Tyr Ser Ser Asp Glu Lys Val Leu Gly Glu Asp Phe
            100                 105                 110

Ser Asp Thr Arg Leu Tyr Lys Ile Glu His Asn Lys Ala Asn Arg Leu
        115                 120                 125

Asp Gly Lys Asn Glu Phe Pro Glu Ile Ser Thr Thr Ser Lys Tyr Glu
    130                 135                 140
```

Ala Asn Met Gly Asp Pro Glu Val Leu Lys Lys Phe Ile Asp Tyr Cys
145                 150                 155                 160

Lys Ser Asn Tyr Glu Ala Asp Lys Tyr Val Leu Ile Met Ala Asn His
            165                 170                 175

Gly Gly Gly Ala Arg Glu Lys Ser Asn Pro Arg Leu Asn Arg Ala Ile
        180                 185                 190

Cys Trp Asp Asp Ser Asn Leu Asp Lys Asn Gly Glu Ala Asp Cys Leu
        195                 200                 205

Tyr Met Gly Glu Ile Ser Asp His Leu Thr Glu Lys Gln Ser Val Asp
210                 215                 220

Leu Leu Ala Phe Asp Ala Cys Leu Met Gly Thr Ala Glu Val Ala Tyr
225                 230                 235                 240

Gln Tyr Arg Pro Gly Asn Gly Gly Phe Ser Ala Asp Thr Leu Val Ala
            245                 250                 255

Ser Ser Pro Val Val Trp Gly Pro Gly Phe Lys Tyr Asp Lys Ile Phe
        260                 265                 270

Asp Arg Ile Lys Ala Gly Gly Thr Asn Asn Glu Asp Asp Leu Thr
        275                 280                 285

Leu Gly Gly Lys Glu Gln Asn Phe Asp Pro Ala Thr Ile Thr Asn Glu
290                 295                 300

Gln Leu Gly Ala Leu Phe Val Glu Gln Arg Asp Ser Thr His Ala
305                 310                 315                 320

Asn Gly Arg Tyr Asp Gln His Leu Ser Phe Tyr Asp Leu Lys Lys Ala
            325                 330                 335

Glu Ser Val Lys Arg Ala Ile Asp Asn Leu Ala Val Asn Leu Ser Asn
        340                 345                 350

Glu Asn Lys Lys Ser Glu Ile Glu Lys Leu Arg Gly Ser Gly Ile His
        355                 360                 365

Thr Asp Leu Met His Tyr Phe Asp Glu Tyr Ser Glu Gly Glu Trp Val
370                 375                 380

Glu Tyr Pro Tyr Phe Asp Val Tyr Asp Leu Cys Glu Lys Ile Asn Lys
385                 390                 395                 400

Ser Glu Asn Phe Ser Ser Lys Thr Lys Asp Leu Ala Ser Asn Ala Met
            405                 410                 415

Asn Lys Leu Asn Glu Met Ile Val Tyr Ser Phe Gly Asp Pro Ser Asn
        420                 425                 430

Asn Phe Lys Glu Gly Lys Asn Gly Leu Ser Ile Phe Leu Pro Asn Gly
        435                 440                 445

Asp Lys Lys Tyr Ser Thr Tyr Tyr Thr Ser Thr Lys Ile Pro His Trp
450                 455                 460

Thr Met Gln Ser Trp Tyr Asn Ser Ile Asp Thr Val Lys Tyr Gly Leu
465                 470                 475                 480

Asn Pro Tyr Gly Lys Leu Ser Trp Cys Lys Asp Gly Gln Asp Pro Glu
            485                 490                 495

Ile Asn Lys Val Gly Asn Trp Phe Glu Leu Leu Asp Ser Trp Phe Asp
        500                 505                 510

Lys Thr Asn Asp Val Thr Gly Gly Val Asn His Tyr Gln Trp
515                 520                 525

<210> SEQ ID NO 35
<211> LENGTH: 530
<212> TYPE: PRT
<213> ORGANISM: Clostridium novyi

<400> SEQUENCE: 35

```
Met Leu Arg Lys Lys Val Ile His Leu Leu Ala Ala Ile Leu Gly
 1               5                  10                  15

Met Ser Phe Ile Asn Ile Gln Pro Val Tyr Ala Thr Pro Lys Pro Thr
                20                  25                  30

Ala Asn Asn Ala Lys Ser Ser Ile Thr Lys Lys Ala Lys Asp Glu Ser
                35                  40                  45

Lys Lys Glu Gln Lys Val Thr Ile Leu Tyr Tyr Cys Asp Ala Asp Asn
 50                  55                  60

Asn Leu Glu Asp Ala Leu Met Ser Asp Ile Ala Glu Met Lys Lys Gly
 65                  70                  75                  80

Tyr Val Asn Asn Pro Asn Leu Asn Leu Ile Ala Leu Val Asp Arg Thr
                 85                  90                  95

Pro Gly Tyr Ser Glu Asp Ser Thr Ala Leu Gly Glu Asn Phe Glu Asp
                100                 105                 110

Thr Arg Leu Tyr Lys Ile Glu His Asn Lys Ala Thr Arg Leu Asp Gly
                115                 120                 125

Gly Lys Tyr Phe Pro Glu Ile Lys Val Asn Gly Thr Tyr Glu Ala Asn
                130                 135                 140

Met Gly Asp Pro Glu Thr Leu Lys Lys Phe Ile Glu Phe Gly Lys Asn
145                 150                 155                 160

Asn Tyr Lys Ala Asp Lys Tyr Val Leu Ile Met Ser Asn His Gly Gly
                165                 170                 175

Gly Ala Lys Asn Lys Pro Asn Val Asn Glu Lys Leu Asn Lys Ala Ile
                180                 185                 190

Cys Trp Asp Asp Ser Asn Leu Asp Gly Glu Asn Pro Asp Cys Leu Tyr
                195                 200                 205

Ile Gly Glu Ile Ser Asp His Leu Asp Glu Ser His Ser Val Asp Val
210                 215                 220

Leu Ala Phe Asp Ala Cys Leu Met Gly Thr Ala Glu Val Ala Tyr Gln
225                 230                 235                 240

Tyr Arg Pro Gly Asn Gly Arg Phe Ser Ala Lys Thr Met Ile Ala Ser
                245                 250                 255

Ser Pro Val Val Trp Gly Ala Gly Phe Lys Tyr Asp Asp Ile Phe Ser
                260                 265                 270

Arg Ile Arg Ser Gly Asn Thr Phe Thr Leu Gln Lys Asp Leu Thr Leu
                275                 280                 285

Gly Gly Arg Glu Arg Cys Phe Asp Pro Ala Thr Ile Thr Asn Glu Gln
                290                 295                 300

Ile Gly Ala Leu Phe Val Glu Glu Gln Arg Asp Ser Thr Ser Arg Tyr
305                 310                 315                 320

Phe Arg Ser Asp Gln Gln Leu Ser Cys Tyr Asp Leu Thr Lys Ala Glu
                325                 330                 335

Asn Ile Lys Lys Ser Phe Asp Lys Leu Ala Val Asp Leu Ser Thr Lys
                340                 345                 350

Asn Lys Lys Ser Ala Ile Glu Lys Leu Arg Gly Ser Lys Thr Asn Val
                355                 360                 365

Asn Leu Met His Tyr Phe Asn Glu Lys Asp Gln Leu Asp Trp Ile Glu
                370                 375                 380

Tyr Pro Tyr Phe Asp Ile Tyr Asp Leu Cys Glu Gly Ile Ser Lys Ser
385                 390                 395                 400

Asn Asp Phe Asp Glu Glu Thr Gln Lys Leu Ala Lys Asp Val Met Lys
                405                 410                 415

Asn Val Asp Ser Met Val Leu Tyr Ser Phe Gly Gly Lys Lys Phe Lys
                420                 425                 430
```

```
Gly Val Gly Lys Phe Lys Glu Gly Lys Asn Gly Leu Ser Val Phe Leu
            435                 440                 445

Pro Asp Gly Asn Arg Ile Tyr Thr Ser Arg Tyr Ser Asn Ala Lys Ile
450                 455                 460

Pro His Trp Leu Ile Gln Ser Trp Tyr Asn Ser Ile Asp Thr Val Ala
465                 470                 475                 480

Ser Gly Leu Asn Asn Pro Tyr Gly Lys Leu Ser Trp Cys Lys Asp Gly
            485                 490                 495

Gln Asp Pro Glu Ile Asn Lys Val Gly Asn Trp Phe Glu Leu Leu Asp
                500                 505                 510

Ser Trp Phe Asp Lys Thr Asn Gly Pro Asp Gly Gly Phe Asn His Tyr
            515                 520                 525

Gln Trp
    530
```

<210> SEQ ID NO 36
<211> LENGTH: 522
<212> TYPE: PRT
<213> ORGANISM: Clostridium perfringens

<400> SEQUENCE: 36

```
Met Phe Lys Lys Lys Leu Ser Leu Leu Met Ala Thr Ile Thr Ile Gly
  1               5                  10                  15

Ser Val Leu Leu Gly Gly Ala Ser Thr Val Ser Ala Ala Pro Arg Gln
                 20                  25                  30

Lys His Lys Thr Val Ser Glu Lys Ile Lys Glu Ala Lys Thr Glu
             35                  40                  45

Gly Asp Lys Lys Leu Thr Val Met Val Tyr Ala Asp Cys Asp Asn Asn
 50                  55                  60

Leu Glu Glu Tyr Ile Leu Asn Asp Ile Glu Glu Met Lys Glu Gly Tyr
 65                  70                  75                  80

Lys Asn Asn Pro Asn Leu Asn Ile Val Val Leu Val Asp Arg Ile Pro
                 85                  90                  95

Gly Tyr Ser Asn Asp Ser Lys Val Leu Gly Ser Asn Phe Glu Asp Thr
            100                 105                 110

Arg Leu Tyr Lys Ile Gly Glu Asn Ser Ala Glu Arg Ile Ser Gly Lys
        115                 120                 125

Ser Glu Phe Pro Glu Ile Thr Thr Thr Ser Asn Tyr Glu Ala Asn Met
    130                 135                 140

Gly Asp Ala Asn Thr Leu Lys Lys Phe Ile Lys Phe Cys Lys Lys Asn
145                 150                 155                 160

Tyr Glu Ala Asp Lys Tyr Met Leu Ile Met Ser Asn His Gly Gly Gly
                165                 170                 175

Ala Lys Asp Asp Lys Asp Arg Ala Ser Thr Val Asn Lys Ala Ile Cys
            180                 185                 190

Trp Asp Ser Asn Asn Lys Asp Cys Leu Tyr Thr Gly Glu Ile Ser
        195                 200                 205

Asp Val Leu Thr Lys Asp Glu Ser Val Asp Val Leu Phe Asp Ala
    210                 215                 220

Cys Leu Met Gly Thr Ser Glu Val Ala Tyr Gln Tyr Arg Pro Asn Asn
225                 230                 235                 240

Gly Ser Phe Glu Ala Lys Thr Leu Val Ala Ser Ala Pro Val Val Trp
                245                 250                 255

Gly Asn Gly Tyr Pro Tyr Asp Lys Ile Phe Ser Arg Leu Lys Ser Thr
            260                 265                 270
```

```
Lys Gly Asp Asn Gly Glu Val Asp Ser Thr Leu Gly Lys Glu Lys
            275                 280                 285

Ile Phe Glu Pro Ser Leu Val Thr Asn Asn Glu Leu Gly Ala Leu Phe
            290                 295                 300

Val Glu Glu Gln Arg Asp Ser Val Asn Ser Tyr Gly Val Thr Asp Gln
305                 310                 315                 320

Gln Leu Ser Cys Tyr Asp Leu Ser Lys Ile Glu Thr Val Lys Lys Ser
                325                 330                 335

Val Asp Ala Leu Ala Arg Asn Leu Ser Lys Asn Asn Lys Lys Asp Ala
            340                 345                 350

Ile Glu Asn Leu Arg Gly Thr Gly Lys Asn Ala Pro Thr Met His Tyr
            355                 360                 365

Phe Lys Asn Tyr Asp Glu Tyr Glu Trp Ile Glu Tyr Pro Tyr Phe Asp
            370                 375                 380

Leu Tyr Asp Leu Cys Glu Lys Ile Ser Leu Ser Asn Glu Phe Asp Glu
385                 390                 395                 400

Thr Thr Lys Lys Leu Ser Lys Asn Val Met Lys Asn Val Asp Gln Leu
                405                 410                 415

Ile Leu Tyr Ser Phe Ala Gly Asn Asp Phe Lys Gly Phe Lys Glu Gly
            420                 425                 430

Lys Asn Gly Ile Ser Ile Phe Leu Pro Asp Gly Asn Arg Asn Tyr Tyr
            435                 440                 445

Asp Gln Tyr Ser Gly Gln Val Ile Pro His Trp Ala Ile Gln Arg Trp
450                 455                 460

Tyr Asn Pro Leu Asp Thr Asn Ala Tyr Arg Leu Arg Ser Gly Tyr Gly
465                 470                 475                 480

Lys Leu Ala Trp Cys Lys Asp Gly Leu Asp Pro Lys Ile Asn Lys Val
                485                 490                 495

Gly Asn Trp Phe Glu Leu Leu Asp Ser Trp Phe Asp Lys Asp Asn Thr
            500                 505                 510

Ser Leu Gly Gly Tyr Asn Arg Tyr Arg Tyr
            515                 520

<210> SEQ ID NO 37
<211> LENGTH: 522
<212> TYPE: PRT
<213> ORGANISM: Clostridium perfringens

<400> SEQUENCE: 37

Met Phe Lys Lys Lys Leu Ser Leu Leu Met Ala Thr Ile Thr Ile Gly
 1                5                  10                  15

Ser Val Leu Leu Gly Gly Val Ser Thr Val Ser Ala Ala Pro Arg Gln
                20                  25                  30

Lys His Lys Thr Val Ser Glu Lys Ile Lys Glu Ala Glu Lys Thr Glu
            35                  40                  45

Gly Asp Lys Lys Leu Thr Val Met Val Tyr Ala Asp Cys Asp Asn Asn
        50                  55                  60

Leu Glu Glu Tyr Ile Leu Asn Asp Ile Glu Glu Met Lys Glu Gly Tyr
65                  70                  75                  80

Lys Asn Asn Pro Asn Leu Asn Ile Ile Val Leu Val Asp Arg Ile Pro
                85                  90                  95

Gly Tyr Ser Asn Asp Ser Lys Val Leu Gly Ser Asn Phe Glu Asp Thr
            100                 105                 110

Arg Leu Tyr Lys Ile Gly Glu Asn Ser Ala Glu Arg Ile Ser Gly Lys
        115                 120                 125
```

```
Ser Glu Phe Pro Glu Ile Thr Thr Thr Ser Asn Tyr Glu Ala Asn Met
        130                 135                 140

Gly Asp Ala Asn Thr Leu Lys Lys Phe Ile Lys Phe Cys Lys Lys Asn
145                 150                 155                 160

Tyr Glu Ala Asp Lys Tyr Met Leu Ile Met Ser Asn His Gly Gly Gly
                165                 170                 175

Ala Lys Asp Asp Lys Asp Arg Ala Ser Thr Val Asn Lys Ala Ile Cys
            180                 185                 190

Trp Asp Asp Ser Asn Asn Lys Asp Cys Leu Tyr Thr Gly Glu Ile Ser
        195                 200                 205

Asp Val Leu Thr Lys Asp Glu Ser Val Asp Val Leu Val Phe Asp Ala
        210                 215                 220

Cys Leu Met Gly Asn Ser Glu Val Ala Tyr Gln Tyr Arg Pro Asn Asn
225                 230                 235                 240

Gly Ser Phe Glu Ala Lys Thr Leu Val Ala Ser Ala Pro Val Val Trp
                245                 250                 255

Gly Phe Gly Tyr Pro Tyr Asp Lys Ile Phe Ser Arg Leu Arg Ser Thr
            260                 265                 270

Lys Gly Asp Asn Gly Glu Val Asp Ser Thr Leu Gly Gly Lys Glu Lys
        275                 280                 285

Ile Phe Asp Pro Ser Thr Val Thr Asn Asn Glu Leu Gly Ala Leu Phe
        290                 295                 300

Val Glu Glu Gln Arg Asp Ser Val Asn Ser Cys Gly Val Thr Asp Gln
305                 310                 315                 320

Gln Leu Ser Cys Tyr Asp Leu Ser Lys Ile Glu Lys Val Lys Lys Ser
                325                 330                 335

Val Asp Thr Leu Ala Arg Asn Leu Ser Lys Asn Lys Lys Asp Ala
            340                 345                 350

Ile Glu Ser Leu Arg Gly Thr Gly Lys Asn Ala Pro Thr Met His Tyr
        355                 360                 365

Phe Lys Asn Tyr Asp Glu Tyr Glu Trp Ile Glu Tyr Pro Tyr Phe Asp
        370                 375                 380

Leu Tyr Asp Leu Cys Glu Lys Ile Ser Leu Ser Asp Glu Phe Asn Glu
385                 390                 395                 400

Thr Thr Lys Lys Leu Ser Lys Asn Val Met Lys Asn Val Asp Gln Leu
                405                 410                 415

Ile Leu Tyr Ser Phe Ala Gly Asn Asp Phe Lys Gly Phe Lys Glu Gly
            420                 425                 430

Lys Asn Gly Ile Ser Ile Phe Leu Pro Asp Gly Asn Arg Asn Tyr Tyr
        435                 440                 445

Asp Gln Tyr Ser Gly Gln Ala Ile Pro His Trp Ala Ile Gln Arg Trp
        450                 455                 460

Tyr Asn Pro Leu Asp Thr Asn Ala Tyr Arg Leu Arg Ser Gly Tyr Gly
465                 470                 475                 480

Lys Leu Ser Trp Cys Lys Asp Gly Leu Asp Pro Lys Ile Asn Lys Val
                485                 490                 495

Gly Asn Trp Phe Glu Leu Leu Asp Ser Trp Phe Asp Lys Asp Asn Thr
            500                 505                 510

Ser Leu Gly Gly Tyr Asn Arg Tyr Arg Tyr
        515                 520

<210> SEQ ID NO 38
<211> LENGTH: 524
<212> TYPE: PRT
```

<213> ORGANISM: Clostridium perfringens

<400> SEQUENCE: 38

```
Met Tyr Met Phe Lys Lys Leu Ser Leu Met Ala Thr Ile Thr
 1               5                  10                  15

Ile Gly Ser Val Leu Leu Gly Val Ser Thr Val Ser Ala Ala Pro
                20                  25                  30

Arg Gln Lys His Lys Thr Val Ser Glu Lys Ile Lys Glu Ala Glu Lys
                35                  40                  45

Thr Glu Gly Asp Lys Lys Leu Thr Val Met Val Tyr Ala Asp Cys Asp
    50                  55                  60

Asn Asn Leu Glu Glu Tyr Ile Leu Asn Asp Ile Glu Glu Met Lys Glu
65                  70                  75                  80

Gly Tyr Lys Asn Asn Pro Asn Leu Asn Ile Ile Val Leu Val Asp Arg
                85                  90                  95

Ile Pro Gly Tyr Ser Asn Asp Ser Lys Val Leu Gly Ser Asn Phe Glu
                100                 105                 110

Asp Thr Arg Leu Tyr Lys Ile Gly Glu Asn Ser Ala Glu Arg Ile Ser
                115                 120                 125

Gly Lys Ser Glu Phe Pro Glu Ile Thr Thr Thr Ser Asn Tyr Glu Ala
    130                 135                 140

Asn Met Gly Asp Ala Asn Thr Leu Lys Lys Phe Ile Lys Phe Cys Lys
145                 150                 155                 160

Lys Asn Tyr Glu Ala Asp Lys Tyr Met Leu Ile Met Ser Asn His Gly
                165                 170                 175

Gly Gly Ala Lys Asp Asp Lys Asp Arg Ala Ser Thr Val Asn Lys Ala
                180                 185                 190

Ile Cys Trp Asp Ser Asn Asn Lys Asp Cys Leu Tyr Thr Gly Glu
                195                 200                 205

Ile Ser Asp Val Leu Thr Lys Asp Glu Ser Val Asp Val Leu Val Phe
    210                 215                 220

Asp Ala Cys Leu Met Gly Asn Ser Glu Val Ala Tyr Gln Tyr Arg Pro
225                 230                 235                 240

Asn Asn Gly Ser Phe Glu Ala Lys Thr Leu Val Ala Ser Ala Pro Val
                245                 250                 255

Val Trp Gly Phe Gly Tyr Pro Tyr Asp Lys Ile Phe Ser Arg Leu Arg
                260                 265                 270

Ser Thr Lys Gly Asp Asn Gly Glu Val Asp Ser Thr Leu Gly Gly Lys
    275                 280                 285

Glu Lys Ile Phe Asp Pro Ser Thr Val Thr Asn Asn Glu Leu Gly Ala
    290                 295                 300

Leu Phe Val Glu Glu Gln Arg Asp Ser Val Asn Ser Cys Arg Val Thr
305                 310                 315                 320

Asp Gln Gln Leu Ser Cys Tyr Asp Leu Ser Lys Ile Glu Lys Val Lys
                325                 330                 335

Lys Ser Val Asp Ala Leu Ala Arg Asn Leu Ser Lys Asn Asn Lys Lys
                340                 345                 350

Asp Ala Ile Glu Lys Leu Arg Gly Thr Gly Lys Asn Ala Pro Thr Met
    355                 360                 365

His Tyr Phe Lys Asn Tyr Asp Glu Tyr Glu Trp Ile Glu Tyr Pro Tyr
    370                 375                 380

Phe Asp Leu Tyr Asp Leu Cys Glu Lys Ile Ser Leu Ser Asp Glu Phe
385                 390                 395                 400

Asn Glu Thr Thr Lys Lys Leu Ser Lys Asn Val Met Lys Asn Val Asp
```

-continued

```
                    405                 410                 415
Gln Leu Ile Leu Tyr Ser Phe Ala Gly Lys Asp Phe Lys Gly Phe Lys
            420                 425                 430

Glu Gly Lys Asn Gly Ile Ser Ile Phe Leu Pro Asp Gly Asn Arg Asn
        435                 440                 445

Tyr Tyr Asp Gln Tyr Ser Gly Gln Ala Ile Pro His Trp Ala Ile Gln
    450                 455                 460

Arg Trp Tyr Asn Pro Leu Asp Thr Asn Ala Tyr Arg Leu Arg Ser Gly
465                 470                 475                 480

Tyr Gly Lys Leu Ala Trp Cys Lys Asp Gly Leu Asp Pro Lys Ile Asn
                485                 490                 495

Lys Val Gly Asn Trp Phe Glu Leu Leu Asp Ser Trp Phe Asp Lys Asp
            500                 505                 510

Asn Thr Ser Leu Gly Gly Tyr Asn Arg Tyr Arg Tyr
        515                 520

<210> SEQ ID NO 39
<211> LENGTH: 772
<212> TYPE: PRT
<213> ORGANISM: Clostridium botulinum serotype A

<400> SEQUENCE: 39

Met Leu Arg Lys Ile Glu Ser Lys Asp Leu Leu Tyr Asn Leu Glu Leu
1               5                   10                  15

Asp Asp Ile Asn Ile Asp Arg Thr Gln Lys Tyr Thr Pro Glu Tyr Asn
            20                  25                  30

Ser Ile Tyr Glu Lys Ile Asn Leu Ala Leu Asp Ile Asp Lys Ser Gly
        35                  40                  45

Tyr Asn Leu Tyr Leu Val Asp Asp Phe Ser Lys Glu Lys Leu Asn Ser
    50                  55                  60

Ile Ile Asn Phe Ile Asn Gln Lys Leu Glu Lys Lys Ser Lys Pro Lys
65                  70                  75                  80

Asp Ile Cys Tyr Val Val Leu Glu Glu Arg Tyr Pro Tyr Ser Ile
                85                  90                  95

Tyr Leu Glu Asn Gly Lys Gly Lys Ile Leu Lys Glu Lys Leu Lys Asp
            100                 105                 110

Ile Gln Thr Lys Tyr Asn Glu Cys Ile Tyr Asp Phe Tyr Asn Lys Ser
        115                 120                 125

Ser Asn Lys Glu Lys Glu Ile Ile Leu Glu Ser Met Glu Lys Lys Arg
    130                 135                 140

Ser Glu Ile Val Asn Glu Leu Ile Glu Ser Lys Lys Glu Gly Phe
145                 150                 155                 160

Glu Ile Lys Thr Gly Val Ser Gly Phe Val Phe Met Pro Ile Lys Asp
                165                 170                 175

Gly Asn Ser Leu Ser Glu Ser Glu Tyr Glu Asp Leu Asn Lys Glu Asp
            180                 185                 190

Lys Glu Glu Ile Leu Glu Lys Val Ser Lys Leu Lys Glu Lys Ala Glu
        195                 200                 205

Ser Ser Leu Glu Val Leu Ala Asp Met Glu Arg Glu Gly Leu Glu Lys
    210                 215                 220

Leu Lys Asp Ile Met Arg Thr Tyr Leu Glu Met Glu Lys Gly Ser
225                 230                 235                 240

Lys Glu Glu Tyr Arg Met Glu Phe Glu Asp Asn Ile Gln Thr Leu Asp
                245                 250                 255

Phe Leu Asn Ser Val Cys Arg Asn Ile Glu Lys Glu Leu Ile Glu Ser
```

-continued

```
                260                 265                 270
Tyr Thr Ser Ser Tyr Glu Glu Asp Gln Glu Ser Ile Ile Asn Val Ile
            275                 280                 285
Tyr Lys Tyr Lys Val Asn Val Ile Val Asp Asn Thr Leu Asn Lys Ser
        290                 295                 300
Pro Leu Val Ile Phe Glu Glu Asn Pro Ser Val Asn Asn Leu Val Gly
305                 310                 315                 320
Ser Ile Glu Tyr Glu Asn Lys Ser Gly Val Tyr Tyr Thr Asp Ala Ser
                325                 330                 335
Leu Ile Lys Ala Gly Ser Leu Leu Lys Ala Asn Glu Gly Cys Leu Ile
            340                 345                 350
Val Arg Ala Asn Ser Leu Phe Thr Asn Gly Ser Ala Tyr Phe Tyr Leu
        355                 360                 365
Lys Lys Ala Leu Ile Asn Asp Lys Ile Asp Phe Asp Tyr Asn Lys Gly
370                 375                 380
Tyr Leu Glu Leu Leu Ser Leu Gly Gly Leu Lys Pro Glu Pro Ile Asn
385                 390                 395                 400
Thr Lys Leu Lys Val Ile Ile Gly Asp Tyr Glu Thr Tyr Asn Leu
            405                 410                 415
Leu Tyr Asn Tyr Asp Glu Asp Phe Lys Lys Ile Phe Lys Leu Lys Ser
            420                 425                 430
Glu Tyr Asn Lys Val Val Asp Ile Asn Ser Lys Ser Lys Glu Gln Ile
            435                 440                 445
Cys Lys Asn Ile Tyr Asp Ile Cys Glu Asn Lys Asp Leu Lys Asn Ile
        450                 455                 460
Asn Glu Glu Ala Val Lys Glu Val Cys Lys Tyr Leu Ser Arg Lys Ala
465                 470                 475                 480
Glu Asn Lys Asn Lys Phe Tyr Phe Asp Asn Tyr Glu Ile Asp Arg Leu
                485                 490                 495
Leu Ile Gln Ala Asp Ser Lys Ala Arg Ile Glu Asp Arg Asp Ile Ile
            500                 505                 510
Thr Lys Glu Asp Ile Gln Phe Val Ala Tyr Glu Lys Glu Glu Ile Glu
        515                 520                 525
Lys Glu Val Met Glu Gly Tyr Glu Lys Glu Arg Ile Phe Ile Asp Val
        530                 535                 540
Lys Gly Asp Lys Val Gly Gln Val Asn Gly Leu Ser Val Ile Asp Leu
545                 550                 555                 560
Gly Tyr Ala Ser Phe Gly Arg Pro Ile Arg Ile Thr Cys Cys Cys Tyr
                565                 570                 575
Lys Gly Asn Gly Asp Ile Ile Asp Ile Gln Lys Glu Ser Asn Leu Ser
                580                 585                 590
Gly Asn Ile His Asn Lys Ala Ile Ser Thr Leu Lys Gly Tyr Ile Asn
            595                 600                 605
Ser Ile Ile Gly Lys Tyr Asp Thr Leu Pro Val Asp Phe His Leu Ser
        610                 615                 620
Phe Glu Gln Ile Tyr Gly Thr Val Asp Gly Asp Ser Ala Ser Val Ala
625                 630                 635                 640
Glu Ala Ile Ala Met Leu Ser Ala Leu Ser Asn Ile Pro Val Arg Gln
                645                 650                 655
Ser Ile Ala Val Thr Gly Ser Ile Asn Gln Phe Gly Gln Val Gln Pro
            660                 665                 670
Ile Gly Gly Val Asn Glu Lys Ile Glu Gly Phe Tyr Glu Val Cys Arg
        675                 680                 685
```

```
Tyr Lys Lys Asp Ile Lys Asp Lys Gly Ile Leu Ile Pro Lys Ser Asn
        690             695                 700
Lys Glu Asn Leu Val Leu Asn Lys Glu Val Glu Ala Ile Lys Asn
705             710                 715                 720
Gly Glu Phe Ser Ile Tyr Thr Met Glu Thr Leu Glu Asp Ala Val Lys
                725                 730                 735
Ile Leu Leu Gly Glu Lys Asn Leu Lys Phe Asn Glu Leu Ile Val Glu
            740                 745                 750
Ile Glu Lys Glu Leu Lys Lys Tyr Asn Lys Ser Lys Lys Cys Arg
        755                 760                 765
Lys Ile Lys Leu
    770
```

<210> SEQ ID NO 40
<211> LENGTH: 575
<212> TYPE: PRT
<213> ORGANISM: Clostridium botulinum serotype A

<400> SEQUENCE: 40

```
Met Lys Ser Lys Lys Leu Leu Thr Ile Leu Leu Ser Ala Ile Ile Thr
1               5                   10                  15
Ala Ser Ser Ile Ser Ser Val Tyr Ala Ala Glu Ser Val Gly Ile Lys
                20                  25                  30
Ser Lys Tyr Gln Pro Lys Thr Thr Ile Phe Trp Glu Lys Gly Lys
            35                  40                  45
Gln Asn Asn Lys Lys Ser Ala Thr Asn Ile Ala Ser Glu Gln Phe Asn
    50                  55                  60
Asn Phe Glu Glu Ile Asn Gln Phe Phe Gln Gln Asn Ile Ser Arg Phe
65                  70                  75                  80
Gly Leu Lys Lys Gly Ser Leu Lys Ser Thr Lys Ala Leu Lys Asp Glu
                85                  90                  95
Lys Gly Lys Thr His Tyr His Thr Ile Tyr Gln Val Glu Gly Ile Pro
            100                 105                 110
Val Tyr Tyr Gly Arg Ile Val Phe Thr Thr Glu Lys Asp Ser Thr Ile
        115                 120                 125
Ser Ser Ile Asn Gly Gly Val Asp Ile Ser Phe Glu Asn Glu Asn Trp
    130                 135                 140
Lys Asn Lys Ile Lys Leu Ser Lys Ser Asp Ala Ile Ala Lys Ala Lys
145                 150                 155                 160
Asn Asn Ile Lys Tyr Glu Glu Leu His Asp Ser Lys Ala Asp Leu Tyr
                165                 170                 175
Leu Tyr Asn Phe Glu Glu Lys Pro Tyr Val Val Tyr Leu Ile Asp Leu
            180                 185                 190
Ser Thr Asp Thr Gly Asp Trp Asn Val Phe Val Asn Ala Glu Asp Gly
        195                 200                 205
Ser Ile Val Asn Lys Phe Asn Asn Ile Pro Thr Leu Thr Asn Thr Arg
    210                 215                 220
Asp Lys Lys Phe Thr Ser Thr Lys Lys Thr Asn Thr Lys Val Asn Lys
225                 230                 235                 240
Ser Asn Asn Leu Ile Asp Val Gln Gly Asn Thr Ile Lys Gly Lys Gly
                245                 250                 255
Lys Ser Ser Leu Asn Gly Ile Val Asp Ile Asp Leu Thr Tyr Lys Asp
            260                 265                 270
Gly Lys Tyr Tyr Leu Lys Asn Ser Asn Lys Asn Ile Tyr Val Tyr Asp
        275                 280                 285
```

-continued

Leu Asn Asn Lys Tyr Ile Asn Thr Phe Thr Thr Pro Lys Ser Ser Ile
    290                 295                 300

Leu Lys Ala Ser Lys Leu Val Glu Asn Asn Asn Glu Phe Ile Asp
305                 310                 315                 320

Asp Lys His Ile Ile Ala Val Asp Ala Tyr Ile Asn Leu Glu Lys Thr
                325                 330                 335

Tyr Asp Tyr Tyr Lys Asn Lys Phe Asn Arg Asn Ser Ile Asp Asn Lys
            340                 345                 350

Gly Met Asn Val Glu Ala Phe Ile His His Gly Glu Lys Tyr Ala Gly
        355                 360                 365

Ala Glu Trp Ser Glu Asn Leu Gly Ser Met Leu Leu Gly Asp Gly Asp
370                 375                 380

Gly Arg Asn Ser Ser His Met Ser Lys Ala Leu Asp Val Val Gly His
385                 390                 395                 400

Glu Phe Ser His Gly Val Thr Arg Lys Glu Ser Asn Leu Lys Tyr Glu
                405                 410                 415

Asn Glu Ser Gly Ala Leu Asn Glu Ser Phe Ser Asp Ile Met Gly Ile
            420                 425                 430

Ala Ile Lys Gly Lys Asn Phe Lys Leu Gly Asp Cys Trp Thr Pro
        435                 440                 445

Asp Ile Glu Gly Asp Ala Ile Arg Asp Met Gln Asp Pro Ser Lys Gly
450                 455                 460

Tyr Gln Pro Ala His Met Lys Asp Tyr Arg Ser Met Asp Ile Arg Tyr
465                 470                 475                 480

Asp Asn Gly Gly Val His Val Asn Ser Gly Ile Ile Asn His Ala Ala
                485                 490                 495

Tyr Leu Ile Ala Asp Gly Ile Glu Lys Leu Gly Val Glu Asn Ser Lys
            500                 505                 510

Asp Ile Met Ala Lys Leu Phe Tyr Thr Ala Asn Cys Tyr Glu Trp Asp
        515                 520                 525

Glu Thr Thr Asn Phe Ser Lys Cys Arg Asn Asp Leu Ile Lys Val Thr
530                 535                 540

Lys Asp Leu Tyr Gly Glu Asn Ser Lys Tyr Val Gln Ile Val Glu Asn
545                 550                 555                 560

Ala Phe Asp Lys Val Gly Ile Thr Ala Thr Pro Gln Leu Pro Leu
                565                 570                 575

<210> SEQ ID NO 41
<211> LENGTH: 592
<212> TYPE: PRT
<213> ORGANISM: Clostridium botulinum serotype A

<400> SEQUENCE: 41

Met Lys Ser Lys Lys Leu Leu Ala Thr Val Leu Ser Ala Val Ile Thr
1               5                   10                  15

Phe Ser Ala Val Ser Ala Val Ser Ala Ala Pro Val Gly Lys Glu Ser
                20                  25                  30

Lys Ser Glu Pro Lys Ile Thr Thr Ile Ser Trp Asp Lys Ser Glu Gln
            35                  40                  45

Asn Thr Lys Lys Asp Ala Thr Asp Ile Lys Gln Lys Lys Phe Asn Asn
        50                  55                  60

Ala Gln Glu Val Thr Asn Phe Phe Glu Lys Asn Ile Ser Lys Phe Gly
65                  70                  75                  80

Val Lys Lys Gly Thr Leu Lys Ser Thr Lys Thr Leu Lys Asp Asp Lys
                85                  90                  95

```
Gly Lys Thr His Tyr His Thr Ile Tyr Glu Val Glu Gly Ile Pro Val
            100                 105                 110

Tyr Tyr Gly Arg Ile Val Phe Thr Glu Lys Asp Ser Thr Met Asn
        115                 120                 125

Ser Ile Asn Gly Arg Val Asp Thr Val Phe Glu Asn Gly Asn Trp Lys
130                 135                 140

Asn Lys Ile Lys Leu Ser Lys Glu Asp Ala Ile Ala Lys Ala Lys Gly
145                 150                 155                 160

Asp Ile Lys Asp Gln Lys Ser Asn Ser Glu Lys Ala Asp Leu Tyr Leu
                165                 170                 175

Tyr Asn Phe Glu Gly Lys Pro Tyr Val Val Tyr Leu Val Asn Thr Met
            180                 185                 190

Thr Asp Ser Gly Asn Trp Asn Val Phe Val Asn Ala Glu Asp Gly Ser
        195                 200                 205

Ile Val Asn Lys Phe Asp Thr Thr Pro Thr Leu Val Glu Asn Lys Asp
    210                 215                 220

Lys Lys Leu Pro Asn Ala Lys Lys Ile Lys Asp Glu Ala Glu Lys Asn
225                 230                 235                 240

Glu Ala Lys Lys Ala Asn Ala Ser Asn Val Asn Ser Val Thr Asp Val
                245                 250                 255

Gln Gly Gln Ser Val Lys Gly Met Gly Arg Thr Ser Leu Asp Gly Leu
            260                 265                 270

Val Asn Leu Asp Leu Thr Tyr Gly Ser Gly Arg Tyr Tyr Leu Lys Asp
        275                 280                 285

Asn Asn Arg Lys Ile Tyr Leu Tyr Asp Leu Lys Asn Gln Val Ser Gly
    290                 295                 300

Asp Asp Leu Tyr Arg Tyr Ile Ile Glu His Tyr Tyr Tyr Gly Ala Pro
305                 310                 315                 320

Glu Tyr Lys Gln Arg Leu Met Ser Gln Ser Glu Leu Val Ser Asn Ser
                325                 330                 335

Asn Asn Asn Phe Ile Asn Asp Asn Gln Val Asn Ser Val Asp Ala Tyr
            340                 345                 350

Val Asn Thr Ala Lys Thr Tyr Asp Tyr Tyr Lys Asn Lys Leu Ser Arg
        355                 360                 365

Asn Ser Ile Asp Asn Lys Gly Met Asn Val Asn Gly Phe Val His Val
    370                 375                 380

Asp Lys Asn Leu Gly Asn Ala Phe Trp Tyr Gly Pro Tyr Asp Ser Met
385                 390                 395                 400

Phe Phe Gly Asp Gly Asp Gly Val Arg Phe Ser Ala Leu Ala Lys Ser
                405                 410                 415

Leu Asp Val Val Gly His Glu Leu Ser His Gly Val Thr Asn Lys Gln
            420                 425                 430

Ser Asn Leu Asn Tyr Ala Asn Glu Ser Gly Ala Leu Asn Glu Ser Phe
        435                 440                 445

Ser Asp Ile Met Gly Thr Ala Val Glu Gly Lys Asn Phe Val Leu Gly
    450                 455                 460

Glu Asp Cys Trp Ile Ala Gly Gly Val Met Arg Asp Met Glu Asn Pro
465                 470                 475                 480

Ser Arg Gly Asn Gln Pro Ala His Met Lys Asp Tyr Val Tyr Met Ser
                485                 490                 495

Glu Asp Asn Gly Gly Val His Lys Asn Ser Gly Ile Ile Asn His Ala
            500                 505                 510

Ala Tyr Leu Ile Ala Asp Gly Phe Glu Lys Met Gly Ala Lys Asp Ser
        515                 520                 525
```

```
Lys Asp Ile Met Gly Lys Leu Phe Tyr Ile Ala Asn Cys Tyr Tyr Trp
    530                 535                 540

Asp Gln Thr Thr Asp Phe Ala Lys Cys Arg Asn Asp Val Val Arg Val
545                 550                 555                 560

Ala Lys Asp Leu Tyr Gly Glu Asn Ser Lys Glu Val Gln Ile Val Lys
                565                 570                 575

Asn Ala Phe Asp Lys Val Gly Val Ser Ala Thr Pro Gln Leu Ser Leu
                580                 585                 590

<210> SEQ ID NO 42
<211> LENGTH: 594
<212> TYPE: PRT
<213> ORGANISM: Clostridium botulinum serotype A

<400> SEQUENCE: 42

Met Lys Ser Lys Lys Leu Leu Ala Thr Val Leu Ser Ala Val Ile Thr
 1               5                  10                  15

Phe Ser Ala Val Ser Ala Val Ser Ala Ala Pro Val Gly Lys Glu Ser
                 20                  25                  30

Lys Ser Asp Pro Lys Thr Thr Thr Ile Ser Trp Asp Lys Ser Glu Gln
             35                  40                  45

Asn Ala Lys Lys Ala Thr Thr Asp Ile Lys Gln Lys Lys Phe Asp Asn
 50                  55                  60

Ala Gln Glu Ile Thr Lys Phe Phe Glu Lys Asn Ile Ser Lys Phe Gly
 65                  70                  75                  80

Val Lys Lys Gly Thr Leu Asn Ser Thr Lys Thr Leu Lys Asp Asp Lys
                 85                  90                  95

Gly Lys Thr His Tyr His Thr Ile Tyr Glu Val Glu Gly Ile Pro Val
            100                 105                 110

Tyr Tyr Gly Arg Ile Val Phe Thr Thr Glu Lys Asp Ser Thr Met Asp
                115                 120                 125

Ser Ile Asn Gly Arg Val Asp Thr Val Phe Glu Asn Gly Asn Trp Lys
    130                 135                 140

Asn Lys Ile Lys Leu Ser Lys Glu Asp Ala Ile Ala Lys Ala Lys Ala
145                 150                 155                 160

Asp Ile Lys Asn Glu Lys Ser Asn Lys Glu Lys Ala Glu Leu Tyr Leu
                165                 170                 175

Tyr Asn Phe Glu Gly Lys Pro Tyr Val Val Tyr Leu Val Asn Ser Ile
                180                 185                 190

Thr Asn Ser Gly Asn Trp Asp Ile Phe Val Asn Ala Glu Asp Gly Ser
    195                 200                 205

Ile Val Asn Lys Phe Asn Asn Thr Pro Thr Leu Leu Asp Thr Lys Ala
    210                 215                 220

Glu Lys Leu Pro Asn Ala Lys Lys Ile Lys Asp Glu Ala Glu Lys Asn
225                 230                 235                 240

Glu Ala Lys Lys Ala Asn Asn Met Asn Asn Ile Ile Asp Val Gln Gly
                245                 250                 255

Gln Ser Val Lys Gly Leu Gly Arg Thr Ser Leu Asp Gly Leu Val Asn
            260                 265                 270

Ile Asn Leu Thr Tyr Asp Asn Gly Arg Tyr Tyr Leu Lys Asp Asn Asn
        275                 280                 285

Arg Lys Ile Tyr Leu Tyr Asp Leu Lys Asn Gln Val Asp Leu Asp Asp
    290                 295                 300

Leu Asn Asp Phe Tyr Asp Ser Pro Lys Gly Gly His Asn Glu Glu Leu
305                 310                 315                 320
```

Met Arg Arg Ser Glu Leu Val Ser Asn Ser Asn Asn Asn Phe Val Asp
            325                 330                 335

Asp Asn Gln Val Asn Ser Val Asp Ala Tyr Ala Asn Met Ala Lys Ser
        340                 345                 350

Tyr Asp Tyr Tyr Lys Asn Lys Leu Ser Arg Asn Ser Leu Asp Asn Lys
            355                 360                 365

Gly Met Asn Ile Lys Gly Phe Val His Phe Asp Lys Asn Leu Gly Asn
    370                 375                 380

Ala Phe Trp Val Gly Glu Tyr Asp Ser Met Phe Phe Gly Asp Gly Asp
385                 390                 395                 400

Gly Val Arg Leu Ser Pro Leu Ala Lys Ala Leu Asp Val Val Gly His
            405                 410                 415

Glu Leu Ser His Gly Val Thr Asn Lys Gln Ser Asp Leu Lys Tyr Glu
        420                 425                 430

Lys Glu Ser Gly Ala Leu Asn Glu Ser Phe Ser Asp Ile Met Gly Thr
    435                 440                 445

Ala Ile Glu Gly Lys Asn Phe Glu Ile Gly Glu Asp Cys Trp Ile Pro
450                 455                 460

Ser Asp Arg Tyr Gly Glu Ile Met Arg Asp Met Lys Asp Pro Ser Arg
465                 470                 475                 480

Gly Asn Gln Pro Ala His Met Lys Asp Phe Arg Asp Leu Pro Val Asp
            485                 490                 495

Glu Asp His Asp Trp Gly Gly Val His Thr Asn Ser Gly Ile Ile Asn
        500                 505                 510

His Ala Ala Tyr Leu Ile Ala Asp Gly Phe Glu Lys Met Gly Glu Lys
    515                 520                 525

Asp Ser Lys Asp Ile Met Ala Lys Ile Phe Tyr Ile Ala Asn Cys Tyr
530                 535                 540

Tyr Trp Asp Gln Ile Thr Asp Phe Ser Lys Cys Arg Asn Asp Val Val
545                 550                 555                 560

Lys Val Ala Lys Asp Leu Tyr Gly Asp Asn Ser Lys Glu Val Gln Ile
            565                 570                 575

Val Lys Asn Ala Phe Asp Gln Val Gly Ile Thr Ala Thr Pro Gln Leu
        580                 585                 590

Pro Leu

<210> SEQ ID NO 43
<211> LENGTH: 581
<212> TYPE: PRT
<213> ORGANISM: Clostridium botulinum serotype A

<400> SEQUENCE: 43

Met Lys Ser Lys Lys Leu Leu Ala Thr Val Leu Ser Ala Val Ile Thr
1               5                   10                  15

Phe Ser Thr Val Ser Ala Val Tyr Ala Ala Pro Val Gly Lys Glu Ser
            20                  25                  30

Lys Val Glu Pro Lys Thr Thr Thr Ile Thr Trp Glu Lys Asn Glu Gln
        35                  40                  45

Asn Thr Lys Lys Ala Ala Thr Asp Ile Thr Glu Lys Lys Phe Asn Asn
    50                  55                  60

Ser Glu Glu Ile Thr Lys Phe Phe Glu Lys Asn Ile Ser Lys Phe Gly
65                  70                  75                  80

Val Gln Lys Gly Ser Leu Lys Asn Thr Lys Thr Val Lys Asp Glu Lys
            85                  90                  95

```
Gly Lys Thr Asn Tyr His Met Ile Tyr Glu Val Gly Ile Pro Val
                100                 105                 110

Tyr Tyr Gly Arg Ile Val Phe Thr Glu Lys Asp Ser Ser Met Asp
            115                 120                 125

Ser Ile Asn Gly Arg Ile Asp Thr Val Phe Glu Asn Gly Asn Trp Lys
130                 135                 140

Asn Lys Ile Lys Leu Ser Lys Glu Asp Ala Ile Ala Lys Ala Lys Asn
145                 150                 155                 160

Asp Ile Lys Asp Glu Lys Ala Thr Ser Lys Lys Thr Asp Leu Tyr Leu
                165                 170                 175

Tyr Asn Phe Glu Gly Lys Pro Tyr Val Val Tyr Leu Val Asp Leu Ile
            180                 185                 190

Thr Asp Asn Gly Ser Trp Thr Val Phe Val Asn Ala Glu Asp Gly Ser
        195                 200                 205

Ile Val Asn Lys Phe Asn Asn Thr Pro Thr Leu Ile Asp Thr Lys Asp
    210                 215                 220

Gln Lys Leu Pro Asn Ala Lys Lys Ile Lys Asp Glu Ala Lys Lys Ala
225                 230                 235                 240

Ser Asn Ala Asn Asn Val Ile Asp Val Gln Gly Gln Ser Val Lys Gly
                245                 250                 255

Val Gly Lys Thr Ser Leu Asp Gly Leu Val Asn Ile Asp Val Thr Tyr
            260                 265                 270

Gly Asn Gly Lys Tyr Tyr Leu Lys Asp Ser Asn Lys Asn Ile Tyr Leu
        275                 280                 285

Tyr Asp Leu Lys Asn Gln Val Asp Glu Tyr Asp Leu Tyr Asn Tyr Leu
    290                 295                 300

Ser Arg Pro Asn Tyr Lys Gln Ile Leu Met Ser Lys Ser Glu Leu Ile
305                 310                 315                 320

Ser Asn Tyr Asn Asn Phe Ile Ala Asn Asn Gln Val Asn Ser Val
                325                 330                 335

Asp Ala Tyr Val Asn Thr Asn Lys Thr Tyr Asp Tyr Lys Asn Lys
            340                 345                 350

Leu Asn Arg Asn Ser Ile Asp Asn Lys Gly Met Asn Ile Asn Gly Phe
        355                 360                 365

Val His Val Gly Arg Asn Tyr Gly Asn Ala Phe Trp Tyr Gly Pro Tyr
    370                 375                 380

Asp Gly Met Phe Phe Gly Asp Gly Asp Gly Ile Tyr Phe Ser Ser Leu
385                 390                 395                 400

Ala Lys Ser Leu Asp Val Val Gly His Glu Leu Ser His Gly Val Thr
                405                 410                 415

Asn Lys Glu Ser Asn Leu Lys Tyr Glu Asn Glu Ser Gly Ala Leu Asn
            420                 425                 430

Glu Ser Phe Ser Asp Ile Met Gly Val Ala Val Glu Gly Lys Asn Phe
        435                 440                 445

Val Leu Gly Glu Asp Cys Trp Val Ala Gly Val Met Arg Asp Met
    450                 455                 460

Glu Asn Pro Ser Arg Gly Gly Gln Pro Ala His Met Lys Asp Tyr Lys
465                 470                 475                 480

Tyr Lys Thr Met Asn Asp Asp Asn Gly Gly Val His Thr Asn Ser Gly
                485                 490                 495

Ile Ile Asn His Ala Ala Tyr Leu Val Ala Asp Gly Ile Glu Lys Thr
            500                 505                 510

Gly Ala Lys Asn Ser Lys Asp Ile Met Gly Lys Ile Phe Tyr Thr Ala
        515                 520                 525
```

```
Asn Cys Tyr Lys Trp Asp Glu Thr Thr Asn Phe Ala Lys Cys Arg Asn
    530                 535                 540
Asp Val Val Gln Val Thr Lys Glu Leu Tyr Gly Glu Asn Ser Asn Tyr
545                 550                 555                 560
Val Lys Ile Val Glu Lys Ala Phe Asp Gln Val Gly Ile Thr Ala Thr
                565                 570                 575
Pro Gln Leu Pro Leu
            580

<210> SEQ ID NO 44
<211> LENGTH: 580
<212> TYPE: PRT
<213> ORGANISM: Clostridium botulinum serotype A

<400> SEQUENCE: 44

Met Lys Ser Lys Lys Leu Leu Ala Thr Val Leu Ser Ala Val Ile Thr
  1               5                  10                  15
Phe Ser Thr Val Ser Ala Val Ser Ala Ala Pro Val Gly Lys Glu Ser
                 20                  25                  30
Lys Ser Glu Pro Lys Thr Thr Thr Ile Phe Trp Glu Lys Ser Glu Gln
             35                  40                  45
Asn Thr Lys Lys Ser Thr Thr Ser Ile Thr Gln Glu Lys Phe Ser Asn
 50                  55                  60
Ser Asp Glu Ile Thr Lys Phe Phe Glu Lys Asn Ile Ser Lys Phe Gly
 65                  70                  75                  80
Val Lys Lys Gly Ser Leu Lys Asn Thr Lys Ala Val Lys Asp Asp Lys
                 85                  90                  95
Gly Lys Thr His Tyr His Met Ile Tyr Gln Val Glu Asp Ile Pro Val
            100                 105                 110
Tyr Tyr Gly Arg Ile Val Phe Thr Thr Lys Lys Asp Ser Ser Leu Asp
            115                 120                 125
Ser Ile Asn Gly Arg Ile Asp Thr Ala Phe Glu Asn Glu Ser Trp Lys
130                 135                 140
Asp Lys Val Lys Leu Ser Lys Asp Asn Ala Ile Glu Lys Ala Lys Ser
145                 150                 155                 160
Ser Ile Lys Tyr Asp Asn Leu Ser Lys Ser Asp Ala Asp Leu Tyr Leu
                165                 170                 175
Tyr Asn Phe Glu Gly Lys Pro Tyr Val Val Tyr Leu Val Asp Leu Val
            180                 185                 190
Thr Asp Asp Gly Asp Trp Asn Val Phe Val Asn Ala Glu Asp Gly Ser
            195                 200                 205
Ile Val Asn Lys Phe Asn Asn Thr Pro Thr Leu Ile Asp Asn Lys Asp
210                 215                 220
Gln Lys Leu Pro Asn Ala Glu Glu Ile Lys Arg Ser Ser Glu Lys Ala
225                 230                 235                 240
Pro Asn Ile Asn Ser Val Ile Asn Val Asn Gly Gln Ser Thr Lys Gly
                245                 250                 255
Gln Gly Lys Thr Ser Leu Asp Gly Ile Val Asp Ile Asp Leu Thr Tyr
            260                 265                 270
Lys Asp Gly Lys Tyr Tyr Leu Lys Asp Ser Asn Lys Asn Ile Tyr Leu
            275                 280                 285
Tyr Asn Leu Asn Asn Ser Trp Ala Pro Thr Ile Gly Ile Phe Ser Lys
290                 295                 300
Asp Tyr Ile Leu Arg Arg Ser Thr Leu Val Glu Asn Asn Ser Asn Lys
305                 310                 315                 320
```

```
Phe Thr Glu Asp Lys His Val Thr Ala Val Asp Gly Tyr Val Asn Leu
            325                 330                 335

Ser Lys Thr Tyr Asp Tyr Tyr Lys Asn Lys Phe Asn Arg Asn Ser Ile
            340                 345                 350

Asp Asn Lys Gly Met Asn Val Glu Gly Phe Ile His Thr Gly Lys Asn
            355                 360                 365

Phe Asn Asn Ala Phe Trp Arg Asp Asp Leu Gly Ser Met Phe Phe Gly
    370                 375                 380

Asp Gly Asp Gly Val Lys Phe Ser Ser Phe Ala Ser Ala Leu Asp Val
385                 390                 395                 400

Val Gly His Glu Val Ser His Gly Ile Thr Ser Lys Glu Ser Lys Leu
            405                 410                 415

Lys Tyr Glu Lys Glu Ser Gly Ala Leu Asn Glu Ser Phe Ser Asp Ile
            420                 425                 430

Met Gly Val Ala Ile Glu Gly Lys Asn Phe Gln Ile Gly Glu Asp Cys
            435                 440                 445

Tyr Thr Pro Asn Ile Pro Gly Asp Ala Leu Arg Asp Met Glu Asp Pro
            450                 455                 460

Ser Lys Gly Asn Gln Pro Ala His Met Lys Asp Phe Gln Tyr Leu Pro
465                 470                 475                 480

Asn Asp Lys Asp His Asp Trp Gly Gly Val His Thr Asn Ser Gly Ile
            485                 490                 495

Ile Asn His Ala Ala Tyr Leu Ile Ala Asp Gly Met Glu Lys Ser Gly
            500                 505                 510

Glu Lys Asn Ser Lys Asp Ile Met Ala Lys Leu Phe Tyr Arg Ala Asn
            515                 520                 525

Cys Tyr Lys Trp Asp Glu Thr Thr Asn Phe Ala Lys Cys Arg Asn Asp
            530                 535                 540

Val Val Gln Val Thr Lys Asp Leu Tyr Gly Glu Asn Ser Lys Tyr Val
545                 550                 555                 560

Lys Ile Val Glu Asn Ala Phe Asp Gln Val Gly Ile Thr Ala Thr Pro
            565                 570                 575

Gln Leu Pro Leu
        580

<210> SEQ ID NO 45
<211> LENGTH: 1209
<212> TYPE: PRT
<213> ORGANISM: Clostridium botulinum serotype A

<400> SEQUENCE: 45

Met Lys Lys Phe Ile Lys Ala Leu Cys Ser Val Ala Leu Ser Cys
  1               5                  10                  15

Met Ile Cys Thr Ser Cys Ile Thr Lys Val Ser Ala Ala Pro Thr Asn
            20                  25                  30

Asn Thr Lys Ile Asn Ser Asn Glu Ile Asn Ile Ser Glu Asp Ser Ser
            35                  40                  45

Lys Ser Glu Arg Ile Pro Ser Thr Lys Ser Lys Pro Leu Gly Leu Asn
    50                  55                  60

Ala Thr Lys Ala Asn Thr Ala Lys Tyr Ser Phe Asn Asp Leu Asn Lys
65                  70                  75                  80

Leu Ser Asn Lys Glu Ile Leu Asp Leu Thr Ser Arg Ile Lys Trp Asn
            85                  90                  95

Asp Ile Ser Asp Leu Phe Gln Tyr Asn Asp Asp Ser Tyr Ala Phe Tyr
            100                 105                 110
```

```
Ser Asn Lys Glu Arg Val Gln Ala Leu Ile Asp Gly Leu Tyr Glu Lys
        115                 120                 125

Ala Ser Thr Tyr Thr Gly Thr Asp Lys Gly Ile Asp Thr Leu Val
130                 135                 140

Glu Ile Leu Arg Ser Gly Phe Tyr Leu Gly Phe Tyr Asn Asp Ser Leu
145                 150                 155                 160

Lys Tyr Leu Asn Asp Arg Ser Phe Gln Asp Lys Cys Ile Pro Ala Met
                165                 170                 175

Leu Ala Ile Glu Asn Asn Lys Asn Phe Lys Leu Gly Glu Lys Gly Gln
            180                 185                 190

Asp Thr Val Ile Ser Ala Leu Gly Lys Leu Ile Gly Asn Ala Ser Cys
        195                 200                 205

Asn Ala Glu Val Val Asn Lys Thr Val Pro Ile Leu Glu Gln Tyr Tyr
210                 215                 220

Arg Glu Met Asn Lys Tyr Pro Lys Asp Lys Leu Lys Ala Asp Ala Val
225                 230                 235                 240

Tyr Ser Leu Met Lys Glu Ile Asn Tyr Asp Ile Ser Gln Tyr Thr Tyr
                245                 250                 255

Asp His Asn Ile Arg Asp Gly Lys Asn Thr Pro Trp Ser Lys Ile
            260                 265                 270

Asp Pro Phe Ile Asn Thr Ile Ser Lys Phe Ala Gly Ile Ser Lys Val
        275                 280                 285

Thr Glu Asp Asn Gly Trp Ile Ile Asn Asn Gly Ile Tyr Tyr Thr Ser
290                 295                 300

Lys Phe Ala Ile Tyr His Ser Asn Pro Ser Ile Pro His Ser Val Ile
305                 310                 315                 320

Asp Lys Cys Leu Glu Ile Leu Pro Ala Tyr Ser Glu Gln Tyr Tyr Ile
                325                 330                 335

Ala Val Glu Arg Ile Lys Glu Asp Phe Asn Cys Lys Asp Ser Lys Gly
            340                 345                 350

Asn Val Val Asp Ile Asp Lys Leu Leu Glu Asp Gly Lys Lys His Tyr
        355                 360                 365

Leu Pro Lys Thr Tyr Thr Phe Asp Asn Gly Lys Met Ile Ile Lys Ala
370                 375                 380

Gly Asp Lys Val Asp Glu Ser Lys Ile Gln Arg Leu Tyr Trp Ala Ser
385                 390                 395                 400

Lys Glu Val Lys Ser Gln Phe His Arg Ile Ile Gly Asn Asp Lys Pro
                405                 410                 415

Leu Glu Ala Gly Asn Ala Asp Asp Val Leu Thr Met Val Ile Tyr Asn
            420                 425                 430

Ser Pro Glu Glu Tyr Lys Leu Asn Arg Thr Leu Tyr Gly Tyr Ser Val
        435                 440                 445

Asp Asn Gly Gly Ile Tyr Ile Glu Gly Ile Gly Thr Phe Phe Thr Tyr
450                 455                 460

Glu Arg Thr Pro Glu Glu Ser Ile Tyr Ser Leu Glu Glu Leu Phe Arg
465                 470                 475                 480

His Glu Phe Thr His Tyr Leu Gln Gly Arg Tyr Leu Val Pro Gly Leu
                485                 490                 495

Phe Asn Glu Gly Asp Phe Tyr Lys Gly Asn Ser Gly Arg Ile Thr Trp
            500                 505                 510

Phe Glu Glu Gly Ser Ala Glu Phe Phe Ala Gly Ser Thr Arg Thr Ser
        515                 520                 525

Val Leu Pro Arg Lys Ser Met Val Gly Gly Leu Ser Glu Asn Pro Lys
```

```
            530                 535                 540
Glu Arg Phe Ser Ala Asp Lys Ile Leu His Ser Lys Tyr Asp Asp Gly
545                 550                 555                 560

Trp Glu Phe Tyr Lys Tyr Gly Tyr Ala Phe Ser Asp Tyr Met Tyr Asn
                565                 570                 575

Asn Ser Lys Lys Leu Phe Ser Asp Leu Val Ser Thr Met Lys Asn Asn
                580                 585                 590

Asp Val Lys Gly Tyr Glu Asn Leu Ile Glu Asn Ala Ser Lys Asp Pro
                595                 600                 605

Asn Val Asn Lys Ser Tyr Gln Asn His Met Gln Lys Leu Val Asp Asn
                610                 615                 620

Tyr Asn Asn Tyr Thr Ile Pro Leu Val Ser Asp Asp Tyr Met Lys Lys
625                 630                 635                 640

Tyr Ser Asn Lys Ser Leu Asn Glu Ile Lys Ser Asp Ile Glu Ser Thr
                645                 650                 655

Met Asn Leu Thr Asn Ser Glu Ile Thr Lys Glu Ser Ser Gln Tyr Phe
                660                 665                 670

Asp Thr Tyr Thr Leu Lys Ala Asn Tyr Thr Leu Asp Ser Asn Lys Gly
                675                 680                 685

Glu Ile Asp Asn Trp Asn Cys Met Asn Asn Lys Val Asn Glu Ser Leu
690                 695                 700

Glu Lys Leu Asn Lys Leu Gly Trp Gly Tyr Lys Thr Val Thr Ala
705                 710                 715                 720

Tyr Phe Ser Asn Pro Lys Val Asn Ser His Asn Gln Val Glu Tyr Asn
                725                 730                 735

Val Val Phe His Gly Leu Leu Thr His Asn Lys Asn Phe Asn Glu Ala
                740                 745                 750

Pro Thr Ile Lys Leu Asp Phe Pro Lys Glu Ala Asn Thr Asp Glu Lys
                755                 760                 765

Ile Lys Phe Ser Ser Glu Gly Ser Thr Asp Asp Gly Lys Ile Val Ser
                770                 775                 780

Tyr Ala Trp Asp Leu Gly Asp Gly Glu Thr Ser Ser Glu Lys Asn Pro
785                 790                 795                 800

Thr His Val Tyr Lys Ala Pro Gly Thr Tyr Thr Val Lys Leu Thr Val
                805                 810                 815

Thr Asp Asp Lys Gly Leu Lys Ser Glu Lys Ser Ala Ser Ile Asn Ile
                820                 825                 830

Lys Lys Val Leu Thr Gly Asn Ala Val Ser Glu Lys Glu Asn Asn Asn
                835                 840                 845

Asp Tyr Val Asn Ala Asn Pro Val Tyr Ser Lys Asp Leu Val Ser Gly
850                 855                 860

Ser Val Ser Ser Ser Asp Asp Arg Asp Ile Phe Tyr Phe Asn Val Thr
865                 870                 875                 880

Lys Pro Ser Asp Ile Thr Ile Asn Ala Glu Lys Ile Asn Lys Asp Lys
                885                 890                 895

Ser Glu Phe Thr Trp Leu Leu Phe Ser Glu Glu Asp Lys Ser Asn Tyr
                900                 905                 910

Ile Ala Tyr Pro Asn Lys Lys Leu Glu Asn Leu Phe Tyr Ser Thr Val
                915                 920                 925

Lys Ile Asp Lys Pro Gly Lys Tyr Tyr Leu Val Ile Tyr Lys Val Ser
                930                 935                 940

Gly Asp Lys Ser Asp Tyr Arg Phe Asn Ile Glu Gly Asp Ile Ser Ala
945                 950                 955                 960
```

-continued

```
Ser Thr Lys Asp Asp Thr Asp Lys Asn Glu Leu Val Ile Ser Glu Lys
            965                 970                 975

Glu Asp Asn Asn Ser Phe Asp Lys Ala Asn Arg Val Cys Lys Asn Gln
            980                 985                 990

Ser Val Ile Ala Thr Leu Asp Thr Asn Asp Pro Arg Asp Thr Tyr Tyr
            995                1000                1005

Phe Asp Ala Leu Thr Val Gly Asn Ile Glu Val Thr Met Glu Asn Thr
           1010                1015                1020

Asp Asn Asn Ser Asn Glu Phe Asn Trp Leu Ala Tyr Ser Ser Asp Asn
1025                1030                1035                1040

Thr Asn Asn Tyr Ile Gly Tyr Ala Thr Lys Arg Glu Gly Asn Lys Ile
           1045                1050                1055

Ile Gly Asn Phe Lys Val Asp Lys Pro Gly Arg Tyr Tyr Ile Val Ala
           1060                1065                1070

Tyr Lys Thr Ser Ser Asn Lys Ile Asn Tyr Lys Leu Asn Ile Lys Gly
           1075                1080                1085

Asp Ile Asp Asn Val Pro Lys Asn Asp Glu Ile Tyr Glu Lys Glu Ser
           1090                1095                1100

Asn Asp Ser Phe Glu Thr Ala Asn Lys Ile Met Leu Asn Thr Thr Val
1105                1110                1115                1120

Leu Gly Asn Leu Asn Gly Lys Asp Val Arg Asp Ile Tyr Ser Phe Asp
           1125                1130                1135

Ile Lys Glu Ala Lys Asp Leu Asp Ile Lys Leu Asn Asn Leu Asn Asn
           1140                1145                1150

Leu Gly Leu Ala Trp Asn Leu Tyr Lys Glu Ser Asp Leu Asn Asn Tyr
           1155                1160                1165

Ile Ala Tyr Gly Ser Val Ser Gly Asn Thr Ile Gln Gly Lys Cys Asn
           1170                1175                1180

Val Thr Pro Gly Lys Tyr Tyr Leu Tyr Val Tyr Lys Tyr Ser Gly Asp
1185                1190                1195                1200

Asn Gly Asn Tyr Ser Leu Thr Ile Lys
           1205

<210> SEQ ID NO 46
<211> LENGTH: 212
<212> TYPE: PRT
<213> ORGANISM: Clostridium botulinum serotype A

<400> SEQUENCE: 46

Met Leu Asn Glu Phe Tyr Thr Lys Gly Glu Glu Ile Ala Asn Ala Ile
  1               5                  10                  15

Thr His Gly Ile Gly Ala Leu Leu Ser Ile Ala Ala Leu Val Ile Leu
             20                  25                  30

Ile Val Phe Ser Ala Lys Tyr Gly Asp Ala Trp Tyr Val Thr Ser Tyr
         35                  40                  45

Ser Ile Phe Gly Ser Cys Leu Phe Ile Leu Tyr Leu Glu Ser Thr Leu
     50                  55                  60

Tyr His Ser Leu Gln Gly Ser Lys Val Lys Lys Ile Phe Arg Ile Phe
65                  70                  75                  80

Asp His Ser Ser Ile Phe Leu Leu Ile Ala Gly Thr Tyr Thr Pro Phe
                 85                  90                  95

Ile Leu Thr Ser Leu Arg Asp Pro Leu Gly Trp Thr Ile Phe Gly Ile
            100                 105                 110

Glu Trp Gly Leu Thr Leu Ile Gly Ile Ile Leu Lys Val Phe Thr Thr
        115                 120                 125
```

Gly Lys Tyr Glu Lys Leu Ser Thr Ala Ile Tyr Ile Phe Met Gly Trp
                130                 135                 140

Leu Ile Met Leu His Ala Lys Lys Leu Val Leu Val Ile Pro Arg Ile
145                 150                 155                 160

Ser Leu Ile Tyr Leu Ile Val Gly Gly Val Ile Tyr Thr Val Gly Ala
                165                 170                 175

Phe Leu Phe Met Leu Asp Asp Ile Pro Tyr Asn His Pro Ile Trp His
                180                 185                 190

Leu Phe Val Ile Gly Gly Ser Val Phe His Phe Phe Ser Leu Phe Tyr
                195                 200                 205

Met Ile Pro Arg
    210

<210> SEQ ID NO 47
<211> LENGTH: 216
<212> TYPE: PRT
<213> ORGANISM: Clostridium botulinum serotype A

<400> SEQUENCE: 47

Met Phe Lys Lys Phe Arg Asp Pro Val Ser Gly Leu Thr His Leu Phe
1               5                   10                  15

Gly Ala Ile Met Ser Ile Val Gly Leu Ile Val Leu Val Asn Tyr Ser
                20                  25                  30

Ile Phe Gln Asp Ser Pro Leu His Ile Thr Val Phe Ala Ile Phe Gly
            35                  40                  45

Ala Ser Leu Ile Leu Leu Tyr Ser Ala Ser Ser Ile Tyr His Leu Val
        50                  55                  60

Thr Ala Ser Lys Lys Ser Ile Arg Ile Leu Arg Arg Ile Asp His Ser
65                  70                  75                  80

Met Ile Tyr Val Leu Ile Ala Gly Ser Tyr Thr Pro Ile Cys Leu Leu
                85                  90                  95

Ala Leu Lys Gly Thr Phe Gly Leu Ala Met Leu Thr Ile Ile Trp Thr
                100                 105                 110

Leu Ala Ile Ile Gly Ile Leu Val Lys Asn Phe Trp Phe Ser Ala Pro
            115                 120                 125

Arg Trp Ile Ser Thr Gly Phe Tyr Leu Ile Met Gly Trp Leu Ile Val
        130                 135                 140

Val Ala Ile Phe Pro Leu Ser Lys Thr Leu Ser Ile Gly Gly Leu Phe
145                 150                 155                 160

Trp Leu Ile Ala Gly Gly Val Ala Tyr Ser Ile Gly Ala Val Ile Tyr
                165                 170                 175

Gly Thr Lys Arg Pro Lys Ile Ala Ser Lys Tyr Phe Thr Phe His Asp
                180                 185                 190

Ile Phe His Ile Phe Val Leu Leu Gly Ser Leu Cys His Phe Ile Leu
            195                 200                 205

Met Leu Asn Tyr Ile Met Tyr Met
    210                 215

<210> SEQ ID NO 48
<211> LENGTH: 401
<212> TYPE: PRT
<213> ORGANISM: Clostridium botulinum serotype A

<400> SEQUENCE: 48

Met Lys Lys Asn Lys Lys Trp Ile Ile Trp Thr Val Val Ile Val Leu
1               5                   10                  15

Val Thr Asn Ile Phe Thr Phe Leu Gly Thr Asn Leu Val Ser Leu Tyr

```
                    20                  25                  30
Leu Pro Asn Gly Lys Val Ile Ile Gly Ala Asp Gln Tyr Lys Asp Ile
                35                  40                  45
Leu Lys Tyr Gln Lys Met Phe Leu Ile Arg Asn Gln Ile Tyr Lys Tyr
 50                  55                  60
Tyr Asp Gly Lys Ile Asp Glu Ser Lys Met Val Glu Gly Ala Val Lys
 65                  70                  75                  80
Gly Met Thr Glu Ser Leu Asn Asp Pro Tyr Thr Val Phe Met Asn Ala
                85                  90                  95
Lys Glu Tyr Lys Glu Phe Asn Ala Gln Thr Glu Gly Asn Tyr Ser Gly
                100                 105                 110
Val Gly Ile Gln Ile Gln Ala Lys Asp Lys Ile Ile Val Ala Ser
                115                 120                 125
Thr Phe Glu Gly Ser Pro Ala Lys Glu Ala Gly Ile Leu Pro Lys Asp
                130                 135                 140
Glu Ile Gln Lys Val Asn Asn Thr Thr Val Ser Gly Lys Glu Leu Glu
145                 150                 155                 160
Lys Ala Val Ser Ile Met Lys Gly Lys Glu Gly Thr Asp Val Lys Leu
                165                 170                 175
Gln Leu Tyr Arg Lys Glu Lys Gly Ser Phe Glu Val Thr Leu Lys Arg
                180                 185                 190
Lys Lys Ile Asp Ile Pro Thr Ile Lys Ser Glu Met Ile Asp Asn Asn
                195                 200                 205
Ile Gly Tyr Ile Gln Val Ser Met Phe Asp Gly Asn Thr Ser Lys Asn
                210                 215                 220
Phe Lys Asn Ala Leu Asn Asp Leu Lys Asp Lys Gly Met Lys Ser Leu
225                 230                 235                 240
Leu Leu Asp Leu Arg Gly Asn Pro Gly Gly Leu Leu Asp Glu Cys Ile
                245                 250                 255
Asn Met Ala Ser Asn Phe Ile Glu Lys Gly Lys Val Val Val Ser Thr
                260                 265                 270
Ile Asp Lys Tyr Gly Ser Lys Lys Glu Tyr Lys Ser Lys Gly Gly Asp
                275                 280                 285
Phe Ile Gly Phe Pro Val Thr Ile Leu Val Asp Glu Gly Ser Ala Ser
                290                 295                 300
Ala Ser Glu Val Phe Leu Gly Ala Met Lys Asp Tyr Asn Val Ala Thr
305                 310                 315                 320
Ser Ile Gly Lys Lys Thr Phe Gly Lys Gly Val Val Gln Thr Ile Ile
                325                 330                 335
Glu Thr Gly Asp Asn Thr Ala Leu Lys Val Thr Ile Ser Lys Tyr Tyr
                340                 345                 350
Ser Pro Lys Gly Val Asn Ile Asn His Lys Gly Ile Thr Pro Asp Met
                355                 360                 365
Glu Ile Asp Tyr Pro Glu Glu Leu Arg Lys Lys Glu Tyr Asp Arg Lys
                370                 375                 380
Val Asp Pro Gln Phe Asn Lys Ala Leu Asn Ile Ala Lys Ser Lys Ile
385                 390                 395                 400
Arg

<210> SEQ ID NO 49
<211> LENGTH: 311
<212> TYPE: PRT
<213> ORGANISM: Clostridium botulinum serotype A

<400> SEQUENCE: 49
```

```
Met Ser Lys Asp Ile Gly Lys Arg Leu Ile Leu Leu Ser Ile Gly
 1               5                  10                 15

Val Thr Ile Leu Val Ile Thr Tyr Ala Tyr Ile Tyr Thr Lys Pro Asn
                20                  25                  30

Ala Tyr Glu Val Leu Val Asn Asn Pro Val Ala Tyr Val Lys Asn
            35                  40                  45

Lys Glu Asp Phe Asn Lys Ile Tyr Lys Val Glu Asn Asn Ile Lys
        50                  55                  60

Lys Arg Phe Asn Leu Asp Met Arg Asn Asn Ile Asn Phe Glu Asn Ile
 65              70                  75                  80

Lys Val Lys Gly Asp Ile Leu Thr Ser Asn Asp Phe Ile Lys Lys Ser
                85                  90                  95

Ile Leu Glu Asn Ser Asn Ile Lys Val Thr Ala Phe Lys Val Lys Phe
                100                 105                 110

Gln Asp Glu Phe Ile Gly Ile Leu Ser Asn Lys Lys Glu Ile Gln Asp
                115                 120                 125

Leu Ser Lys Ile Ile Ser Lys Lys Tyr Ser Val Asn Ile Ile Asn His
        130                 135                 140

Ile Lys Ile Lys Glu Glu Thr Ile Ser Val Glu Glu Ile Asn Thr Ile
145                 150                 155                 160

Asp Glu Leu Ala Ile Asn Ile Ser Lys Ser Gln Lys Leu Gln Asn Phe
                165                 170                 175

Met Asn Ser Lys Arg Leu Ser Arg Gly Asp Ile Asn Glu Glu Ile Ala
        180                 185                 190

Leu Ala Met Pro Thr Asn Gly Cys Ile Thr Ser Lys Phe Gly Lys Arg
        195                 200                 205

Trp Gly Lys Phe His Lys Gly Leu Asp Ile Gly Ala Pro Asn Gly Thr
210                 215                 220

Asp Ile Tyr Ser Ser Leu Asp Gly Lys Val Ile Tyr Ser Gly Trp Glu
225                 230                 235                 240

Glu Gly Tyr Gly Lys Val Ile Lys Ile Gln His Ser Ser Glu Leu Ile
                245                 250                 255

Thr Ile Tyr Ala His Cys Ser Asn Leu Tyr Val Lys Val Gly Gln Tyr
                260                 265                 270

Val Lys Lys Gly Glu Lys Ile Gly Glu Val Gly Ser Thr Gly Arg Ser
        275                 280                 285

Thr Gly Pro His Val His Phe Glu Leu Arg Lys Asn Asn Glu Pro Cys
        290                 295                 300

Asn Pro Leu Thr Tyr Ile Lys
305                 310

<210> SEQ ID NO 50
<211> LENGTH: 1262
<212> TYPE: PRT
<213> ORGANISM: Artificial Sequence
<220> FEATURE:
<223> OTHER INFORMATION: BoNT/E-DiA

<400> SEQUENCE: 50

Met Pro Lys Ile Asn Ser Phe Asn Tyr Asn Asp Pro Val Asn Asp Arg
 1               5                  10                 15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
                35                  40                  45
```

-continued

```
Gly Thr Thr Pro Gln Asp Phe His Pro Pro Thr Ser Leu Lys Asn Gly
 50                  55                  60

Asp Ser Ser Tyr Tyr Asp Pro Asn Tyr Leu Gln Ser Asp Glu Glu Lys
 65                  70                  75                  80

Asp Arg Phe Leu Lys Ile Val Thr Lys Ile Phe Asn Arg Ile Asn Asn
                 85                  90                  95

Asn Leu Ser Gly Gly Ile Leu Leu Glu Glu Leu Ser Lys Ala Asn Pro
                100                 105                 110

Tyr Leu Gly Asn Asp Asn Thr Pro Asp Asn Gln Phe His Ile Gly Asp
                115                 120                 125

Ala Ser Ala Val Glu Ile Lys Phe Ser Asn Gly Ser Gln Asp Ile Leu
                130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
                180                 185                 190

Arg Phe Asn Asp Asn Ser Met Asn Glu Phe Ile Gln Asp Pro Ala Leu
                195                 200                 205

Thr Leu Met His Glu Leu Ile His Ser Leu His Gly Leu Tyr Gly Ala
                210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
                275                 280                 285

Val Gln Val Ser Asn Pro Leu Leu Asn Pro Tyr Lys Asp Val Phe Glu
                290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
                355                 360                 365

Tyr Asn Ile Ser Glu Gly Tyr Asn Ile Asn Asn Leu Lys Val Asn Phe
                370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Lys Thr Lys Ser Leu Asp Lys Gly Tyr Asn Lys Ala Leu
                420                 425                 430

Asn Asp Leu Cys Ile Glu Ile Asn Asn Gly Glu Leu Phe Phe Val Ala
                435                 440                 445

Ser Glu Asn Ser Tyr Asn Asp Asp Asn Ile Asn Thr Pro Lys Glu Ile
                450                 455                 460

Asp Asp Thr Val Thr Ser Asn Asn Asn Tyr Glu Asn Asp Leu Asp Gln
465                 470                 475                 480
```

Val Ile Leu Asn Phe Asn Ser Glu Ser Ala Pro Gly Leu Ser Asp Glu
                485                 490                 495

Lys Leu Asn Leu Thr Ile Gln Asn Asp Ala Tyr Ile Pro Lys Tyr Asp
            500                 505                 510

Ser Asn Gly Thr Ser Asp Ile Glu Gln His Asp Val Asn Glu Leu Asn
        515                 520                 525

Val Phe Phe Tyr Leu Asp Ala Gln Lys Val Pro Glu Gly Glu Asn Asn
    530                 535                 540

Val Asn Leu Thr Ser Ser Ile Asp Thr Ala Leu Leu Glu Gln Pro Lys
545                 550                 555                 560

Ile Tyr Thr Phe Phe Ser Ser Glu Phe Ile Asn Asn Val Asn Lys Pro
                565                 570                 575

Val Gln Ala Ala Leu Phe Val Ser Trp Ile Gln Gln Val Leu Val Asp
            580                 585                 590

Phe Thr Thr Glu Ala Asn Gln Lys Ser Thr Val Asp Lys Ile Ala Asp
        595                 600                 605

Ile Ser Ile Val Val Pro Tyr Ile Gly Leu Ala Leu Asn Ile Gly Asn
    610                 615                 620

Glu Ala Gln Lys Gly Asn Phe Lys Asp Ala Leu Glu Leu Leu Gly Ala
625                 630                 635                 640

Gly Ile Leu Leu Glu Phe Glu Pro Glu Leu Leu Ile Pro Thr Ile Leu
                645                 650                 655

Val Phe Thr Ile Lys Ser Phe Leu Gly Ser Ser Asp Asn Lys Asn Lys
            660                 665                 670

Val Ile Lys Ala Ile Asn Asn Ala Leu Lys Glu Arg Asp Glu Lys Trp
        675                 680                 685

Lys Glu Val Tyr Ser Phe Ile Val Ser Asn Trp Met Thr Lys Ile Asn
    690                 695                 700

Thr Gln Phe Asn Lys Arg Lys Glu Gln Met Tyr Gln Ala Leu Gln Asn
705                 710                 715                 720

Gln Val Asn Ala Ile Lys Thr Ile Ile Glu Ser Lys Tyr Asn Ser Tyr
                725                 730                 735

Thr Leu Glu Glu Lys Asn Glu Leu Thr Asn Lys Tyr Asp Ile Lys Gln
            740                 745                 750

Ile Glu Asn Glu Leu Asn Gln Lys Val Ser Ile Ala Met Asn Asn Ile
        755                 760                 765

Asp Arg Phe Leu Thr Glu Ser Ser Ile Ser Tyr Leu Met Lys Leu Ile
    770                 775                 780

Asn Glu Val Lys Ile Asn Lys Leu Arg Glu Tyr Asp Glu Asn Val Lys
785                 790                 795                 800

Thr Tyr Leu Leu Asn Tyr Ile Ile Gln His Gly Ser Ile Leu Gly Glu
                805                 810                 815

Ser Gln Gln Glu Leu Asn Ser Met Val Thr Asp Thr Leu Asn Asn Ser
            820                 825                 830

Ile Pro Phe Lys Leu Ser Ser Tyr Thr Asp Asp Lys Ile Leu Ile Ser
        835                 840                 845

Tyr Phe Asn Lys Phe Phe Lys Arg Ile Lys Ser Ser Ser Val Leu Asn
    850                 855                 860

Met Arg Tyr Lys Asn Asp Lys Tyr Val Asp Thr Ser Gly Tyr Asp Ser
865                 870                 875                 880

Asn Ile Asn Ile Asn Gly Asp Val Tyr Lys Tyr Pro Thr Asn Lys Asn
                885                 890                 895

Gln Phe Gly Ile Tyr Asn Asp Lys Leu Ser Glu Val Asn Ile Ser Gln

```
                    900                 905                 910
Asn Asp Tyr Ile Ile Tyr Asp Asn Lys Tyr Asn Phe Ser Ile Ser
            915                 920                 925

Phe Trp Val Arg Ile Pro Asn Tyr Asp Asn Lys Ile Val Asn Val Asn
        930                 935                 940

Asn Glu Tyr Thr Ile Ile Asn Cys Met Arg Asp Asn Asn Ser Gly Trp
945                 950                 955                 960

Lys Val Ser Leu Asn His Asn Glu Ile Ile Trp Thr Leu Gln Asp Asn
                965                 970                 975

Ala Gly Ile Asn Gln Lys Leu Ala Phe Asn Tyr Gly Asn Ala Asn Gly
            980                 985                 990

Ile Ser Asp Tyr Ile Asn Lys Trp Ile Phe Val Thr Ile Thr Asn Asp
        995                 1000                1005

Arg Leu Gly Asp Ser Lys Leu Tyr Ile Asn Gly Asn Leu Ile Asp Gln
    1010                1015                1020

Lys Ser Ile Leu Asn Leu Gly Asn Ile His Val Ser Asp Asn Ile Leu
1025                1030                1035                1040

Phe Lys Ile Val Asn Cys Ser Tyr Thr Arg Tyr Ile Gly Ile Arg Tyr
                1045                1050                1055

Phe Asn Ile Phe Asp Lys Glu Leu Asp Glu Thr Glu Ile Gln Thr Leu
            1060                1065                1070

Tyr Ser Asn Glu Pro Asn Thr Asn Ile Leu Lys Asp Phe Trp Gly Asn
        1075                1080                1085

Tyr Leu Leu Tyr Asp Lys Glu Tyr Tyr Leu Leu Asn Val Leu Lys Pro
    1090                1095                1100

Asn Asn Phe Ile Asp Arg Arg Lys Asp Ser Thr Leu Ser Ile Asn Asn
1105                1110                1115                1120

Ile Arg Ser Thr Ile Leu Leu Ala Asn Arg Leu Tyr Ser Gly Ile Lys
                1125                1130                1135

Val Lys Ile Gln Arg Val Asn Asn Ser Ser Thr Asn Asp Asn Leu Val
            1140                1145                1150

Arg Lys Asn Asp Gln Val Tyr Ile Asn Phe Val Ala Ser Lys Thr His
        1155                1160                1165

Leu Phe Pro Leu Tyr Ala Asp Thr Ala Thr Thr Asn Lys Glu Lys Thr
    1170                1175                1180

Ile Lys Ile Ser Ser Ser Gly Asn Arg Phe Asn Gln Val Val Val Met
1185                1190                1195                1200

Asn Ser Val Gly Asn Asn Cys Thr Met Asn Phe Lys Asn Asn Asn Gly
                1205                1210                1215

Asn Asn Ile Gly Leu Leu Gly Phe Lys Ala Asp Thr Val Val Ala Ser
            1220                1225                1230

Thr Trp Tyr Tyr Thr His Met Arg Asp His Thr Asn Ser Asn Gly Cys
        1235                1240                1245

Phe Trp Asn Phe Ile Ser Glu Glu His Gly Trp Gln Glu Lys
    1250                1255                1260

<210> SEQ ID NO 51
<211> LENGTH: 1306
<212> TYPE: PRT
<213> ORGANISM: Artificial Sequence
<220> FEATURE:
<223> OTHER INFORMATION: BoNT/B-DiA

<400> SEQUENCE: 51

Met Pro Val Thr Ile Asn Asn Phe Asn Tyr Asn Asp Pro Ile Asp Asn
1               5                   10                  15
```

-continued

```
Asn Asn Ile Ile Met Met Glu Pro Pro Phe Ala Arg Gly Thr Gly Arg
             20                  25                  30
Tyr Tyr Lys Ala Phe Lys Ile Thr Asp Arg Ile Trp Ile Ile Pro Glu
         35                  40                  45
Arg Tyr Thr Phe Gly Tyr Lys Pro Glu Asp Phe Asn Lys Ser Ser Gly
 50                  55                  60
Ile Phe Asn Arg Asp Val Cys Glu Tyr Tyr Asp Pro Asp Tyr Leu Asn
 65                  70                  75                  80
Thr Asn Asp Lys Lys Asn Ile Phe Leu Gln Thr Met Ile Lys Leu Phe
                 85                  90                  95
Asn Arg Ile Lys Ser Lys Pro Leu Gly Glu Lys Leu Leu Glu Met Ile
            100                 105                 110
Ile Asn Gly Ile Pro Tyr Leu Gly Asp Arg Arg Val Pro Leu Glu Glu
        115                 120                 125
Phe Asn Thr Asn Ile Ala Ser Val Thr Val Asn Lys Leu Ile Ser Asn
130                 135                 140
Pro Gly Glu Val Glu Arg Lys Lys Gly Ile Phe Ala Asn Leu Ile Ile
145                 150                 155                 160
Phe Gly Pro Gly Pro Val Leu Asn Glu Asn Glu Thr Ile Asp Ile Gly
                165                 170                 175
Ile Gln Asn His Phe Ala Ser Arg Glu Gly Phe Gly Gly Ile Met Gln
            180                 185                 190
Met Lys Phe Cys Pro Glu Tyr Val Ser Val Phe Asn Asn Val Gln Glu
        195                 200                 205
Asn Lys Gly Ala Ser Ile Phe Asn Arg Arg Gly Tyr Phe Ser Asp Pro
210                 215                 220
Ala Leu Ile Leu Met His Glu Leu Ile His Val Leu His Gly Leu Tyr
225                 230                 235                 240
Gly Ile Lys Val Asp Asp Leu Pro Ile Val Pro Asn Glu Lys Lys Phe
                245                 250                 255
Phe Met Gln Ser Thr Asp Ala Ile Gln Ala Glu Glu Leu Tyr Thr Phe
            260                 265                 270
Gly Gly Gln Asp Pro Ser Ile Ile Thr Pro Ser Thr Asp Lys Ser Ile
        275                 280                 285
Tyr Asp Lys Val Leu Gln Asn Phe Arg Gly Ile Val Asp Arg Leu Asn
290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
                325                 330                 335
Lys Tyr Ser Ile Asp Val Glu Ser Phe Asp Lys Leu Tyr Lys Ser Leu
            340                 345                 350
Met Phe Gly Phe Thr Glu Thr Asn Ile Ala Glu Asn Tyr Lys Ile Lys
        355                 360                 365
Thr Arg Ala Ser Tyr Phe Ser Asp Ser Leu Pro Pro Val Lys Ile Lys
370                 375                 380
Asn Leu Leu Asp Asn Glu Ile Tyr Thr Ile Glu Glu Gly Phe Asn Ile
385                 390                 395                 400
Ser Asp Lys Asp Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
            420                 425                 430
Lys Ile Gln Met Cys Val Arg Gly Ile Ile Thr Ser Lys Thr Lys Ser
```

-continued

```
            435                 440                 445
Leu Asp Lys Gly Tyr Asn Lys Ala Leu Asn Asp Leu Cys Ile Asp Val
450                 455                 460
Asp Asn Glu Asp Leu Phe Phe Ile Ala Asp Lys Asn Ser Phe Ser Asp
465                 470                 475                 480
Asp Leu Ser Lys Asn Glu Arg Ile Glu Tyr Asn Thr Gln Ser Asn Tyr
                485                 490                 495
Ile Glu Asn Asp Phe Pro Ile Asn Glu Leu Ile Leu Asp Thr Asp Leu
                500                 505                 510
Ile Ser Lys Ile Glu Leu Pro Ser Glu Asn Thr Glu Ser Leu Thr Asp
            515                 520                 525
Phe Asn Val Asp Val Pro Val Tyr Glu Lys Gln Pro Ala Ile Lys Lys
        530                 535                 540
Ile Phe Thr Asp Glu Asn Thr Ile Phe Gln Tyr Leu Tyr Ser Gln Thr
545                 550                 555                 560
Phe Pro Leu Asp Ile Arg Asp Ile Ser Leu Thr Ser Ser Phe Asp Asp
                565                 570                 575
Ala Leu Leu Phe Ser Asn Lys Val Tyr Ser Phe Phe Ser Met Asp Tyr
            580                 585                 590
Ile Lys Thr Ala Asn Lys Val Val Glu Ala Gly Leu Phe Ala Gly Trp
        595                 600                 605
Val Lys Gln Ile Val Asn Asp Phe Val Ile Glu Ala Asn Lys Ser Asn
    610                 615                 620
Thr Met Asp Lys Ile Ala Asp Ile Ser Leu Ile Val Pro Tyr Ile Gly
625                 630                 635                 640
Leu Ala Leu Asn Val Gly Asn Glu Thr Ala Lys Gly Asn Phe Glu Asn
                645                 650                 655
Ala Phe Glu Ile Ala Gly Ala Ser Ile Leu Leu Glu Phe Ile Pro Glu
            660                 665                 670
Leu Leu Ile Pro Val Val Gly Ala Phe Leu Leu Glu Ser Tyr Ile Asp
        675                 680                 685
Asn Lys Asn Lys Ile Ile Lys Thr Ile Asp Asn Ala Leu Thr Lys Arg
    690                 695                 700
Asn Glu Lys Trp Ser Asp Met Tyr Gly Leu Ile Val Ala Gln Trp Leu
705                 710                 715                 720
Ser Thr Val Asn Thr Gln Phe Tyr Thr Ile Lys Glu Gly Met Tyr Lys
                725                 730                 735
Ala Leu Asn Tyr Gln Ala Gln Ala Leu Glu Glu Ile Ile Lys Tyr Arg
            740                 745                 750
Tyr Asn Ile Tyr Ser Glu Lys Glu Lys Ser Asn Ile Asn Ile Asp Phe
        755                 760                 765
Asn Asp Ile Asn Ser Lys Leu Asn Glu Gly Ile Asn Gln Ala Ile Asp
    770                 775                 780
Asn Ile Asn Asn Phe Ile Asn Gly Cys Ser Val Ser Tyr Leu Met Lys
785                 790                 795                 800
Lys Met Ile Pro Leu Ala Val Glu Lys Leu Leu Asp Phe Asp Asn Thr
                805                 810                 815
Leu Lys Lys Asn Leu Leu Asn Tyr Ile Asp Glu Asn Lys Leu Tyr Leu
            820                 825                 830
Ile Gly Ser Ala Glu Tyr Glu Lys Ser Lys Val Asn Lys Tyr Leu Lys
        835                 840                 845
Thr Ile Met Pro Phe Asp Leu Ser Ile Tyr Thr Asn Asp Thr Ile Leu
    850                 855                 860
```

-continued

Ile Glu Met Phe Asn Lys Tyr Asn Ser Glu Ile Leu Asn Asn Ile Ile
865                 870                  875                 880

Leu Asn Leu Arg Tyr Lys Asp Asn Asn Leu Ile Asp Leu Ser Gly Tyr
            885                 890                 895

Gly Ala Lys Val Glu Val Tyr Asp Gly Val Glu Leu Asn Asp Lys Asn
            900                 905                 910

Gln Phe Lys Leu Thr Ser Ser Ala Asn Ser Lys Ile Arg Val Thr Gln
            915                 920                 925

Asn Gln Asn Ile Ile Phe Asn Ser Val Phe Leu Asp Phe Ser Val Ser
            930                 935                 940

Phe Trp Ile Arg Ile Pro Lys Tyr Lys Asn Asp Gly Ile Gln Asn Tyr
945                 950                 955                 960

Ile His Asn Glu Tyr Thr Ile Ile Asn Cys Met Lys Asn Asn Ser Gly
            965                 970                 975

Trp Lys Ile Ser Ile Arg Gly Asn Arg Ile Ile Trp Thr Leu Ile Asp
            980                 985                 990

Ile Asn Gly Lys Thr Lys Ser Val Phe Phe Glu Tyr Asn Ile Arg Glu
            995                 1000                1005

Asp Ile Ser Glu Tyr Ile Asn Arg Trp Phe Phe Val Thr Ile Thr Asn
            1010                1015                1020

Asn Leu Asn Asn Ala Lys Ile Tyr Ile Asn Gly Lys Leu Glu Ser Asn
1025                1030                1035                1040

Thr Asp Ile Lys Asp Ile Arg Glu Val Ile Ala Asn Gly Glu Ile Ile
            1045                1050                1055

Phe Lys Leu Asp Gly Asp Ile Asp Arg Thr Gln Phe Ile Trp Met Lys
            1060                1065                1070

Tyr Phe Ser Ile Phe Asn Thr Glu Leu Ser Gln Ser Asn Ile Glu Glu
            1075                1080                1085

Arg Tyr Lys Ile Gln Ser Tyr Ser Glu Tyr Leu Lys Asp Phe Trp Gly
            1090                1095                1100

Asn Pro Leu Met Tyr Asn Lys Glu Tyr Tyr Met Phe Asn Ala Gly Asn
1105                1110                1115                1120

Lys Asn Ser Tyr Ile Lys Leu Lys Lys Asp Ser Pro Val Gly Glu Ile
            1125                1130                1135

Leu Thr Arg Ser Lys Tyr Asn Gln Asn Ser Lys Tyr Ile Asn Tyr Arg
            1140                1145                1150

Asp Leu Tyr Ile Gly Glu Lys Phe Ile Ile Arg Arg Lys Ser Asn Ser
            1155                1160                1165

Gln Ser Ile Asn Asp Asp Ile Val Arg Lys Glu Asp Tyr Ile Tyr Leu
            1170                1175                1180

Asp Phe Phe Asn Leu Asn Gln Glu Trp Arg Val Tyr Thr Tyr Lys Tyr
1185                1190                1195                1200

Phe Lys Lys Glu Glu Glu Lys Leu Phe Leu Ala Pro Ile Ser Asp Ser
            1205                1210                1215

Asp Glu Phe Tyr Asn Thr Ile Gln Ile Lys Glu Tyr Asp Glu Gln Pro
            1220                1225                1230

Thr Tyr Ser Cys Gln Leu Leu Phe Lys Lys Asp Glu Glu Ser Thr Asp
            1235                1240                1245

Glu Ile Gly Leu Ile Gly Ile His Arg Phe Tyr Glu Ser Gly Ile Val
            1250                1255                1260

Phe Glu Glu Tyr Lys Asp Tyr Phe Cys Ile Ser Lys Trp Tyr Leu Lys
1265                1270                1275                1280

Glu Val Lys Arg Lys Pro Tyr Asn Leu Lys Leu Gly Cys Asn Trp Gln
            1285                1290                1295

Phe Ile Pro Lys Asp Glu Gly Trp Thr Glu
            1300                1305

<210> SEQ ID NO 52
<211> LENGTH: 1299
<212> TYPE: PRT
<213> ORGANISM: Artificial Sequence
<220> FEATURE:
<223> OTHER INFORMATION: BoNT/C1-DiA

<400> SEQUENCE: 52

Met Pro Ile Thr Ile Asn Asn Phe Asn Tyr Ser Asp Pro Val Asp Asn
  1               5                  10                  15

Lys Asn Ile Leu Tyr Leu Asp Thr His Leu Asn Thr Leu Ala Asn Glu
                 20                  25                  30

Pro Glu Lys Ala Phe Arg Ile Thr Gly Asn Ile Trp Val Ile Pro Asp
             35                  40                  45

Arg Phe Ser Arg Asn Ser Asn Pro Asn Leu Asn Lys Pro Pro Arg Val
 50                  55                  60

Thr Ser Pro Lys Ser Gly Tyr Tyr Asp Pro Asn Tyr Leu Ser Thr Asp
 65                  70                  75                  80

Ser Asp Lys Asp Pro Phe Leu Lys Glu Ile Ile Lys Leu Phe Lys Arg
                 85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
            115                 120                 125

Phe Asp Val Asp Phe Asn Ser Val Asp Val Lys Thr Arg Gln Gly Asn
            130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
            195                 200                 205

Val Gly Glu Gly Arg Phe Ser Lys Ser Glu Phe Cys Met Asp Pro Ile
            210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
            275                 280                 285

Phe Glu Glu Lys Ala Leu Asp Tyr Tyr Arg Ser Ile Ala Lys Arg Leu
            290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

```
Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
        370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
                420                 425                 430

Phe Thr Lys Phe Cys Val Arg Gly Ile Ile Thr Ser Lys Thr Lys Ser
        435                 440                 445

Leu Asp Lys Gly Tyr Asn Lys Ala Leu Asn Asp Leu Cys Arg Glu Leu
        450                 455                 460

Leu Val Lys Asn Thr Asp Leu Pro Phe Ile Gly Asp Ile Ser Asp Val
465                 470                 475                 480

Lys Thr Asp Ile Phe Leu Arg Lys Asp Ile Asn Glu Glu Thr Glu Val
                485                 490                 495

Ile Tyr Tyr Pro Asp Asn Val Ser Val Asp Gln Val Ile Leu Ser Lys
                500                 505                 510

Asn Thr Ser Glu His Gly Gln Leu Asp Leu Leu Tyr Pro Ser Ile Asp
        515                 520                 525

Ser Glu Ser Glu Ile Leu Pro Gly Glu Asn Gln Val Phe Tyr Asp Asn
        530                 535                 540

Arg Thr Gln Asn Val Asp Tyr Leu Asn Ser Tyr Tyr Tyr Leu Glu Ser
545                 550                 555                 560

Gln Lys Leu Ser Asp Asn Val Glu Asp Phe Thr Phe Thr Arg Ser Ile
                565                 570                 575

Glu Glu Ala Leu Asp Asn Ser Ala Lys Val Tyr Thr Tyr Phe Pro Thr
                580                 585                 590

Leu Ala Asn Lys Val Asn Ala Gly Val Gln Gly Gly Leu Phe Leu Met
        595                 600                 605

Trp Ala Asn Asp Val Val Glu Asp Phe Thr Thr Asn Ile Leu Arg Lys
        610                 615                 620

Asp Thr Leu Asp Lys Ile Ser Asp Val Ser Ala Ile Ile Pro Tyr Ile
625                 630                 635                 640

Gly Pro Ala Leu Asn Ile Ser Asn Ser Val Arg Arg Gly Asn Phe Thr
                645                 650                 655

Glu Ala Phe Ala Val Thr Gly Val Thr Ile Leu Leu Glu Ala Phe Pro
                660                 665                 670

Glu Phe Thr Ile Pro Ala Leu Gly Ala Phe Val Ile Tyr Ser Lys Val
        675                 680                 685

Gln Glu Arg Asn Glu Ile Ile Lys Thr Ile Asp Asn Cys Leu Glu Gln
        690                 695                 700

Arg Ile Lys Arg Trp Lys Asp Ser Tyr Glu Trp Met Met Gly Thr Trp
705                 710                 715                 720

Leu Ser Arg Ile Ile Thr Gln Phe Asn Asn Ile Ser Tyr Gln Met Tyr
                725                 730                 735

Asp Ser Leu Asn Tyr Gln Ala Gly Ala Ile Lys Ala Lys Ile Asp Leu
                740                 745                 750

Glu Tyr Lys Lys Tyr Ser Gly Ser Asp Lys Glu Asn Ile Lys Ser Gln
        755                 760                 765

Val Glu Asn Leu Lys Asn Ser Leu Asp Val Lys Ile Ser Glu Ala Met
        770                 775                 780
```

```
Asn Asn Ile Asn Lys Phe Ile Arg Glu Cys Ser Val Thr Tyr Leu Phe
785                 790                 795                 800

Lys Asn Met Leu Pro Lys Val Ile Asp Glu Leu Asn Glu Phe Asp Arg
            805                 810                 815

Asn Thr Lys Ala Lys Leu Ile Asn Leu Ile Asp Ser His Asn Ile Ile
        820                 825                 830

Leu Val Gly Glu Val Asp Lys Leu Lys Ala Lys Val Asn Asn Ser Phe
            835                 840                 845

Gln Asn Thr Ile Pro Phe Asn Ile Phe Ser Tyr Thr Asn Asn Ser Leu
        850                 855                 860

Leu Lys Asp Ile Ile Asn Glu Tyr Phe Asn Asn Ile Asn Asp Ser Lys
865                 870                 875                 880

Ile Leu Ser Leu Gln Asn Arg Lys Asn Thr Leu Val Asp Thr Ser Gly
            885                 890                 895

Tyr Asn Ala Glu Val Ser Glu Glu Gly Asp Val Gln Leu Asn Pro Ile
            900                 905                 910

Phe Pro Phe Asp Phe Lys Leu Gly Ser Ser Gly Glu Asp Arg Gly Lys
        915                 920                 925

Val Ile Val Thr Gln Asn Glu Asn Ile Val Tyr Asn Ser Met Tyr Glu
            930                 935                 940

Ser Phe Ser Ile Ser Phe Trp Ile Arg Ile Asn Lys Trp Val Ser Asn
945                 950                 955                 960

Leu Pro Gly Tyr Thr Ile Ile Asp Ser Val Lys Asn Asn Ser Gly Trp
            965                 970                 975

Ser Ile Gly Ile Ile Ser Asn Phe Leu Val Phe Thr Leu Lys Gln Asn
            980                 985                 990

Glu Asp Ser Glu Gln Ser Ile Asn Phe Ser Tyr Asp Ile Ser Asn Asn
            995                 1000                1005

Ala Pro Gly Tyr Asn Lys Trp Phe Phe Val Thr Val Thr Asn Asn Met
    1010                1015                1020

Met Gly Asn Met Lys Ile Tyr Ile Asn Gly Lys Leu Ile Asp Thr Ile
1025                1030                1035                1040

Lys Val Lys Glu Leu Thr Gly Ile Asn Phe Ser Lys Thr Ile Thr Phe
            1045                1050                1055

Glu Ile Asn Lys Ile Pro Asp Thr Gly Leu Ile Thr Ser Asp Ser Asp
            1060                1065                1070

Asn Ile Asn Met Trp Ile Arg Asp Phe Tyr Ile Phe Ala Lys Glu Leu
        1075                1080                1085

Asp Gly Lys Asp Ile Asn Ile Leu Phe Asn Ser Leu Gln Tyr Thr Asn
        1090                1095                1100

Val Val Lys Asp Tyr Trp Gly Asn Asp Leu Arg Tyr Asn Lys Glu Tyr
1105                1110                1115                1120

Tyr Met Val Asn Ile Asp Tyr Leu Asn Arg Tyr Met Tyr Ala Asn Ser
            1125                1130                1135

Arg Gln Ile Val Phe Asn Thr Arg Arg Asn Asn Asn Asp Phe Asn Glu
            1140                1145                1150

Gly Tyr Lys Ile Ile Ile Lys Arg Ile Arg Gly Asn Thr Asn Asp Thr
        1155                1160                1165

Arg Val Arg Gly Gly Asp Ile Leu Tyr Phe Asp Met Thr Ile Asn Asn
        1170                1175                1180

Lys Ala Tyr Asn Leu Phe Met Lys Asn Glu Thr Met Tyr Ala Asp Asn
1185                1190                1195                1200

His Ser Thr Glu Asp Ile Tyr Ala Ile Gly Leu Arg Glu Gln Thr Lys
```

-continued

Asp Ile Asn Asp Asn Ile Ile Phe Gln Ile Gln Pro Met Asn Asn Thr
         1205                1210                1215
         1220                1225                1230

Tyr Tyr Tyr Ala Ser Gln Ile Phe Lys Ser Asn Phe Asn Gly Glu Asn
         1235                1240                1245

Ile Ser Gly Ile Cys Ser Ile Gly Thr Tyr Arg Phe Arg Leu Gly Gly
         1250                1255                1260

Asp Trp Tyr Arg His Asn Tyr Leu Val Pro Thr Val Lys Gln Gly Asn
1265                1270                1275                1280

Tyr Ala Ser Leu Leu Glu Ser Thr Ser Thr His Trp Gly Phe Val Pro
              1285                1290                1295

Val Ser Glu

<210> SEQ ID NO 53
<211> LENGTH: 1287
<212> TYPE: PRT
<213> ORGANISM: Artificial Sequence
<220> FEATURE:
<223> OTHER INFORMATION: BoNT/D-DiA

<400> SEQUENCE: 53

Met Thr Trp Pro Val Lys Asp Phe Asn Tyr Ser Asp Pro Val Asn Asp
 1               5                  10                  15

Asn Asp Ile Leu Tyr Leu Arg Ile Pro Gln Asn Lys Leu Ile Thr Thr
             20                  25                  30

Pro Val Lys Ala Phe Met Ile Thr Gln Asn Ile Trp Val Ile Pro Glu
         35                  40                  45

Arg Phe Ser Ser Asp Thr Asn Pro Ser Leu Ser Lys Pro Pro Arg Pro
     50                  55                  60

Thr Ser Lys Tyr Gln Ser Tyr Tyr Asp Pro Ser Tyr Leu Ser Thr Asp
 65                  70                  75                  80

Glu Gln Lys Asp Thr Phe Leu Lys Gly Ile Ile Lys Leu Phe Lys Arg
                 85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Thr Pro Ser Val Leu Ile Phe Gly Pro
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

-continued

```
Phe Gly Gly Leu Asp Val Glu Ile Ile Pro Gln Ile Glu Arg Ser Gln
            275                 280                 285

Leu Arg Glu Lys Ala Leu Gly His Tyr Lys Asp Ile Ala Lys Arg Leu
        290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Val Arg Gly Ile Ile Thr Ser Lys Thr Lys Ser
        435                 440                 445

Leu Asp Lys Gly Tyr Asn Lys Ala Leu Asn Asp Leu Cys Ile Lys Val
    450                 455                 460

Lys Asn Asn Arg Leu Pro Tyr Val Ala Asp Lys Asp Ser Ile Ser Gln
465                 470                 475                 480

Glu Ile Phe Glu Asn Lys Ile Ile Thr Asp Glu Thr Asn Val Gln Asn
                485                 490                 495

Tyr Ser Asp Lys Phe Ser Leu Asp Glu Ser Ile Leu Asp Gly Gln Val
            500                 505                 510

Pro Ile Asn Pro Glu Ile Val Asp Pro Leu Leu Pro Asn Val Asn Met
        515                 520                 525

Glu Pro Leu Asn Leu Pro Gly Glu Glu Ile Val Phe Tyr Asp Asp Ile
    530                 535                 540

Thr Lys Tyr Val Asp Tyr Leu Asn Ser Tyr Tyr Tyr Leu Glu Ser Gln
545                 550                 555                 560

Lys Leu Ser Asn Asn Val Glu Asn Ile Thr Leu Thr Thr Ser Val Glu
                565                 570                 575

Glu Ala Leu Gly Tyr Ser Asn Lys Ile Tyr Thr Phe Leu Pro Ser Leu
            580                 585                 590

Ala Glu Lys Val Asn Lys Gly Val Gln Ala Gly Leu Phe Leu Asn Trp
        595                 600                 605

Ala Asn Glu Val Val Glu Asp Phe Thr Thr Asn Ile Met Lys Lys Asp
    610                 615                 620

Thr Leu Asp Lys Ile Ser Asp Val Ser Val Ile Ile Pro Tyr Ile Gly
625                 630                 635                 640

Pro Ala Leu Asn Ile Gly Asn Ser Ala Leu Arg Gly Asn Phe Asn Gln
                645                 650                 655

Ala Phe Ala Thr Ala Gly Val Ala Phe Leu Leu Glu Gly Phe Pro Glu
            660                 665                 670

Phe Thr Ile Pro Ala Leu Gly Val Phe Thr Phe Tyr Ser Ser Ile Gln
        675                 680                 685

Glu Arg Glu Lys Ile Ile Lys Thr Ile Glu Asn Cys Leu Glu Gln Arg
    690                 695                 700
```

```
Val Lys Arg Trp Lys Asp Ser Tyr Gln Trp Met Val Ser Asn Trp Leu
705                 710                 715                 720

Ser Arg Ile Thr Thr Gln Phe Asn His Ile Asn Tyr Gln Met Tyr Asp
            725                 730                 735

Ser Leu Ser Tyr Gln Ala Asp Ala Ile Lys Ala Lys Ile Asp Leu Glu
            740                 745                 750

Tyr Lys Lys Tyr Ser Gly Ser Asp Lys Glu Asn Ile Lys Ser Gln Val
        755                 760                 765

Glu Asn Leu Lys Asn Ser Leu Asp Val Lys Ile Ser Glu Ala Met Asn
        770                 775                 780

Asn Ile Asn Lys Phe Ile Arg Glu Cys Ser Val Thr Tyr Leu Phe Lys
785                 790                 795                 800

Asn Met Leu Pro Lys Val Ile Asp Glu Leu Asn Lys Phe Asp Leu Arg
                805                 810                 815

Thr Lys Thr Glu Leu Ile Asn Leu Ile Asp Ser His Asn Ile Ile Leu
            820                 825                 830

Val Gly Glu Val Asp Arg Leu Lys Ala Lys Val Asn Glu Ser Phe Glu
        835                 840                 845

Asn Thr Met Pro Phe Asn Ile Phe Ser Tyr Thr Asn Asn Ser Leu Leu
        850                 855                 860

Lys Asp Ile Ile Asn Glu Tyr Phe Asn Ser Ile Asn Asp Ser Lys Ile
865                 870                 875                 880

Leu Ser Leu Gln Asn Lys Lys Asn Ala Leu Val Asp Thr Ser Gly Tyr
                885                 890                 895

Asn Ala Glu Val Arg Val Gly Asp Asn Val Gln Leu Asn Thr Ile Tyr
            900                 905                 910

Thr Asn Asp Phe Lys Leu Ser Ser Ser Gly Asp Lys Ile Ile Val Asn
        915                 920                 925

Leu Asn Asn Asn Ile Leu Tyr Ser Ala Ile Tyr Glu Asn Ser Ser Val
        930                 935                 940

Ser Phe Trp Ile Lys Ile Ser Lys Asp Leu Thr Asn Ser His Asn Glu
945                 950                 955                 960

Tyr Thr Ile Ile Asn Ser Ile Glu Gln Asn Ser Gly Trp Lys Leu Cys
                965                 970                 975

Ile Arg Asn Gly Asn Ile Glu Trp Ile Leu Gln Asp Val Asn Arg Lys
            980                 985                 990

Tyr Lys Ser Leu Ile Phe Asp Tyr Ser Glu Ser Leu Ser His Thr Gly
        995                 1000                1005

Tyr Thr Asn Lys Trp Phe Phe Val Thr Ile Thr Asn Asn Ile Met Gly
        1010                1015                1020

Tyr Met Lys Leu Tyr Ile Asn Gly Glu Leu Lys Gln Ser Gln Lys Ile
1025                1030                1035                1040

Glu Asp Leu Asp Glu Val Lys Leu Asp Lys Thr Ile Val Phe Gly Ile
                1045                1050                1055

Asp Glu Asn Ile Asp Glu Asn Gln Met Leu Trp Ile Arg Asp Phe Asn
            1060                1065                1070

Ile Phe Ser Lys Glu Leu Ser Asn Glu Asp Ile Asn Ile Val Tyr Glu
        1075                1080                1085

Gly Gln Ile Leu Arg Asn Val Ile Lys Asp Tyr Trp Gly Asn Pro Leu
        1090                1095                1100

Lys Phe Asp Thr Glu Tyr Tyr Ile Ile Asn Asp Asn Tyr Ile Asp Arg
1105                1110                1115                1120

Tyr Ile Ala Pro Glu Ser Asn Val Leu Val Leu Val Gln Tyr Pro Asp
```

-continued

```
                1125                1130                1135

Arg Ser Lys Leu Tyr Thr Gly Asn Pro Ile Thr Ile Lys Ser Val Ser
            1140                1145                1150

Asp Lys Asn Pro Tyr Ser Arg Ile Leu Asn Gly Asp Asn Ile Ile Leu
        1155                1160                1165

His Met Leu Tyr Asn Ser Arg Lys Tyr Met Ile Ile Arg Asp Thr Asp
    1170                1175                1180

Thr Ile Tyr Ala Thr Gln Gly Gly Glu Cys Ser Gln Asn Cys Val Tyr
1185                1190                1195                1200

Ala Leu Lys Leu Gln Ser Asn Leu Gly Asn Tyr Gly Ile Gly Ile Phe
                1205                1210                1215

Ser Ile Lys Asn Ile Val Ser Lys Asn Lys Tyr Cys Ser Gln Ile Phe
            1220                1225                1230

Ser Ser Phe Arg Glu Asn Thr Met Leu Leu Ala Asp Ile Tyr Lys Pro
        1235                1240                1245

Trp Arg Phe Ser Phe Lys Asn Ala Tyr Thr Pro Val Ala Val Thr Asn
    1250                1255                1260

Tyr Glu Thr Lys Leu Leu Ser Thr Ser Ser Phe Trp Lys Phe Ile Ser
1265                1270                1275                1280

Arg Asp Pro Gly Trp Val Glu
                1285

<210> SEQ ID NO 54
<211> LENGTH: 1282
<212> TYPE: PRT
<213> ORGANISM: Artificial Sequence
<220> FEATURE:
<223> OTHER INFORMATION: BoNT/F-DiA

<400> SEQUENCE: 54

Met Pro Val Ala Ile Asn Ser Phe Asn Tyr Asn Asp Pro Val Asn Asp
 1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205
```

```
Gly His Asn Ser Ser Thr Glu Ser Phe Ile Ala Asp Pro Ala Ile Ser
            210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
            275                 280                 285

Asn Leu Leu Ala Asn Tyr Glu Lys Ile Ala Thr Arg Leu Ser Glu Val
290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
            355                 360                 365

Phe Ile Lys Tyr Glu Phe Leu Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Val Arg Gly
                420                 425                 430

Ile Ile Thr Ser Lys Thr Lys Ser Leu Asp Lys Gly Tyr Asn Lys Ala
            435                 440                 445

Leu Asn Asp Leu Cys Ile Arg Val Asn Asn Ser Glu Leu Phe Phe Val
450                 455                 460

Ala Ser Glu Ser Ser Tyr Asn Glu Asn Asp Ile Asn Thr Pro Lys Glu
465                 470                 475                 480

Ile Asp Asp Thr Thr Asn Leu Asn Asn Asn Tyr Arg Asn Asn Leu Asp
                485                 490                 495

Glu Val Ile Leu Asp Tyr Asn Ser Gln Thr Ile Pro Gln Ile Ser Asn
                500                 505                 510

Arg Thr Leu Asn Thr Leu Val Gln Asp Asn Ser Tyr Val Pro Arg Tyr
            515                 520                 525

Asp Ser Asn Gly Thr Ser Glu Ile Glu Glu Tyr Asp Val Val Asp Phe
530                 535                 540

Asn Val Phe Phe Tyr Leu His Ala Gln Lys Val Pro Glu Gly Glu Thr
545                 550                 555                 560

Asn Ile Ser Leu Thr Ser Ser Ile Asp Thr Ala Leu Leu Glu Glu Ser
                565                 570                 575

Lys Asp Ile Phe Phe Ser Ser Glu Phe Ile Asp Thr Ile Asn Lys Pro
            580                 585                 590

Val Asn Ala Ala Leu Phe Ile Asp Trp Ile Ser Lys Val Ile Arg Asp
            595                 600                 605

Phe Thr Thr Glu Ala Thr Gln Lys Ser Thr Val Asp Lys Ile Ala Asp
610                 615                 620

Ile Ser Leu Ile Val Pro Tyr Val Gly Leu Ala Leu Asn Ile Ile Ile
```

```
            625                 630                 635                 640
Glu Ala Glu Lys Gly Asn Phe Glu Ala Phe Glu Leu Leu Gly Val
                645                 650                 655
Gly Ile Leu Leu Glu Phe Val Pro Glu Leu Thr Ile Pro Val Ile Leu
                660                 665                 670
Val Phe Thr Ile Lys Ser Tyr Ile Asp Ser Tyr Glu Asn Lys Asn Lys
                675                 680                 685
Ala Ile Lys Ala Ile Asn Asn Ser Leu Ile Glu Arg Glu Ala Lys Trp
                690                 695                 700
Lys Glu Ile Tyr Ser Trp Ile Val Ser Asn Trp Leu Thr Arg Ile Asn
705                 710                 715                 720
Thr Gln Phe Asn Lys Arg Lys Glu Gln Met Tyr Gln Ala Leu Gln Asn
                725                 730                 735
Gln Val Asp Ala Ile Lys Thr Ala Ile Glu Tyr Lys Tyr Asn Asn Tyr
                740                 745                 750
Thr Ser Asp Glu Lys Asn Arg Leu Glu Ser Glu Tyr Asn Ile Asn Asn
                755                 760                 765
Ile Glu Glu Glu Leu Asn Lys Lys Val Ser Leu Ala Met Lys Asn Ile
                770                 775                 780
Glu Arg Phe Met Thr Glu Ser Ser Ile Ser Tyr Leu Met Lys Leu Ile
785                 790                 795                 800
Asn Glu Ala Lys Val Gly Lys Leu Lys Lys Tyr Asp Asn His Val Lys
                805                 810                 815
Ser Asp Leu Leu Asn Tyr Ile Leu Asp His Arg Ser Ile Leu Gly Glu
                820                 825                 830
Gln Thr Asn Glu Leu Ser Asp Leu Val Thr Ser Thr Leu Asn Ser Ser
                835                 840                 845
Ile Pro Phe Glu Leu Ser Ser Tyr Thr Asn Asp Lys Ile Leu Ile Ile
                850                 855                 860
Tyr Phe Asn Arg Leu Tyr Lys Lys Ile Lys Asp Ser Ser Ile Leu Asp
865                 870                 875                 880
Met Arg Tyr Glu Asn Asn Lys Phe Ile Asp Ile Ser Gly Tyr Gly Ser
                885                 890                 895
Asn Ile Ser Ile Asn Gly Asn Val Tyr Ile Tyr Ser Thr Asn Arg Asn
                900                 905                 910
Gln Phe Gly Ile Tyr Asn Ser Arg Leu Ser Glu Val Asn Ile Ala Gln
                915                 920                 925
Asn Asn Asp Ile Ile Tyr Asn Ser Arg Tyr Gln Asn Phe Ser Ile Ser
                930                 935                 940
Phe Trp Val Arg Ile Pro Lys His Tyr Lys Pro Met Asn His Asn Arg
945                 950                 955                 960
Glu Tyr Thr Ile Ile Asn Cys Met Gly Asn Asn Asn Ser Gly Trp Lys
                965                 970                 975
Ile Ser Leu Arg Thr Val Arg Asp Cys Glu Ile Ile Trp Thr Leu Gln
                980                 985                 990
Asp Thr Ser Gly Asn Lys Glu Asn Leu Ile Phe Arg Tyr Glu Glu Leu
                995                 1000                1005
Asn Arg Ile Ser Asn Tyr Ile Asn Lys Trp Ile Phe Val Thr Ile Thr
                1010                1015                1020
Asn Asn Arg Leu Gly Asn Ser Arg Ile Tyr Ile Asn Gly Asn Leu Ile
1025                1030                1035                1040
Val Glu Lys Ser Ile Ser Asn Leu Gly Asp Ile His Val Ser Asp Asn
                1045                1050                1055
```

```
Ile Leu Phe Lys Ile Val Gly Cys Asp Asp Glu Thr Tyr Val Gly Ile
            1060                1065                1070

Arg Tyr Phe Lys Val Phe Asn Thr Glu Leu Asp Lys Thr Glu Ile Glu
            1075                1080                1085

Thr Leu Tyr Ser Asn Glu Pro Asp Pro Ser Ile Leu Lys Asn Tyr Trp
            1090                1095                1100

Gly Asn Tyr Leu Leu Tyr Asn Lys Lys Tyr Tyr Leu Phe Asn Leu Leu
1105                1110                1115                1120

Arg Lys Asp Lys Tyr Ile Thr Leu Asn Ser Gly Ile Leu Asn Ile Asn
            1125                1130                1135

Gln Gln Arg Gly Val Thr Glu Gly Ser Val Phe Leu Asn Tyr Lys Leu
            1140                1145                1150

Tyr Glu Gly Val Glu Val Ile Ile Arg Lys Asn Gly Pro Ile Asp Ile
            1155                1160                1165

Ser Asn Thr Asp Asn Phe Val Arg Lys Asn Asp Leu Ala Tyr Ile Asn
            1170                1175                1180

Val Val Asp Arg Gly Val Glu Tyr Arg Leu Tyr Ala Asp Thr Lys Ser
1185                1190                1195                1200

Glu Lys Glu Lys Ile Ile Arg Thr Ser Asn Leu Asn Asp Ser Leu Gly
            1205                1210                1215

Gln Ile Ile Val Met Asp Ser Ile Gly Asn Asn Cys Thr Met Asn Phe
            1220                1225                1230

Gln Asn Asn Asn Gly Ser Asn Ile Gly Leu Leu Gly Phe His Ser Asn
            1235                1240                1245

Asn Leu Val Ala Ser Ser Trp Tyr Tyr Asn Asn Ile Arg Arg Asn Thr
            1250                1255                1260

Ser Ser Asn Gly Cys Phe Trp Ser Ser Ile Ser Lys Glu Asn Gly Trp
1265                1270                1275                1280

Lys Glu

<210> SEQ ID NO 55
<211> LENGTH: 1307
<212> TYPE: PRT
<213> ORGANISM: Artificial Sequence
<220> FEATURE:
<223> OTHER INFORMATION: BoNT/G-DiA

<400> SEQUENCE: 55

Met Pro Val Asn Ile Lys Asn Phe Asn Tyr Asn Asp Pro Ile Asn Asn
 1               5                  10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
            35                  40                  45

Arg Phe Thr Tyr Gly Phe Gln Pro Asp Gln Phe Asn Ala Ser Thr Gly
 50                  55                  60

Val Phe Ser Lys Asp Val Tyr Glu Tyr Tyr Asp Pro Thr Tyr Leu Lys
 65                  70                  75                  80

Thr Asp Ala Glu Lys Asp Lys Phe Leu Lys Thr Met Ile Lys Leu Phe
            85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
            115                 120                 125

Phe Ala Ala Asn Val Ala Asn Val Ser Ile Asn Lys Lys Ile Ile Gln
            130                 135                 140
```

```
Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
            165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
                195                 200                 205

Asn Lys Asp Thr Ser Ile Phe Ser Arg Arg Ala Tyr Phe Ala Asp Pro
            210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
            275                 280                 285

Tyr Asn Lys Ala Leu Gln Asn Phe Gln Asp Ile Ala Asn Arg Leu Asn
            290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
            355                 360                 365

Arg Tyr Ser Tyr Phe Ser Glu Tyr Leu Pro Pro Ile Lys Thr Glu Lys
370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
            405                 410                 415

Lys Glu Ala Tyr Glu Glu Ile Ser Leu Glu His Leu Val Ile Tyr Arg
            420                 425                 430

Ile Ala Met Cys Val Arg Gly Ile Ile Thr Ser Lys Thr Lys Ser Leu
            435                 440                 445

Asp Lys Gly Tyr Asn Lys Ala Leu Asn Asp Leu Cys Ile Ile Val Asn
            450                 455                 460

Asn Glu Asp Leu Phe Phe Ile Ala Asn Lys Asp Ser Phe Ser Lys Asp
465                 470                 475                 480

Leu Ala Lys Ala Glu Thr Ile Ala Tyr Asn Thr Gln Asn Asn Thr Ile
            485                 490                 495

Glu Asn Asn Phe Ser Ile Asp Gln Leu Ile Leu Asp Asn Asp Leu Ser
            500                 505                 510

Ser Gly Ile Asp Leu Pro Asn Glu Asn Thr Glu Pro Phe Thr Asn Phe
            515                 520                 525

Asp Asp Ile Asp Ile Pro Val Tyr Ile Lys Gln Ser Ala Leu Lys Lys
            530                 535                 540

Ile Phe Val Asp Gly Asp Ser Leu Phe Glu Tyr Leu His Ala Gln Thr
545                 550                 555                 560

Phe Pro Ser Asn Ile Glu Asn Leu Gln Leu Thr Asn Ser Leu Asn Asp
```

-continued

```
                565                 570                 575
Ala Leu Arg Asn Asn Asn Lys Val Tyr Thr Phe Phe Ser Thr Asn Leu
            580                 585                 590
Val Glu Lys Ala Asn Thr Val Val Gly Ala Ser Leu Phe Val Asn Trp
            595                 600                 605
Val Lys Gly Val Ile Asp Asp Phe Thr Ser Glu Ser Thr Gln Lys Ser
            610                 615                 620
Thr Ile Asp Lys Val Ser Asp Val Ser Ile Ile Pro Tyr Ile Gly
625                 630                 635                 640
Pro Ala Leu Asn Val Gly Asn Glu Thr Ala Lys Glu Asn Phe Lys Asn
            645                 650                 655
Ala Phe Glu Ile Gly Gly Ala Ala Ile Leu Met Glu Phe Ile Pro Glu
            660                 665                 670
Leu Ile Val Pro Ile Val Gly Phe Phe Thr Leu Glu Ser Tyr Val Gly
            675                 680                 685
Asn Lys Gly His Ile Ile Met Thr Ile Ser Asn Ala Leu Lys Lys Arg
            690                 695                 700
Asp Gln Lys Trp Thr Asp Met Tyr Gly Leu Ile Val Ser Gln Trp Leu
705                 710                 715                 720
Ser Thr Val Asn Thr Gln Phe Tyr Thr Ile Lys Glu Arg Met Tyr Asn
                725                 730                 735
Ala Leu Asn Asn Gln Ser Gln Ala Ile Glu Lys Ile Ile Glu Asp Gln
            740                 745                 750
Tyr Asn Arg Tyr Ser Glu Glu Asp Lys Met Asn Ile Asn Ile Asp Phe
            755                 760                 765
Asn Asp Ile Asp Phe Lys Leu Asn Gln Ser Ile Asn Leu Ala Ile Asn
            770                 775                 780
Asn Ile Asp Asp Phe Ile Asn Gln Cys Ser Ile Ser Tyr Leu Met Asn
785                 790                 795                 800
Arg Met Ile Pro Leu Ala Val Lys Lys Leu Lys Asp Phe Asp Asp Asn
                805                 810                 815
Leu Lys Arg Asp Leu Leu Glu Tyr Ile Asp Thr Asn Glu Leu Tyr Leu
            820                 825                 830
Leu Asp Glu Val Asn Ile Leu Lys Ser Lys Val Asn Arg His Leu Lys
            835                 840                 845
Asp Ser Ile Pro Phe Asp Leu Ser Leu Tyr Thr Lys Asp Thr Ile Leu
            850                 855                 860
Ile Gln Val Phe Asn Asn Tyr Ile Ser Asn Ile Ser Ser Asn Ala Ile
865                 870                 875                 880
Leu Ser Leu Ser Tyr Arg Gly Gly Arg Leu Ile Asp Ser Ser Gly Tyr
                885                 890                 895
Gly Ala Thr Met Asn Val Gly Ser Asp Val Ile Phe Asn Asp Ile Gly
            900                 905                 910
Asn Gly Gln Phe Lys Leu Asn Asn Ser Glu Asn Ser Asn Ile Thr Ala
            915                 920                 925
His Gln Ser Lys Phe Val Val Tyr Asp Ser Met Phe Asp Asn Phe Ser
            930                 935                 940
Ile Asn Phe Trp Val Arg Thr Pro Lys Tyr Asn Asn Asn Asp Ile Gln
945                 950                 955                 960
Thr Tyr Leu Gln Asn Glu Tyr Thr Ile Ile Ser Cys Ile Lys Asn Asp
                965                 970                 975
Ser Gly Trp Lys Val Ser Ile Lys Gly Asn Arg Ile Ile Trp Thr Leu
            980                 985                 990
```

```
Ile Asp Val Asn Ala Lys Ser Lys Ser Ile Phe Phe Glu Tyr Ser Ile
    995                 1000                1005

Lys Asp Asn Ile Ser Asp Tyr Ile Asn Lys Trp Phe Ser Ile Thr Ile
    1010                1015                1020

Thr Asn Asp Arg Leu Gly Asn Ala Asn Ile Tyr Ile Asn Gly Ser Leu
1025                1030                1035                1040

Lys Lys Ser Glu Lys Ile Leu Asn Leu Asp Arg Ile Asn Ser Ser Asn
            1045                1050                1055

Asp Ile Asp Phe Lys Leu Ile Asn Cys Thr Asp Thr Lys Phe Val
        1060                1065                1070

Trp Ile Lys Asp Phe Asn Ile Phe Gly Arg Glu Leu Asn Ala Thr Glu
    1075                1080                1085

Val Ser Ser Leu Tyr Trp Ile Gln Ser Ser Thr Asn Thr Leu Lys Asp
    1090                1095                1100

Phe Trp Gly Asn Pro Leu Arg Tyr Asp Thr Gln Tyr Tyr Leu Phe Asn
1105                1110                1115                1120

Gln Gly Met Gln Asn Ile Tyr Ile Lys Tyr Phe Ser Lys Ala Ser Met
                1125                1130                1135

Gly Glu Thr Ala Pro Arg Thr Asn Phe Asn Asn Ala Ala Ile Asn Tyr
    1140                1145                1150

Gln Asn Leu Tyr Leu Gly Leu Arg Phe Ile Ile Lys Lys Ala Ser Asn
    1155                1160                1165

Ser Arg Asn Ile Asn Asn Asp Asn Ile Val Arg Glu Gly Asp Tyr Ile
    1170                1175                1180

Tyr Leu Asn Ile Asp Asn Ile Ser Asp Glu Ser Tyr Arg Val Tyr Val
1185                1190                1195                1200

Leu Val Asn Ser Lys Glu Ile Gln Thr Gln Leu Phe Leu Ala Pro Ile
                1205                1210                1215

Asn Asp Asp Pro Thr Phe Tyr Asp Val Leu Gln Ile Lys Lys Tyr Tyr
            1220                1225                1230

Glu Lys Thr Thr Tyr Asn Cys Gln Ile Leu Cys Glu Lys Asp Thr Lys
    1235                1240                1245

Thr Phe Gly Leu Phe Gly Ile Gly Lys Phe Val Lys Asp Tyr Gly Tyr
    1250                1255                1260

Val Trp Asp Thr Tyr Asp Asn Tyr Phe Cys Ile Ser Gln Trp Tyr Leu
1265                1270                1275                1280

Arg Arg Ile Ser Glu Asn Ile Asn Lys Leu Arg Leu Gly Cys Asn Trp
                1285                1290                1295

Gln Phe Ile Pro Val Asp Glu Gly Trp Thr Glu
            1300                1305

<210> SEQ ID NO 56
<211> LENGTH: 1311
<212> TYPE: PRT
<213> ORGANISM: Artificial Sequence
<220> FEATURE:
<223> OTHER INFORMATION: TeNT-DiA

<400> SEQUENCE: 56

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
                20                  25                  30

Tyr Tyr Lys Ala Phe Lys Ile Thr Asp Arg Ile Trp Ile Val Pro Glu
            35                  40                  45

Arg Tyr Glu Phe Gly Thr Lys Pro Glu Asp Phe Asn Pro Pro Ser Ser
```

```
                  50                  55                  60
Leu Ile Glu Gly Ala Ser Glu Tyr Tyr Asp Pro Asn Tyr Leu Arg Thr
 65                  70                  75                  80

Asp Ser Asp Lys Asp Arg Phe Leu Gln Thr Met Val Lys Leu Phe Asn
                 85                  90                  95

Arg Ile Lys Asn Asn Val Ala Gly Glu Ala Leu Leu Asp Lys Ile Ile
                100                 105                 110

Asn Ala Ile Pro Tyr Leu Gly Asn Ser Tyr Ser Leu Leu Asp Lys Phe
                115                 120                 125

Asp Thr Asn Ser Asn Ser Val Ser Phe Asn Leu Leu Glu Gln Asp Pro
                130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
                180                 185                 190

Ile Met Gln Met Ala Phe Cys Pro Glu Tyr Val Pro Thr Phe Asp Asn
                195                 200                 205

Val Ile Glu Asn Ile Thr Ser Leu Thr Ile Gly Lys Ser Lys Tyr Phe
210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
                260                 265                 270

Phe Thr Phe Gly Gly Gln Asp Ala Asn Leu Ile Ser Ile Asp Ile Lys
                275                 280                 285

Asn Asp Leu Tyr Glu Lys Thr Leu Asn Asp Tyr Lys Ala Ile Ala Asn
                290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
                340                 345                 350

Ser Ile Met Tyr Gly Phe Thr Glu Ile Glu Leu Gly Lys Lys Phe Asn
                355                 360                 365

Ile Lys Thr Arg Leu Ser Tyr Phe Ser Met Asn His Asp Pro Val Lys
                370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
                420                 425                 430

Ser Lys Leu Ile Gly Leu Cys Val Arg Gly Ile Ile Thr Ser Lys Thr
                435                 440                 445

Lys Ser Leu Asp Lys Gly Tyr Asn Lys Ala Leu Asn Asp Leu Cys Ile
                450                 455                 460

Lys Ile Lys Asn Glu Asp Leu Thr Phe Ile Ala Glu Lys Asn Ser Phe
465                 470                 475                 480
```

-continued

```
Ser Glu Glu Pro Phe Gln Asp Glu Ile Val Ser Tyr Asn Thr Lys Asn
            485                 490                 495

Lys Pro Leu Asn Phe Asn Tyr Ser Leu Asp Lys Ile Ile Val Asp Tyr
        500                 505                 510

Asn Leu Gln Ser Lys Ile Thr Leu Pro Asn Asp Arg Thr Thr Pro Val
        515                 520                 525

Thr Lys Gly Ile Pro Tyr Ala Pro Glu Tyr Lys Ser Asn Ala Ala Ser
        530                 535                 540

Thr Ile Glu Ile His Asn Ile Asp Asp Asn Thr Ile Tyr Gln Tyr Leu
545                 550                 555                 560

Tyr Ala Gln Lys Ser Pro Thr Thr Leu Gln Arg Ile Thr Met Thr Asn
                565                 570                 575

Ser Val Asp Asp Ala Leu Ile Asn Ser Thr Lys Ile Tyr Ser Tyr Phe
                580                 585                 590

Pro Ser Val Ile Ser Lys Val Asn Gln Gly Ala Gln Gly Ile Leu Phe
            595                 600                 605

Leu Gln Trp Val Arg Asp Ile Ile Asp Asp Phe Thr Asn Glu Ser Ser
        610                 615                 620

Gln Lys Thr Thr Ile Asp Lys Ile Ser Asp Val Ser Thr Ile Val Pro
625                 630                 635                 640

Tyr Ile Gly Pro Ala Leu Asn Ile Val Lys Gln Gly Tyr Glu Gly Asn
                645                 650                 655

Phe Ile Gly Ala Leu Glu Thr Thr Gly Val Val Leu Leu Leu Glu Tyr
            660                 665                 670

Ile Pro Glu Ile Thr Leu Pro Val Ile Ala Ala Leu Ser Ile Ala Glu
        675                 680                 685

Ser Ser Thr Gln Lys Glu Lys Ile Ile Lys Thr Ile Asp Asn Phe Leu
        690                 695                 700

Glu Lys Arg Tyr Glu Lys Trp Ile Glu Val Tyr Lys Leu Val Lys Ala
705                 710                 715                 720

Lys Trp Leu Gly Thr Val Asn Thr Gln Phe Gln Lys Arg Ser Tyr Gln
                725                 730                 735

Met Tyr Arg Ser Leu Glu Tyr Gln Val Asp Ala Ile Lys Lys Ile Ile
                740                 745                 750

Asp Tyr Glu Tyr Lys Ile Tyr Ser Gly Pro Asp Lys Glu Gln Ile Ala
            755                 760                 765

Asp Glu Ile Asn Asn Leu Lys Asn Lys Leu Glu Glu Lys Ala Asn Lys
        770                 775                 780

Ala Met Ile Asn Ile Asn Ile Phe Met Arg Glu Ser Ser Arg Ser Phe
785                 790                 795                 800

Leu Val Asn Gln Met Ile Asn Glu Ala Lys Lys Gln Leu Leu Glu Phe
                805                 810                 815

Asp Thr Gln Ser Lys Asn Ile Leu Met Gln Tyr Ile Lys Ala Asn Ser
                820                 825                 830

Lys Phe Ile Gly Ile Thr Glu Leu Lys Lys Leu Glu Ser Lys Ile Asn
            835                 840                 845

Lys Val Phe Ser Thr Pro Ile Pro Phe Ser Tyr Ser Lys Asn Leu Asp
        850                 855                 860

Cys Trp Val Asp Asn Glu Glu Asp Ile Asp Val Ile Leu Lys Lys Ser
865                 870                 875                 880

Thr Ile Leu Asn Leu Asp Ile Asn Asn Asp Ile Ile Ser Asp Ile Ser
                885                 890                 895

Gly Phe Asn Ser Ser Val Ile Thr Tyr Pro Asp Ala Gln Leu Val Pro
            900                 905                 910
```

Gly Ile Asn Gly Lys Ala Ile His Leu Val Asn Asn Glu Ser Ser Glu
            915                 920                 925

Val Ile Val His Lys Ala Met Asp Ile Glu Tyr Asn Asp Met Phe Asn
        930                 935                 940

Asn Phe Thr Val Ser Phe Trp Leu Arg Val Pro Lys Val Ser Ala Ser
945                 950                 955                 960

His Leu Glu Gln Tyr Gly Thr Asn Glu Tyr Ser Ile Ile Ser Ser Met
                965                 970                 975

Lys Lys His Ser Leu Ser Ile Gly Ser Gly Trp Ser Val Ser Leu Lys
            980                 985                 990

Gly Asn Asn Leu Ile Trp Thr Leu Lys Asp Ser Ala Gly Glu Val Arg
        995                 1000                1005

Gln Ile Thr Phe Arg Asp Leu Pro Asp Lys Phe Asn Ala Tyr Leu Ala
    1010                1015                1020

Asn Lys Trp Val Phe Ile Thr Ile Thr Asn Asp Arg Leu Ser Ser Ala
1025                1030                1035                1040

Asn Leu Tyr Ile Asn Gly Val Leu Met Gly Ser Ala Glu Ile Thr Gly
                1045                1050                1055

Leu Gly Ala Ile Arg Glu Asp Asn Asn Ile Thr Leu Lys Leu Asp Arg
            1060                1065                1070

Cys Asn Asn Asn Gln Tyr Val Ser Ile Asp Lys Phe Arg Ile Phe
        1075                1080                1085

Cys Lys Ala Leu Asn Pro Lys Glu Ile Glu Lys Leu Tyr Thr Ser Tyr
    1090                1095                1100

Leu Ser Ile Thr Phe Leu Arg Asp Phe Trp Gly Asn Pro Leu Arg Tyr
1105                1110                1115                1120

Asp Thr Glu Tyr Tyr Leu Ile Pro Val Ala Ser Ser Ser Lys Asp Val
                1125                1130                1135

Gln Leu Lys Asn Ile Thr Asp Tyr Met Tyr Leu Thr Asn Ala Pro Ser
            1140                1145                1150

Tyr Thr Asn Gly Lys Leu Asn Ile Tyr Tyr Arg Arg Leu Tyr Asn Gly
        1155                1160                1165

Leu Lys Phe Ile Ile Lys Arg Tyr Thr Pro Asn Asn Glu Ile Asp Ser
    1170                1175                1180

Phe Val Lys Ser Gly Asp Phe Ile Lys Leu Tyr Val Ser Tyr Asn Asn
1185                1190                1195                1200

Asn Glu His Ile Val Gly Tyr Pro Lys Asp Gly Asn Ala Phe Asn Asn
                1205                1210                1215

Leu Asp Arg Ile Leu Arg Val Gly Tyr Asn Ala Pro Gly Ile Pro Leu
            1220                1225                1230

Tyr Lys Lys Met Glu Ala Val Lys Leu Arg Asp Leu Lys Thr Tyr Ser
        1235                1240                1245

Val Gln Leu Lys Leu Tyr Asp Asp Lys Asn Ala Ser Leu Gly Leu Val
    1250                1255                1260

Gly Thr His Asn Gly Gln Ile Gly Asn Asp Pro Asn Arg Asp Ile Leu
1265                1270                1275                1280

Ile Ala Ser Asn Trp Tyr Phe Asn His Leu Lys Asp Lys Ile Leu Gly
                1285                1290                1295

Cys Asp Trp Tyr Phe Val Pro Thr Asp Glu Gly Trp Thr Asn Asp
            1300                1305                1310

<210> SEQ ID NO 57
<211> LENGTH: 1278
<212> TYPE: PRT

<213> ORGANISM: Artificial Sequence
<220> FEATURE:
<223> OTHER INFORMATION: BaNT-DiA

<400> SEQUENCE: 57

```
Met Pro Val Asn Ile Asn Asn Phe Asn Tyr Asn Asp Pro Ile Asn Asn
 1               5                  10                  15

Thr Thr Ile Leu Tyr Met Lys Met Pro Tyr Tyr Glu Asp Ser Asn Lys
            20                  25                  30

Tyr Tyr Lys Ala Phe Glu Ile Met Asp Asn Val Trp Ile Ile Pro Glu
        35                  40                  45

Arg Asn Ile Ile Gly Lys Lys Pro Ser Asp Phe Tyr Pro Pro Ile Ser
    50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95

Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
        115                 120                 125

Cys Ala Asn Asn Arg Ser Thr Ser Val Glu Ile Lys Glu Ser Asn Gly
    130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
        195                 200                 205

Phe Ile Ala Asp Pro Ala Ile Ser Leu Ala His Glu Leu Ile His Val
    210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
                245                 250                 255

Glu Glu Phe Ile Thr Phe Gly Gly Gln Asp Leu Asn Ile Ile Thr Asn
            260                 265                 270

Ser Thr Asn Gln Lys Ile Tyr Val Ile Leu Leu Ser Asn Tyr Thr Ala
        275                 280                 285

Ile Ala Ser Arg Leu Ser Gln Val Asn Arg Asn Asn Ser Ala Leu Asn
    290                 295                 300

Thr Thr Tyr Tyr Lys Asn Phe Phe Gln Trp Lys Tyr Gly Leu Asp Gln
305                 310                 315                 320

Asp Ser Asn Gly Asn Tyr Thr Val Asn Ile Ser Lys Phe Asn Ala Ile
                325                 330                 335

Tyr Lys Lys Leu Phe Ser Phe Thr Glu Cys Asp Leu Ala Gln Lys Phe
            340                 345                 350

Gln Val Lys Asn Arg Ser Asn Tyr Leu Phe His Phe Lys Pro Phe Arg
        355                 360                 365

Leu Leu Asp Leu Leu Asp Asp Asn Ile Tyr Ser Ile Ser Glu Gly Phe
    370                 375                 380

Asn Ile Gly Ser Leu Arg Val Asn Asn Asn Gly Gln Asn Ile Asn Leu
385                 390                 395                 400
```

```
Asn Ser Arg Ile Val Gly Pro Ile Pro Asp Asn Gly Leu Val Glu Arg
                405                 410                 415
Phe Val Gly Leu Cys Val Arg Gly Ile Ile Thr Ser Lys Thr Lys Ser
            420                 425                 430
Leu Asp Lys Gly Tyr Asn Lys Ala Leu Asn Asp Leu Cys Ile Lys Val
            435                 440                 445
Asn Asn Arg Asp Leu Phe Phe Val Ala Ser Glu Ser Ser Tyr Asn Glu
450                 455                 460
Asn Gly Ile Asn Ser Pro Lys Glu Ile Asp Asp Thr Thr Ile Thr Asn
465                 470                 475                 480
Asn Asn Tyr Lys Lys Asn Leu Asp Glu Val Ile Leu Asp Tyr Asn Ser
                485                 490                 495
Asp Ala Ile Pro Asn Leu Ser Ser Arg Leu Leu Asn Thr Thr Ala Gln
                500                 505                 510
Asn Asp Ser Tyr Val Pro Lys Tyr Asp Ser Asn Gly Thr Ser Glu Ile
            515                 520                 525
Lys Glu Tyr Thr Val Asp Lys Leu Asn Val Phe Phe Tyr Leu Tyr Ala
            530                 535                 540
Gln Lys Ala Pro Glu Gly Glu Ser Ala Ile Ser Leu Thr Ser Ser Val
545                 550                 555                 560
Asn Thr Ala Leu Leu Asp Ala Ser Lys Val Tyr Thr Phe Phe Ser Ser
                565                 570                 575
Asp Phe Ile Asn Thr Val Asn Lys Pro Val Gln Ala Ala Leu Phe Ile
                580                 585                 590
Ser Trp Ile Gln Gln Val Ile Asn Asp Phe Thr Thr Glu Ala Thr Gln
            595                 600                 605
Lys Ser Thr Ile Asp Lys Ile Ala Asp Ile Ser Leu Ile Val Pro Tyr
            610                 615                 620
Val Gly Leu Ala Leu Asn Ile Gly Asn Glu Val Gln Lys Gly Asn Phe
625                 630                 635                 640
Lys Glu Ala Ile Glu Leu Leu Gly Ala Gly Ile Leu Leu Glu Phe Val
                645                 650                 655
Pro Glu Leu Leu Ile Pro Thr Ile Leu Val Phe Thr Ile Lys Ser Phe
                660                 665                 670
Ile Asn Ser Asp Asp Ser Lys Asn Lys Ile Ile Lys Ala Ile Asn Asn
            675                 680                 685
Ala Leu Arg Glu Arg Glu Leu Lys Trp Lys Glu Val Tyr Ser Trp Ile
            690                 695                 700
Val Ser Asn Trp Leu Thr Arg Ile Asn Thr Gln Phe Asn Lys Arg Lys
705                 710                 715                 720
Glu Gln Met Tyr Gln Ala Leu Gln Asn Gln Val Asp Gly Ile Lys Lys
                725                 730                 735
Ile Ile Glu Tyr Lys Tyr Asn Asn Tyr Thr Leu Asp Glu Lys Asn Arg
                740                 745                 750
Leu Arg Ala Glu Tyr Asn Ile Tyr Ser Ile Lys Glu Glu Leu Asn Lys
            755                 760                 765
Lys Val Ser Leu Ala Met Gln Asn Ile Asp Arg Phe Leu Thr Glu Ser
            770                 775                 780
Ser Ile Ser Tyr Leu Met Lys Leu Ile Asn Glu Ala Lys Ile Asn Lys
785                 790                 795                 800
Leu Ser Glu Tyr Asp Lys Arg Val Asn Gln Tyr Leu Leu Asn Tyr Ile
                805                 810                 815
Leu Glu Asn Ser Ser Thr Leu Gly Thr Ser Ser Val Pro Glu Leu Asn
```

```
                820             825             830
Asn Leu Val Ser Asn Thr Leu Asn Asn Ser Ile Pro Phe Glu Leu Ser
            835             840             845
Glu Tyr Thr Asn Asp Lys Ile Leu Ile His Ile Leu Ile Arg Phe Tyr
        850             855             860
Lys Arg Ile Ile Asp Ser Ser Ile Leu Asn Met Lys Tyr Glu Asn Asn
865             870             875             880
Arg Phe Ile Asp Ser Ser Gly Tyr Gly Ser Asn Ile Ser Ile Asn Gly
            885             890             895
Asp Ile Tyr Ile Tyr Ser Thr Asn Arg Asn Gln Phe Gly Ile Tyr Ser
        900             905             910
Ser Arg Leu Ser Glu Val Asn Ile Thr Gln Asn Asn Thr Ile Ile Tyr
            915             920             925
Asn Ser Arg Tyr Gln Asn Phe Ser Val Ser Phe Trp Val Arg Ile Pro
        930             935             940
Lys Tyr Asn Asn Leu Lys Asn Leu Asn Asn Glu Tyr Thr Ile Ile Asn
945             950             955             960
Cys Met Arg Asn Asn Ser Gly Trp Lys Ile Ser Leu Asn Tyr Asn
            965             970             975
Asn Ile Ile Trp Thr Leu Gln Asp Thr Thr Gly Asn Asn Gln Lys Leu
        980             985             990
Val Phe Asn Tyr Thr Gln Met Ile Asp Ile Ser Asp Tyr Ile Asn Lys
            995             1000            1005
Trp Thr Phe Val Thr Ile Thr Asn Asn Arg Leu Gly His Ser Lys Leu
        1010            1015            1020
Tyr Ile Asn Gly Asn Leu Thr Asp Gln Lys Ser Ile Leu Asn Leu Gly
1025            1030            1035            1040
Asn Ile His Val Asp Asp Asn Ile Leu Phe Lys Ile Val Gly Cys Asn
            1045            1050            1055
Asp Thr Arg Tyr Val Gly Ile Arg Tyr Phe Lys Ile Phe Asn Met Glu
        1060            1065            1070
Leu Asp Lys Thr Glu Ile Glu Thr Leu Tyr His Ser Glu Pro Asp Ser
            1075            1080            1085
Thr Ile Leu Lys Asp Phe Trp Gly Asn Tyr Leu Leu Tyr Asn Lys Lys
        1090            1095            1100
Tyr Tyr Leu Leu Asn Leu Leu Lys Pro Asn Met Ser Val Thr Lys Asn
1105            1110            1115            1120
Ser Asp Ile Leu Asn Ile Asn Arg Gln Arg Gly Ile Tyr Ser Lys Thr
            1125            1130            1135
Asn Ile Phe Ser Asn Ala Arg Leu Tyr Thr Gly Val Glu Val Ile Ile
            1140            1145            1150
Arg Lys Val Gly Ser Thr Asp Thr Ser Asn Thr Asp Asn Phe Val Arg
        1155            1160            1165
Lys Asn Asp Thr Val Tyr Ile Asn Val Val Asp Gly Asn Ser Glu Tyr
            1170            1175            1180
Gln Leu Tyr Ala Asp Val Ser Thr Ser Ala Val Glu Lys Thr Ile Lys
1185            1190            1195            1200
Leu Arg Arg Ile Ser Asn Ser Asn Tyr Asn Ser Asn Gln Met Ile Ile
            1205            1210            1215
Met Asp Ser Ile Gly Asp Asn Cys Thr Met Asn Phe Lys Thr Asn Asn
        1220            1225            1230
Gly Asn Asp Ile Gly Leu Leu Gly Phe His Leu Asn Asn Leu Val Ala
            1235            1240            1245
```

```
Ser Ser Trp Tyr Tyr Lys Asn Ile Arg Asn Asn Thr Arg Asn Asn Gly
    1250                1255                1260

Cys Phe Trp Ser Phe Ile Ser Lys Glu His Gly Trp Gln Glu
1265                1270                1275

<210> SEQ ID NO 58
<211> LENGTH: 1261
<212> TYPE: PRT
<213> ORGANISM: Artificial Sequence
<220> FEATURE:
<223> OTHER INFORMATION: BuNT-DiA

<400> SEQUENCE: 58

Met Pro Thr Ile Asn Ser Phe Asn Tyr Asn Asp Pro Val Asn Asn Arg
 1               5                  10                  15

Thr Ile Leu Tyr Ile Lys Pro Gly Gly Cys Gln Gln Phe Tyr Lys Ser
            20                  25                  30

Phe Asn Ile Met Lys Asn Ile Trp Ile Ile Pro Glu Arg Asn Val Ile
        35                  40                  45

Gly Thr Ile Pro Gln Asp Phe Leu Pro Pro Thr Ser Leu Lys Asn Gly
    50                  55                  60

Asp Ser Ser Tyr Tyr Asp Pro Asn Tyr Leu Gln Ser Asp Gln Glu Lys
65                  70                  75                  80

Asp Lys Phe Leu Lys Ile Val Thr Lys Ile Phe Asn Arg Ile Asn Asp
                85                  90                  95

Asn Leu Ser Gly Arg Ile Leu Leu Glu Glu Leu Ser Lys Ala Asn Pro
            100                 105                 110

Tyr Leu Gly Asn Asp Asn Thr Pro Asp Gly Asp Phe Ile Ile Asn Asp
        115                 120                 125

Ala Ser Ala Val Pro Ile Gln Phe Ser Asn Gly Ser Gln Ser Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Lys Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
```

```
                     340               345               350
Gly Gln Tyr Lys Tyr Phe Lys Leu Ser Asn Leu Leu Asn Asp Ser Ile
                355               360               365

Tyr Asn Ile Ser Glu Gly Tyr Asn Ile Asn Asn Leu Lys Val Asn Phe
    370               375               380

Arg Gly Gln Asn Ala Asn Leu Asn Pro Arg Ile Ile Thr Pro Ile Thr
385               390               395               400

Gly Arg Gly Leu Val Lys Lys Ile Ile Arg Phe Cys Val Arg Gly Ile
                405               410               415

Ile Thr Ser Lys Thr Lys Ser Leu Asp Lys Gly Tyr Asn Lys Ala Leu
                420               425               430

Asn Asp Leu Cys Ile Glu Ile Asn Asn Gly Glu Leu Phe Phe Val Ala
                435               440               445

Ser Glu Asn Ser Tyr Asn Asp Asn Ile Asn Thr Pro Lys Glu Ile
    450               455               460

Asp Asp Thr Val Thr Ser Asn Asn Asn Tyr Glu Asn Asp Leu Asp Gln
465               470               475               480

Val Ile Leu Asn Phe Asn Ser Glu Ser Ala Pro Gly Leu Ser Asp Glu
                485               490               495

Lys Leu Asn Leu Thr Ile Gln Asn Asp Ala Tyr Ile Pro Lys Tyr Asp
                500               505               510

Ser Asn Gly Thr Ser Asp Ile Glu Gln His Asp Val Asn Glu Leu Asn
                515               520               525

Val Phe Phe Tyr Leu Asp Ala Gln Lys Val Pro Glu Gly Glu Asn Asn
                530               535               540

Val Asn Leu Thr Ser Ser Ile Asp Thr Ala Leu Leu Glu Gln Pro Lys
545               550               555               560

Ile Tyr Thr Phe Phe Ser Ser Glu Phe Ile Asn Asn Val Asn Lys Pro
                565               570               575

Val Gln Ala Ala Leu Phe Val Gly Trp Ile Gln Gln Val Leu Val Asp
                580               585               590

Phe Thr Thr Glu Ala Asn Gln Lys Ser Thr Val Asp Lys Ile Ala Asp
                595               600               605

Ile Ser Ile Val Val Pro Tyr Ile Gly Leu Ala Leu Asn Ile Gly Asn
                610               615               620

Glu Ala Gln Lys Gly Asn Phe Lys Asp Ala Leu Glu Leu Leu Gly Ala
625               630               635               640

Gly Ile Leu Leu Glu Phe Glu Pro Glu Leu Leu Ile Pro Thr Ile Leu
                645               650               655

Val Phe Thr Ile Lys Ser Phe Leu Gly Ser Ser Asp Asn Lys Asn Lys
                660               665               670

Val Ile Lys Ala Ile Asn Asn Ala Leu Lys Glu Arg Asp Glu Lys Trp
                675               680               685

Lys Glu Val Tyr Ser Phe Ile Val Ser Asn Trp Met Thr Lys Ile Asn
                690               695               700

Thr Gln Phe Asn Lys Arg Lys Glu Gln Met Tyr Gln Ala Leu Gln Asn
705               710               715               720

Gln Val Asn Ala Leu Lys Ala Ile Ile Glu Ser Lys Tyr Asn Ser Tyr
                725               730               735

Thr Leu Glu Glu Lys Asn Glu Leu Thr Asn Lys Tyr Asp Ile Glu Gln
                740               745               750

Ile Glu Asn Glu Leu Asn Gln Lys Val Ser Ile Ala Met Asn Asn Ile
                755               760               765
```

```
Asp Arg Phe Leu Thr Glu Ser Ser Ile Ser Tyr Leu Met Lys Leu Ile
770                 775                 780

Asn Glu Val Lys Ile Asn Lys Leu Arg Glu Tyr Asp Glu Asn Val Lys
785                 790                 795                 800

Thr Tyr Leu Leu Asp Tyr Ile Ile Lys His Gly Ser Ile Leu Gly Glu
                805                 810                 815

Ser Gln Gln Glu Leu Asn Ser Met Val Ile Asp Thr Leu Asn Asn Ser
            820                 825                 830

Ile Pro Phe Lys Leu Ser Ser Tyr Thr Asp Asp Lys Ile Leu Ile Ser
        835                 840                 845

Tyr Phe Asn Lys Phe Phe Lys Arg Ile Lys Ser Ser Val Leu Asn
    850                 855                 860

Met Arg Tyr Lys Asn Asp Lys Tyr Val Asp Thr Ser Gly Tyr Asp Ser
865                 870                 875                 880

Asn Ile Asn Ile Asn Gly Asp Val Tyr Lys Tyr Pro Thr Asn Lys Asn
                885                 890                 895

Gln Phe Gly Ile Tyr Asn Asp Lys Leu Ser Glu Val Asn Ile Ser Gln
            900                 905                 910

Asn Asp Tyr Ile Ile Tyr Asp Asn Lys Tyr Lys Asn Phe Ser Ile Ser
        915                 920                 925

Phe Trp Val Arg Ile Pro Asn Tyr Asp Asn Lys Ile Val Asn Val Asn
    930                 935                 940

Asn Glu Tyr Thr Ile Ile Asn Cys Met Arg Asp Asn Asn Ser Gly Trp
945                 950                 955                 960

Lys Val Ser Leu Asn His Asn Glu Ile Ile Trp Thr Leu Gln Asp Asn
                965                 970                 975

Ser Gly Ile Asn Gln Lys Leu Ala Phe Asn Tyr Gly Asn Ala Asn Gly
            980                 985                 990

Ile Ser Asp Tyr Ile Asn Lys Trp Ile Phe Val Thr Ile Thr Asn Asp
        995                 1000                1005

Arg Leu Gly Asp Ser Lys Leu Tyr Ile Asn Gly Asn Leu Ile Asp Lys
    1010                1015                1020

Lys Ser Ile Leu Asn Leu Gly Asn Ile His Val Ser Asp Asn Ile Leu
1025                1030                1035                1040

Phe Lys Ile Val Asn Cys Ser Tyr Thr Arg Tyr Ile Gly Ile Arg Tyr
                1045                1050                1055

Phe Asn Ile Phe Asp Lys Glu Leu Asp Glu Thr Glu Ile Gln Thr Leu
            1060                1065                1070

Tyr Asn Asn Glu Pro Asn Ala Asn Ile Leu Lys Asp Phe Trp Gly Asn
        1075                1080                1085

Tyr Leu Leu Tyr Asp Lys Glu Tyr Tyr Leu Leu Asn Val Leu Lys Pro
    1090                1095                1100

Asn Asn Phe Ile Asn Arg Arg Thr Asp Ser Thr Leu Ser Ile Asn Asn
1105                1110                1115                1120

Ile Arg Ser Thr Ile Leu Leu Ala Asn Arg Leu Tyr Ser Gly Ile Lys
                1125                1130                1135

Val Lys Ile Gln Arg Val Asn Asn Ser Ser Thr Asn Asp Asn Leu Val
            1140                1145                1150

Arg Lys Asn Asp Gln Val Tyr Ile Asn Phe Val Ala Ser Lys Thr His
        1155                1160                1165

Leu Leu Pro Leu Tyr Ala Asp Thr Ala Thr Thr Asn Lys Glu Lys Thr
    1170                1175                1180

Ile Lys Ile Ser Ser Ser Gly Asn Arg Phe Asn Gln Val Val Val Met
1185                1190                1195                1200
```

```
Asn Ser Val Gly Asn Cys Thr Met Asn Phe Lys Asn Asn Asn Gly Asn
            1205                1210               1215

Asn Ile Gly Leu Leu Gly Phe Lys Ala Asp Thr Val Val Ala Ser Thr
            1220                1225                1230

Trp Tyr Tyr Thr His Met Arg Asp Asn Thr Asn Ser Asn Gly Phe Phe
            1235                1240                1245

Trp Asn Phe Ile Ser Glu Glu His Gly Trp Gln Glu Lys
        1250                1255                1260
```